US011985890B2

(12) United States Patent
Kawakami et al.

(10) Patent No.: US 11,985,890 B2
(45) Date of Patent: May 14, 2024

(54) ORGANIC COMPOUND, LIGHT-EMITTING ELEMENT, LIGHT-EMITTING DEVICE, ELECTRONIC DEVICE, DISPLAY DEVICE, AND LIGHTING DEVICE

(71) Applicant: Semiconductor Energy Laboratory Co., Ltd., Kanagawa-ken (JP)

(72) Inventors: Sachiko Kawakami, Kanagawa (JP); Anna Tada, Kanagawa (JP); Yusuke Takita, Kanagawa (JP); Tsunenori Suzuki, Kanagawa (JP); Naoaki Hashimoto, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 183 days.

(21) Appl. No.: 17/166,217

(22) Filed: Feb. 3, 2021

(65) Prior Publication Data

US 2021/0159410 A1 May 27, 2021

Related U.S. Application Data

(63) Continuation of application No. 15/855,113, filed on Dec. 27, 2017, now Pat. No. 10,916,707.

(30) Foreign Application Priority Data

Dec. 28, 2016 (JP) ................................ 2016-255514

(51) Int. Cl.
*H01L 51/50* (2006.01)
*C07C 211/54* (2006.01)
(Continued)

(52) U.S. Cl.
CPC .......... *H10K 85/633* (2023.02); *C07C 211/54* (2013.01); *C07C 211/58* (2013.01);
(Continued)

(58) Field of Classification Search
None
See application file for complete search history.

(56) References Cited

U.S. PATENT DOCUMENTS 6,582,837 B1 6/2003 Toguchi et al.
8,203,262 B2 6/2012 Seo et al.
(Continued)

FOREIGN PATENT DOCUMENTS

JP 11-152253 A 6/1999
JP 2010-202633 A 9/2010
(Continued)

OTHER PUBLICATIONS

Taiwanese Office Action (Application No. 106145661) dated Aug. 23, 2021.

*Primary Examiner* — Gregory D Clark
(74) *Attorney, Agent, or Firm* — Husch Blackwell LLP

(57) ABSTRACT

An object of one embodiment of the present invention is to provide a novel organic compound. The organic compound is a triarylamine derivative. The triarylamine derivative has an aryl group including a skeleton in which a naphthyl group is bonded to a naphthylene group. The other two aryl groups are each independently a phenyl group, a biphenyl group, or a terphenyl group. These groups may each have a substituent. As the substituent, an alkyl group having 1 to 6 carbon atoms or a cycloalkyl group having 3 to 6 carbon atoms can be selected.

6 Claims, 62 Drawing Sheets

(51) Int. Cl.

| | |
|---|---|
| ***C07C 211/58*** | (2006.01) |
| ***H10K 85/60*** | (2023.01) |
| *H10K 50/11* | (2023.01) |
| *H10K 50/15* | (2023.01) |
| *H10K 50/16* | (2023.01) |
| *H10K 59/12* | (2023.01) |
| *H10K 59/17* | (2023.01) |
| *H10K 71/00* | (2023.01) |
| *H10K 71/13* | (2023.01) |
| *H10K 101/10* | (2023.01) |
| *H10K 101/30* | (2023.01) |
| *H10K 102/00* | (2023.01) |

(52) U.S. Cl.

CPC ......... *H10K 85/626* (2023.02); *H10K 85/631* (2023.02); *C07C 2601/16* (2017.05); *C07C 2602/10* (2017.05); *H10K 50/11* (2023.02); *H10K 50/156* (2023.02); *H10K 50/16* (2023.02); *H10K 59/12* (2023.02); *H10K 59/17* (2023.02); *H10K 71/00* (2023.02); *H10K 71/13* (2023.02); *H10K 2101/10* (2023.02); *H10K 2101/30* (2023.02); *H10K 2102/311* (2023.02)

(56) References Cited

U.S. PATENT DOCUMENTS

| | | | | |
|---|---|---|---|---|
| 8,822,434 | B2 | 9/2014 | Liang et al. | |
| 8,841,655 | B2 | 9/2014 | Okamoto | |
| 8,921,548 | B2 | 12/2014 | Inoue et al. | |
| 9,093,649 | B2 | 7/2015 | Kawakami et al. | |
| 9,184,398 | B2 | 11/2015 | Inoue et al. | |
| 9,343,681 | B2 | 5/2016 | Suzuki et al. | |
| 9,985,223 | B2 | 5/2018 | Inoue et al. | |
| 10,916,707 | B2 | 2/2021 | Kawakami et al. | |
| 2002/0050786 | A1 | 5/2002 | Yamazaki et al. | |
| 2004/0245542 | A1 | 12/2004 | Kim | |
| 2004/0265630 | A1 | 12/2004 | Suh et al. | |
| 2005/0208331 | A1 | 9/2005 | Maeda | |
| 2007/0037011 | A1 | 2/2007 | Nakashima et al. | |
| 2007/0096639 | A1 | 5/2007 | Nakashima et al. | |
| 2007/0149784 | A1 | 6/2007 | Murata et al. | |
| 2007/0215867 | A1 | 9/2007 | Kawakami et al. | |
| 2007/0215889 | A1 | 9/2007 | Kawakami et al. | |
| 2008/0206598 | A1 | 8/2008 | Ohsawa et al. | |
| 2009/0284140 | A1 | 11/2009 | Osaka et al. | |
| 2010/0245217 | A1 | 9/2010 | Nomura et al. | |
| 2010/0301744 | A1 | 12/2010 | Osaka et al. | |
| 2011/0168992 | A1 | 7/2011 | Bae et al. | |
| 2012/0305898 | A1 | 12/2012 | Okamoto | |
| 2013/0321361 | A1 | 12/2013 | Lynch et al. | |
| 2014/0084273 | A1 | 3/2014 | Nakayama et al. | |
| 2014/0183500 | A1 | 7/2014 | Ikeda et al. | |
| 2015/0041795 | A1 | 2/2015 | Suzuki et al. | |
| 2015/0060813 | A1 | 3/2015 | Kawakami et al. | |
| 2015/0188057 | A1 | 7/2015 | Itoi et al. | |
| 2015/0318495 | A1 | 11/2015 | Kawakami et al. | |
| 2016/0079314 | A1 | 3/2016 | Seo et al. | |
| 2016/0336519 | A1 | 11/2016 | Seo et al. | |
| 2017/0040535 | A1 | 2/2017 | Ogita et al. | |
| 2017/0062734 | A1 | 3/2017 | Suzuki et al. | |
| 2017/0125689 | A1 | 5/2017 | Lee et al. | |
| 2017/0222156 | A1 | 8/2017 | Kawakami et al. | |
| 2017/0317289 | A1* | 11/2017 | Lee | C07D 307/91 |

FOREIGN PATENT DOCUMENTS

| | | | | |
|---|---|---|---|---|
| JP | 2011-009498 A | | 1/2011 | |
| JP | 2014-167946 A | | 9/2014 | |
| JP | 7016695 | | 2/2022 | |
| KR | 2013-0022071 A | | 3/2013 | |
| KR | 2016-0120609 A | | 10/2016 | |
| KR | 2016120609 | * | 10/2016 | H01L 51/50 |
| TW | 201336969 | | 9/2013 | |
| WO | WO 2012/053627 A1 | | 4/2012 | |

* cited by examiner

ORGANIC COMPOUND, LIGHT-EMITTING ELEMENT, LIGHT-EMITTING DEVICE, ELECTRONIC DEVICE, DISPLAY DEVICE, AND LIGHTING DEVICE

This application is a continuation of copending U.S. application Ser. No. 15/855,113, filed on Dec. 27, 2017 which is incorporated herein by reference.

BACKGROUND OF THE INVENTION

1. Field of the Invention

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. Another embodiment of the present invention relates to a process, a machine, manufacture, or a composition of matter. Specific examples of the technical field of one embodiment of the present invention disclosed in this specification include a semiconductor device, a display device, a liquid crystal display device, a light-emitting device, a lighting device, a power storage device, a memory device, an imaging device, a method for driving any of them, and a method for manufacturing any of them.

2. Description of the Related Art

Some display devices and light-emitting devices including organic EL elements are practically used and are increasingly finding diverse applications. With an increase in usage scenes, there arises a possibility of the use in a severe environment, which requires higher reliability.

Meanwhile, higher emission characteristics and higher display characteristics are also demanded. Regarding a carrier-transport material, importance is placed not only on reliability but also on its transport property and level.

Patent Document 1 discloses a hole-transport material which has a triarylamine structure and exhibits favorable characteristics.

REFERENCE

Patent Document

[Patent Document 1] Japanese Published Patent Application No. 2010-202633

SUMMARY OF THE INVENTION

An object of one embodiment of the present invention is to provide a novel organic compound. Another object of one embodiment of the present invention is to provide a novel carrier-transport material. Another object of one embodiment of the present invention is to provide a novel hole-transport material. Another object of one embodiment of the present invention is to provide a hole-transport material with a high glass transition temperature (Tg). Another object of one embodiment of the present invention is to provide a novel material for alight-emitting element. Another object of one embodiment of the present invention is to provide a material for a light-emitting element, which enables the light-emitting element to have a long lifetime.

Another object of one embodiment of the present invention is to provide a novel light-emitting element. Another object is to provide a light-emitting element with a long lifetime.

Another object of one embodiment of the present invention is to provide a highly reliable light-emitting device, a highly reliable electronic device, and a highly reliable display device. Another object of one embodiment of the present invention is to provide a light-emitting device, an electronic device, and a display device each having high display quality.

It is only necessary that at least one of the above objects be achieved in the present invention.

One embodiment of the present invention is an organic compound represented by the following general formula (G1).

(G1)

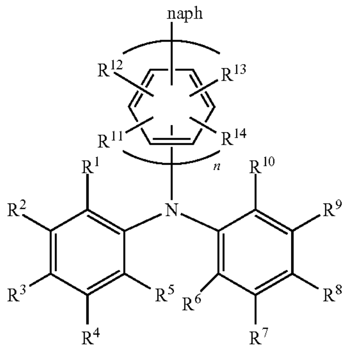

In the general formula (G1), $R^1$ to $R^{10}$ each independently represent hydrogen, an alkyl group having 1 to 6 carbon atoms, a cycloalkyl group having 3 to 6 carbon atoms, or one of groups represented by the following general formulae (R-1) to (R-4), and $R^{11}$ to $R^{14}$ each independently represent hydrogen, an alkyl group having 1 to 6 carbon atoms, or a cycloalkyl group having 3 to 6 carbon atoms. Furthermore, n represents 0, 1, or 2; in the case where n is 2, two phenylene groups may have different substituents. Furthermore, naph represents a group represented by the following general formula (g1-1) or (g1-2).

(R-1)

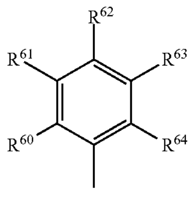

-continued (R-2)

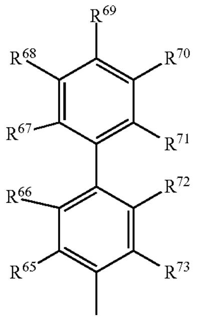

(R-3)

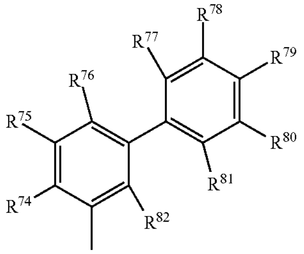

(R-4)

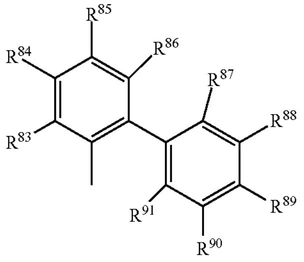

In the general formulae (R-1) to (R-4), $R^{60}$ to $R^{91}$ each independently represent hydrogen, an alkyl group having 1 to 6 carbon atoms, or a cycloalkyl group having 3 to 6 carbon atoms.

(gl-1)

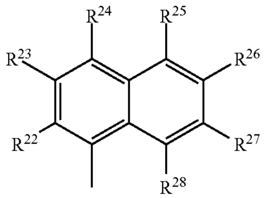

(gl-2)

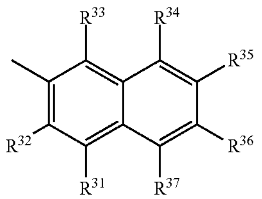

In the general formula (gl-1), one of $R^{22}$ to $R^{28}$ represents a group represented by the following general formula (g2-1) or (g2-2), and the others each independently represent hydrogen, an alkyl group having 1 to 6 carbon atoms, or a cycloalkyl group having 3 to 6 carbon atoms. In the general formula (gl-2), one of $R^{31}$ to $R^{37}$ represents the group represented by the following general formula (g2-1) or (g2-2), and the others each independently represent hydrogen, an alkyl group having 1 to 6 carbon atoms, or a cycloalkyl group having 3 to 6 carbon atoms.

(g2-1)

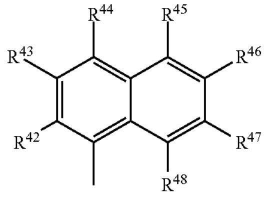

(g2-2)

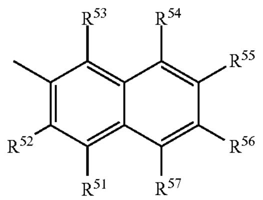

In the general formula (g2-1), $R^{42}$ to $R^{48}$ each independently represent hydrogen, an alkyl group having 1 to 6 carbon atoms, or a cycloalkyl group having 3 to 6 carbon atoms. In the general formula (g2-2), $R^{51}$ to $R^{57}$ each independently represent hydrogen, an alkyl group having 1 to 6 carbon atoms, or a cycloalkyl group having 3 to 6 carbon atoms.

Another embodiment of the present invention is an organic compound represented by the following general formula (G1).

(G1)

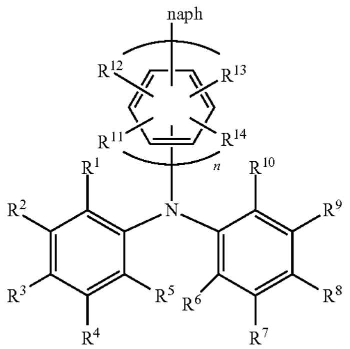

In the general formula (G1), $R^1$ to $R^{10}$ each independently represent hydrogen, an alkyl group having 1 to 6 carbon atoms, a cycloalkyl group having 3 to 6 carbon atoms, or one of groups represented by the following general formulae (R-1) to (R-4), and $R^{11}$ to $R^{14}$ each independently represent hydrogen, an alkyl group having 1 to 6 carbon atoms, or a cycloalkyl group having 3 to 6 carbon atoms. Furthermore, n represents 0, 1, or 2; in the case where n is 2, two phenylene groups may have different substituents. Furthermore, naph represents a group represented by the following general formula (g1-2).

(R-1)

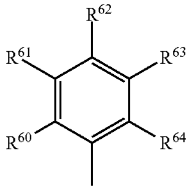

(R-2)

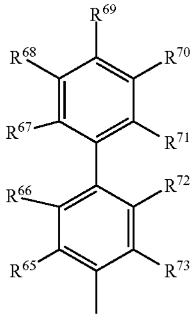

(R-3)

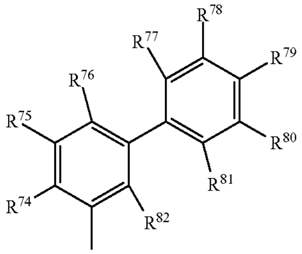

(R-4)

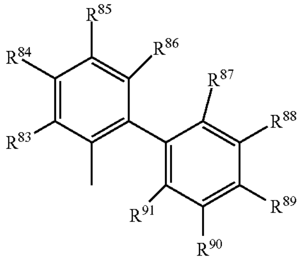

In the general formulae (R-1) to (R-4), $R^{60}$ to $R^{91}$ each independently represent hydrogen, an alkyl group having 1 to 6 carbon atoms, or a cycloalkyl group having 3 to 6 carbon atoms.

(g1-2)

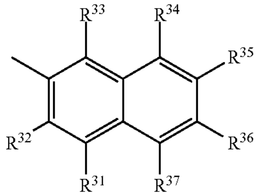

In the general formula (g1-2), one of $R^{31}$ to $R^{37}$ represents a group represented by the following general formula (g2-1) or (g2-2), and the others each independently represent hydrogen, an alkyl group having 1 to 6 carbon atoms, or a cycloalkyl group having 3 to 6 carbon atoms.

(g2-1)

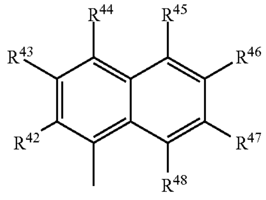

(g2-2)

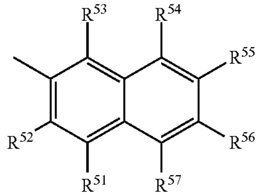

In the general formula (g2-1), $R^{42}$ to $R^{48}$ each independently represent hydrogen, an alkyl group having 1 to 6 carbon atoms, or a cycloalkyl group having 3 to 6 carbon atoms. In the general formula (g2-2), $R^{51}$ to $R^{57}$ each independently represent hydrogen, an alkyl group having 1 to 6 carbon atoms, or a cycloalkyl group having 3 to 6 carbon atoms.

Another embodiment of the present invention is an organic compound represented by the following general formula (G2).

(G2)

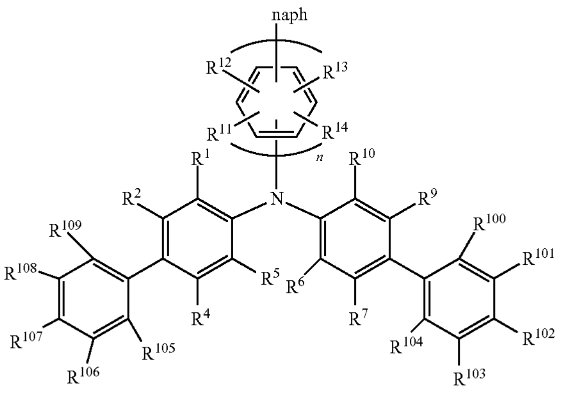

In the general formula (G2), $R^1$, $R^2$, $R^4$ to $R^7$, $R^9$ to $R^{14}$, and $R^{100}$ to $R^{109}$ each independently represent hydrogen, an alkyl group having 1 to 6 carbon atoms, or a cycloalkyl group having 3 to 6 carbon atoms. Furthermore, n represents 0, 1, or 2; in the case where n is 2, two phenylene groups may have different substituents. Furthermore, naph represents a group represented by the following general formula (g1-2).

(g1-2)

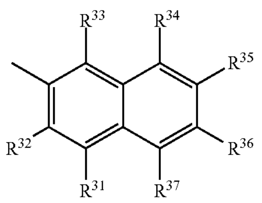

In the general formula (g1-2), one of $R^{31}$ to $R^{37}$ represents a group represented by the following general formula (g2-1) or (g2-2), and the others each independently represent hydrogen, an alkyl group having 1 to 6 carbon atoms, or a cycloalkyl group having 3 to 6 carbon atoms.

(g2-1)

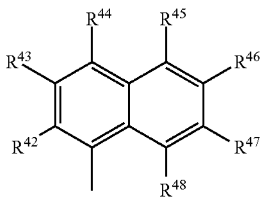

(g2-2)

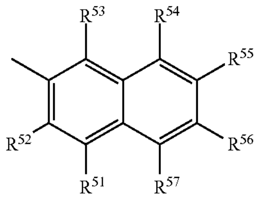

In the general formula (g2-1), $R^{42}$ to $R^{48}$ each independently represent hydrogen, an alkyl group having 1 to 6 carbon atoms, or a cycloalkyl group having 3 to 6 carbon atoms. In the general formula (g2-2), $R^{51}$ to $R^{17}$ each independently represent hydrogen, an alkyl group having 1 to 6 carbon atoms, or a cycloalkyl group having 3 to 6 carbon atoms.

Another embodiment of the present invention is an organic compound represented by the following general formula (G3).

(G3)

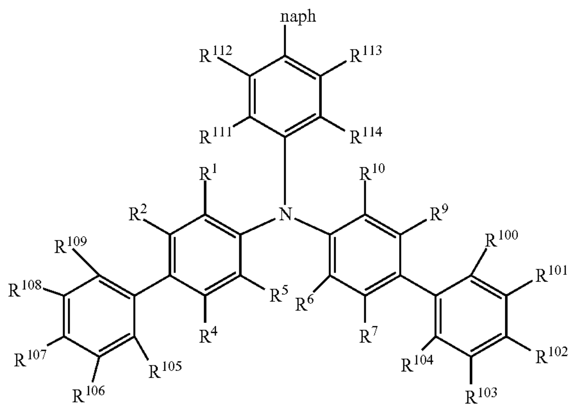

In the general formula (G3), $R^1$, $R^2$, $R^4$ to $R^7$, $R^9$, $R^{10}$, $R^{100}$ to $R^{109}$, and $R^{111}$ to $R^{114}$ each independently represent hydrogen, an alkyl group having 1 to 6 carbon atoms, or a cycloalkyl group having 3 to 6 carbon atoms. Furthermore, naph represents a group represented by the following general formula (g1-2).

(g1-2)

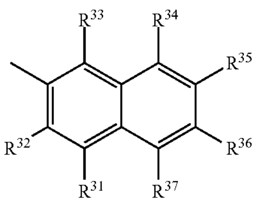

In the general formula (g1-2), one of $R^{31}$ to $R^{37}$ represents a group represented by the following general formula (g2-1) or (g2-2), and the others each independently represent hydrogen, an alkyl group having 1 to 6 carbon atoms, or a cycloalkyl group having 3 to 6 carbon atoms.

(g2-1)

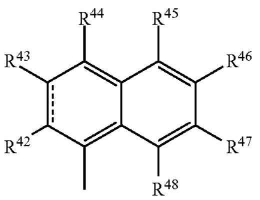

(g2-2)

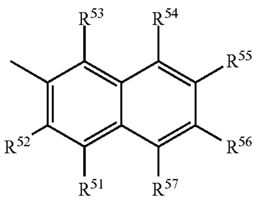

In the general formula (g2-1), $R^{42}$ to $R^{48}$ each independently represent hydrogen, an alkyl group having 1 to 6 carbon atoms, or a cycloalkyl group having 3 to 6 carbon atoms. In the general formula (g2-2), $R^{51}$ to $R^{57}$ each independently represent hydrogen, an alkyl group having 1 to 6 carbon atoms, or a cycloalkyl group having 3 to 6 carbon atoms.

Another embodiment of the present invention is an organic compound represented by the following general formula (G4).

(G4)

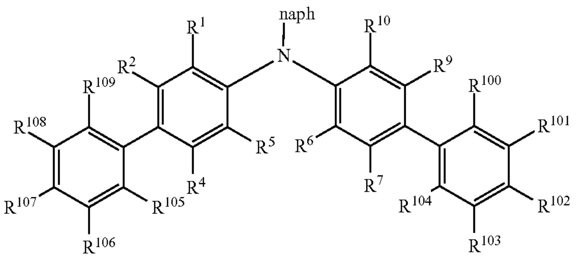

In the general formula (G4), $R^1$, $R^2$, $R^4$ to $R^7$, $R^9$, $R^{10}$, and $R^{100}$ to $R^{19}$ each independently represent hydrogen, an alkyl group having 1 to 6 carbon atoms, or a cycloalkyl group having 3 to 6 carbon atoms. Furthermore, naph represents a group represented by the following general formula (g1-2).

(g1-2)

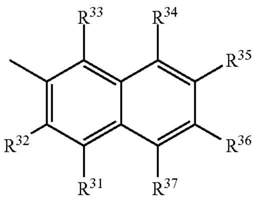

In the general formula (g1-2), one of $R^{31}$ to $R^{37}$ represents a group represented by the following general formula (g2-1) or (g2-2), and the others each independently represent hydrogen, an alkyl group having 1 to 6 carbon atoms, or a cycloalkyl group having 3 to 6 carbon atoms.

(g2-1)

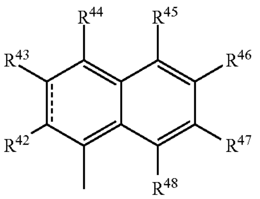

(g2-2)

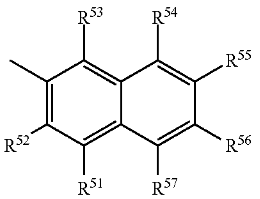

In the general formula (g2-1), $R^{42}$ to $R^{48}$ each independently represent hydrogen, an alkyl group having 1 to 6 carbon atoms, or a cycloalkyl group having 3 to 6 carbon atoms. In the general formula (g2-2), $R^{51}$ to $R^{57}$ each independently represent hydrogen, an alkyl group having 1 to 6 carbon atoms, or a cycloalkyl group having 3 to 6 carbon atoms.

Another embodiment of the present invention is an organic compound represented by the following general formula (G1).

(G1)

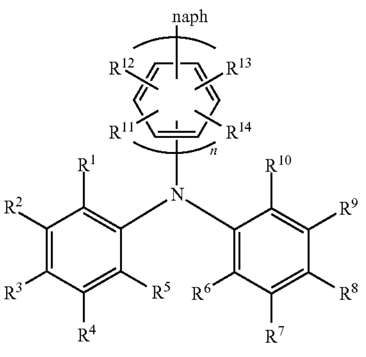

In the general formula (G1), $R^1$ to $R^{10}$ each independently represent hydrogen, an alkyl group having 1 to 6 carbon atoms, a cycloalkyl group having 3 to 6 carbon atoms, or one of groups represented by the following general formulae (R-1) to (R-4), and $R^{11}$ to $R^{14}$ each independently represent hydrogen, an alkyl group having 1 to 6 carbon atoms, or a cycloalkyl group having 3 to 6 carbon atoms. Furthermore, n represents 0, 1, or 2; in the case where n is 2, two phenylene groups may have different substituents. Furthermore, naph represents a group represented by the following general formula (g1-1) or (g1-2).

(R-1)

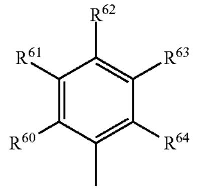

(R-2)

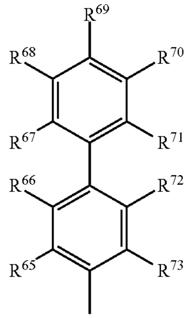

(R-3)

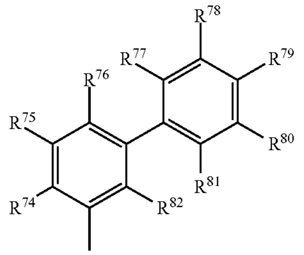

(R-4)

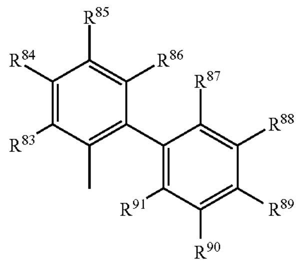

In the general formulae (R-1) to (R-4), $R^{60}$ to $R^{91}$ each independently represent hydrogen, an alkyl group having 1 to 6 carbon atoms, or a cycloalkyl group having 3 to 6 carbon atoms.

(g1-1)

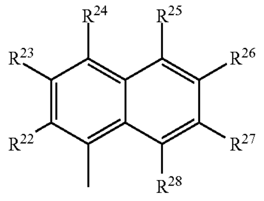

(g1-2)

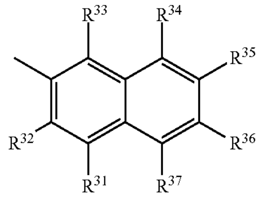

In the general formula (g1-1), one of $R^{22}$ to $R^{28}$ represents a group represented by the following general formula (g2-2), and the others each independently represent hydrogen, an alkyl group having 1 to 6 carbon atoms, or a cycloalkyl group having 3 to 6 carbon atoms. In the general formula (g1-2), one of $R^{31}$ to $R^{37}$ represents the group represented by the following general formula (g2-2), and the others each independently represent hydrogen, an alkyl group having 1 to 6 carbon atoms, or a cycloalkyl group having 3 to 6 carbon atoms.

(g2-2)

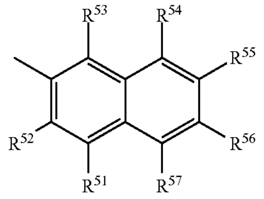

In the general formula (g2-2), $R^{51}$ to $R^{57}$ each independently represent hydrogen, an alkyl group having 1 to 6 carbon atoms, or a cycloalkyl group having 3 to 6 carbon atoms.

Another embodiment of the present invention is an organic compound represented by the following general formula (G1).

(G1)

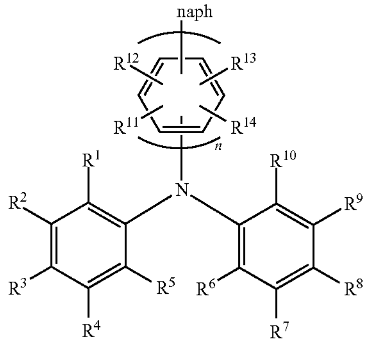

In the general formula (G1), $R^1$ to $R^{10}$ each independently represent hydrogen, an alkyl group having 1 to 6 carbon atoms, a cycloalkyl group having 3 to 6 carbon atoms, or one of groups represented by the following general formulae (R-1) to (R-4), and $R^{11}$ to $R^{14}$ each independently represent hydrogen, an alkyl group having 1 to 6 carbon atoms, or a cycloalkyl group having 3 to 6 carbon atoms. Furthermore, n represents 0, 1, or 2; in the case where n is 2, two phenylene groups may have different substituents. Furthermore, naph represents a group represented by the following general formula (g1-1) or (g1-2).

(R-1)

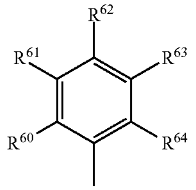

(R-2)

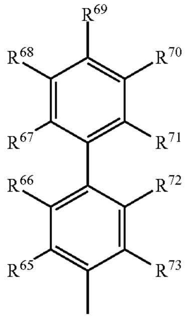

(R-3)

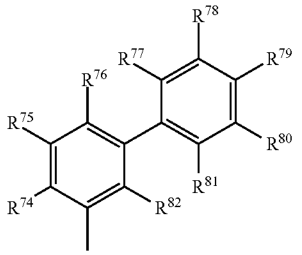

(R-4)

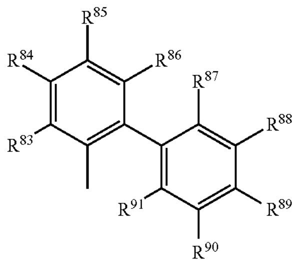

In the general formulae (R-1) to (R-4), $R^{60}$ to $R^{91}$ each independently represent hydrogen, an alkyl group having 1 to 6 carbon atoms, or a cycloalkyl group having 3 to 6 carbon atoms.

(g1-1)

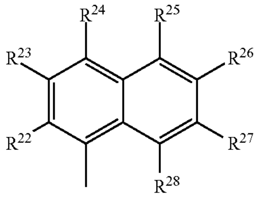

(g1-2)

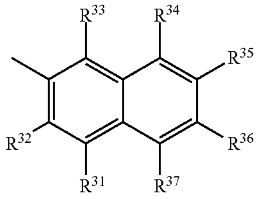

In the general formula (g1-1), one of $R^{22}$ to $R^{28}$ represents a group represented by the following general formula (g2-1), and the others each independently represent hydrogen, an alkyl group having 1 to 6 carbon atoms, or a cycloalkyl group having 3 to 6 carbon atoms. In the general formula (g1-2), one of $R^{31}$ to $R^{37}$ represents the group represented by the following general formula (g2-1), and the others each independently represent hydrogen, an alkyl group having 1 to 6 carbon atoms, or a cycloalkyl group having 3 to 6 carbon atoms.

(g2-1)

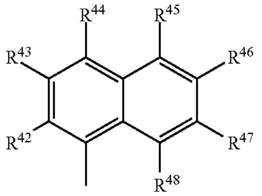

In the general formula (g2-1), $R^{42}$ to $R^{48}$ each independently represent hydrogen, an alkyl group having 1 to 6 carbon atoms, or a cycloalkyl group having 3 to 6 carbon atoms.

Another embodiment of the present invention is an organic compound with the above structure. In the organic compound, one of $R^{31}$ to $R^{37}$ represents a group represented by the following general formula (g2-2), and the others each independently represent hydrogen, an alkyl group having 1 to 6 carbon atoms, or a cycloalkyl group having 3 to 6 carbon atoms.

(g2-2)

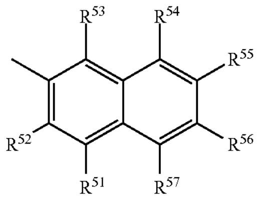

In the general formula (g2-2), $R^{51}$ to $R^{57}$ each independently represent hydrogen, an alkyl group having 1 to 6 carbon atoms, or a cycloalkyl group having 3 to 6 carbon atoms.

Another embodiment of the present invention is an organic compound with the above structure. In the organic compound, $R^{36}$ represents the group represented by the general formula (g2-2), and $R^{31}$ to $R^{35}$ and $R^{37}$ each independently represent hydrogen, an alkyl group having 1 to 6 carbon atoms, or a cycloalkyl group having 3 to 6 carbon atoms.

Another embodiment of the present invention is an organic compound with the above structure. In the organic compound, one of $R^{31}$ to $R^{37}$ represents a group represented by the following general formula (g2-1), and the others each independently represent hydrogen, an alkyl group having 1 to 6 carbon atoms, or a cycloalkyl group having 3 to 6 carbon atoms.

(g2-1)

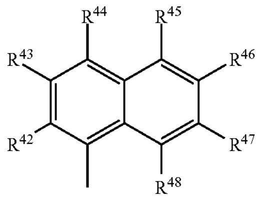

In the general formula (g2-1), $R^{42}$ to $R^{48}$ each independently represent hydrogen, an alkyl group having 1 to 6 carbon atoms, or a cycloalkyl group having 3 to 6 carbon atoms.

One embodiment of the present invention is a light-emitting element containing the organic compound with the above structure.

Another embodiment of the present invention is a light-emitting device including the light-emitting element with the above structure and a transistor or a substrate.

Another embodiment of the present invention is an electronic device including the light-emitting device with the above structure and a sensor, an operation button, a speaker, or a microphone.

Another embodiment of the present invention is a lighting device including the light-emitting device with the above structure and a housing.

Note that the light-emitting device in this specification includes an image display device with a light-emitting element. The light-emitting device may include a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may also be included in lighting equipment or the like.

According to one embodiment of the present invention, a novel light-emitting element can be provided. Furthermore, a light-emitting element with a long lifetime can be provided. Furthermore, a light-emitting element with high emission efficiency can be provided. Furthermore, a light-emitting element with high heat resistance can be provided.

According to another embodiment of the present invention, a highly reliable light-emitting device, a highly reliable electronic device, and a highly reliable display device can be provided. According to another embodiment of the present invention, a light-emitting device, an electronic device, and a display device each having low power consumption can be provided.

Note that the description of these effects does not preclude the existence of other effects. One embodiment of the present invention does not necessarily have all the effects listed above. Other effects will be apparent from and can be derived from the description of the specification, the drawings, the claims, and the like.

BRIEF DESCRIPTION OF THE DRAWINGS

FIGS. 9A, 9B1, 9B2, 9C, and 9D each illustrate an electronic device.

DETAILED DESCRIPTION OF THE INVENTION

Figure 1A:
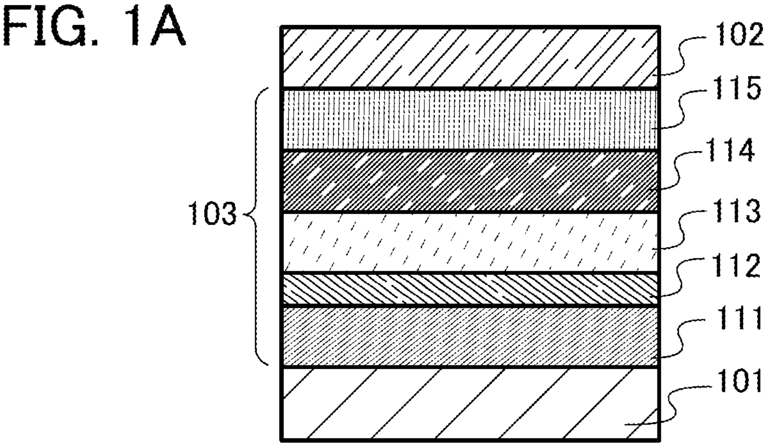
FIGS. 1A to 1C are schematic views of light-emitting elements.

Embodiments of the present invention will be described in detail below with reference to the drawings. Note that the present invention is not limited to the following description, and it will be readily appreciated by those skilled in the art that the modes and details can be changed in various ways without departing from the spirit and the scope of the present invention. Accordingly, the present invention should not be interpreted as being limited to the description of the embodiments below.

Embodiment 1

An organic compound of one embodiment of the present invention is a triarylamine derivative in which one aryl group includes a binaphthyl skeleton. That is, the aryl group includes a skeleton of a naphthylene group having a naphthyl group. The other two aryl groups of the triarylamine derivative are each independently a phenyl group, a biphenyl group, or a terphenyl group. These groups may each have a substituent. As the substituent, an alkyl group having 1 to 6 carbon atoms or a cycloalkyl group having 3 to 6 carbon atoms can be selected.

The aryl group including the skeleton of the naphthylene group having the naphthyl group may further have an arylene group between the naphthylene group and nitrogen of an amine. As the arylene group, a phenylene group or a biphenylene group can be selected. The arylene group may have a substituent. As the substituent, an alkyl group having 1 to 6 carbon atoms or a cycloalkyl group having 3 to 6 carbon atoms can be selected.

In consideration of the reactivity of a naphthalene skeleton, the following structure is preferred: the naphthylene group has bonds at two of the 2-, 3-, 6-, and 7-positions, one of the bonds is bonded to nitrogen of the amine or to the arylene group, and the other is bonded to the naphthyl group. This structure can facilitate the synthesis of a source material and reduce the production cost of the target substance. In consideration of the reactivity of the naphthalene skeleton, it is preferable that the 2-position of the naphthylene group be bonded to the nitrogen of the amine or to the arylene group and one of the 3-, 6-, and 7-positions be bonded to the naphthyl group. This can facilitate the synthesis of a source material and reduce the production cost of the target substance. Furthermore, a material with high heat resistance, high reliability, or a high carrier-transport property can be provided. To obtain a light-emitting element with high heat resistance, high reliability, or a high carrier-transport property, the following structure is preferred: the naphthylene group has bonds at the 2- and 6-positions, one of the bonds is bonded to the nitrogen of the amine or to the arylene group, and the other is bonded to the naphthyl group.

To provide a highly reliable light-emitting element, the naphthyl group is preferably a 2-naphthyl group.

The above organic compound of one embodiment of the present invention can be represented by the following general formula (G1).

(G1)

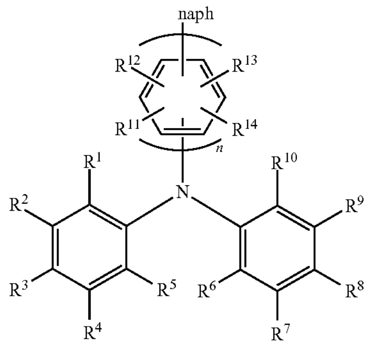

In the general formula (G1), $R^1$ to $R^{10}$ each independently represent hydrogen, an alkyl group having 1 to 6 carbon atoms, a cycloalkyl group having 3 to 6 carbon atoms, or one of groups represented by the following general formulae (R-1) to (R-4). It is preferable that one of $R^1$ to $R^5$ and one of $R^6$ to $R^{10}$ each represent one of the general formulae (R-1) to (R-4) and the others each independently represent hydrogen, an alkyl group having 1 to 6 carbon atoms, or a cycloalkyl group having 3 to 6 carbon atoms. When one of $R^1$ to $R^5$ and one of R to $R^{10}$ each represent one of the general formulae (R-1) to (R-4), all of the others preferably represent hydrogen, in which case the synthesis can be easy and the production cost can be low.

(R-1)

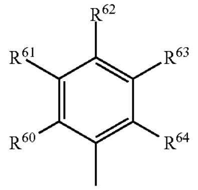

-continued (R-2)

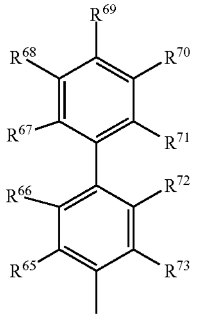

(R-3)

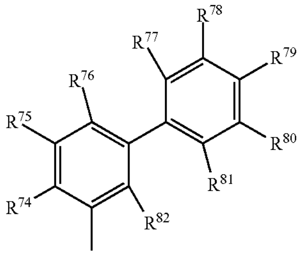

(R-4)

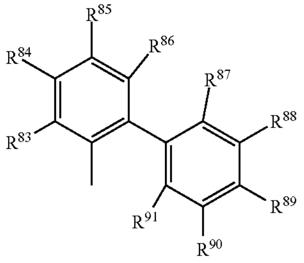

In the groups represented by the general formulae (R-1) to (R-4), $R^{60}$ to $R^{91}$ each independently represent hydrogen, an alkyl group having 1 to 6 carbon atoms, or a cycloalkyl group having 3 to 6 carbon atoms. Considering the cost, all of $R^{60}$ to $R^{91}$ preferably represent hydrogen.

In the general formula (G1), $R^{11}$ to $R^{14}$ each independently represent hydrogen, an alkyl group having 1 to 6 carbon atoms, or a cycloalkyl group having 3 to 6 carbon atoms. Furthermore, n represents 0, 1, or 2. In the case where n is 2, two phenylene groups are bonded to each other; the kinds or the positions of substituents of the phenylene groups may be different from each other. Note that n is preferably 1, in which case the substance has both high sublimability and high heat resistance.

In the general formula (G1), naph represents a group represented by the following general formula (g1-1) or (g1-2).

(g1-1)

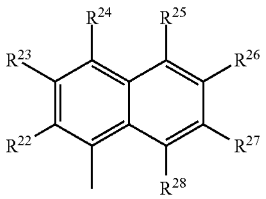

-continued (g1-2)

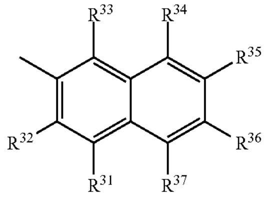

In the case where naph in the general formula (G1) represents the general formula (g1-1), one of $R^{22}$ to $R^{28}$ represents a group represented by the following general formula (g2-1) or (g2-2), and the others each independently represent hydrogen, an alkyl group having 1 to 6 carbon atoms, or a cycloalkyl group having 3 to 6 carbon atoms.

In the organic compound represented by the general formula (G1), naph preferably represents the group represented by the general formula (g1-2), in which case a highly reliable light-emitting element can be easily provided.

In the case where naph in the general formula (G1) represents the general formula (g1-2), one of $R^{31}$ to $R^{37}$ represents the group represented by the following general formula (g2-1) or (g2-2), and the others each independently represent hydrogen, an alkyl group having 1 to 6 carbon atoms, or a cycloalkyl group having 3 to 6 carbon atoms.

(g2-1)

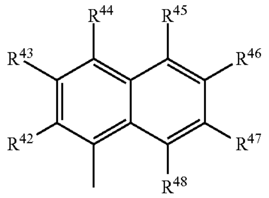

(g2-2)

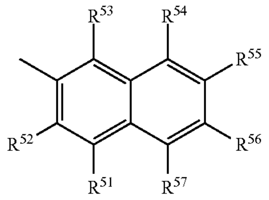

In the case where a substituent in the general formula (g1-1) or (g1-2) is the group represented by the general formula (g2-1), $R^{42}$ to $R^{48}$ each independently represent hydrogen, an alkyl group having 1 to 6 carbon atoms, or a cycloalkyl group having 3 to 6 carbon atoms.

In the case where a substituent in the general formula (g1-1) or (g1-2) is represented by the general formula (g2-2), $R^{51}$ to $R^{57}$ each independently represent hydrogen, an alkyl group having 1 to 6 carbon atoms, or a cycloalkyl group having 3 to 6 carbon atoms.

As for the groups represented by the general formulae (g2-1) and (g2-2), the group represented by the general formula (g2-2) is preferably selected to provide a highly reliable light-emitting element, and the group represented by the general formula (g2-1) is preferably selected to provide a light-emitting element with high heat resistance or a high carrier-transport property.

In the organic compound represented by the general formula (G1), it is preferable that one of $R^1$ to $R^5$ and one of $R^6$ to $R^{10}$ each represent the group represented by the general formula (R-1) and the others each independently represent hydrogen, an alkyl group having 1 to 6 carbon atoms, or a cycloalkyl group having 3 to 6 carbon atoms. In this case, further preferably, the substituents each represented by the general formula (R-1) are positioned at $R^3$ and $R^8$. That is, a preferred embodiment of the present invention is an organic compound represented by the following general formula (G2).

(G2)

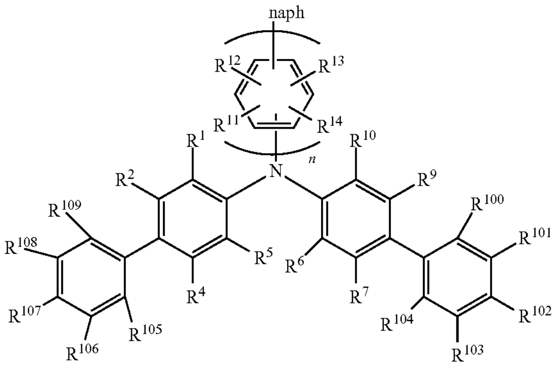

In the organic compound represented by the general formula (G2), $R^1$, $R^2$, $R^4$ to $R^7$, $R^9$, and $R^{10}$ each independently represent hydrogen, an alkyl group having 1 to 6 carbon atoms, or a cycloalkyl group having 3 to 6 carbon atoms. Furthermore, $R^{11}$ to $R^{14}$ and $R^{100}$ to $R^{109}$ each independently represent hydrogen, an alkyl group having 1 to 6 carbon atoms, or a cycloalkyl group having 3 to 6 carbon atoms. Furthermore, n represents 0, 1, or 2. In the case where n is 2, two phenylene groups are bonded to each other; the kinds or the positions of substituents of the phenylene groups may be different from each other.

All of $R^1$, $R^2$, $R^4$ to $R^7$, $R^9$ to $R^{14}$, and $R^{100}$ to $R^{109}$ preferably represent hydrogen, in which case the organic compound can be easily synthesized by using easily available materials, leading to low production cost.

Note that naph in the organic compound represented by the general formula (G2) is similar to naph in the organic compound represented by the general formula (G1) and therefore will not be described here.

In the organic compound represented by the general formula (G2), as described above, n is preferably 1 to provide a substance having both high sublimability and high heat resistance. That is, an organic compound represented by the following general formula (G3) is preferable.

(G3)

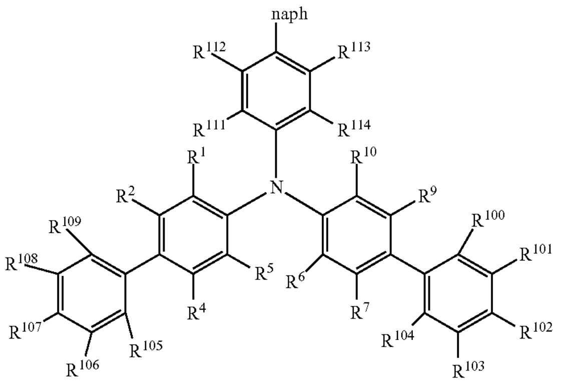

In the organic compound represented by the general formula (G3), naph, $R^1$, $R^2$, $R^4$ to $R^7$, $R^9$, $R^{10}$, and $R^{100}$ to $R^{109}$ are the same as those in the organic compound represented by the general formula (G1) or the organic compound represented by the general formula (G2) and therefore will not be described here. In the general formula (G3), $R^{111}$ to $R^{114}$ each independently represent hydrogen, an alkyl group having 1 to 6 carbon atoms, or a cycloalkyl group having 3 to 6 carbon atoms.

When n in the general formula (G2) is 0, the organic compound has a shallow HOMO level as compared with the case where n is 1 or 2. That is, an organic compound represented by the following general formula (G4) is one embodiment of the structure preferred in the case where a substance with a shallow HOMO level is needed.

(G4)

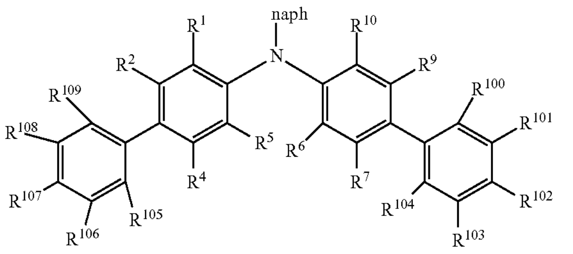

In the organic compound represented by the general formula (G4), naph, $R^1$, $R^2$, $R^4$ to $R^7$, $R^9$, $R^{10}$, and $R^{100}$ to $R^{109}$ are the same as those in the organic compound represented by the general formula (G1) or the organic compound represented by the general formula (G2) and therefore will not be described here.

In each of the organic compounds represented by the general formulae (G1) to (G4), the group represented by naph is preferably a group in which the group represented by the general formula (g2-2) is bonded to the group represented by the general formula (g1-2), in which case a highly reliable element can be provided. Further preferably, $R^{36}$ of the group represented by the general formula (g1-2) represents the group represented by the general formula (g2-2).

Specific structure examples of the organic compound of the present invention are shown below.

-continued
(101)
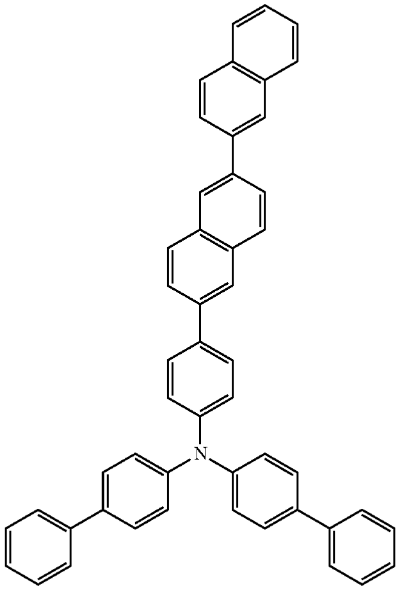
(103)
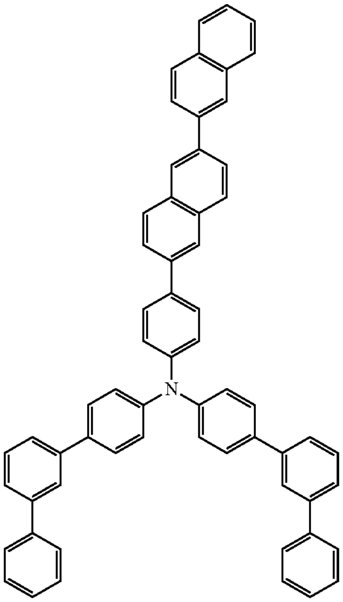
(102)
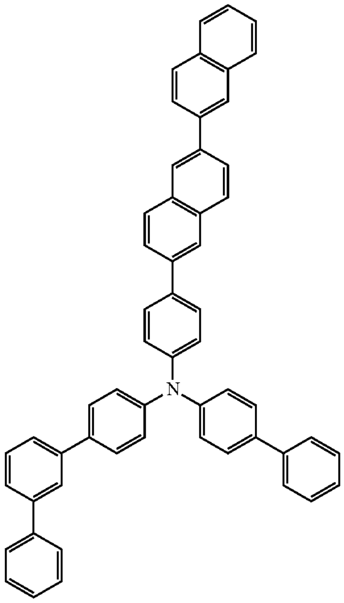
(104)
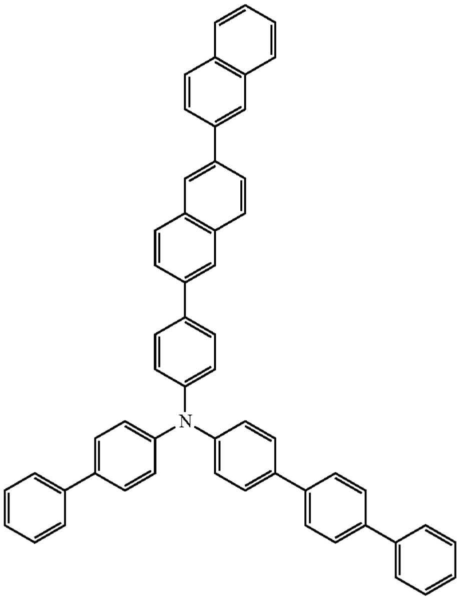

-continued
(105)
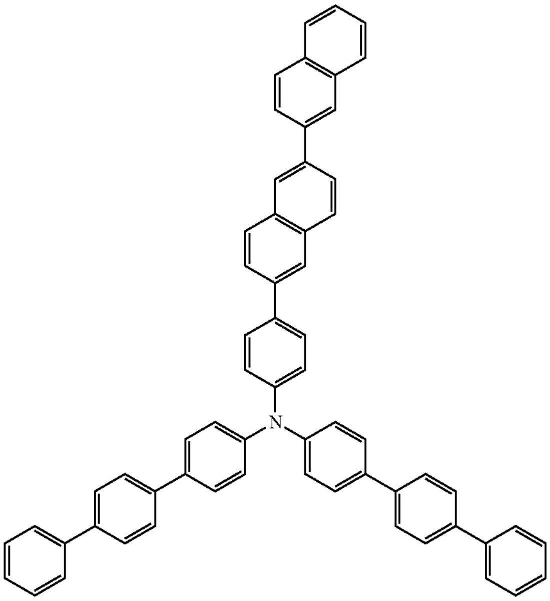
(106)
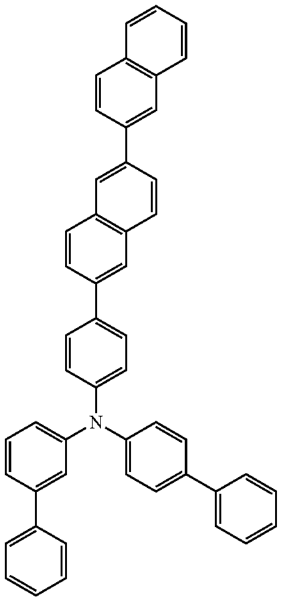
-continued
(107)
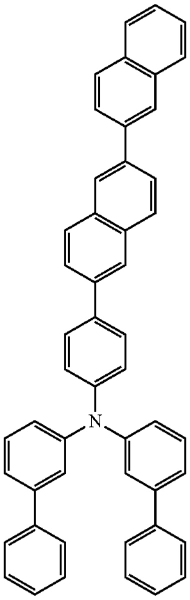
(108)
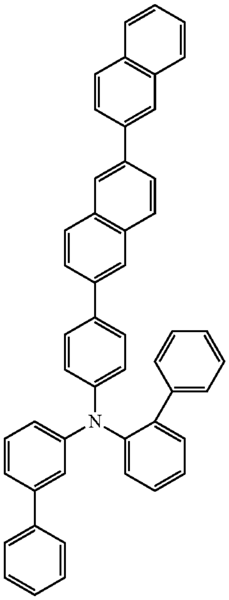

-continued
(109)
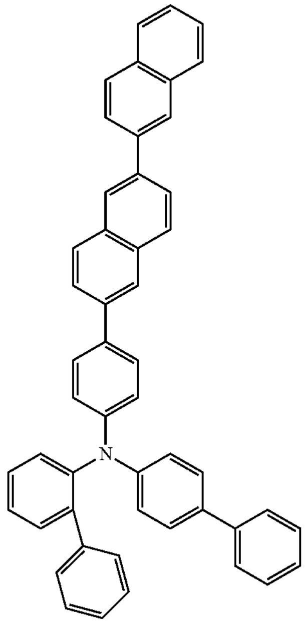
(110)
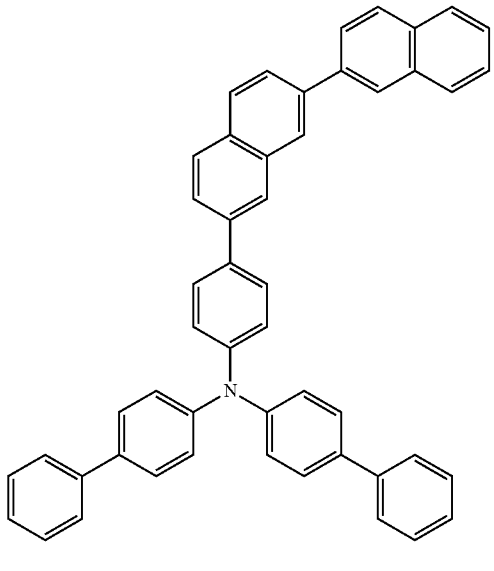
-continued
(111)
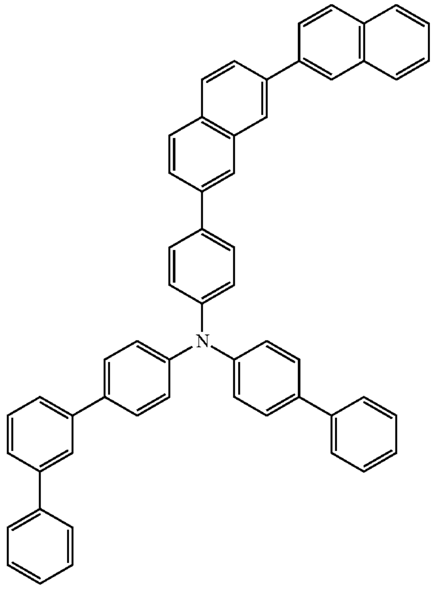
(112)
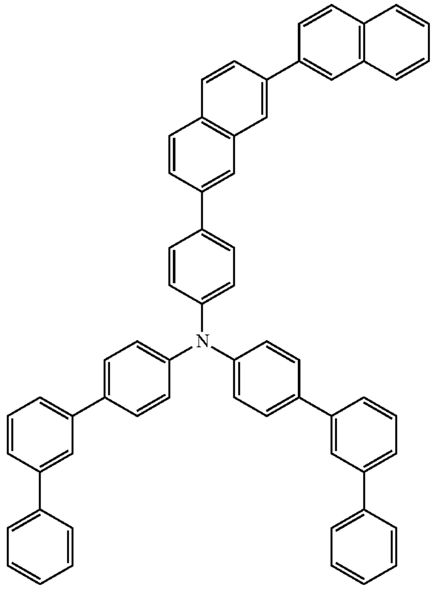

-continued
(113)
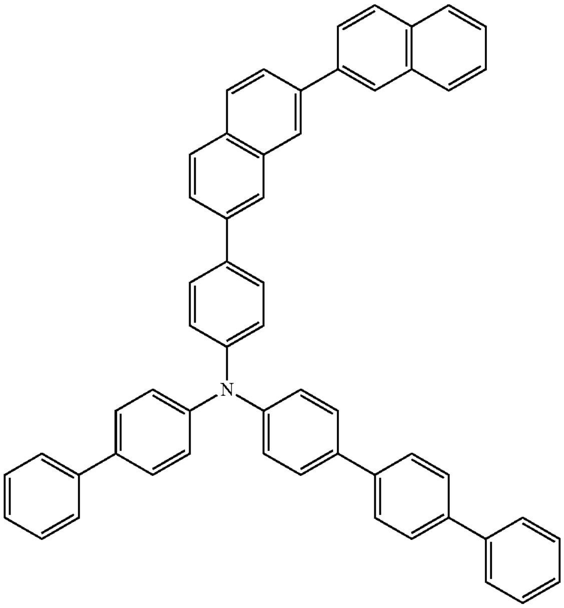
(114)
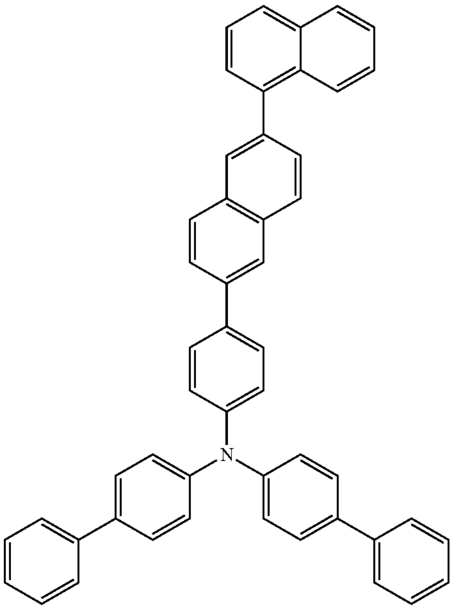
-continued
(115)
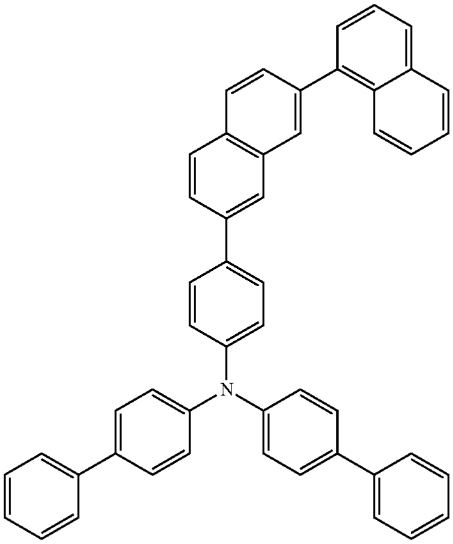
(116)
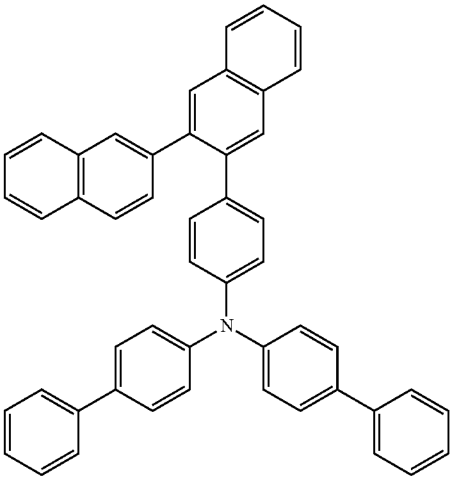
(117)
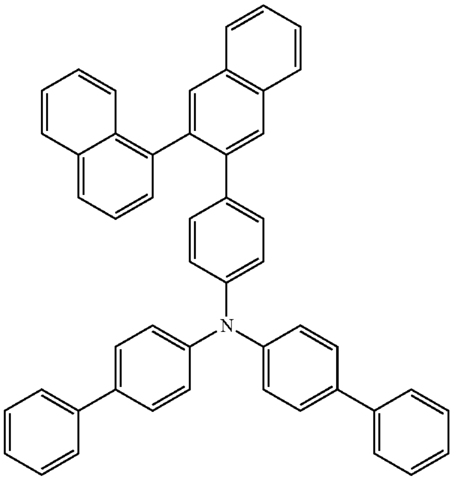

-continued
(118)
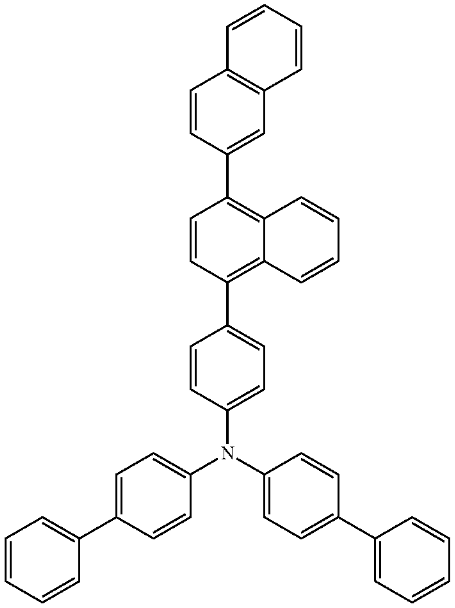
-continued
(120)
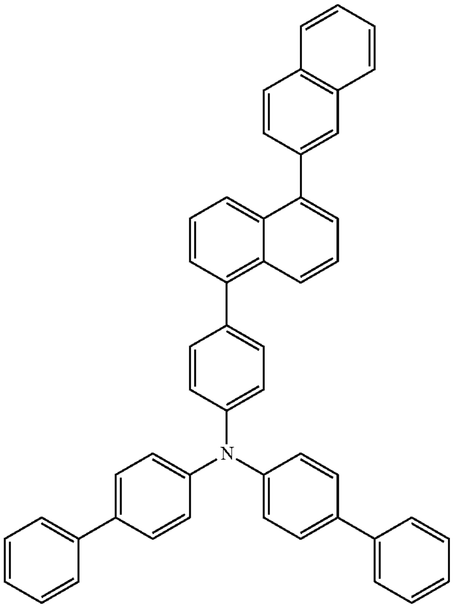
(119)
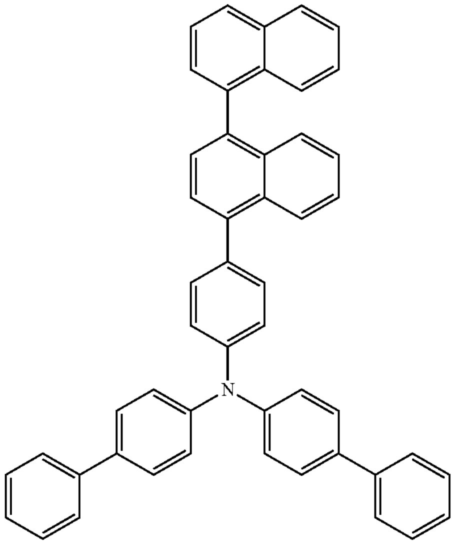
(121)
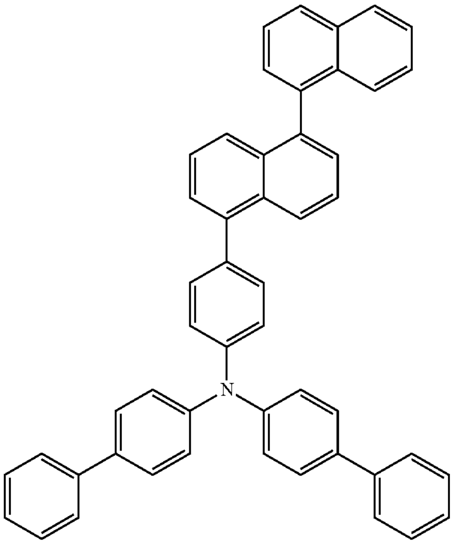

-continued
(122)
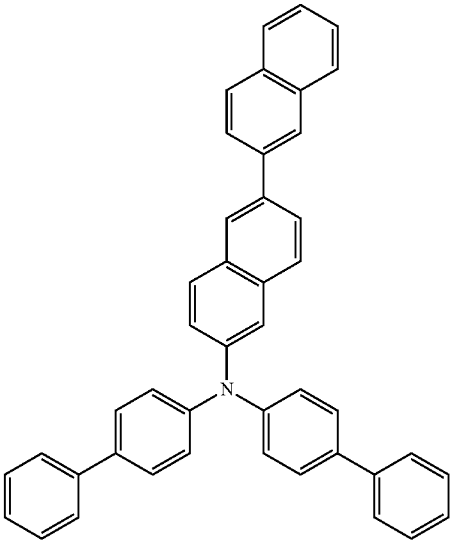
(123)
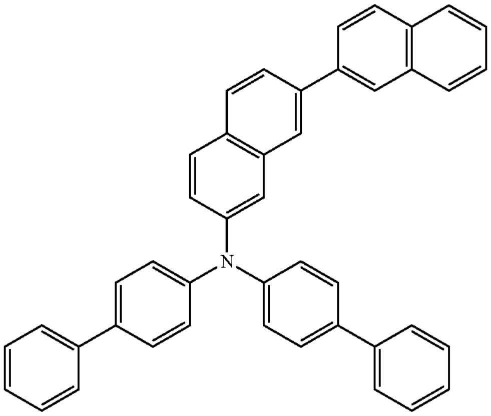
(124)
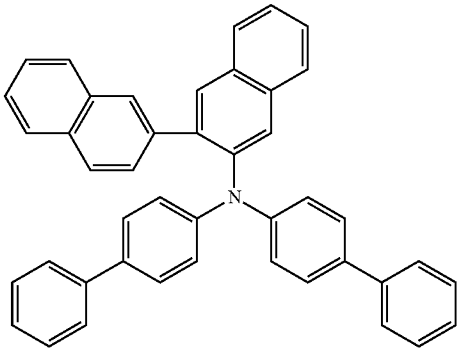
-continued
(125)
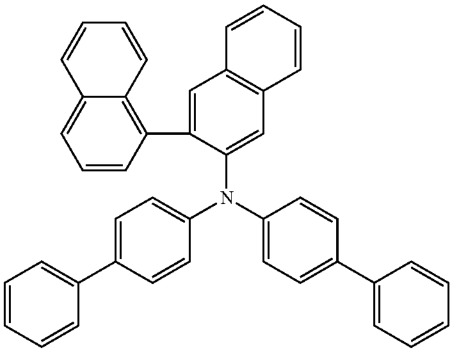
(126)
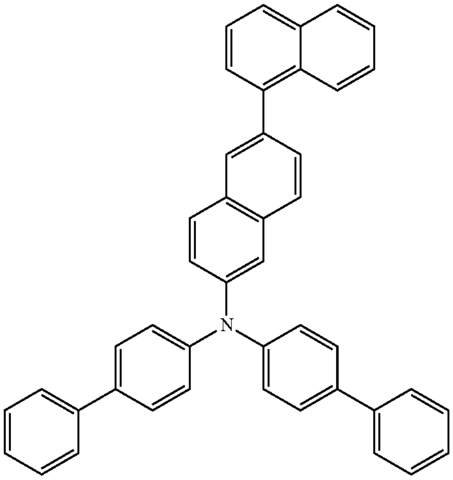
(127)
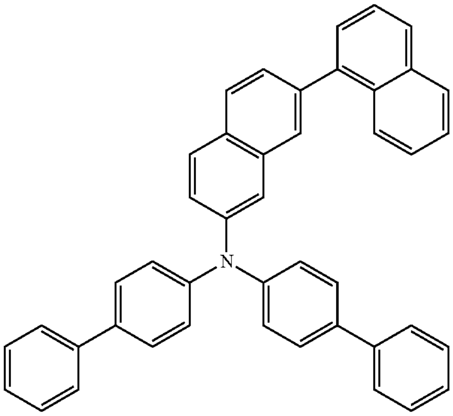

-continued
(128)
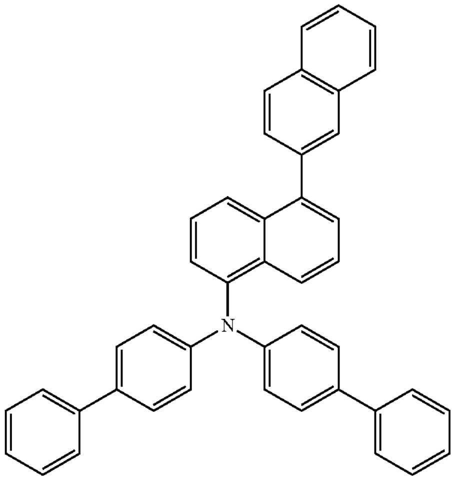
(129)
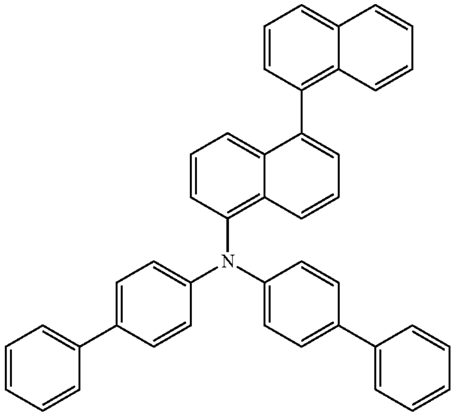
(130)
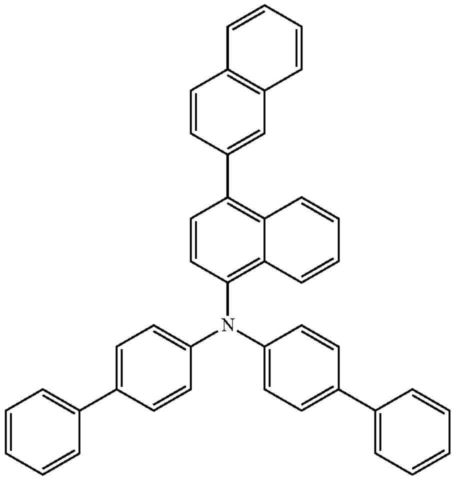
-continued
(131)
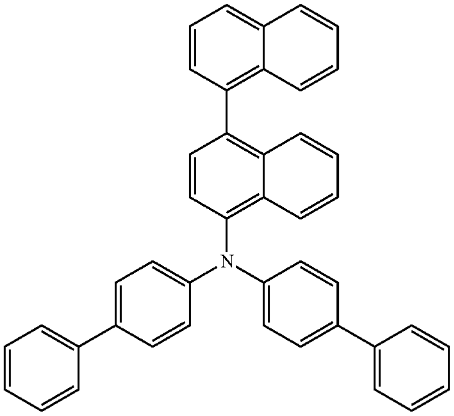
(132)
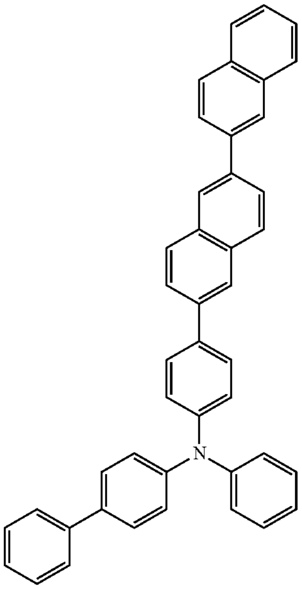
(133)
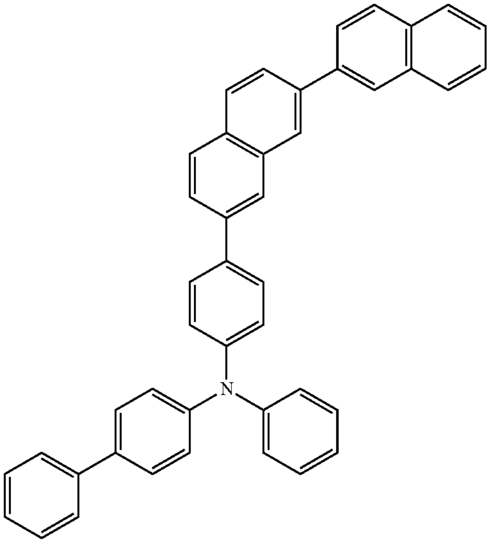

-continued
(134)
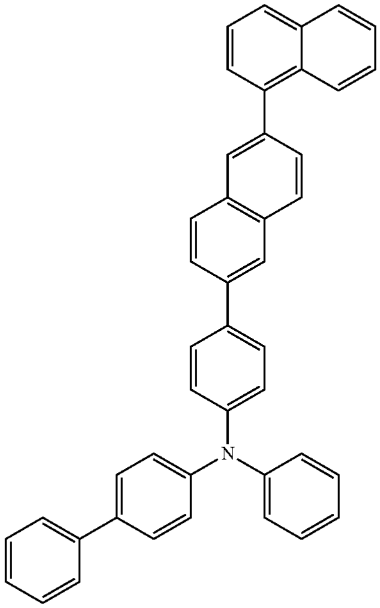
(135)
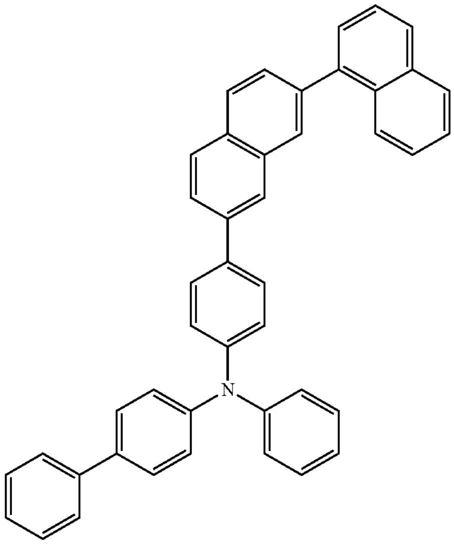
(136)
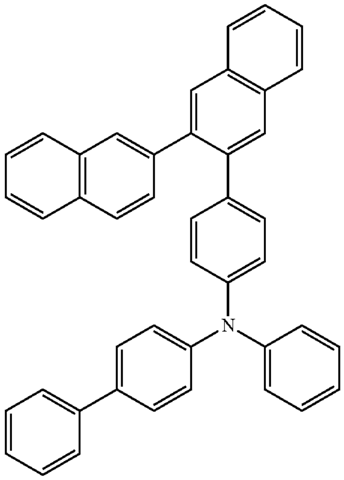
-continued
(137)
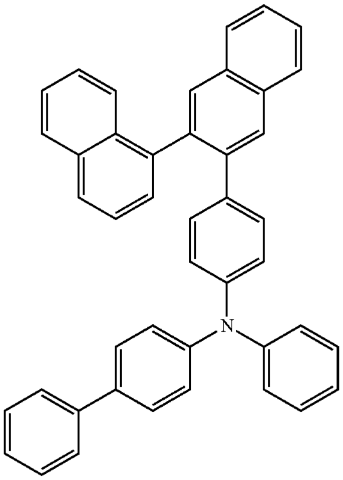
(138)
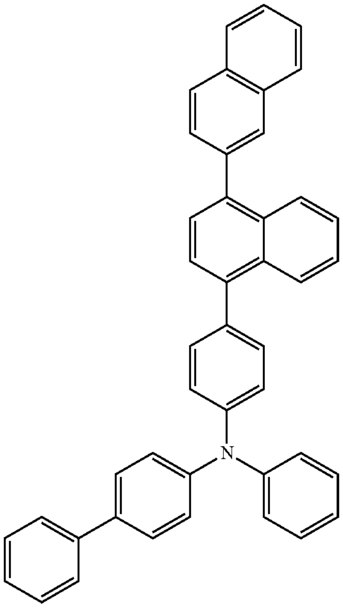
(139)
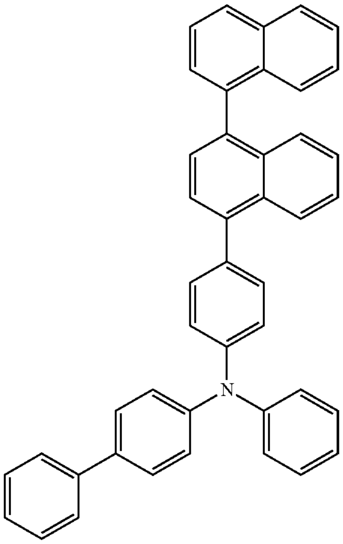

-continued
(140)
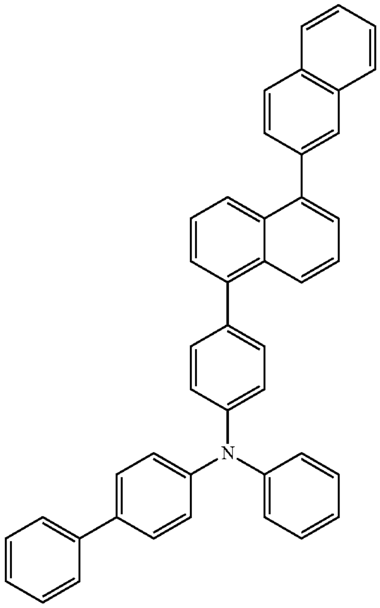
(141)
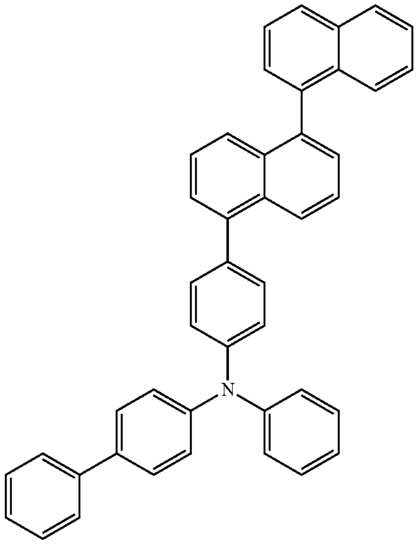
-continued
(142)
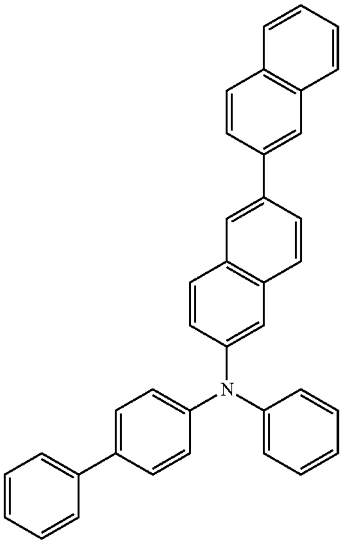
(143)
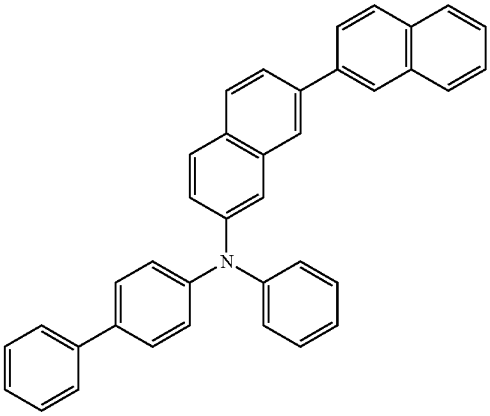
(144)
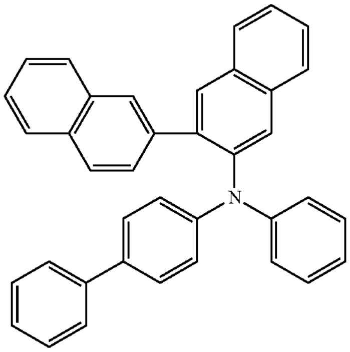

-continued
(145)
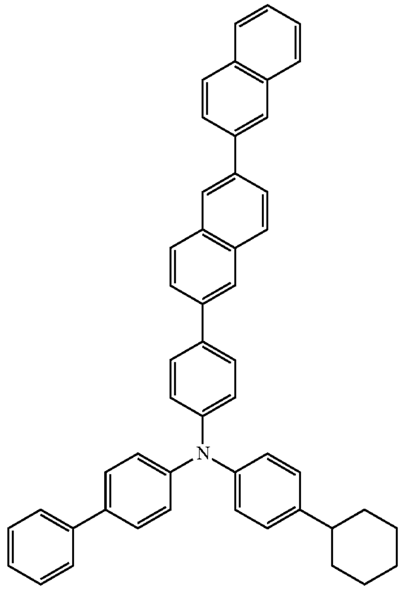
(146)
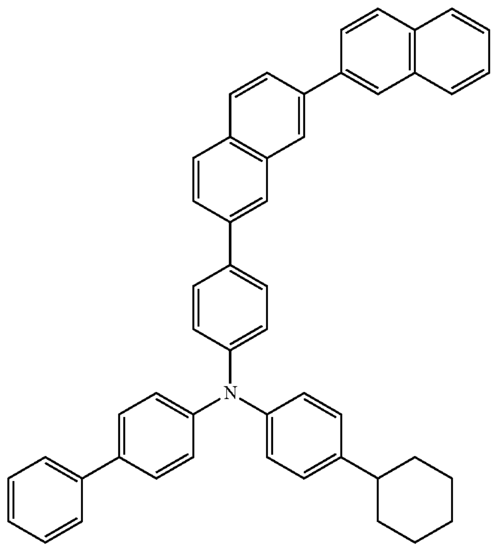
-continued
(147)
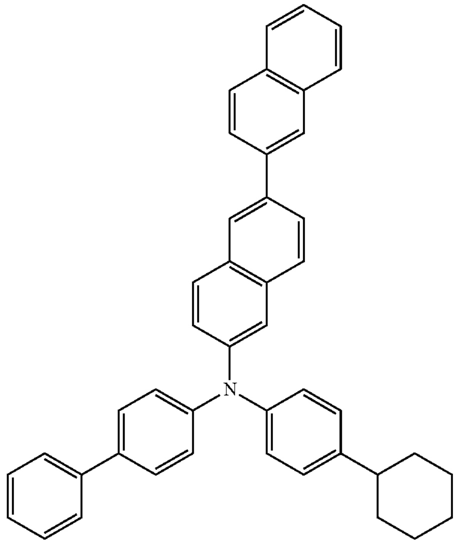
(148)
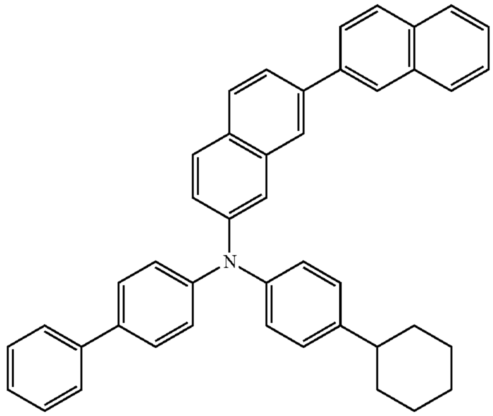
(149)
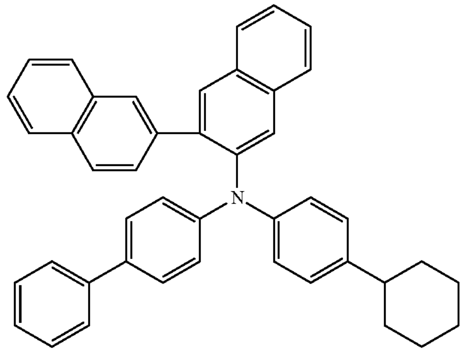

-continued
(150)
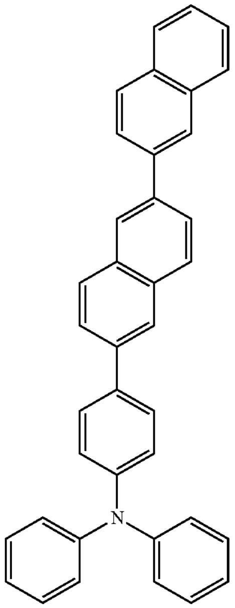
(151)
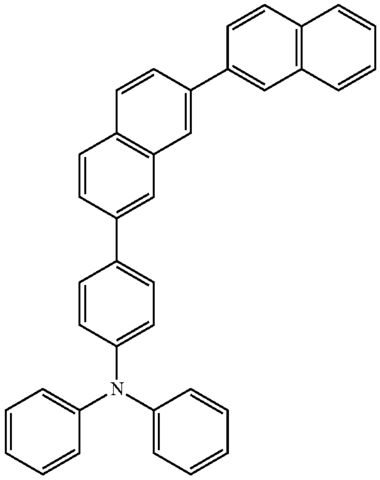
(152)
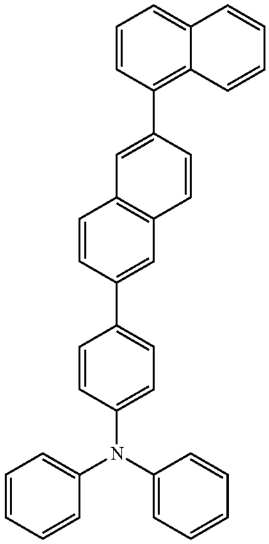
-continued
(153)
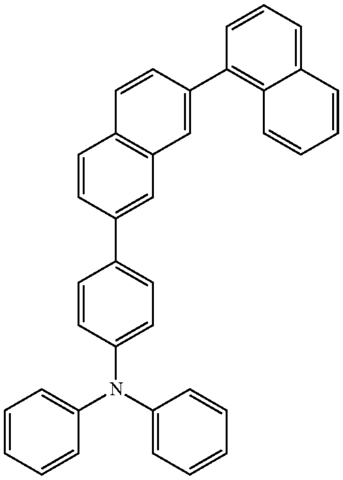
(154)
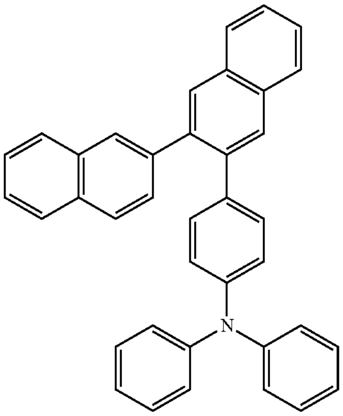
(155)
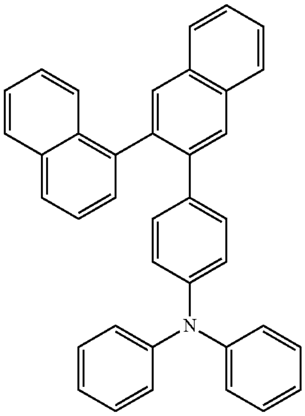

-continued
(156)
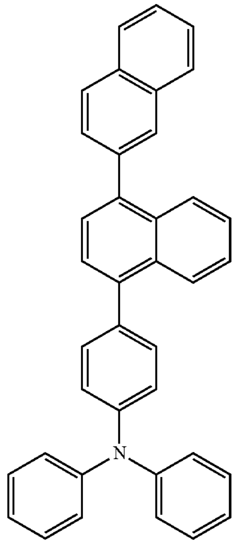
(157)
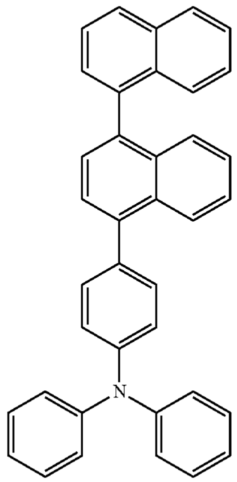
(158)
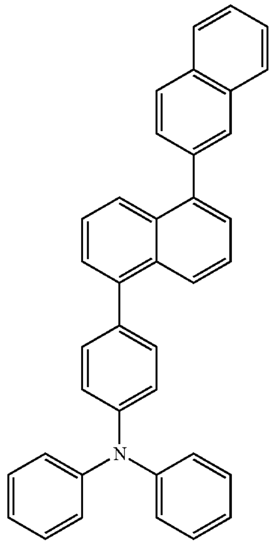
-continued
(159)
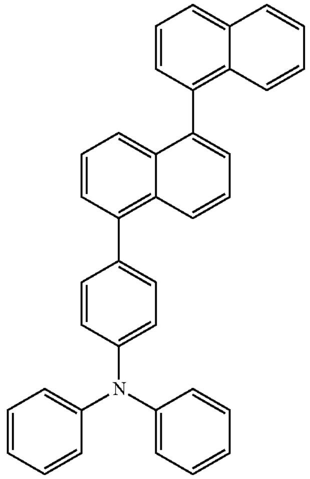
(160)
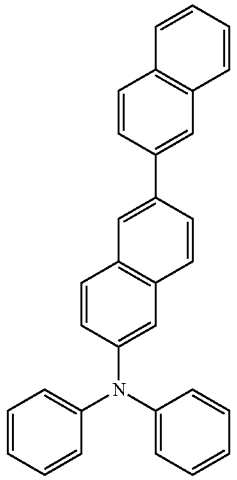
(161)
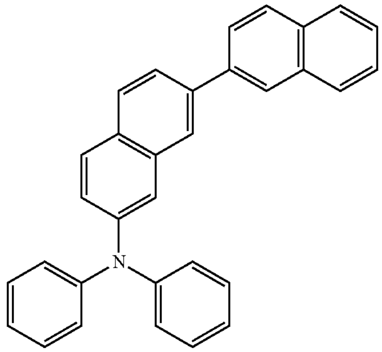
(162)
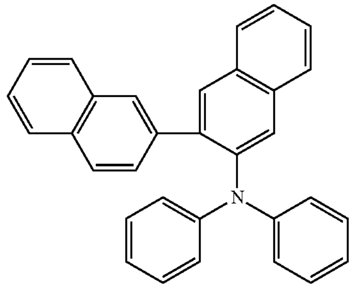

-continued
(163)
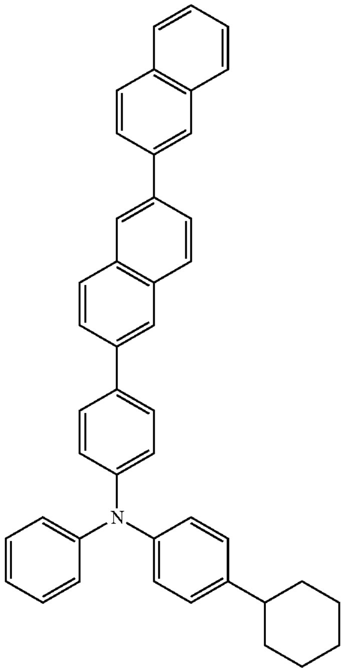
-continued
(165)
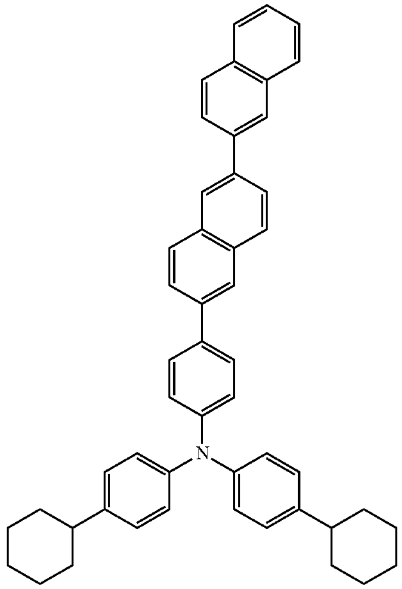
(164)
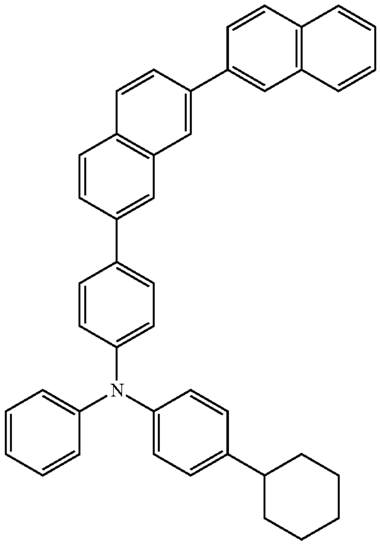
(166)
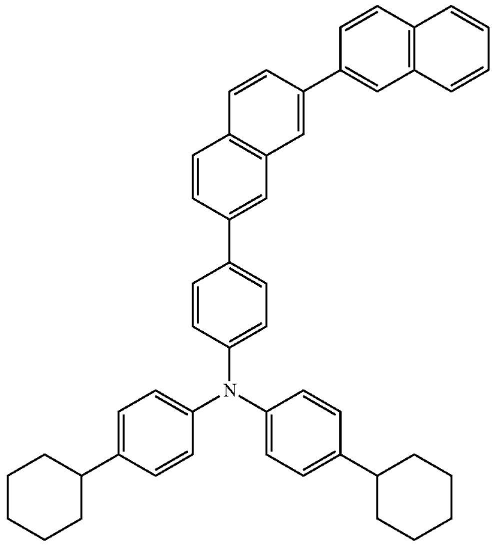

-continued (167)

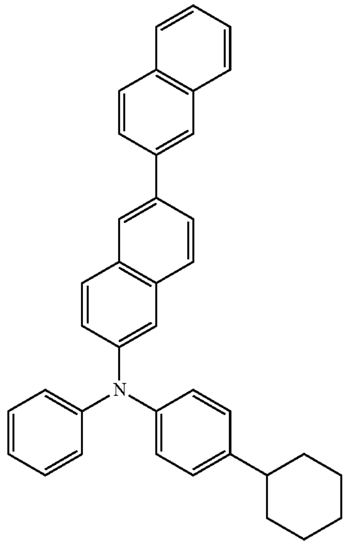

(168)

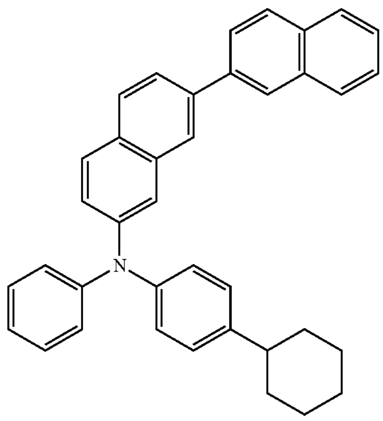

(169)

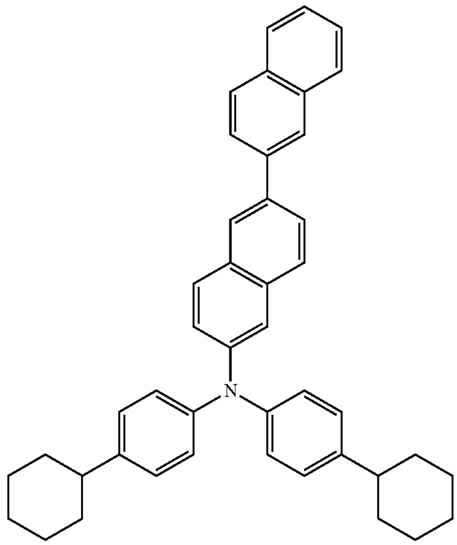

-continued (170)

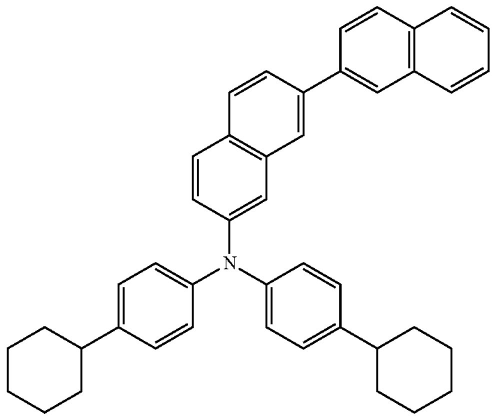

Next, examples of a method for synthesizing the organic compound of the present invention will be described taking the organic compound represented by the general formula (G1) as an example.

The organic compound of one embodiment of the present invention represented by the general formula (G1) can be synthesized according to the following synthesis scheme (a-1). That is, a diarylamine compound (compound 1) is coupled with a binaphthyl compound (compound 2), whereby the target substance (G1) can be obtained. The synthesis scheme (a-1) is shown below.

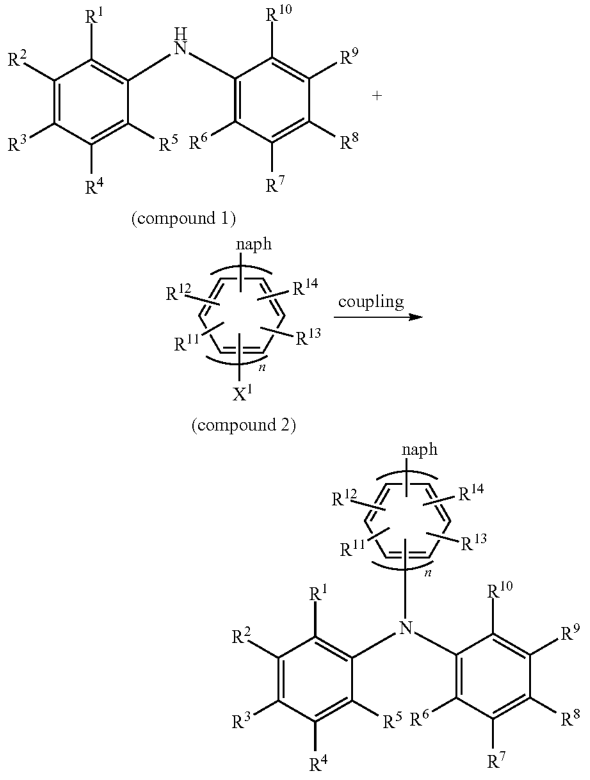

(compound 1)

(compound 2)

(G1)

In the synthesis scheme (a-1), $X^1$ represents chlorine, bromine, iodine, or a triflate group.

In the synthesis scheme (a-1), a Buchwald-Hartwig reaction using a palladium catalyst can be performed. As the palladium catalyst for the reaction, a palladium compound such as bis(dibenzylideneacetone)palladium(0), palladium (II) acetate, [1,1-bis(diphenylphosphino)ferrocene]palladium(II) dichloride, tetrakis(triphenylphosphine)palladium (0), or allylpalladium(II) chloride (dimer) can be used. As a ligand, tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, di-tert-butyl(1-methyl-2,2-diphenylcyclopropyl)phosphine (abbreviation: cBRIDP (registered trademark)), or the like can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. Reagents that can be used for the reaction are not limited to the above reagents.

In the case where the Ullmann reaction is performed in the synthesis scheme (a-1), copper or a copper compound can be used as a reagent, and an inorganic base such as potassium carbonate can be used as a base. Examples of the solvent that can be used for the reaction include 1,3-dimethyl-3,4,5,6-tetrahydro-2(1)pyrimidinone (DMPU), toluene, xylene, and benzene. In the Ullmann reaction, the target substance can be obtained in a shorter time and in a higher yield when the reaction temperature is 100° C. or higher; therefore, it is preferable to use DMPU or xylene, which have high boiling temperatures. A reaction temperature of 150° C. or higher is further preferred, and accordingly, DMPU is further preferably used. Reagents that can be used for the reaction are not limited to the above examples.

The organic compound of one embodiment of the present invention represented by the general formula (G1) can also be synthesized according to the following synthesis scheme (a-2). That is, a triarylamine compound (compound 3) is coupled with a binaphthyl compound (compound 4), whereby the target substance (G1) can be obtained. The synthesis scheme (a-2) is shown below.

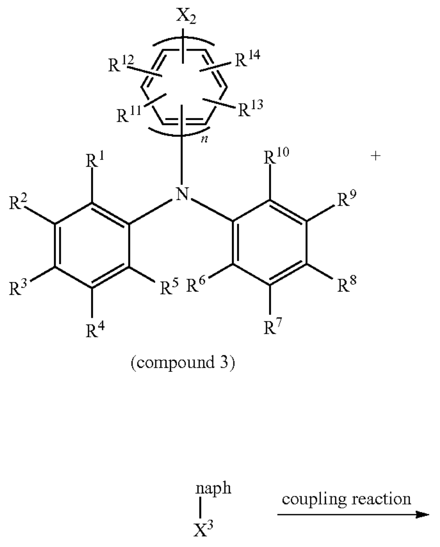

(compound 3)

(compound 4)

-continued

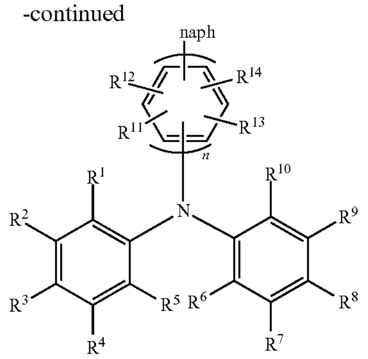

(G1)

In the synthesis scheme (a-2), $X^2$ and $X^3$ each independently represent a halogen, a boronic acid group, an organoboron group, a triflate group, an organotin group, an organozinc group, or a magnesium halide group. The halogen is preferably chlorine, bromine, or iodine; bromine or iodine is preferred in terms of reactivity, and chlorine or bromine is preferred in terms of cost.

When a Suzuki-Miyaura coupling reaction using a palladium catalyst is performed in the synthesis scheme (a-2), $X^2$ and $X^3$ each represent a halogen group, a boronic acid group, an organoboron group, or a triflate group, and the halogen is preferably iodine, bromine, or chlorine. In the reaction, a palladium compound such as bis(dibenzylideneacetone)palladium(0), palladium(II) acetate, [1,1-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In the reaction, an organic base such as sodium tert-butoxide, an inorganic base such as potassium carbonate, cesium carbonate, or sodium carbonate, or the like can be used.

In the reaction, toluene, xylene, benzene, tetrahydrofuran, dioxane, ethanol, methanol, water, diethylene glycol dimethyl ether, ethylene glycol monomethyl ether, or the like can be used as a solvent. Reagents that can be used for the reaction are not limited thereto.

As the reaction represented by the synthesis scheme (a-2), a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be performed.

In the case where the Migita-Kosugi-Stille coupling is employed for the reaction, one of $X^2$ and $X^3$ represents an organotin group, and the other represents a halogen. That is, one of the compounds 3 and 4 is an organotin compound, and the other is a halide. In the case where the Kumada-Tamao-Corriu coupling is employed for the reaction, one of $X^2$ and $X^3$ represents a magnesium halide group, and the other represents a halogen. That is, one of the compounds 3 and 4 is a Grignard reagent, and the other is a halide. In the case where the Negishi coupling is employed for the reaction, one of $X^2$ and $X^3$ represents an organozinc group, and the other represents a halogen. That is, one of the compounds 3 and 4 is an organozinc compound, and the other is a halide.

The method for synthesizing the organic compound (G1) of one embodiment of the present invention is not limited to the synthesis scheme (a-1) or (a-2).

Note that $R^1$ to $R^{14}$, n, and naph in the above reaction schemes are the same as those in the description of the organic compound represented by the general formula (G1); therefore, the description thereof will not be repeated.

Embodiment 2

An example of a light-emitting element which is one embodiment of the present invention will be described in detail below with reference to FIG. 1A.

In this embodiment, the light-emitting element includes a pair of electrodes (an anode 101 and a cathode 102), and an EL layer 103 provided between the anode 101 and the cathode 102.

The anode 101 is preferably formed using a metal, an alloy, or a conductive compound having a high work function (specifically, 4.0 eV or more), a mixture thereof, or the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Films of these conductive metal oxides are usually formed by a sputtering method but may be formed by application of a sol-gel method or the like. For example, Indium oxide-zinc oxide is deposited by a sputtering method using a target obtained by adding 1 wt % or more and 20 wt % or less zinc oxide to indium oxide. Indium oxide containing tungsten oxide and zinc oxide (IWZO) can be deposited by a sputtering method using a target which contains 0.5 wt % or more and 5 wt % or less tungsten oxide and 0.1 wt % or more and 1 wt % or less zinc oxide with respect to indium oxide. Other examples are gold (Au), platinum (Pt), nickel (Ni), tungsten (W), chromium (Cr), molybdenum (Mo), iron (Fe), cobalt (Co), copper (Cu), palladium (Pd), aluminum (Al), and a nitride of a metal material (e.g., titanium nitride). Alternatively, graphene can also be used. In the case where a composite material containing a first substance and a second substance is used for a hole-injection layer 111, an electrode material other than the above can be selected regardless of the work function.

The hole-injection layer 111 is formed using a first substance having a relatively high acceptor property. Preferably, the hole-injection layer 111 is formed using a composite material of the first substance having an acceptor property and a second substance having a hole-transport property. As the first substance, a substance having an acceptor property with respect to the second substance is used. The first substance draws electrons from the second substance, so that electrons are generated in the first substance. In the second substance from which electrons are drawn, holes are generated. By an electric field, the drawn electrons flow to the anode 101 and the generated holes are injected into a light-emitting layer 113 through a hole-transport layer 112.

The first substance is preferably a transition metal oxide, an oxide of a metal belonging to any of Groups 4 to 8 of the periodic table, an organic compound having an electron-withdrawing group (a halogen group or a cyano group), or the like.

As the transition metal oxide or the oxide of a metal belonging to any of Groups 4 to 8 of the periodic table, vanadium oxide, niobium oxide, tantalum oxide, chromium oxide, molybdenum oxide, tungsten oxide, manganese oxide, rhenium oxide, titanium oxide, ruthenium oxide, zirconium oxide, hafnium oxide, or silver oxide is preferable because of its high acceptor property. Molybdenum oxide is particularly preferable because of its high stability in the air, low hygroscopicity, and high handiness.

Examples of the organic compound having an electron-withdrawing group (a halogen group or a cyano group) include 7,7,8,8-tetracyano-2,3,5,6-tetrafluoroquinodimethane (abbreviation: F4TCNQ), chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). A compound in which electron-withdrawing groups are bonded to a condensed aromatic ring having a plurality of hetero atoms, such as HAT-CN, is particularly preferable because it is thermally stable.

The second substance has a hole-transport property and preferably has a hole mobility of $10^{-6}$ $cm^2/Vs$ or higher. Examples of a material that can be used as the second substance include aromatic amines such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B); carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; andaromatichydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, pentacene, coronene, rubrene, perylene, and 2,5,8,11-tetra(tert-butyl)perylene. The aromatic hydrocarbon may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA). Alternatively, the following compound can be used: a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl- 9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]-fluoren-2-amine (abbreviation: PCBAF), or N-phenyl-N-[4-(9-phenyl-9H-carbazol-3-yl)phenyl]-spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); or a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds are highly reliable, have high hole-transport properties, and contribute to a reduction in drive voltage.

A wet process can be used to form the hole-injection layer 111. In this case, a conductive high-molecular compound to which an acid is added, such as a poly(ethylenedioxythiophene)/poly(styrenesulfonic acid) aqueous solution (PEDOT/PSS), a polyaniline/camphor sulfonic acid aqueous solution (PANI/CSA), PTPDES, Et-PTPDEK, PPBA, or polyaniline/poly(styrenesulfonic acid) (PANI/PSS), can be used, for example.

As a material of the hole-transport layer 112, the organic compound described in Embodiment 1, which has a high hole-transport property, can be suitably used. Furthermore, the hole-transport layer 112 is preferably formed of a plurality of layers; in this case, for easy hole injection, the HOMO levels of the hole-transport layer 112 preferably become deeper stepwise from a layer on the hole-injection layer 111 side to a layer on the light-emitting layer 113 side. Such a structure is highly suitable for a blue fluorescence-emitting element in which a host material in the light-emitting layer 113 has a deep HOMO level. In particular, the organic compound described in Embodiment 1 is preferably used for the second and the following layers, which is not indirect contact with the hole-injection layer 111. Further preferably, at least one layer is additionally provided between the layer containing the organic compound and the light-emitting layer 113. That is, when the hole-transport layer 112 is formed of two layers, the layer containing the organic compound described in Embodiment 1 is preferably positioned on the light-emitting layer 113 side, and when formed of three layers, preferably in the middle.

The structure of the hole-transport layer 112 including a plurality of layers so as to have a HOMO level which becomes deeper stepwise toward the light-emitting layer 113 can be applied to an element in which the hole-injection layer 111 is formed using an organic acceptor (an organic compound having the above-mentioned electron-withdrawing group (a halogen group or a cyano group)), whereby a highly favorable element with a high carrier-injection property and a low drive voltage can be obtained.

Note that a wet process can be used to form the hole-transport layer 112. In the case where the hole-transport layer 112 is formed by a wet process, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine](abbreviation: poly-TPD) can be used.

The light-emitting layer 113 may contain any light-emitting substance such as a fluorescent substance, a phosphorescent substance, a substance that emits thermally activated delayed fluorescent (TADF), quantum dots, or a metal halide perovskite. Furthermore, the light-emitting layer 113 may be a single layer or include a plurality of layers. In the case where a light-emitting layer including a plurality of layers is formed, a layer containing a phosphorescent substance and a layer containing a fluorescent substance may be stacked. In this case, an exciplex described later is preferably utilized in the layer containing a phosphorescent substance.

Examples of a fluorescent substance that can be used include, but are not limited to, the following substances: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine, N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7- tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). In particular, condensed aromatic diamine compounds typified by pyrenediamine compounds such as 1,6FLPAPrn and 1,6mMemFLPAPrn are preferable because of their high hole-trapping properties, high emission efficiency, and high reliability.

Examples of a material that can be used as a phosphorescent substance in the light-emitting layer 113 are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κ C}iridium(III) (abbreviation: $[Ir(mpptz\text{-}dmp)_3]$), tris(5-methyl-3,4-diphenyl-4H-1,2,4-triazolato)iridium(III) (abbreviation: $[Ir(Mptz)_3]$), or tris[4-(3-biphenyl)-5-isopropyl-3-phenyl-4H-1,2,4-triazolato]iridium(III) (abbreviation: $[Ir(iPrptz\text{-}3b)_3]$); an organometallic iridium complex having a 1H-triazole skeleton, such as tris[3-methyl-1-(2-methylphenyl)-5-phenyl-1H-1,2,4-triazolato]iridium(III) (abbreviation: $[Ir(Mptz1\text{-}mp)_3]$) or tris(1-methyl-5-phenyl-3-propyl-1H-1,2,4-triazolato)iridium(III) (abbreviation: $[Ir(Prptz1\text{-}Me)_3]$); an organometallic iridium complex a having imidazole skeleton, such as fac-tris[1-(2,6-diisopropylphenyl)-2-phenyl-1H-imidazole]iridium(III) (abbreviation: $[Ir(iPrpmi)_3]$) or tris[3-(2,6-dimethylphenyl)-7-methylimidazo[1,2-f]phenanthridinato]iridium(III) (abbreviation: $[Ir(dmpimpt\text{-}Me)_3]$); and an organometallic iridium complex in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: $[Ir(CF_3ppy)_2(pic)]$), or bis[2-(4',6'-difluorophenyl)pyridinato-N,$C^{2'}$]iridium(III) acetylacetonate (abbreviation: FIr(acac)). These compounds emit blue phosphorescence having an emission peak at 440 nm to 520 nm.

Other examples include an organometallic iridium complex having pyrimidine skeleton, such as tris(4-methyl-6-phenylpyrimidinato)iridium(III) (abbreviation: $[Ir(mppm)_3]$), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), or (acetylacetonato)bis(4,6-diphenylpyrimidinato)iridium(III) (abbreviation: $[Ir(dppm)_2(acac)]$); an organometallic iridium complex having a pyrazine skeleton, such as (acetylacetonato)bis(3,5-dimethyl-2-phenylpyrazinato)iridium(III) (abbreviation: $[Ir(mppr\text{-}Me)_2(acac)]$) or (acetylacetonato)bis(5-isopropyl-3-methyl-2-phenylpyrazinato)iridium(III) (abbreviation: $[Ir(mppr\text{-}iPr)_2(acac)]$); an organometallic iridium complex having a pyridine skeleton, such as tris(2-phenylpyridinato-N,$C^{2'}$)iridium(III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), or bis(2-phenylquinolinato-N,$C^{2'}$)iridium(III) acetylacetonate (abbreviation: $[Ir(pq)_2(acac)]$); and a rare earth metal complex such as tris(acetylacetonato) (monophenanthroline)terbium(III) (abbreviation: $[Tb(acac)_3(Phen)]$). These compounds mainly emit green phosphorescence having an emission peak at 500 nm to 600 nm. Note that an organometallic iridium complex having a pyrimidine skeleton has distinctively high reliability and emission efficiency and thus is especially preferable.

Other examples include an organometallic iridium complex having a pyrimidine skeleton, such as (diisobutyrylmethanato)bis[4,6-bis(3-methylphenyl)pyrimidinato]iridium(III) (abbreviation: $[Ir(5mdppm)_2(dibm)]$), bis[4,6-bis(3-methylphenyl)pyrimidinato](dipivaloylmethanato)iridium(III) (abbreviation: $[Ir(5mdppm)_2(dpm)]$), or bis[4,6-di(naphthalen-1-yl)pyrimidinato](dipivaloylmethanato)iridium(III) (abbreviation: $[Ir(d1npm)_2(dpm)]$); an organometallic iridium complex having a pyrazine skeleton, such as (acetylacetonato)bis(2,3,5-triphenylpyrazinato)iridium(III) (abbreviation: $[Ir(tppr)_2(acac)]$), bis(2,3,5-triphenylpyrazinato) (dipivaloylmethanato)iridium(III) (abbreviation: $[Ir(tppr)_2(dpm)]$), or (acetylacetonato)bis[2,3-bis(4-fluorophenyl)quinoxalinato]iridium(III) (abbreviation: $[Ir(Fdpq)_2(acac)]$); an organometallic iridium complex having a pyridine skeleton, such as tris(1-phenylisoquinolinato-N,$C^{2'}$)iridium(III) (abbreviation: $[Ir(piq)_3]$) or bis(1-phenylisoquinolinato-N,$C^{2'}$)iridium(III) acetylacetonate (abbreviation: $[Ir(piq)_2(acac)]$); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato) (monophenanthroline)europium(III) (abbreviation: $[Eu(DBM)_3(Phen)]$) and tris[1-(2-thenoyl)-3,3,3-trifluoroacetonato] (monophenanthroline)europium(III) (abbreviation: $[Eu(TTA)_3(Phen)]$). These compounds emit red phosphorescence having an emission peak at 600 nm to 700 nm. Furthermore, an organometallic iridium complex having a pyrazine skeleton can emit red light with favorable chromaticity.

Besides the above phosphorescent compounds, a variety of phosphorescent materials may be selected and used.

Examples of the TADF material include a fullerene, a derivative thereof, an acridine, a derivative thereof, and an eosin derivative. Furthermore, porphyrin containing a metal such as magnesium (Mg), zinc (Zn), cadmium (Cd), tin (Sn), platinum (Pt), indium (In), or palladium (Pd) can be used. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$(OEP)), which are represented by the following structural formulae.

-continued
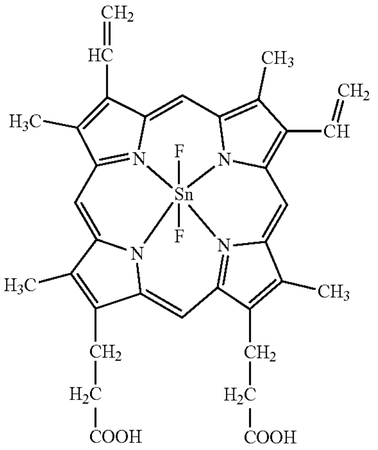
SnF2(Proto IX)
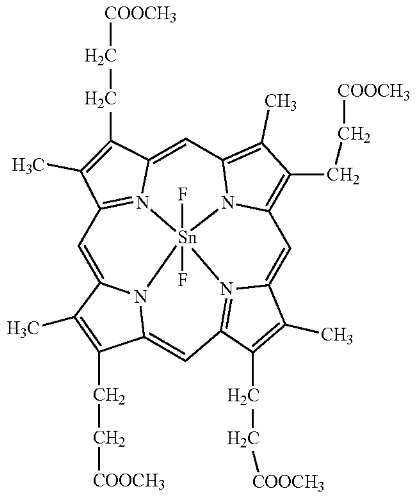
SnF2(Copro III-4Me)
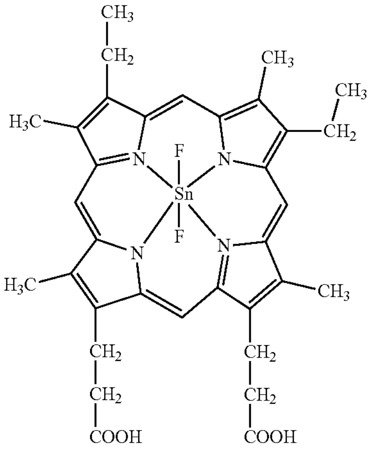
SnF2(Meso IX)
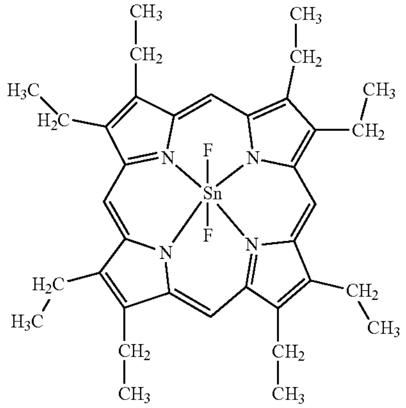
SnF2(OEP)
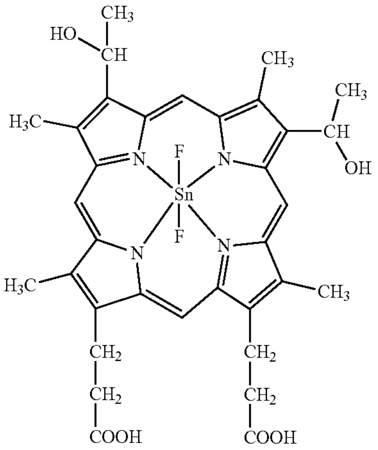
SnF2(Hemato IX)
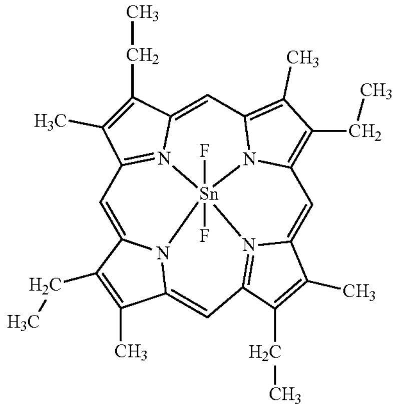
SnF2(Etio I)

-continued

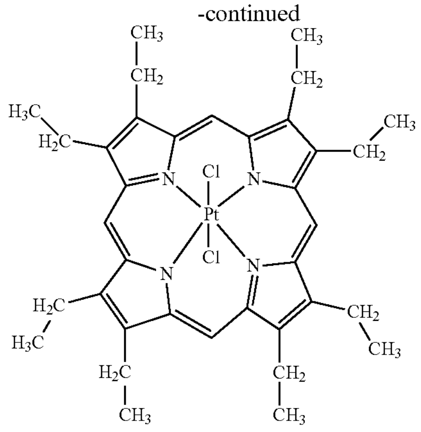

$PtCl_2OEP$

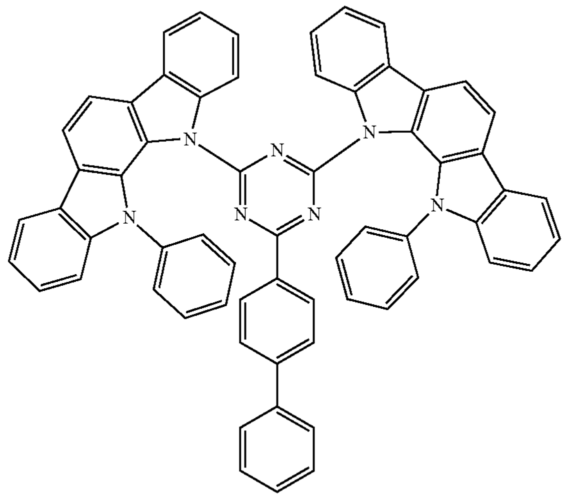

PIC-TRZ

Alternatively, a heterocyclic compound having both a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCz-Tzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACR-XTN), bis[4-(9,9-dimethyl-9,10-dihydroacridine)phenyl] sulfone (abbreviation: DMAC-DPS), or 10-phenyl-10H,10'H-spiro[acridin-9,9'-anthracen]-10'-one (abbreviation: ACRSA), which are represented by the following structural formulae, can be used. Such a heterocyclic compound is preferable because of having high electron-transport and hole-transport properties owing to a 7-electron rich heteroaromatic ring and a 7-electron deficient heteroaromatic ring. Note that a substance in which the 7-electron rich heteroaromatic ring is directly bonded to the 7-electron deficient heteroaromatic ring is particularly preferable because the donor property of the 7-electron rich heteroaromatic ring and the acceptor property of the 7-electron deficient heteroaromatic ring are both increased and the energy difference between the Si level and the Ti level becomes small, so that thermally activated delayed fluorescence can be obtained with high efficiency. Note that an aromatic ring to which an electron-withdrawing group such as a cyano group is bonded may be used instead of the 7-electron deficient heteroaromatic ring.

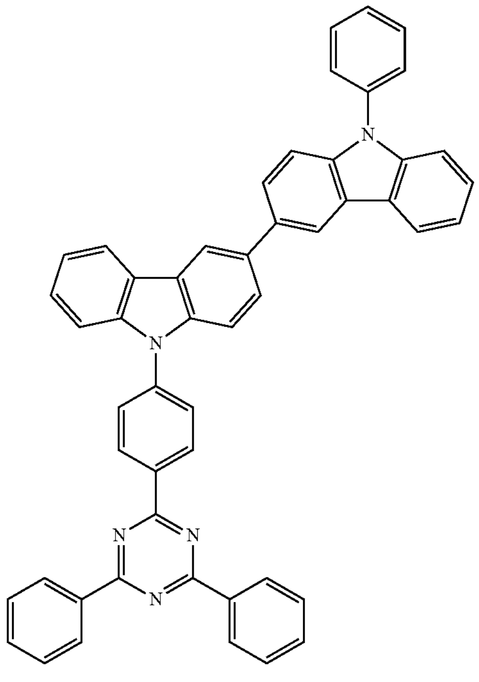

PCCzPTzn

-continued

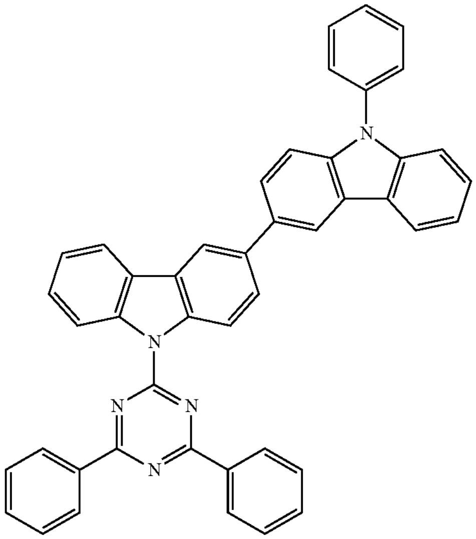

PCCzTzn

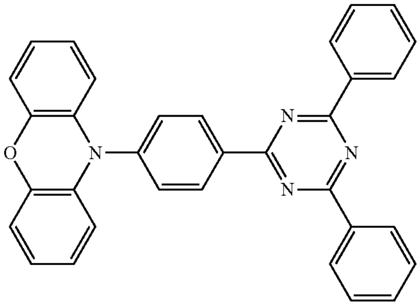

PXZ-TRZ

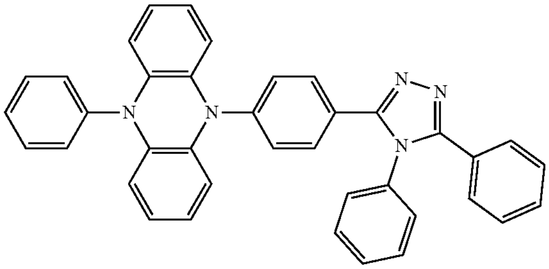

PPZ-3TPT

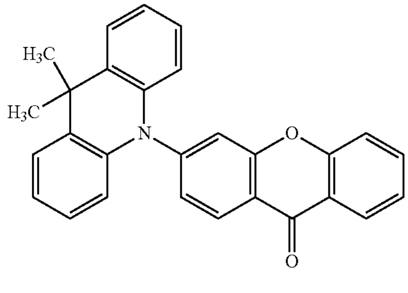

ACRXTN

-continued

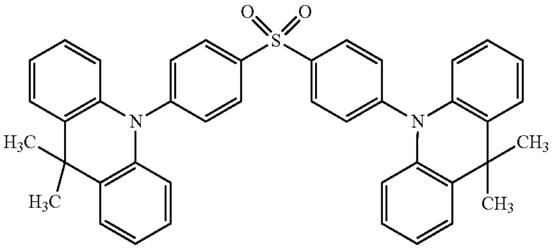

DMAC-DPS

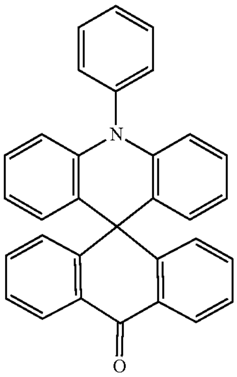

ACRSA

Examples of the quantum dot include nano-sized particles of a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, semiconductor clusters, metal halide perovskites, and the like.

Specific examples include, but are not limited to, cadmium selenide (CdSe), cadmium sulfide (CdS), cadmium telluride (CdTe), zinc selenide (ZnSe), zinc oxide (ZnO), zinc sulfide (ZnS), zinc telluride (ZnTe), mercury sulfide (HgS), mercury selenide (HgSe), mercury telluride (HgTe), indium arsenide (InAs), indium phosphide (InP), gallium arsenide (GaAs), gallium phosphide (GaP), indium nitride (InN), gallium nitride (GaN), indium antimonide (InSb), gallium antimonide (GaSb), aluminum phosphide (AlP), aluminum arsenide (AAs), aluminum antimonide (AlSb), lead(II) selenide (PbSe), lead(II) telluride (PbTe), lead(II) sulfide (PbS), indium selenide ($In_2Se_3$), indium telluride ($In_2Te_3$), indium sulfide ($In_2S_3$), gallium selenide ($Ga_2Se_3$), arsenic(III) sulfide ($As_2S_3$), arsenic(III) selenide ($As_2Se_3$), arsenic(III) telluride ($As_2Te_3$), antimony(III) sulfide ($Sb_2S_3$), antimony(III) selenide ($Sb_2Se_3$), antimony(III) telluride ($Sb_2Te_3$), bismuth(III) sulfide ($Bi_2S_3$), bismuth(III) selenide ($Bi_2Se_3$), bismuth(III) telluride ($Bi_2Te_3$), silicon (Si), silicon carbide (SiC), germanium (Ge), tin (Sn), selenium (Se), tellurium (Te), boron (B), carbon (C), phosphorus (P), boron nitride (BN), boron phosphide (BP), boron arsenide (BAs), aluminum nitride (AN), aluminum sulfide ($A_2S_3$), barium sulfide (BaS), barium selenide (BaSe), barium telluride (BaTe), calcium sulfide (CaS), calcium selenide (CaSe), calcium telluride (CaTe), beryllium sulfide (BeS), beryllium selenide (BeSe), beryllium telluride (BeTe), magnesium sulfide (MgS), magnesium selenide (MgSe), germanium sulfide (GeS), germanium selenide (GeSe), germanium telluride (GeTe), tin(IV) sulfide ($SnS_2$), tin(II) sulfide (SnS), tin(II) selenide (SnSe), tin(II) telluride (SnTe), lead(II) oxide (PbO), copper(I) fluoride (CuF), copper(I) chloride (CuCl), copper(I) bromide (CuBr), copper(I) iodide (CuI), copper(I) oxide ($Cu_2O$), copper(I) selenide ($Cu_2Se$), nickel(II) oxide (NiO), cobalt(II) oxide (CO), cobalt(II) sulfide (CoS), triiron tetraoxide ($Fe_3O_4$), iron(II) sulfide (FeS), manganese(II) oxide (MnO), molybdenum (IV) sulfide ($MoS_2$), vanadium(II) oxide (VO), vanadium (IV) oxide ($VO_2$), tungsten(IV) oxide ($WO_2$), tantalum(V) oxide ($Ta_2O_5$), titanium oxide (e.g., $TiO_2$, $Ti_2O_5$, $Ti_2O_3$, or $Ti_5O_9$), zirconium oxide ($ZrO_2$), silicon nitride ($Si_3N_4$), germanium nitride ($Ge_3N_4$), aluminum oxide ($Al_2O_3$), barium titanate ($BaTiO_3$), a compound of selenium, zinc, and cadmium (CdZnSe), a compound of indium, arsenic, phosphorus (InAsP), a compound of cadmium, selenium, and sulfur (CdSeS), a compound of cadmium, selenium, and tellurium (CdSeTe), a compound of indium, gallium, and arsenic (InGaAs), a compound of indium, gallium, and selenium (InGaSe), a compound of indium, selenium, and sulfur (InSeS), a compound of copper, indium, and sulfur (e.g., $CuInS_2$), and combinations thereof. What is called an alloyed quantum dot, whose composition is represented by a given ratio, may be used. For example, an alloyed quantum dot represented by $CdS_xSe_{1-x}$ (x is a given number between 0 and 1 inclusive) is an effective means for obtaining blue light emission because the emission wavelength can be changed by changing x.

As the quantum dot, a core-type quantum dot, a core-shell quantum dot, a core-multishell quantum dot, or the like may be used. When a core is covered with a shell formed of another inorganic material having a wider band gap, the influence of a defect or a dangling bond existing at the surface of a nanocrystal can be reduced. Since such a structure can significantly improve the quantum efficiency of light emission, it is preferable to use a core-shell or core-multishell quantum dot. Examples of the material of a shell include zinc sulfide (ZnS) and zinc oxide (ZnO).

Quantum dots have a high proportion of surface atoms and thus have high reactivity and easily cohere together. For this reason, it is preferable that a protective agent be attached to or a protective group be provided on the surfaces of the quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

The quantum dots may be quantum rods with rod-like shapes. A quantum rod emits directional light polarized in the c-axis direction; thus, quantum rods can be used as a light-emitting material to obtain a light-emitting element with higher external quantum efficiency.

A light-emitting layer in which the quantum dots are dispersed as a light-emitting material in a host material may be formed as follows: the quantum dots are dispersed in the host material or the host material and the quantum dots are dissolved or dispersed in an appropriate liquid medium, a wet process (e.g., a spin coating method, a casting method, a die coating method, a blade coating method, a roll coating method, an inkjet method, a printing method, a spray coating method, a curtain coating method, or a Langmuir-Blodgett method) is performed to form a layer, and then, the solvent is removed or baking is performed.

Examples of the liquid medium used for the wet process include the following organic solvents: ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); and dimethyl sulfoxide (DMSO).

In the case where a fluorescent substance is used, a host material suitable for the light-emitting layer is a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthryl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), or 9-phenyl-10-{4-(9-phenyl-9H-fluoren-9-yl)biphenyl-4'-yl}anthracene (abbreviation: FLPPA). The use of a substance having an anthracene skeleton as a host material for a fluorescent substance makes it possible to obtain a light-emitting layer with high emission efficiency and high durability. Note that CzPA, cgDBCzPA, 2mBnfPPA, or PCzPA has excellent characteristics and thus is particularly preferably selected.

In the case where a material other than the above materials is used as a host material, various carrier-transport materials, such as a material having an electron-transport property or a material having a hole-transport property, can be used.

Examples of the material with an electron-transport property are a metal complex such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton, such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, the heterocyclic compound having a diazine skeleton and the heterocyclic compound having a pyridine skeleton have high reliability and thus are preferable. In particular, the heterocyclic compound having a diazine (pyrimidine or pyrazine) skeleton has a high electron-transport property and contributes to a reduction in drive voltage.

Examples of a material having a hole-transport property include a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds are highly reliable, have high hole-transport properties, and contribute to a reduction in drive voltage. The hole-transport material may be selected from a variety of substances as well as from the hole-transport materials given above.

In the case where a fluorescent substance is used as a light-emitting substance, a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), or 9-phenyl-10-{4-(9-phenyl-9H-fluoren-9-yl)-biphenyl-4'-yl}-anthracene (abbreviation: FLPPA), is preferably used. The use of a substance having an anthracene skeleton as a host material for a fluorescent substance makes it possible to obtain a light-emitting layer with high emission efficiency and high durability. Note that CzPA, cgDBCzPA, 2mBnfPPA, or PCzPA has excellent characteristics and thus is particularly preferably selected.

Note that a host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

Substances in such a mixed host material may form an exciplex. When a combination of materials is selected so as to form an exciplex that exhibits light emission whose wavelength overlaps with the wavelength of a lowest-energy-side absorption band of a fluorescent substance, a phosphorescent substance, or a TADF material, energy can be transferred smoothly and light emission can be efficiently obtained. Such a structure is preferred to reduce the drive voltage.

The light-emitting layer 113 having the above-described structure can be formed by co-evaporation by a vacuum evaporation method, or a gravure printing method, an offset printing method, an inkjet method, a spin coating method, a dip coating method, or the like using a mixed solution.

An electron-transport layer 114 contains a substance having an electron-transport property. As the substance having an electron-transport property, any of the materials having an electron-transport properties or the materials having anthracene skeletons, which can be used as a host material, can be used.

Between the electron-transport layer and the light-emitting layer, a layer that controls transport of electron carriers may be provided. This layer is formed by addition of a small amount of a substance having a high electron-trapping property to the aforementioned material having a high electron-transport property and is capable of adjusting the carrier balance by retarding transport of electron carriers. Such a structure is very effective in preventing a problem (such as a reduction in element lifetime) caused when electrons pass through the light-emitting layer.

An electron-injection layer 115 may be provided between the electron-transport layer 114 and the cathode 102 and in contact with the cathode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. In addition, an electride may be used for the electron-injection layer 115. Examples of the electride include a substance in which electrons are added at high concentration to calcium oxide-aluminum oxide. Note that a layer that is formed using a substance having an electron-transport property and contains an alkali metal or an alkaline earth metal is preferably used as the electron-injection layer 115, in which case electron injection from the cathode 102 is efficiently performed.

Instead of the electron-injection layer 115, a charge-generation layer 116 may be provided (FIG. 1). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of the material that can be used for the hole-injection layer 111. The p-type layer 117 may be formed by stacking a film containing the above acceptor material as a material included in the composite material and a film containing the above hole-transport material. When a potential is applied to the p-type layer 117, electrons are injected into the electron-transport layer 114 and holes are injected into the cathode 102; thus, the light-emitting element operates. When a layer containing the organic compound of one embodiment of the present invention exists in the electron-transport layer 114 so as to be in contact with the charge-generation layer 116, a luminance decrease over driving time of the light-emitting element can be suppressed, and thus, the light-emitting element can have a long lifetime.

Note that the charge-generation layer 116 preferably includes an electron-relay layer 118 and/or an electron-injection buffer layer 119 in addition to the p-type layer 117.

The electron-relay layer 118 contains at least a substance with an electron-transport property and has a function of preventing an interaction between the electron-injection buffer layer 119 and the p-type layer 117 to transfer electrons smoothly. The LUMO level of the substance with an electron-transport property contained in the electron-relay layer 118 is preferably between the LUMO level of an acceptor substance in the p-type layer 117 and the LUMO level of a substance contained in a layer of the electron-transport layer 114 in contact with the charge-generation layer 116. Specifically, the LUMO energy level of the substance with an electron-transport property used for the electron-relay layer 118 is preferably higher than or equal to −5.0 eV, further preferably higher than or equal to −5.0 eV and lower than or equal to −3.0 eV As the substance with an electron-transport property used for the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)). As the substance having an electron-transport property, a material similar to the above-described material of the electron-transport layer 114 can be used.

For the cathode 102, a metal, an alloy, an electrically conductive compound, or a mixture thereof having a low work function (specifically, 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the cathode 102 and the electron-transport layer, for the cathode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an inkjet method, a spin coating method, or the like. Alternatively, a wet process using a sol-gel method or a wet process using a paste of a metal material may be employed.

A variety of methods, either a dry process or a wet process, can be used to form the EL layer 103. For example, a vacuum evaporation method or a wet process (such as a spin coating method, a casting method, a die coating method, a blade coating method, a roll coating method, an inkjet method, a printing method (e.g., a gravure printing method, an offset printing method, or a screen printing method), a spray coating method, a curtain coating method, or a Langmuir-Blodgett method) may be used.

Different methods may be used to form the electrodes or the layers described above.

Here, a method for forming a layer 786 containing a light-emitting substance by a droplet discharge method will be described with reference to FIGS. 2A to 2D. FIGS. 2A to 2D are cross-sectional views illustrating a method for forming the layer 786 containing a light-emitting substance.

Figure 2A:
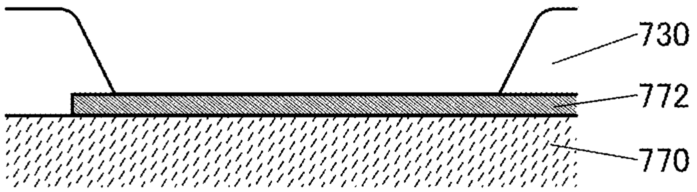
FIGS. 2A to 2D illustrate an example of a method for manufacturing a light-emitting element.
Figure 2B:
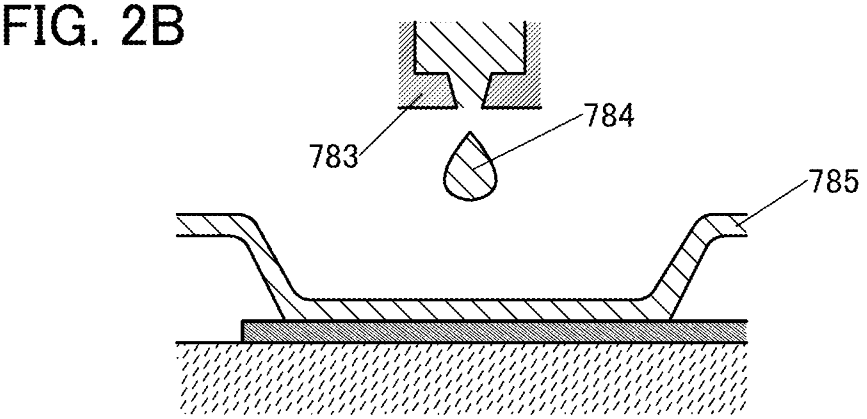

First, a conductive film 772 is formed over a planarization insulating film 770, and an insulating film 730 is formed to cover part of the conductive film 772 (see FIG. 2A).

Then, a droplet 784 is discharged from a droplet discharge apparatus 783 to the conductive film 772 exposed in an opening of the insulating film 730, so that a layer 785 containing a composition is formed. The droplet 784 is a composition containing a solvent and is attached to the conductive film 772 (see FIG. 2B).

Note that the step of discharging the droplet 784 may be performed under reduced pressure.

Figure 2C:
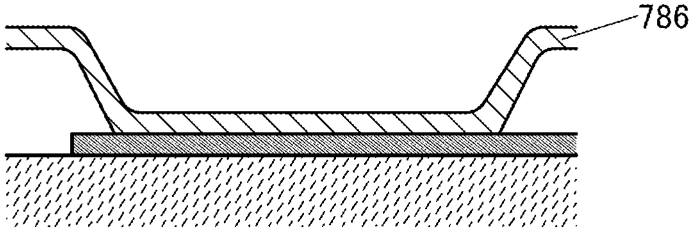

Next, the solvent is removed from the layer 785 containing a composition, and the resulting layer is solidified to form the layer 786 containing a light-emitting substance (see FIG. 2C).

The solvent may be removed by drying or heating.

Figure 2D:
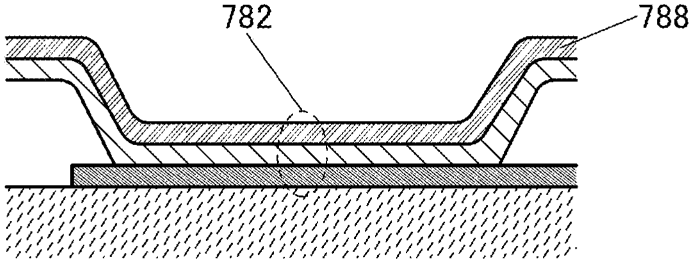

Next, a conductive film 788 is formed over the layer 786 containing a light-emitting substance; thus, a light-emitting element 782 is formed (see FIG. 2D).

When the layer 786 containing a light-emitting substance is formed by a droplet discharge method in this manner, the composition can be selectively discharged; accordingly, waste of material can be reduced. Furthermore, a lithography process or the like for shaping is not needed, and thus, the process can be simplified and cost reduction can be achieved.

The droplet discharge method mentioned above is a general term for a method with a droplet discharge means such as a nozzle having a composition discharge outlet or a head having one or a plurality of nozzles.

Figure 3:
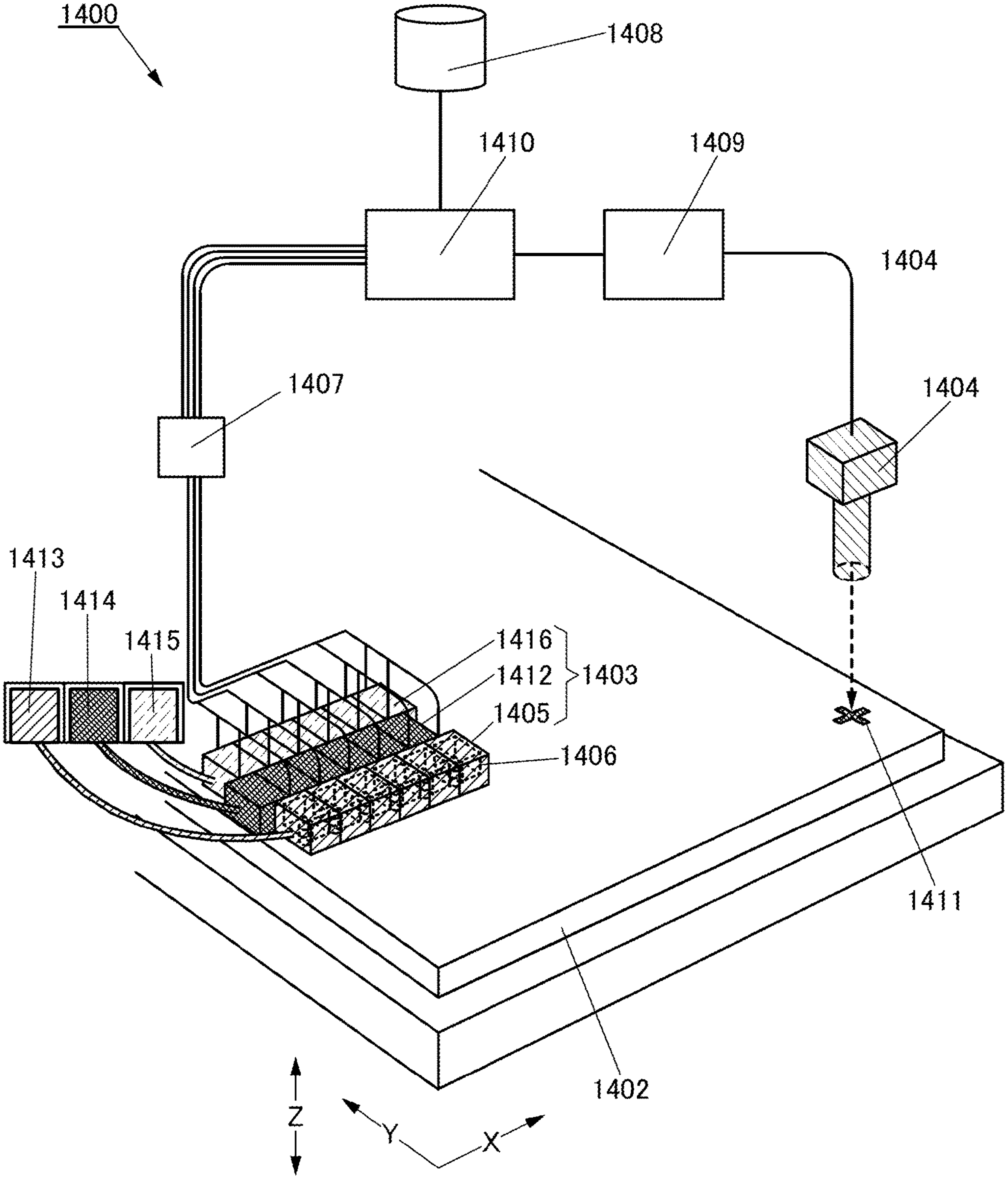
FIG. 3 illustrates an example of a method for manufacturing a light-emitting element.

Next, a droplet discharge apparatus used for the droplet discharge method will be described with reference to FIG. 3. FIG. 3 is a conceptual diagram illustrating a droplet discharge apparatus 1400.

The droplet discharge apparatus 1400 includes a droplet discharge means 1403. The droplet discharge means 1403 includes a head 1405, a head 1412, and a head 1416.

The heads 1405 and 1412 are connected to a control means 1407 which is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The computer 1410 recognizes the digital signal, generates a control signal, and transmits it to the control means 1407.

An image sensor or the like including a charge coupled device (CCD) or a complementary metal oxide semiconductor (CMOS) can be used as the imaging means 1404. Note that information on a pattern to be formed on the substrate 1402 is stored in a storage medium 1408, and a control signal is transmitted to the control means 1407 on the basis of the information, so that the heads 1405, 1412, and 1416 of the droplet discharge means 1403 can be individually controlled. Materials to be discharged are supplied to the heads 1405, 1412, and 1416 from material supply sources 1413, 1414, and 1415, respectively, through pipes.

Inside each of the heads 1405, 1412, and 1416, a space indicated by a dotted line 1406 to be filled with a liquid material and a nozzle serving as a discharge outlet are provided. Although not illustrated, the inside structure of the head 1412 is similar to that of the head 1405. When the nozzle sizes of the heads 1405 and 1412 are different from each other, different materials with different widths can be discharged simultaneously. Each head can discharge a plurality of light-emitting materials or the like to draw a pattern. In the case of drawing a pattern over a large area, the same material can be simultaneously discharged from a plurality of nozzles in order to improve throughput. When a large substrate is used, the heads 1405, 1412, and 1416 can freely scan the substrate in the directions of arrows X, Y, and Z in FIG. 3, and a region in which a pattern is drawn can be freely set. Thus, the same patterns can be drawn on one substrate.

Furthermore, the step of discharging the composition may be performed under reduced pressure. The substrate may be heated when the composition is discharged. The discharge of the composition is followed by drying and/or baking. Both the drying and baking are heat treatments but different in purpose, temperature, and time. The drying and baking are performed under normal pressure or reduced pressure by laser irradiation, rapid thermal annealing, heating in a heating furnace, or the like. Note that there is no particular limitation on the timing of the heat treatment and the number of times of the heat treatment. The temperature for adequately performing the drying and baking depends on the material of the substrate and the properties of the composition.

In the above-described manner, the layer 786 containing a light-emitting substance can be formed with the droplet discharge apparatus.

The layer 786 containing a light-emitting substance can be formed with the droplet discharge apparatus by a wet process using a composition in which any of a variety of organic materials and organic-inorganic halide perovskite materials is dissolved or dispersed in a solvent. In this case, the following various organic solvents can be used to form a coating composition: benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, and cyclohexane. In particular, a less polar benzene derivative such as benzene, toluene, xylene, or mesitylene is preferably used because a solution with a suitable concentration can be obtained and a material contained in ink can be prevented from deteriorating due to oxidation or the like. Furthermore, to form a uniform film or a film with a uniform thickness, a solvent with a boiling point of 100° C. or higher is preferably used, and further preferably, toluene, xylene, or mesitylene is used.

Note that the above-described structure can be combined with any of the structures in this embodiment and the other embodiments.

Next, an embodiment of a light-emitting element in which a plurality of light-emitting units is stacked (also referred to as a stacked element) will be described with reference to FIG. 1C. This light-emitting element includes a plurality of light-emitting units between an anode and a cathode. Each light-emitting unit has a structure similar to that of the EL layer 103 illustrated in FIG. 1A. In other words, the light-emitting element illustrated in FIG. 1A or 1B includes a single light-emitting unit, and the light-emitting element illustrated in FIG. 1C includes a plurality of light-emitting units.

Figure 1B:
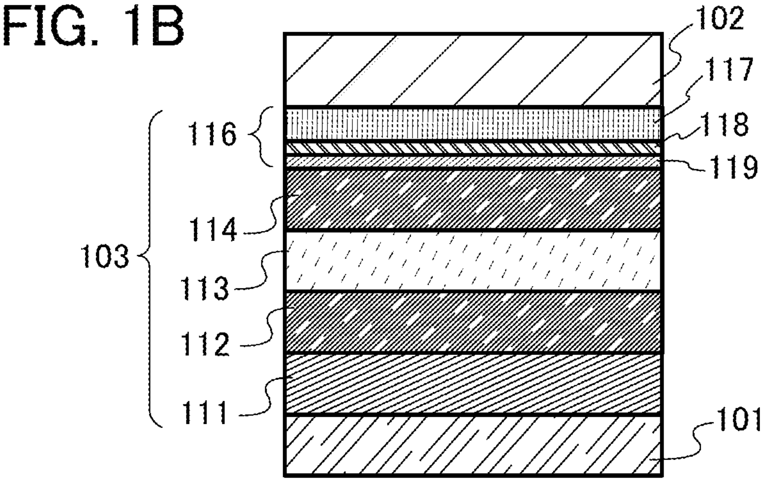
Figure 1C:
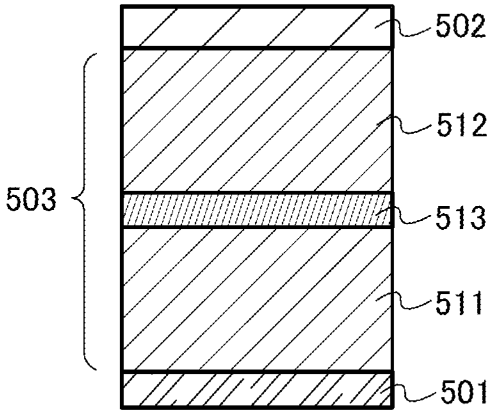

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond to the anode 101 and the cathode 102, respectively, illustrated in FIG. 1A, and the description of FIG. 1A can be applied thereto. Furthermore, the first light-emitting unit 511 and the second light-emitting unit 512 may have the same structure or different structures.

The charge-generation layer 513 has a function of injecting electrons into one of the light-emitting units and injecting holes into the other light-emitting unit when a voltage is applied between the first electrode 501 and the second electrode 502. That is, in FIG. 1C, the charge-generation layer 513 injects electrons into the first light-emitting unit 511 and holes into the second light-emitting unit 512 when a voltage is applied so that the potential of the first electrode is higher than the potential of the second electrode.

The charge-generation layer 513 preferably has a structure similar to that of the charge-generation layer 116 described with reference to FIG. 1B. A composite material of an organic compound and a metal oxide has a high carrier-injection property and a high carrier-transport property; thus, low-voltage driving and low-current driving can be achieved. In the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 serves as an electron-injection layer in the light-emitting unit on the anode side; therefore, the light-emitting unit is not necessarily provided with an additional electron-injection layer.

The light-emitting element having two light-emitting units is described with reference to FIG. 1C; however, one embodiment of the present invention can also be applied to a light-emitting element in which three or more light-emitting units are stacked. With a plurality of light-emitting units partitioned by the charge-generation layer 513 between a pair of electrodes as in the light-emitting element of this embodiment, it is possible to provide a long-life element which can emit light with high luminance at a low current density. A light-emitting device which can be driven at a low voltage and has low power consumption can be provided.

Furthermore, when emission colors of the light-emitting units are different, light emission of a desired color can be obtained from the light-emitting element as a whole.

Embodiment 3

In this embodiment, a light-emitting device including the light-emitting element described in Embodiment 1 will be described.

Figures 4A, 4B:
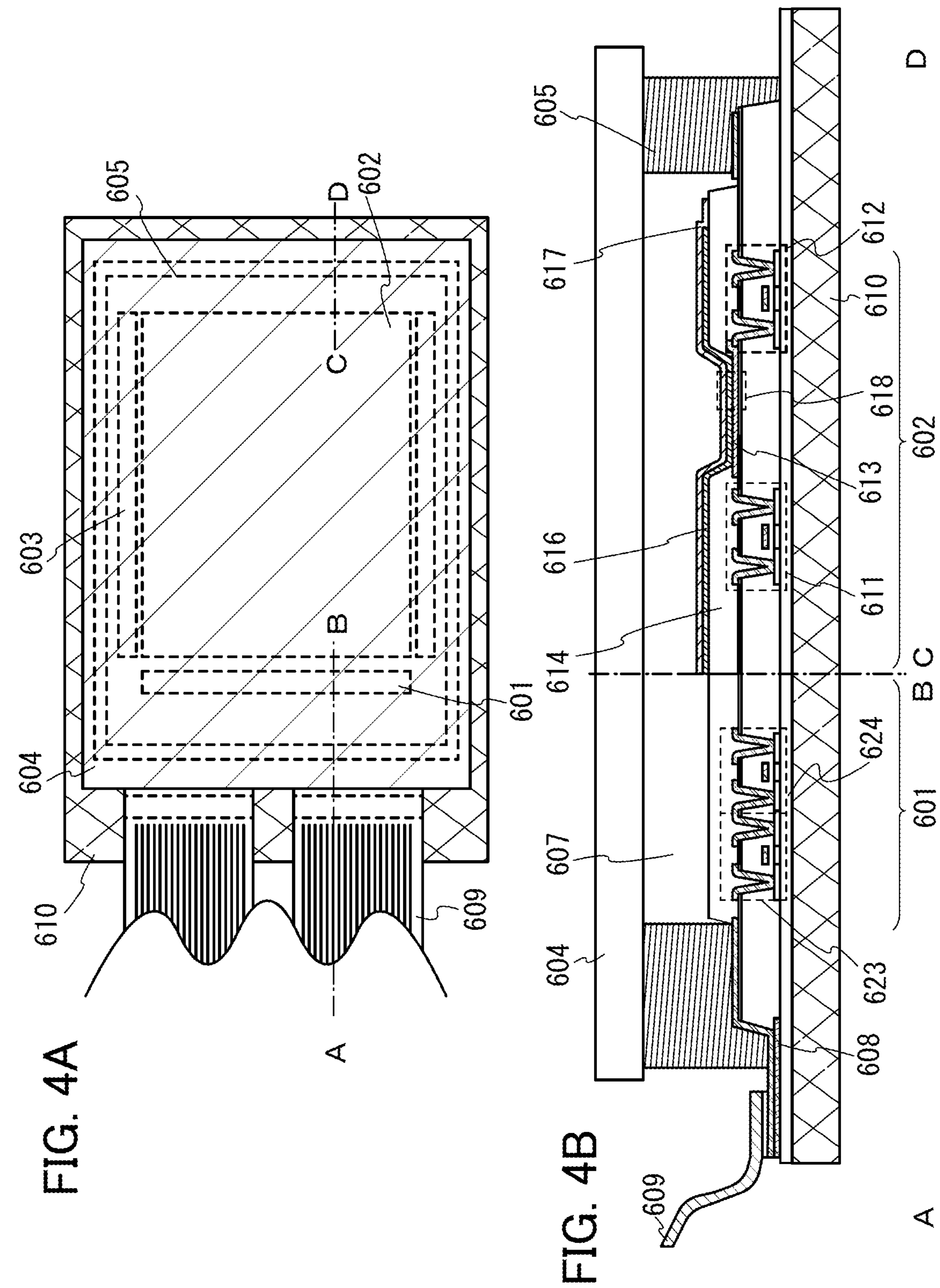
FIGS. 4A and 4B are conceptual diagrams of an active matrix light-emitting device.

A light-emitting device of one embodiment of the present invention will be described with reference to FIGS. 4A and 4B. FIG. 4A is a top view of the light-emitting device, and FIG. 4B is a cross-sectional view taken along the lines A-B and C-D in FIG. 4A. The light-emitting device includes a driver circuit portion (source line driver circuit) 601, a pixel portion 602, and a driver circuit portion (gate line driver circuit) 603, which control light emission of a light-emitting element and are illustrated with dotted lines. A reference numeral 604 denotes a sealing substrate; 605, a sealant; and 607, a space surrounded by the sealant 605.

Note that a lead wiring 608 is a wiring for transmitting signals to be input to the source line driver circuit 601 and the gate line driver circuit 603 and receiving a video signal, a clock signal, a start signal, a reset signal, and the like from a flexible printed circuit (FPC) 609 serving as an external input terminal. Although only the FPC is illustrated here, a printed wiring board (PWB) may be attached to the FPC. The light-emitting device in this specification includes, in its category, not only the light-emitting device itself but also the device provided with the FPC or the PWB.

Next, a cross-sectional structure will be described with reference to FIG. 4B. The driver circuit portion and the pixel portion are formed over an element substrate 610. Here, the source line driver circuit 601, which is the driver circuit portion, and one pixel of the pixel portion 602 are illustrated.

As the source line driver circuit 601, a CMOS circuit in which an n-channel FET 623 and a p-channel FET 624 are combined is formed. The driver circuit may be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and may be formed outside the substrate.

The pixel portion 602 includes a plurality of pixels each including a switching FET 611, a current controlling FET 612, and a first electrode 613 electrically connected to a drain of the current controlling FET 612. One embodiment of the present invention is not limited to this structure. Each pixel of the pixel portion may include three or more FETs and a capacitor in combination.

There is no particular limitation on the kind and crystallinity of a semiconductor used for the FETs; an amorphous semiconductor or a crystalline semiconductor may be used. Examples of the semiconductor used for the FETs include Group 13 semiconductors, Group 14 semiconductors, compound semiconductors, oxide semiconductors, and organic semiconductor materials. Oxide semiconductors are particularly preferable. Examples of the oxide semiconductor include an In—Ga oxide and an In-M-Zn oxide (M is Al, Ga, Y, Zr, La, Ce, or Nd). Note that an oxide semiconductor material that has an energy gap of 2 eV or more, preferably 2.5 eV or more, further preferably 3 eV or more is preferably used, in which case the off-state current of the transistors can be reduced.

Note that an insulator 614 is formed to cover an end portion of the first electrode 613. The insulator 614 can be formed using a positive photosensitive acrylic resin film here.

In order to improve the coverage, the insulator 614 is formed so as to have a curved surface with curvature at its upper or lower end portion. For example, in the case where positive photosensitive acrylic is used as a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. The first electrode 613, the EL layer 616, and the second electrode 617 respectively correspond to the anode 101, the EL layer 103, and the cathode 102 in FIGS. 1A and 1, or to the first electrode 501, an EL layer 503, and the second electrode 502 in FIG. 1C.

The EL layer 616 preferably contains an organometallic complex. The organometallic complex is preferably used as an emission center substance in the light-emitting layer.

The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with a filler and may be filled with an inert gas (e.g., nitrogen or argon) or the sealant 605. It is preferable that the sealing substrate have a recessed portion provided with a desiccant, in which case deterioration due to moisture can be suppressed.

An epoxy-based resin or a glass frit is preferably used as the sealant 605. In this case, it is preferable to use a material that transmits moisture or oxygen as little as possible. As the element substrate 610 and the sealing substrate 604, a glass substrate, a quartz substrate, or a plastic substrate formed of fiber reinforced plastic (FRP), polyvinyl fluoride (PVF), polyester, acrylic, or the like can be used.

In this specification and the like, a transistor or a light-emitting element can be formed using a variety of substrates, for example. The type of the substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used. For the glass substrate, for example, barium borosilicate glass, aluminoborosilicate glass, or soda lime glass can be used. Examples of a material of the flexible substrate, the attachment film, the base material film, or the like are as follows: plastic typified by polyethylene terephthalate (PET), polyethylene naphthalate (PEN), and polyether sulfone (PES). Another example is a synthetic resin such as acrylic. Alternatively, polytetrafluoroethylene (PTFE), polypropylene, polyester, polyvinyl fluoride, polyvinyl chloride, or the like can be used. Alternatively, polyamide, polyimide, aramid, epoxy, an inorganic film formed by evaporation, paper, or the like can be used. Specifically, the use of a semiconductor substrate, a single crystal substrate, an SOI substrate, or the like enables the manufacture of small-sized transistors with high current capability and a small variation in characteristics, size, shape, or the like. A circuit including such transistors achieves lower power consumption or higher integration of the circuit.

Alternatively, a flexible substrate may be used as the substrate, and the transistor or the light-emitting element may be directly formed over the flexible substrate. Alternatively, a separation layer may be provided between a substrate and the transistor or between the substrate and the light-emitting element. The separation layer can be used when part or the whole of a semiconductor device formed over the separation layer is separated from the substrate and transferred to another substrate. In this case, the transistor can be transferred to even a substrate having low heat resistance or a flexible substrate. As the separation layer, a stack of inorganic films, namely a tungsten film and a silicon oxide film, or an organic resin film of polyimide or the like formed over a substrate can be used, for example.

In other words, the transistor or the light-emitting element may be formed using one substrate and then transferred to another substrate. Examples of the substrate to which the transistor or the light-emitting element is transferred include, in addition to the above-described substrates over which the transistor can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent properties or a transistor with low power consumption can be formed, a device with high durability and high heat resistance can be provided, or a reduction in weight or thickness can be achieved.

Figure 5A:
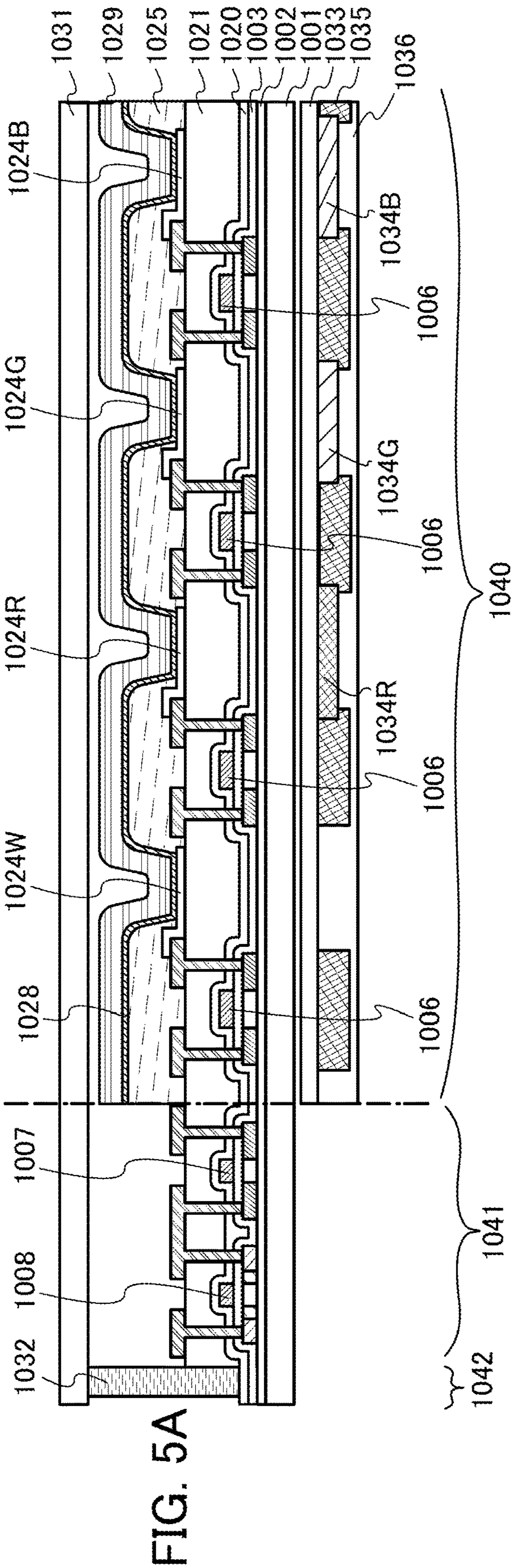
FIGS. 5A and 5B are conceptual diagrams of active matrix light-emitting devices.
Figure 5B:
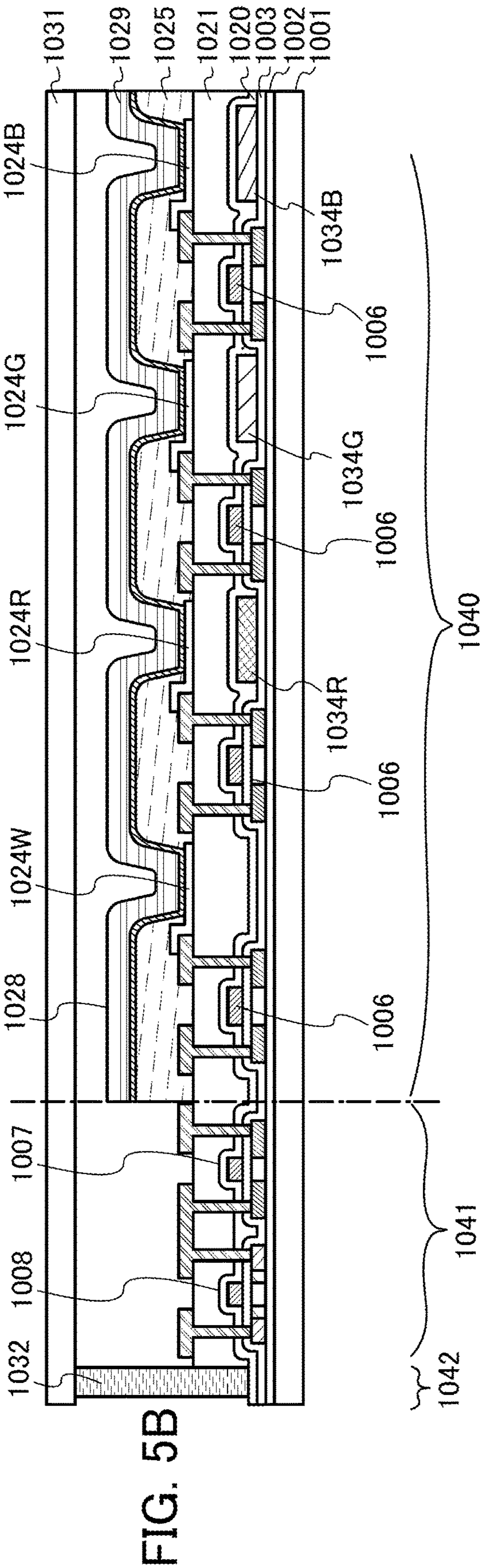

FIGS. 5A and 5B each illustrate an example of a light-emitting device which includes a light-emitting element exhibiting white light emission and coloring layers (color filters) and the like to display a full-color image. FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a cathode 1029 of the light-emitting elements, a sealing substrate 1031, a sealant 1032, and the like.

In FIG. 5A, coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5A, light emitted from some light-emitting layers does not pass through the coloring layers, while light emitted from the other light-emitting layers passes through the respective coloring layers. Since light that does not pass through the coloring layers is white and light that passes through any one of the coloring layers is red, blue, or green, an image can be displayed using pixels of the four colors.

FIG. 5B illustrates an example in which the coloring layers (the red coloring layer 1034R, the green coloring layer 1034G, and the blue coloring layer 1034B) are formed between the gate insulating film 1003 and the first interlayer insulating film 1020. As in this structure, the coloring layers may be provided between the substrate 1001 and the sealing substrate 1031.

Figure 6:
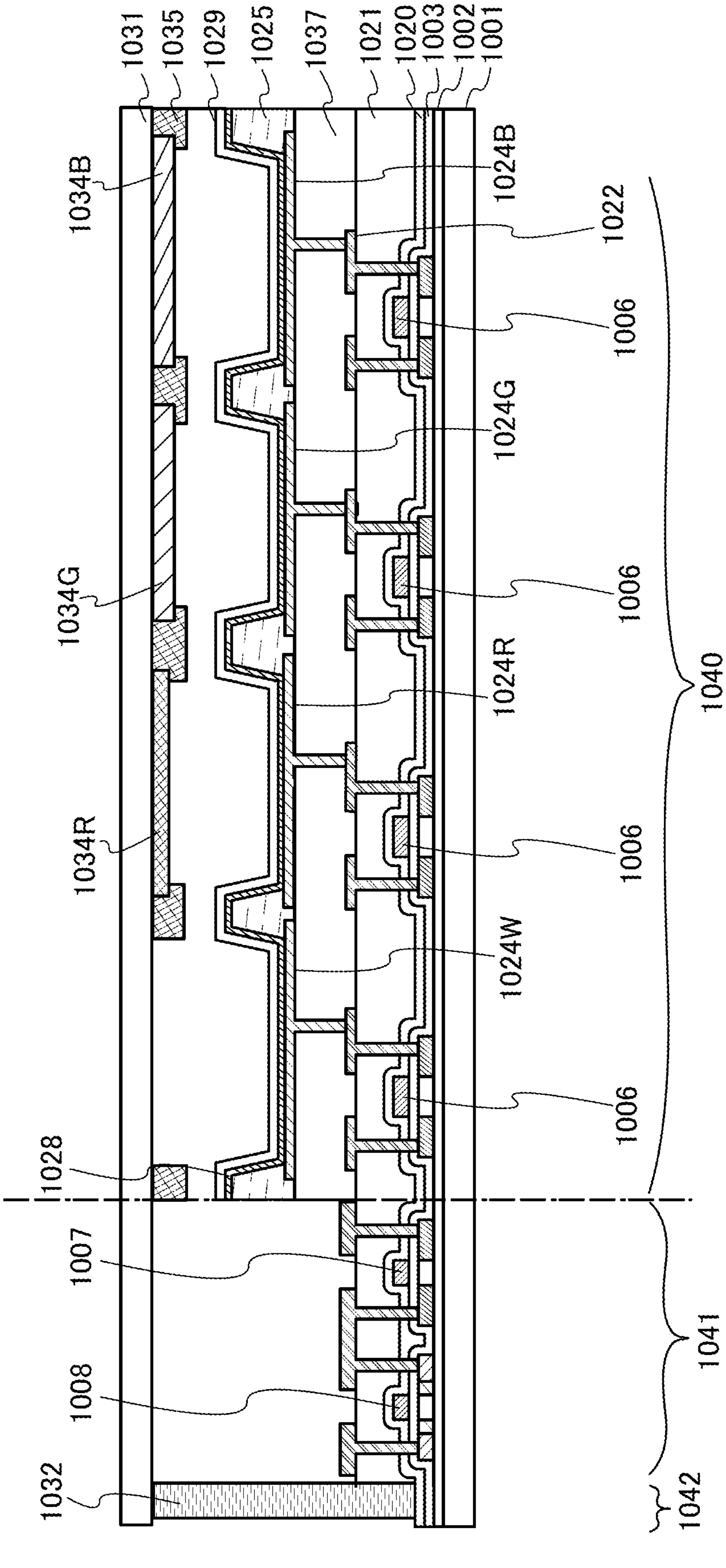
FIG. 6 is a conceptual diagram of an active matrix light-emitting device.

The above-described light-emitting device has a structure in which light is extracted from the substrate 1001 side, over which the FETs are formed (a bottom emission structure), but may have a structure in which light is extracted from the sealing substrate 1031 side (a top emission structure). FIG. 6 is a cross-sectional view of a top-emission light-emitting device. In this case, a substrate that does not transmit light can be used as the substrate 1001. The process up to the step of forming of a connection electrode which connects the FET to the anode of the light-emitting element is performed in a manner similar to that of the bottom-emission light-emitting device. Then, a third interlayer insulating film 1037 is formed to cover an electrode 1022. This insulating film may have a planarization function. The third interlayer insulating film 1037 can be formed using a material similar to that of the second interlayer insulating film or using any other various materials.

The first electrodes 1024W, 1024R, 1024G, and 1024B of the light-emitting elements each serve as an anode here, but may each serve as a cathode. Furthermore, in the case of the top-emission light-emitting device illustrated in FIG. 6, the first electrodes are preferably reflective electrodes. The EL layer 1028 has a structure similar to the structure of the EL layer 103 in FIG. 1A or 1B or the EL layer 503 in FIG. 1C, with which white light emission can be obtained.

In the case of a top emission structure like that in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 which is positioned between pixels. The coloring layers (the red coloring layer 1034R, the green coloring layer 1034G, and the blue coloring layer 1034B) and the black layer may be covered with an overcoat layer. Note that a light-transmitting substrate is used as the sealing substrate 1031.

One embodiment of the present invention is not particularly limited to the example shown here, in which a full-color image is displayed using four colors of red, green, blue, and white; a full-color image may be displayed using three colors of red, green, and blue or four colors of red, green, blue, and yellow.

Figure 7A:
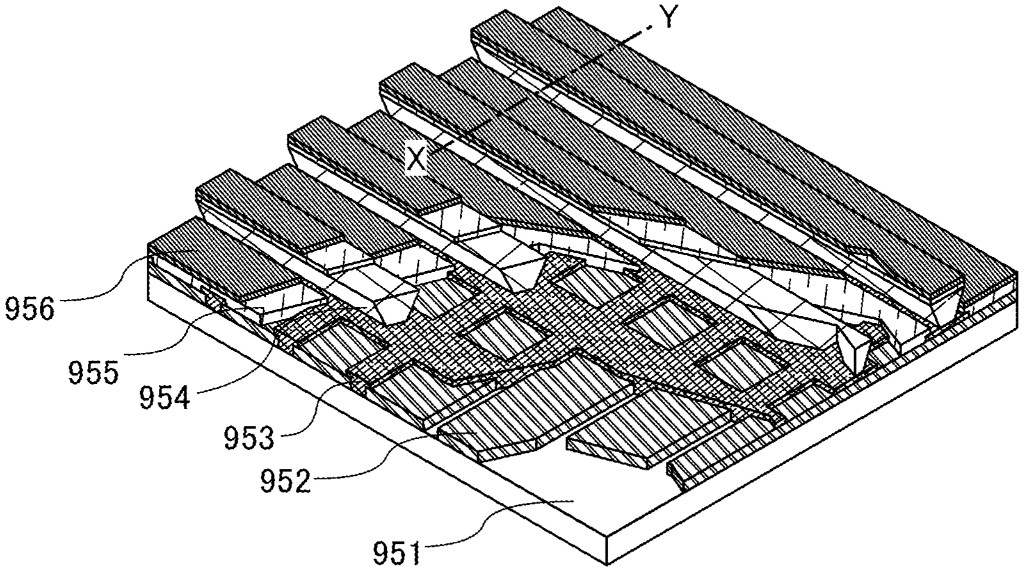
FIGS. 7A and 7B are conceptual diagrams of a passive matrix light-emitting device.
Figure 7B:
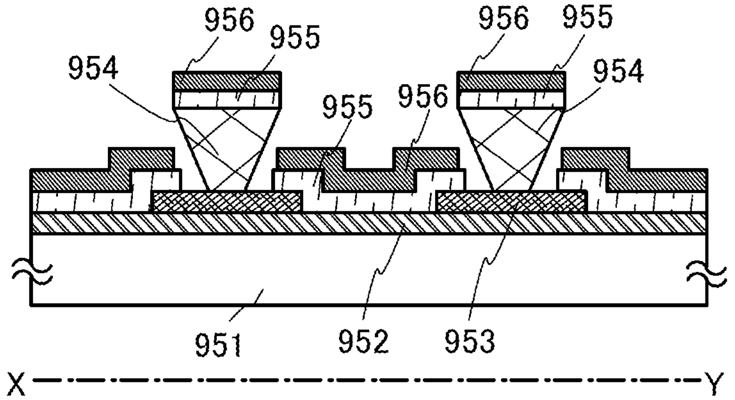

FIGS. 7A and 7B illustrate a passive matrix light-emitting device of one embodiment of the present invention. FIG. 7A is a perspective view of the light-emitting device, and FIG. 7B is a cross-sectional view taken along the line X-Y in FIG. 7A. In FIGS. 7A and 7B, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between the sidewalls is gradually narrowed toward the surface of the substrate. That is, a cross section in the short side direction of the partition layer 954 is a trapezoidal shape, and the lower side (the side which is substantially parallel to the plane direction of the insulating layer 953 and is in contact with the insulating layer 953) is shorter than the upper side (the side which is substantially parallel to the plane direction of the insulating layer 953 and is not in contact with the insulating layer 953). The partition layer 954 provided in this manner can prevent defects of the light-emitting element due to static electricity or the like.

Since many minute light-emitting elements arranged in a matrix can be independently controlled by the FETs formed in the pixel portion, the above-described light-emitting device can be suitably used as an image display device.

<<Lighting Device>>

Figure 8A:
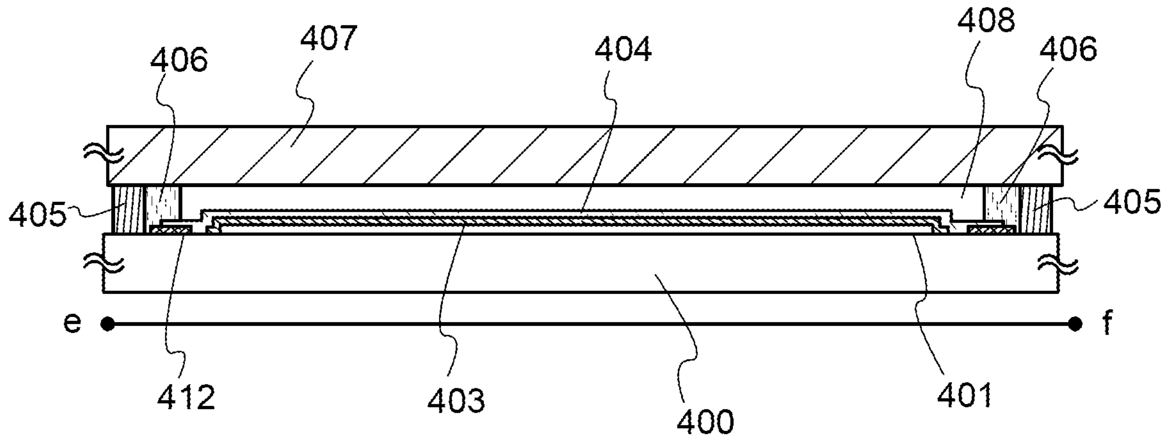
FIGS. 8A and 8B illustrate a lighting device.
Figure 8B:
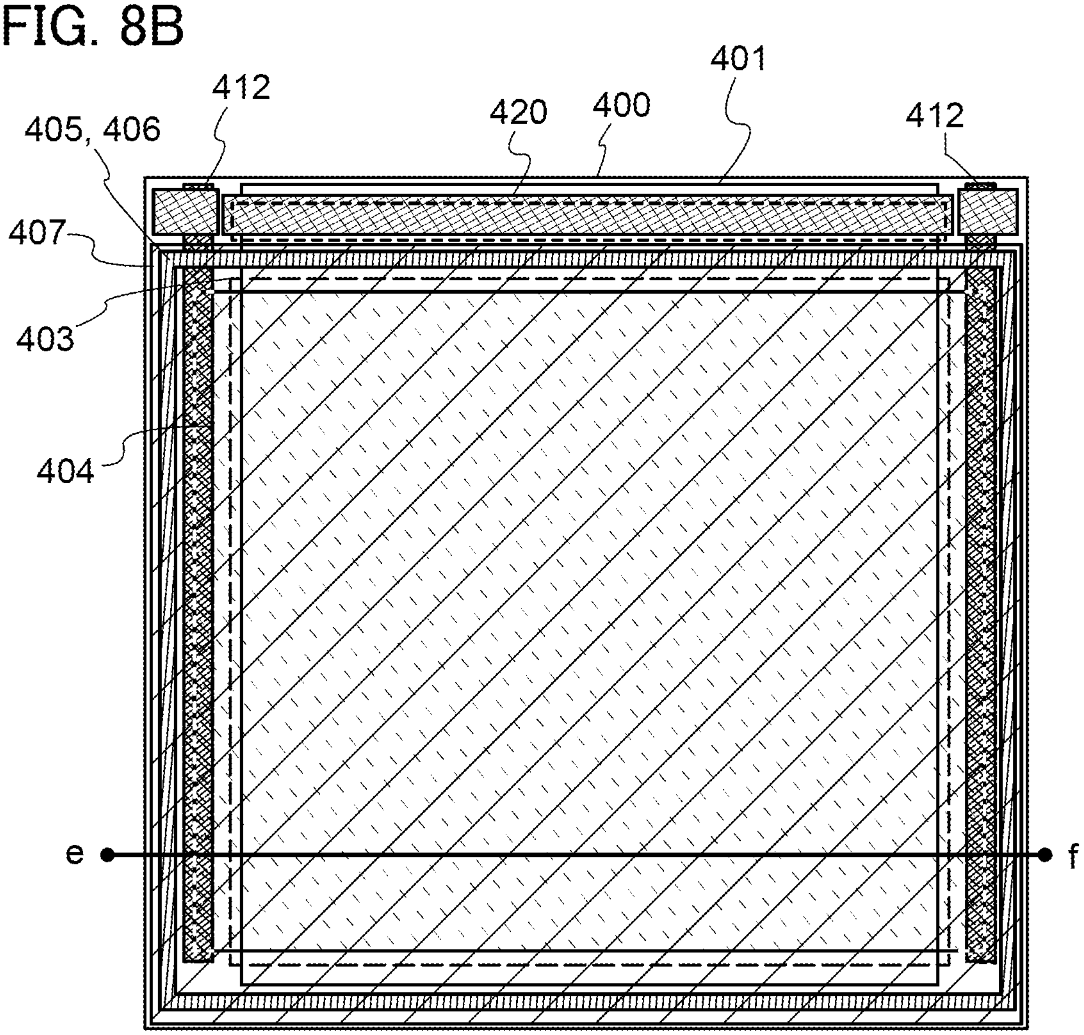

A lighting device of one embodiment of the present invention will be described with reference to FIGS. 8A and 8B. FIG. 8B is a top view of the lighting device, and FIG. 8A is a cross-sectional view taken along the line e-f in FIG. 8B.

In the lighting device, a first electrode 401 is formed over a substrate 400 which is a support and has a light-transmitting property. The first electrode 401 corresponds to the anode 101 in FIGS. 1A and 1B. When light is extracted from the first electrode 401 side, the first electrode 401 is formed using a material having a light-transmitting property.

A pad 412 for applying a voltage to a second electrode 404 is formed over the substrate 400.

An EL layer 403 is formed over the first electrode 401. The EL layer 403 corresponds to, for example, the EL layer 103 in FIGS. 1A and 1B. For these structures, the corresponding description can be referred to.

The second electrode 404 is formed to cover the EL layer 403. The second electrode 404 corresponds to the cathode 102 in FIG. 1A. The second electrode 404 contains a material having high reflectivity when light is extracted from the first electrode 401 side. The second electrode 404 is connected to the pad 412, whereby a voltage is applied thereto.

A light-emitting element is formed with the first electrode 401, the EL layer 403, and the second electrode 404. The light-emitting element is sealed by being fixed to a sealing substrate 407 with sealants 405 and 406, whereby the lighting device is completed. It is possible to omit the sealant 405 or the sealant 406. In addition, the inner sealant 406 can be mixed with a desiccant that enables moisture to be adsorbed, increasing reliability.

When part of the pad 412 and part of the first electrode 401 are extended to the outside of the sealants 405 and 406, the extended parts can serve as external input terminals. An IC chip 420 mounted with a converter or the like may be provided over the external input terminals.

<<Electronic Device>>

Examples of an electronic device of one embodiment of the present invention will be described. Examples of the electronic device include a television device (also referred to as a television or a television receiver), a monitor of a computer or the like, a digital camera, a digital video camera, a digital photo frame, a mobile phone (also referred to as a cellular phone or a mobile phone device), a portable game console, a portable information terminal, an audio reproducing device, and a large-sized game machine such as a pachinko machine. Specific examples of these electronic devices are shown below.

Figure 9A:
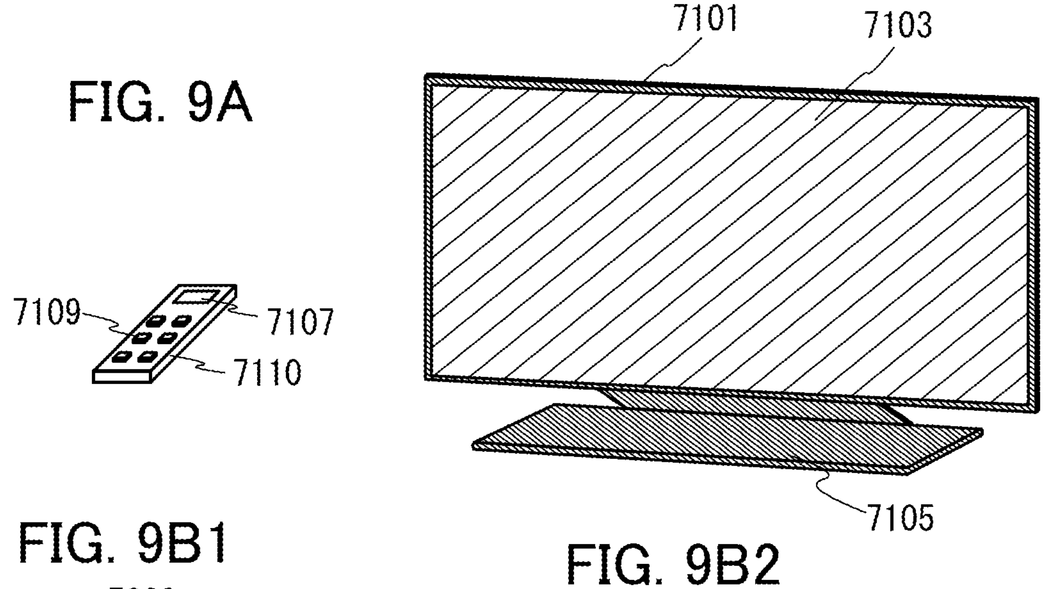
Figure 9A:
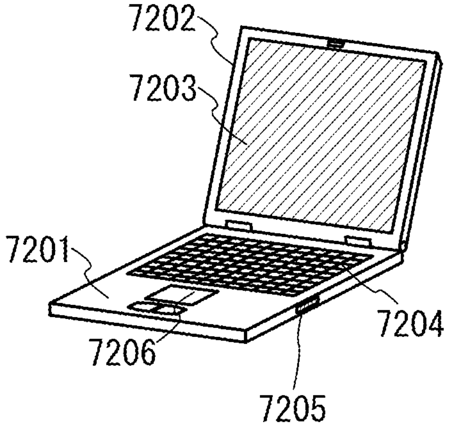
Figure 9A:
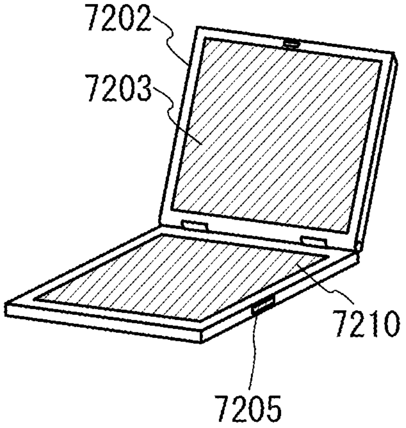

FIG. 9A illustrates an example of a television device. In the television device, a display portion 7103 is incorporated in a housing 7101. Here, the housing 7101 is supported by a stand 7105. Images can be displayed on the display portion 7103 in which light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 9B1 illustrates a computer which includes a main body 7201, a housing 7202, a display portion 7203, a keyboard 7204, an external connection port 7205, a pointing device 7206, and the like. Note that this computer is manufactured by arranging light-emitting elements in a matrix in the display portion 7203. The computer in FIG. 9B1 may have a structure in FIG. 9B2. The computer in FIG. 9B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 9C:
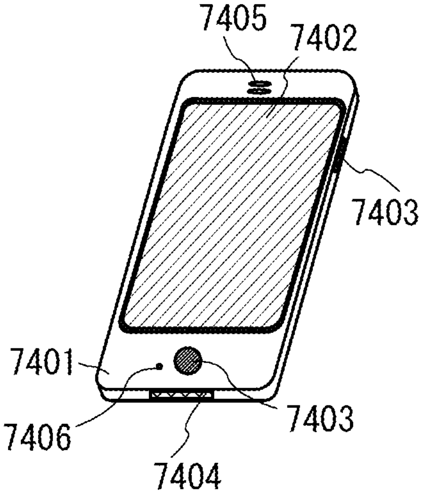
Figure 9D:
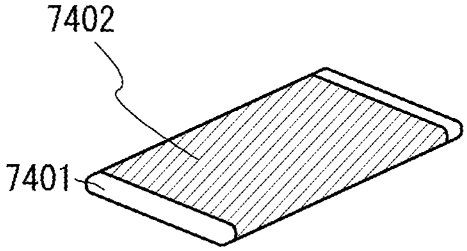

FIGS. 9C and 9D each illustrate an example of a portable information terminal. The portable information terminal is provided with a display portion 7402 incorporated in a housing 7401, operation buttons 7403, an external connection port 7404, a speaker 7405, a microphone 7406, and the like. Note that the portable information terminal includes the display portion 7402 in which light-emitting elements are arranged in a matrix.

Information can be input to each of the portable information terminals illustrated in FIGS. 9C and 9D by touching the display portion 7402 with a finger or the like. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor for sensing inclination, such as a gyroscope sensor or an acceleration sensor, is provided inside the portable information terminal, screen display of the display portion 7402 can be automatically changed by determining the orientation of the portable information terminal (whether the portable information terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Note that in the above electronic devices, any of the structures described in this specification can be combined as appropriate.

The display portion preferably includes the light-emitting element of one embodiment of the present invention. The light-emitting element can have high emission efficiency. In addition, the light-emitting element can be driven at low voltage. Thus, the electronic device including the light-emitting element of one embodiment of the present invention can have low power consumption.

Figure 10:
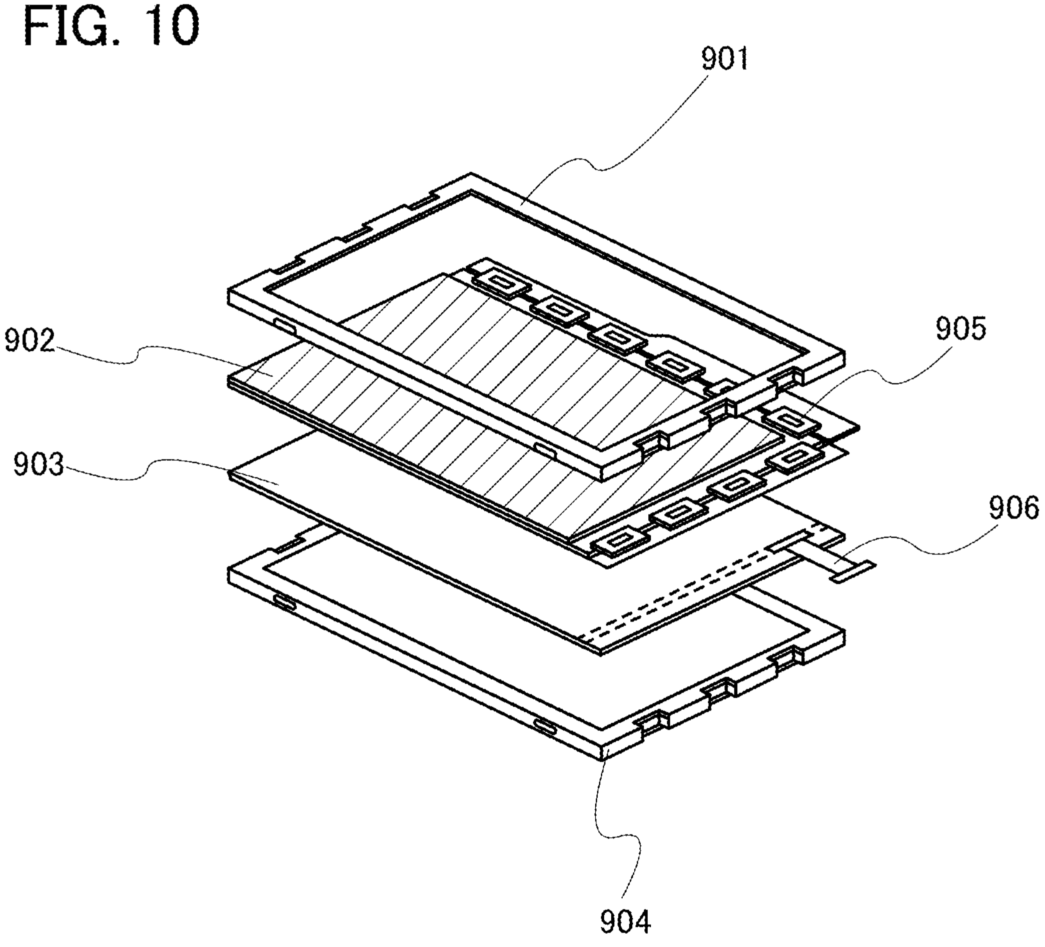
FIG. 10 illustrates alight source device.

FIG. 10 illustrates an example of a liquid crystal display device in which a light-emitting element is used for a backlight. The liquid crystal display device illustrated in FIG. 10 includes a housing 901, a liquid crystal layer 902, a backlight unit 903, and a housing 904. The liquid crystal layer 902 is connected to a driver IC 905. The light-emitting element is used for the backlight unit 903, to which a current is supplied through a terminal 906.

As the light-emitting element, the light-emitting element of one embodiment of the present invention is preferably used. By including the light-emitting element, the backlight of the liquid crystal display device can have low power consumption.

Figure 11:
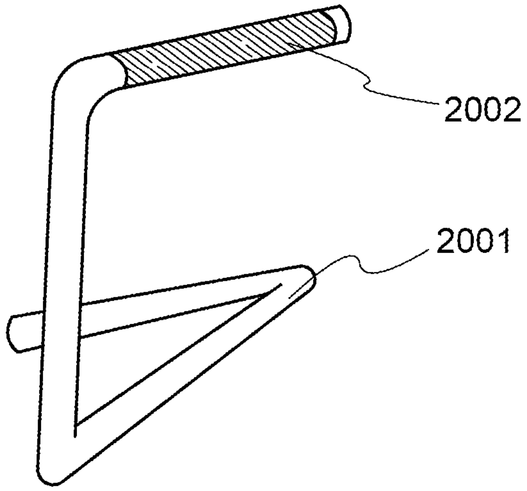
FIG. 11 illustrates a lighting device.

FIG. 11 illustrates an example of a desk lamp of one embodiment of the present invention. The desk lamp illustrated in FIG. 11 includes a housing 2001 and a light source 2002, and a lighting device including a light-emitting element is used as the light source 2002.

Figure 12:
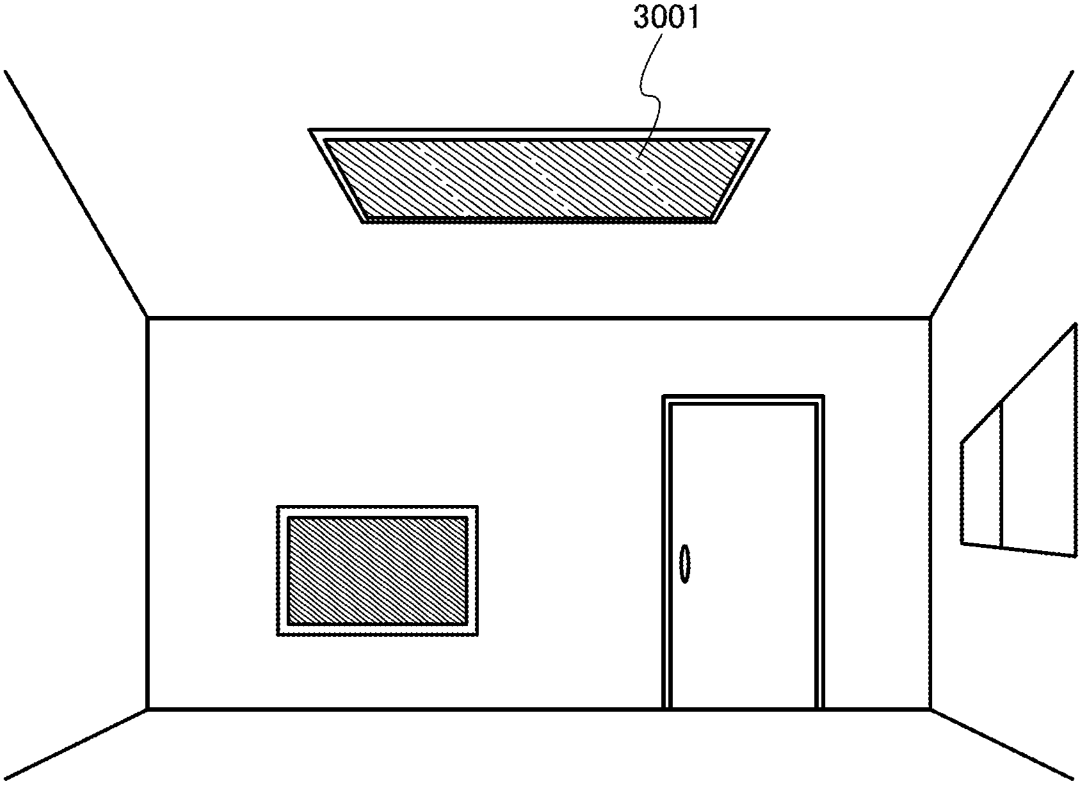
FIG. 12 illustrates a lighting device.

FIG. 12 illustrates an example of an indoor lighting device 3001. The light-emitting element of one embodiment of the present invention is preferably used for the lighting device 3001.

Figure 13:
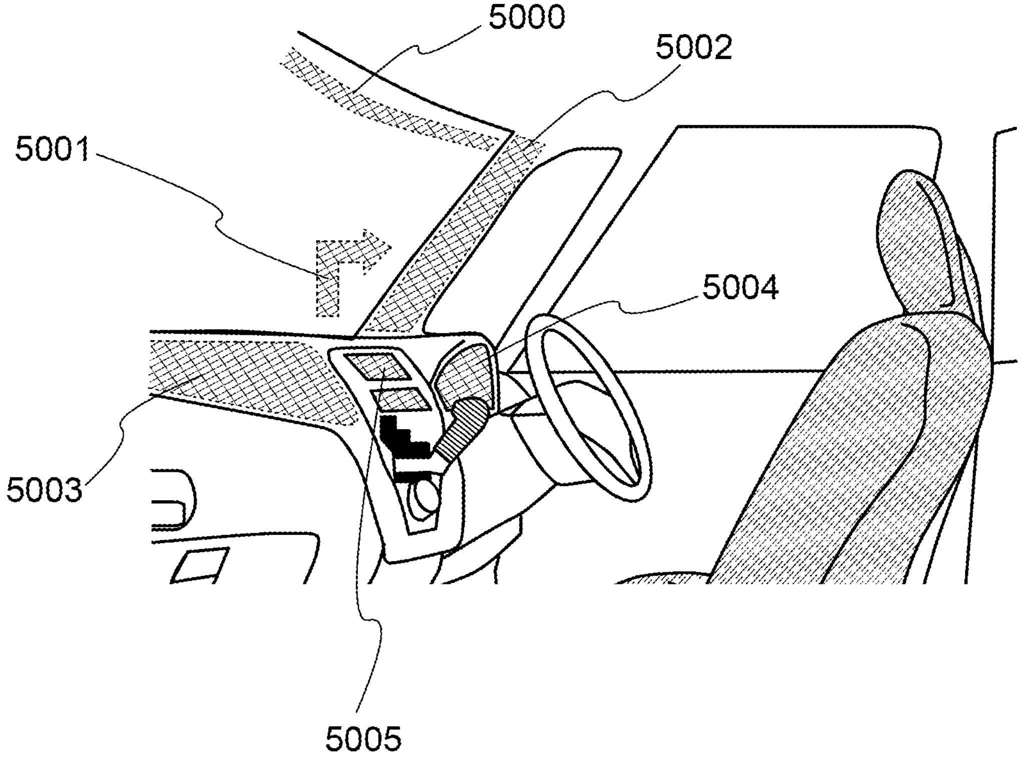
FIG. 13 illustrates car-mounted display devices and lighting devices.

An automobile of one embodiment of the present invention is illustrated in FIG. 13. In the automobile, light-emitting elements are used for a windshield and a dashboard. Display regions 5000 to 5005 are preferably formed using the light-emitting elements of one embodiment of the present invention. This suppresses the power consumption of the display regions 5000 to 5005, showing suitability for use in an automobile.

The display regions 5000 and 5001 are display devices which are provided in the automobile windshield and include the light-emitting elements. When electrodes having light-transmitting properties are used as first electrodes and second electrodes of these light-emitting elements, what is called see-through display devices, through which the opposite side can be seen, can be obtained. Such see-through display devices can be provided even in the automobile windshield without hindering the vision. In the case where a driving transistor or the like is provided, a transistor having a light-transmitting property, such as an organic transistor including an organic semiconductor material or a transistor including an oxide semiconductor, is preferably used.

The display region 5002 is a display device which is provided in a pillar portion and includes the light-emitting element. The display region 5002 can compensate for the view hindered by the pillar by displaying an image taken by an imaging unit provided in the car body. Similarly, the display region 5003 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to confirm safety easily and comfortably.

The display regions 5004 and 5005 can provide a variety of kinds of information such as navigation information, a speedometer, a tachometer, a mileage, a fuel meter, a gearshift indicator, and air-condition setting. The content or layout of the display can be changed freely by a user as appropriate. Note that such information can also be displayed on the display regions 5000 to 5003. The display regions 5000 to 5005 can also be used as lighting devices.

Figure 14A:
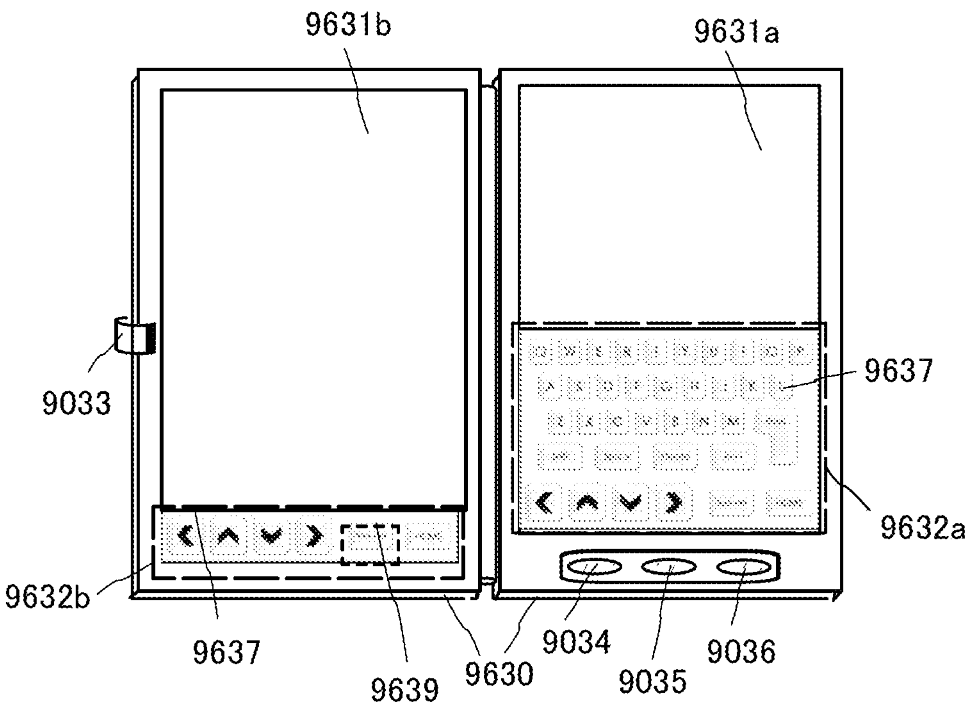
FIGS. 14A to 14C illustrate an electronic device.
Figure 14B:
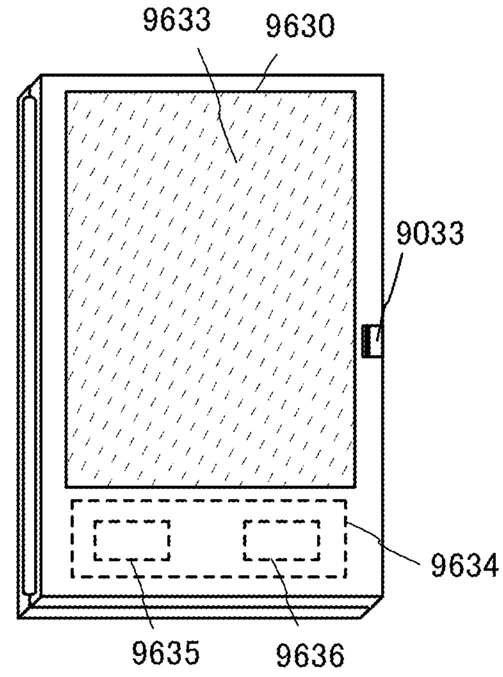

FIGS. 14A and 14B illustrate an example of a foldable tablet terminal. In FIG. 14A, the tablet terminal is opened and includes a housing 9630, a display portion 9631*a*, a display portion 9631*b*, a switch 9034 for switching display modes, a power switch 9035, a switch 9036 for switching to power-saving mode, and a clasp 9033. In the tablet terminal, a light-emitting device which includes the light-emitting element of one embodiment of the present invention is used for the display portion 9631*a* and/or the display portion 9631*b*.

Part of the display portion 9631*a* can be a touch panel region 9632*a*, and data can be input when a displayed operation key 9637 is touched. The structure of the display portion 9631*a* is not limited to the illustrated structure in which a half region has only a display function and the other half region has a touch panel function. The whole region of the display portion 9631*a* may have a touch panel function. For example, the whole area of the display portion 9631*a* can display keyboard buttons to serve as a touch panel, and the display portion 9631*b* can be used as a display screen.

Like the display portion 9631*a*, part of the display portion 9631*b* can be a touch panel region 9632*b*. When a switching button 9639 for showing/hiding a keyboard on the touch panel is touched with a finger, a stylus, or the like, keyboard buttons can be displayed on the display portion 9631*b*.

Touch input can be performed in the touch panel region 9632*a* and the touch panel region 9632*b* at the same time.

The switch 9034 for switching display modes can switch the display between a portrait mode, a landscape mode, and the like, and between monochrome display and color display, for example. With the switch 9036 for switching to power-saving mode, the luminance of display can be optimized in accordance with the amount of external light in use which is sensed by an optical sensor incorporated in the tablet terminal. In addition to the optical sensor, another sensing device such as a sensor for sensing inclination, e.g., a gyroscope sensor or an acceleration sensor, may be incorporated in the tablet terminal.

One embodiment of the present invention is not particularly limited to the example illustrated in FIG. 14A, in which the display portion 9631*a* and the display portion 9631*b* have the same display area. The display portion 9631*a* and the display portion 9631*b* may have different areas or different display quality. For example, one of the display portions 9631*a* and 9631*b* may display higher definition images than the other.

The tablet terminal is closed in FIG. 14B. The tablet terminal of this embodiment includes the housing 9630, a solar cell 9633, a charge/discharge control circuit 9634, a battery 9635, and a DCDC converter 9636. Note that FIG. 14B illustrates an example in which the charge/discharge control circuit 9634 includes the battery 9635 and the DCDC converter 9636.

Since the tablet terminal can be folded, the housing 9630 can be closed when the tablet terminal is not used. Thus, the display portion 9631*a* and the display portion 9631*b* can be protected; accordingly, a tablet terminal which has high durability and high reliability for long-term use can be provided.

In addition, the tablet terminal illustrated in FIGS. 14A and 14B can have a function of displaying a variety of kinds of information (e.g., a still image, a moving image, and a text image), a function of displaying a calendar, a date, the time, or the like on the display portion, a touch-input function of operating or editing information displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 is preferably provided on one or two surfaces of the housing 9630, in which case the battery 9635 can be charged efficiently.

Figure 14C:
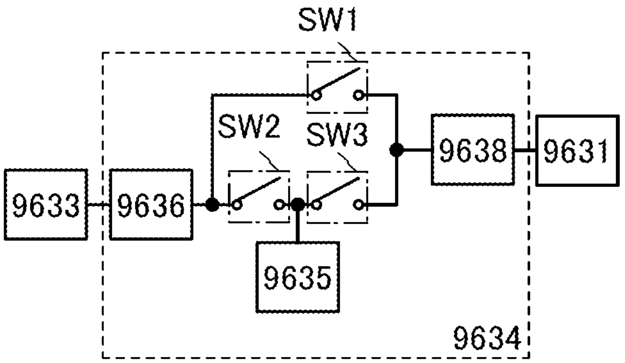

The structure and operation of the charge/discharge control circuit 9634 illustrated in FIG. 14B will be described with reference to a block diagram in FIG. 14C. FIG. 14C illustrates the solar cell 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge/discharge control circuit 9634 illustrated in FIG. 14B.

First, an example of the operation in the case where power is generated by the solar cell 9633 using external light will be described. The voltage of power generated by the solar cell is raised or lowered by the DCDC converter 9636 so as to be a voltage for charging the battery 9635. Then, when the power charged by the solar cell 9633 is used for the operation of the display portion 9631, the switch SW1 is turned on and the voltage of the power is raised or lowered by the converter 9638 so as to be a voltage needed for the display portion 9631. When display on the display portion 9631 is not performed, the switch SW1 is turned off and the switch SW2 is turned on so that the battery 9635 may be charged.

Although the solar cell 9633 is described as an example of a power generation means, there is no particular limitation on the power generation means, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or other charge means may be used in combination; the power generation means is not necessarily provided.

One embodiment of the present invention is not limited to the tablet terminal having the shape illustrated in FIGS. 14A to 14C as long as the display portion 9631 is provided.

Figure 15A:
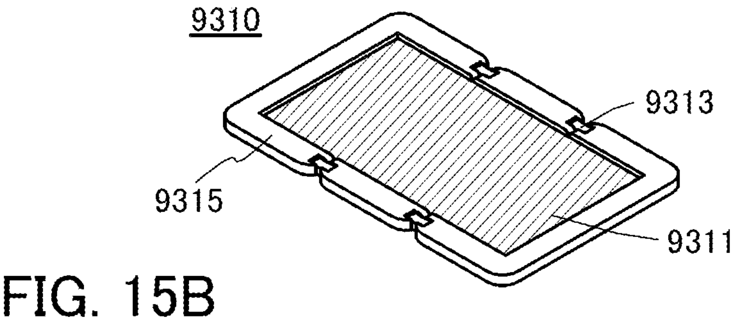
FIGS. 15A to 15C illustrate an electronic device.
Figure 15B:
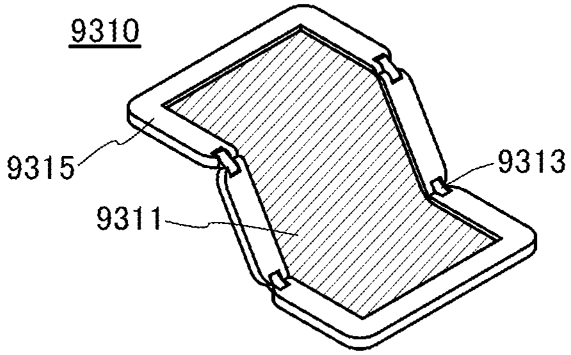
Figure 15C:
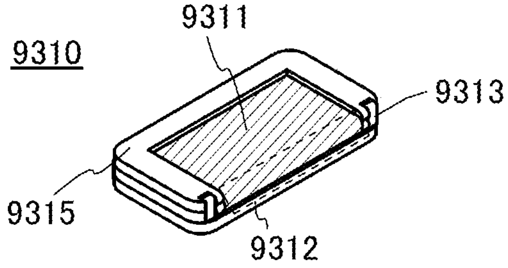

FIGS. 15A to 15C illustrate a foldable portable information terminal 9310. FIG. 15A illustrates the portable information terminal 9310 which is opened. FIG. 15B illustrates the portable information terminal 9310 which is being opened or being folded. FIG. 15C illustrates the portable information terminal 9310 which is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting device of one embodiment of the present invention can be used for the display panel 9311. A display region 9312 of the display panel 9311 is positioned at a side surface of the portable information terminal 9310 which is folded. On the display region 9312, information icons, file shortcuts of frequently used applications or programs, and the like can be displayed, and confirmation of information and start of an application can be easily performed.

Example 1

Synthesis Example 1

This synthesis example discloses a synthesis method of 4-(6;2'-binaphthyl-2-yl)-4',4"-diphenyltriphenylamine (abbreviation: BBA(βN2)B), which is the organic compound of one embodiment of the present invention represented by the structural formula (101) in Embodiment 1. The structural formula of BBA(βN2)B is shown below.

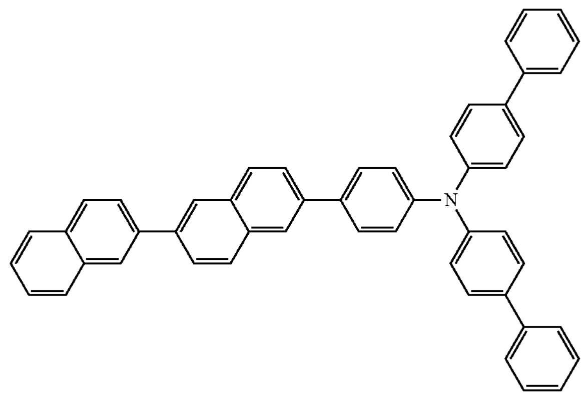 [SMILES: c1ccc(-c2ccc(N(c3ccc(-c4ccccc4)cc3)c3ccc(-c4ccc5cc(-c6ccc7ccccc7c6)ccc5c4)cc3)cc2)cc1]

Step 1: Synthesis of 6-bromo-2,2'-binaphthyl

In a 200-mL three-neck flask, 5.7 g (20 mmol) of 2,6-dibromonaphthalene, 3.4 g (20 mmol) of 2-naphthylboronic acid, 0.30 g (1.0 mmol) of tri(ortho-tolyl)phosphine, 80 mL of toluene, 20 mL of ethanol, and 40 mL of an aqueous solution of potassium carbonate (2.0 mol/L) were mixed. This mixture was degassed under reduced pressure, and then, a nitrogen gas was continuously introduced into the system. The mixture was heated to 60° C. Then, 0.12 g (0.5 mmol) of palladium(II) acetate was added, and stirring was performed at 80° C. for 2 hours. After the stirring, the mixture was cooled to room temperature, and the precipitated solid was collected by suction filtration and washed with water, ethanol, and toluene to give 2.1 g of a target pale brown solid. The filtrate obtained by the suction filtration was washed with water and saturated saline, and the organic layer was dried with magnesium sulfate. This mixture was subjected to gravity filtration, and the filtrate was concentrated to give a solid. The solid was purified by high performance liquid chromatography (HPLC; mobile phase: chloroform) to give 2.8 g of a target white solid. A total of 4.9 g of the target substance (the white solid obtained by the HPLC purification and the pale brown solid collected after the reaction) was obtained in a yield of 74%. The synthesis scheme of Step 1 is shown below.

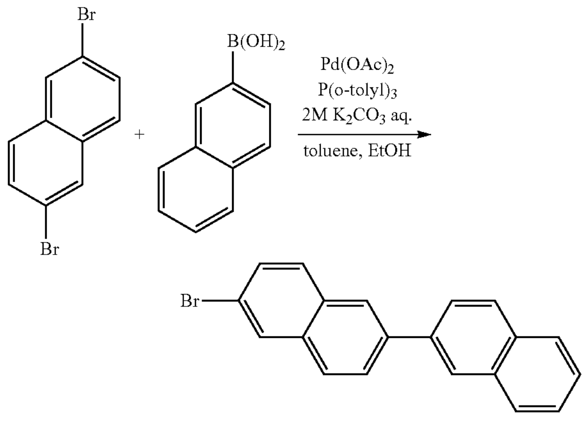

Step 2: Synthesis of 4,4'-diphenyl-4"-(4,4,5,5-tetramethyl-1,3,2-dioxaborolan-2-yl)triphenylamine Into a 200-mL three-neck flask, 2.3 g (5.0 mmol) of 4-bromo-4',4"-diphenyltriphenylamine, 1.3 g (5.0 mmol) of bis(pinacolato)diboron, 0.11 g (0.40 mmol) of 2-di-tert-butylphosphino-2',4',6'-triisopropylbiphenyl (abbreviation: tBuXphos), 0.97 g of potassium acetate, and 25 mL of xylene were put and mixed. This mixture was degassed under reduced pressure, and then, a nitrogen gas was continuously introduced into the system. The mixture was heated to 60° C. Then, 92 mg (0.10 mmol) of [1,1-bis(diphenylphosphino)ferrocene]dichloropalladium(II) (abbreviation: Pd(dppf)$Cl_2$) was added, and stirring was performed at 120° C. for 5 hours. After the stirring, disappearance of the source material was confirmed by thin layer chromatography (TLC), and then, the next reaction was conducted. The synthesis scheme of Step 2 is shown below.

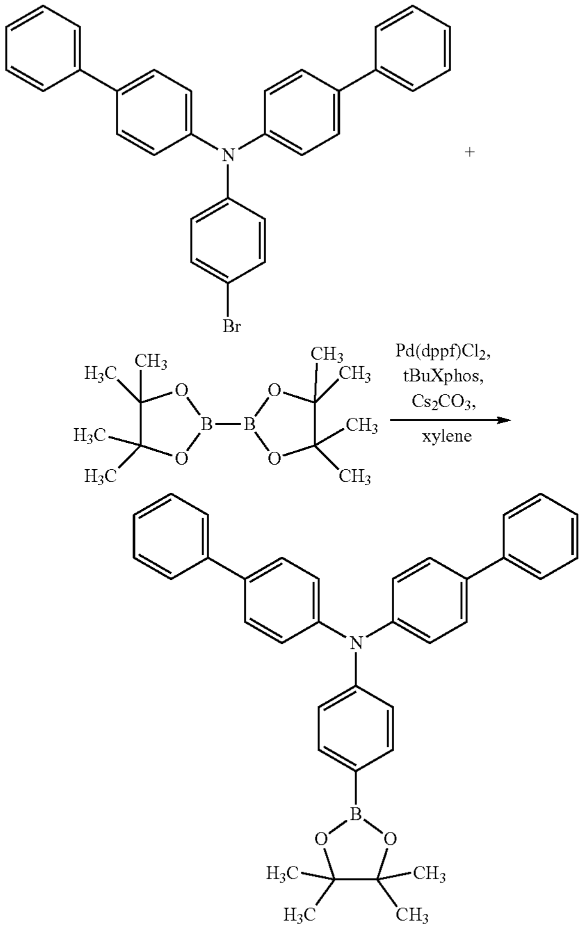

Step 3: Synthesis of 4-(6;2'-binaphthyl-2-yl)-4',4"-diphenyltriphenylamine (Abbreviation: BBA(βN2)B)

To the mixture obtained in Step 2, 1.7 g (5.0 mmol) of 6-bromo-2,2'-binaphthyl, 0.88 g (0.20 mmol) of 2-di-tert-butylphosphino-2',4',6'-triisopropylbiphenyl (abbreviation: tBuXphos), and 3.2 g (10 mmol) of cesium carbonate were added. This mixture was degassed under reduced pressure, and then, a nitrogen gas was continuously introduced into the system. The mixture was heated to 60° C. After that, 87 mg (0.12 mmol) of [1,1-bis(diphenylphosphino)ferrocene]dichloropalladium(II) (abbreviation: Pd(dppf)$Cl_2$) was added, and then, stirring was performed at 120° C. for 8.5 hours. After the stirring, the precipitated solid was collected by suction filtration and washed with toluene, water, and ethanol to give 3.3 g of a target brown solid in a yield of 99% or higher. The synthesis scheme of Step 3 is shown below.

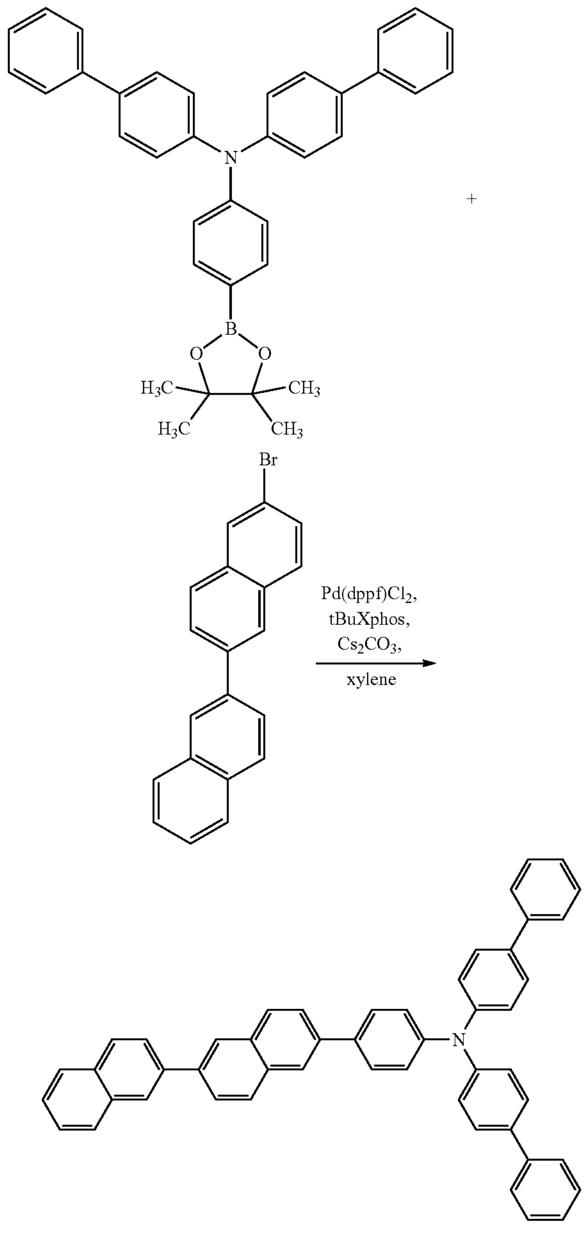

Figure 16A:
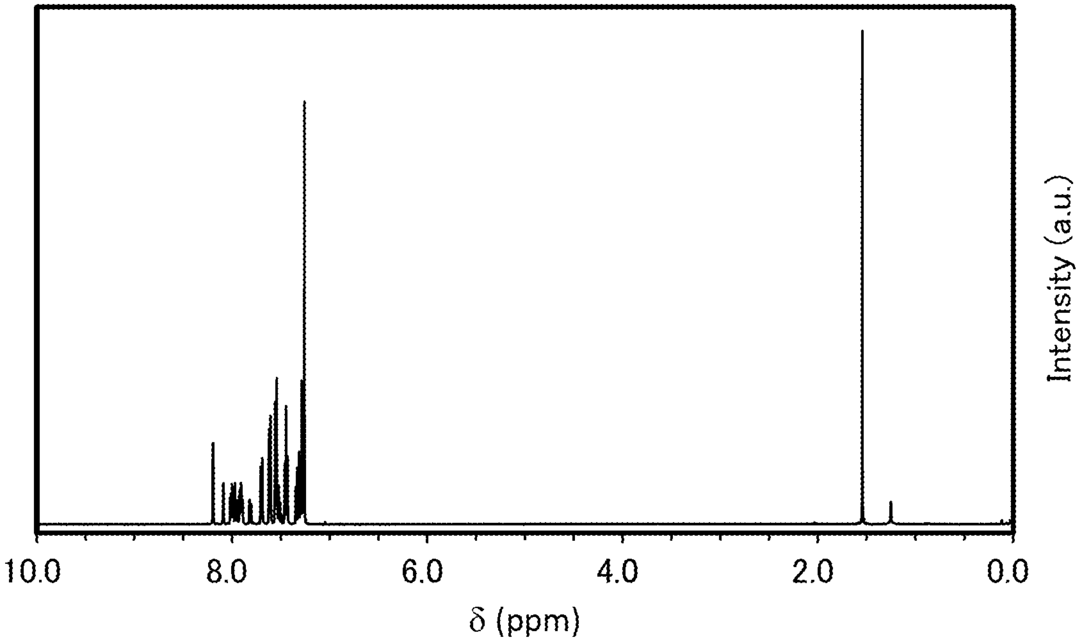
FIGS. 16A and 16B show $^{1}$H NMR spectra of BBA(βN2)B.
Figure 16B:
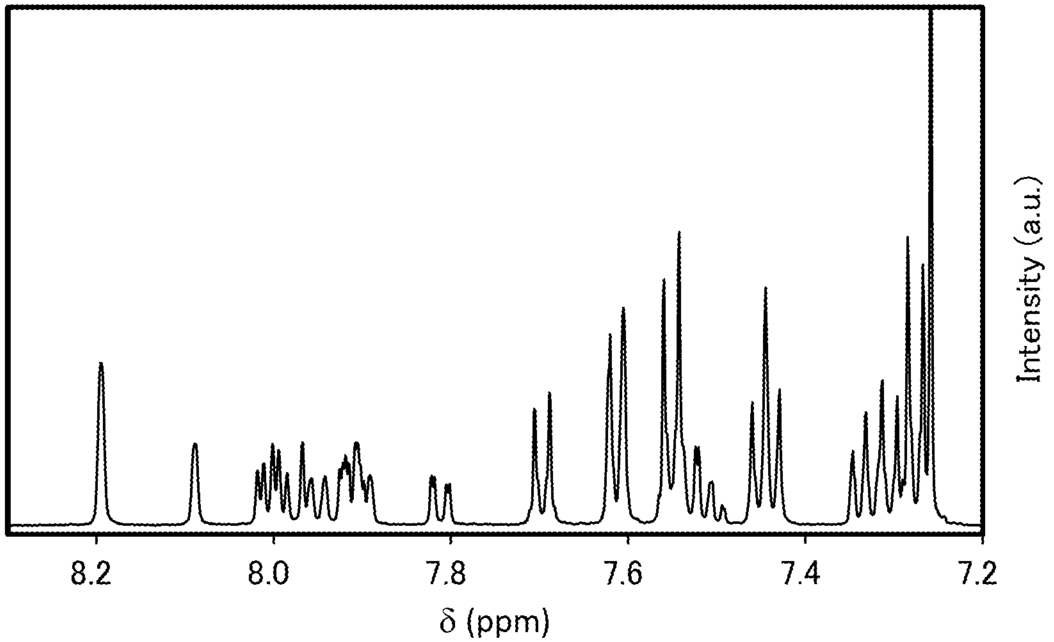

FIGS. 16A and 16B show $^1$H NMR data of the obtained substance, whose numerical data is shown below. These results indicate that BBA(βN2)B, which is the organic compound of one embodiment of the present invention, was obtained in this synthesis example.

$^1$H NMR (chloroform-d, 500 MHz): δ=7.26-7.35 (m, 8H), 7.45 (t, J=7.5 Hz, 4H), 7.49-7.57 (m, 6H), 7.61 (d, J=7.5 Hz, 4H), 7.70 (d, J=8.5 Hz, 2H), 7.81 (dd, $J_1$=8.5 Hz, $J_2$=1.5 Hz, 1H), 7.89-7.93 (m, 3H), 7.95 (d, J=7.5 Hz, 1H), 7.98 (d, J=8.5 Hz, 1H), 8.0 (dd, $J_1$=8.5 Hz, $J_2$=3.5 Hz, 2H), 8.09 (s, 1H), 8.20 (s, 2H).

By a train sublimation method, 3.3 g of the obtained solid was purified. In the sublimation purification, the solid was heated at 320° C. for 15 hours under a pressure of 2.5 Pa with an argon flow rate of 15 mL/min. After the sublimation purification, 2.1 g of a target pale yellow solid was obtained at a collection rate of 64%.

Figure 17:
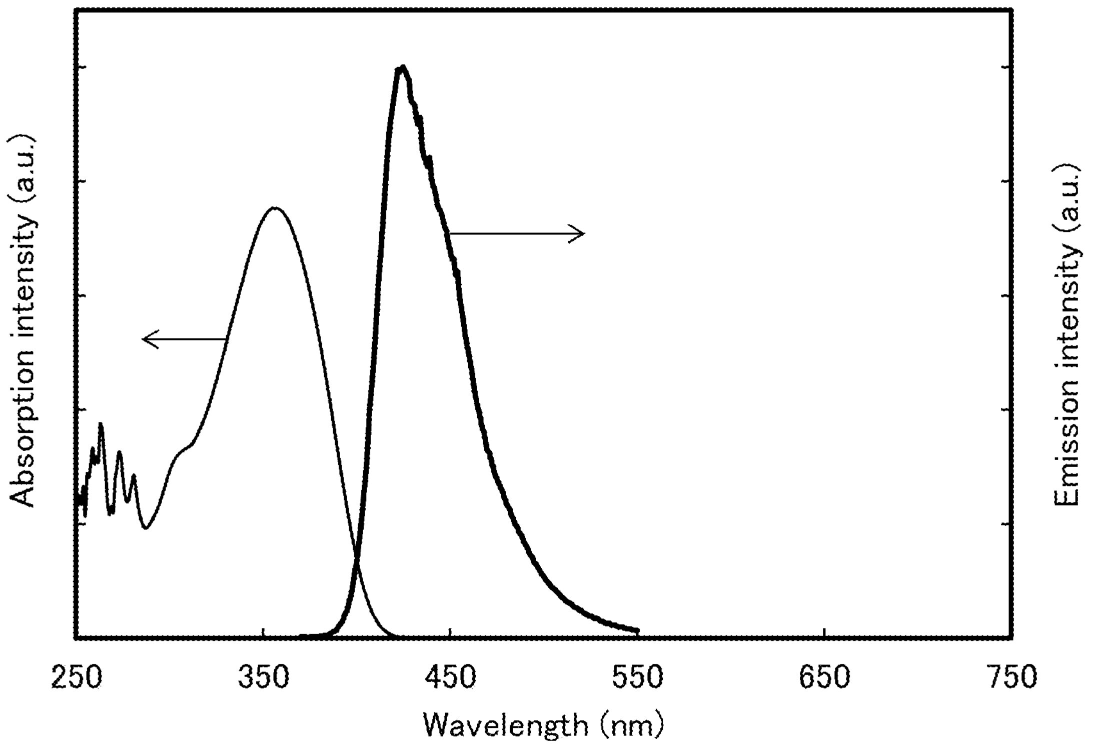
FIG. 17 shows absorption and emission spectra of BBA(βN2)B in a solution.
Figure 18:
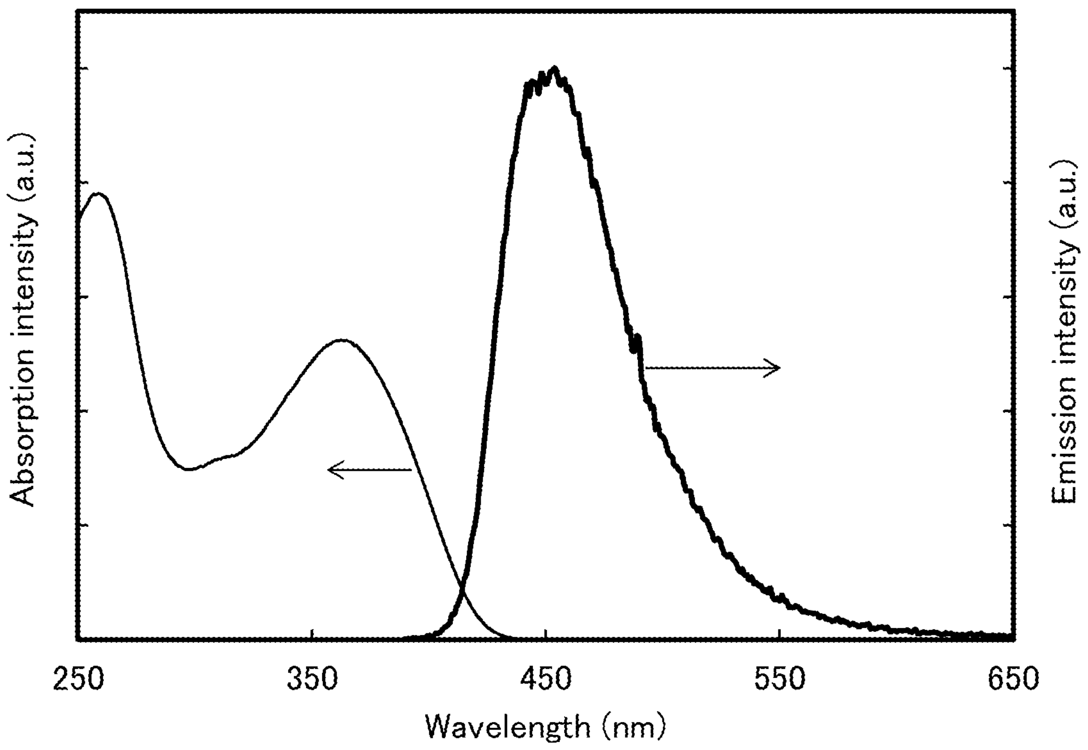
FIG. 18 shows absorption and emission spectra of a thin film of BBA(βN2)B.

Next, FIG. 17 shows the measurement results of the absorption and emission spectra of BBA(βN2)B in a toluene solution. FIG. 18 shows the absorption and emission spectra of a thin film of BBA(βN2)B. The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectra were measured with a fluorescence spectrophotometer (FS920, manufactured by Hamamatsu Photonics K.K.).

FIG. 17 shows that BBA(βN2)B in the toluene solution has absorption peaks at around 358 nm and 305 nm and an emission wavelength peak at 425 nm (excitation wavelength: 360 nm). FIG. 18 shows that the thin film of BBA(βN2)B has absorption peaks at around 365 nm, 309 nm, 258 nm, and 210 nm and an emission wavelength peak at around 452 nm (excitation wavelength: 380 nm). These results indicate that BBA(βN2)B emits blue light and can be used as a host for a light-emitting substance or a substance which emits fluorescence in the visible region.

Furthermore, the thin film of BBA(βN2)B was found to be a high-quality film that is not easily aggregated even in the air and is less likely to change in shape.

Next, the HOMO level and the LUMO level of BBA (βN2)B were calculated by cyclic voltammetry (CV) measurement. The calculation method is shown below.

An electrochemical analyzer (ALS model 600A or 600C, manufactured by BAS Inc.) was used as a measurement apparatus. To prepare a solution for the CV measurement, dehydrated dimethylformamide (DMF; produced by Sigma-Aldrich Inc., 99.8%, catalog No. 22705-6) was used as a solvent, and tetra-n-butylammonium perchlorate (n-$Bu_4NClO_4$; produced by Tokyo Chemical Industry Co., Ltd., catalog No. T0836) as a supporting electrolyte was dissolved at a concentration of 100 mmol/L. Furthermore, the object to be measured was also dissolved at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an $Ag/Ag^+$ electrode (RE7 non-aqueous reference electrode, manufactured by BAS Inc.) was used as a reference electrode. Note that the measurement was performed at room temperature (20° C. to 25° C.). In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

The CV measurement was repeated 100 times, and the oxidation-reduction wave in the hundredth cycle was compared with the oxidation-reduction wave in the first cycle to examine the electrical stability of the compound.

According to the results, BBA(βN2)B has a HOMO level of −5.47 eV and a LUMO level of −2.48 eV Furthermore, the oxidation-reduction wave was repeatedly measured. In the measurement of the oxidation potential Ea [V], 85% of the peak intensity in the first cycle was maintained after the hundredth cycle; accordingly, BBA(βN2)B is highly resistant to oxidation.

Differential scanning calorimetry (DSC) measurement of BBA(βN2)B was performed with Pyris1DSC manufactured by PerkinElmer, Inc. The DSC measurement was performed in the following manner: the temperature was raised from −10° C. to 280° C. at a temperature rising rate of 40° C./min and held for a minute; then, the temperature was decreased to −10° C. at a temperature decreasing rate of 100° C./min and held at −10° C. for three minutes. This operation was performed twice in succession. The result of the DSC measurement in the second cycle proves that BBA(βN2)B has a glass transition point of 110° C., a crystallization temperature of 161° C., and a melting point of 266° C. and is thus a substance with extremely high heat resistance.

The thermogravimetry-differential thermal analysis (TG-DTA) of BBA(βN2)B was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 500° C. or higher, which shows that BBA(βN2)B is a substance with high heat resistance.

Example 2

Synthesis Example 2

In this synthesis example, a synthesis method of N,N-bis (4-biphenylyl)-2,2'-binaphthyl-6-amine (abbreviation: BBA (βN2)), which is the organic compound of one embodiment of the present invention represented by the structural formula (122) in Embodiment 1, will be described. The structural formula of BBA(βN2) is shown below.

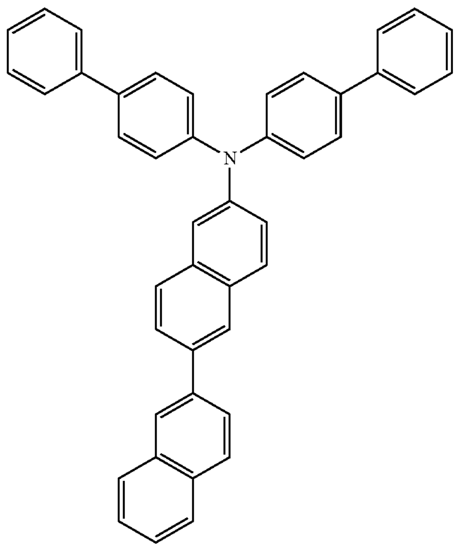 [SMILES: c1ccc(-c2ccc(N(c3ccc(-c4ccccc4)cc3)c3ccc4cc(-c5ccc6ccccc6c5)ccc4c3)cc2)cc1]

Step 1: Synthesis of 6-bromo-2,2'-binaphthyl

In a manner similar to Step 1 of Example 1, 6-bromo-2, 2'-binaphthyl was synthesized.

Step 2: Synthesis of N,N-bis(4-biphenylyl)-2,2'-binaphthyl-6-amine (Abbreviation: BBA(βN2))

Into a 200-mL three-neck flask, 1.7 g (5.1 mmol) of 6-bromo-2,2'-binaphthyl, 1.6 g (5.1 mmol) of bis(4-biphenylyl)amine, 96 mg (0.20 mmol) of 2-dicyclohexylphosphino-2',4',6'-triisopropylbiphenyl (abbreviation: XPhos), and 1.5 g (15 mmol) of t-butoxysodium were put, and the air in the system was replaced with nitrogen. After 26 mL of xylene was added to this mixture, which was then degassed under reduced pressure, a nitrogen gas was continuously introduced into the system. This mixture was heated to 80° C., and then, 62 mg (0.10 mmol) of bis(dibenzylideneacetone)palladium(0) (abbreviation: $Pd(dba)_2$) was added thereto. This mixture was stirred at 120° C. for 5 hours. After the stirring, cooling to room temperature was performed, the resulting mixture was washed with water and saturated saline, and an organic layer and an inorganic layer were separated from each other. Then, the organic layer was dried with magnesium sulfate. The mixture was gravity filtered, and the filtrate was concentrated to give a solid. The obtained solid was purified by high performance liquid chromatography (HPLC; mobile phase: chloroform) to give 2.5 g of a target white solid in a yield of 87%. The synthesis scheme of Step 2 is shown below.

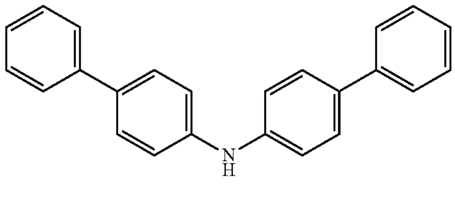

+

-continued

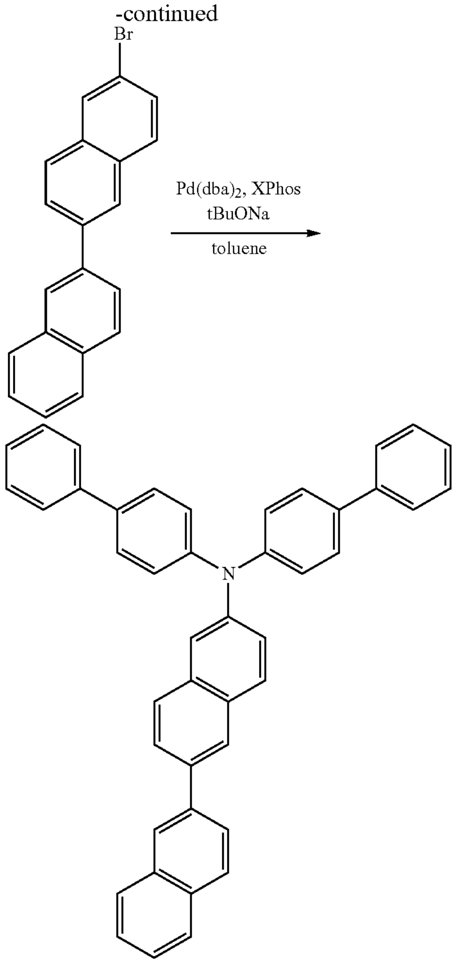

Figure 19A:
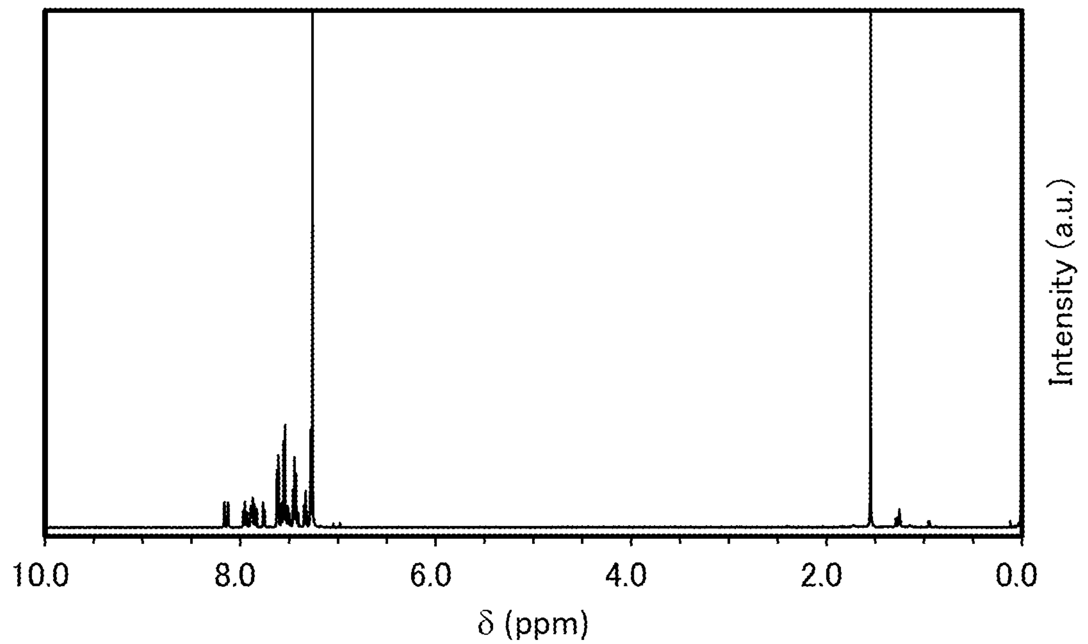
FIGS. 19A and 19B show $^{1}$H NMR spectra of BBA(βN2).
Figure 19B:
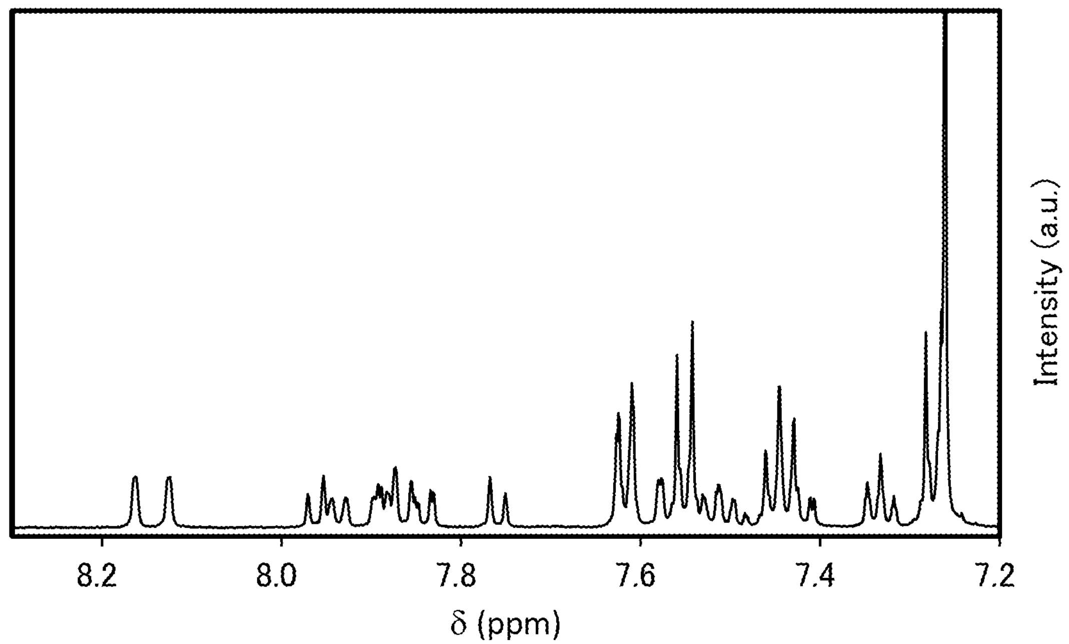

FIGS. 19A and 19B show $^1$H NMR data of the obtained substance, whose numerical data is shown below. These results indicate that BBA(βN2), which is the organic compound of one embodiment of the present invention, was obtained in this synthesis example.

$^1$H NMR (chloroform-d, 500 MHz): δ=7.27 (d, J=8.5 Hz, 4H), 7.33 (t, J=7.5 Hz, 2H), 7.41-7.46 (m, 5H), 7.48-7.58 (m, 7H), 7.62 (d, J=7.5 Hz, 4H), 7.76 (d, J=8.5 Hz, 1H), 7.83-7.89 (m, 4H), 7.94 (d, J=7.5 Hz, 1H), 7.96 (d, J=9.0 Hz, 1H), 8.12 (s, 1H), 8.16 (s, 1H).

By a train sublimation method, 2.5 g of the obtained solid was purified. In the sublimation purification, the solid was heated at 310° C. for 15 hours under a pressure of 3.5 Pa with an argon flow rate of 15 mL/min. After the sublimation purification, 2.0 g of a target pale yellow solid was obtained at a collection rate of 80%.

Figure 20:
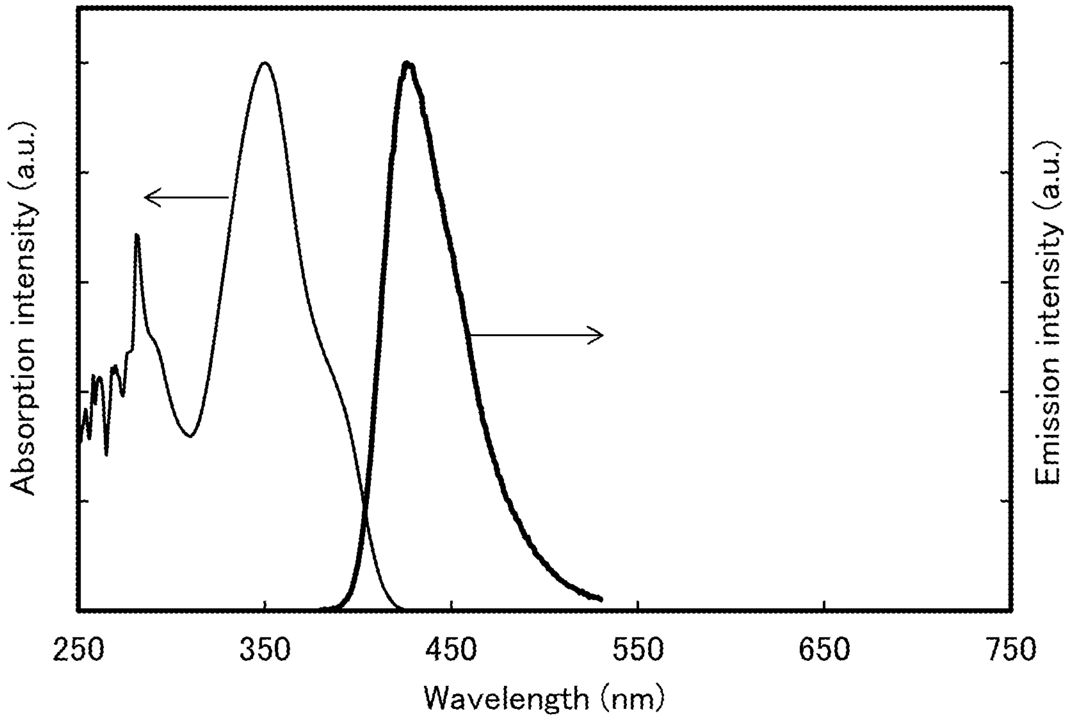
FIG. 20 shows absorption and emission spectra of BBA(βN2) in a solution.
Figure 21:
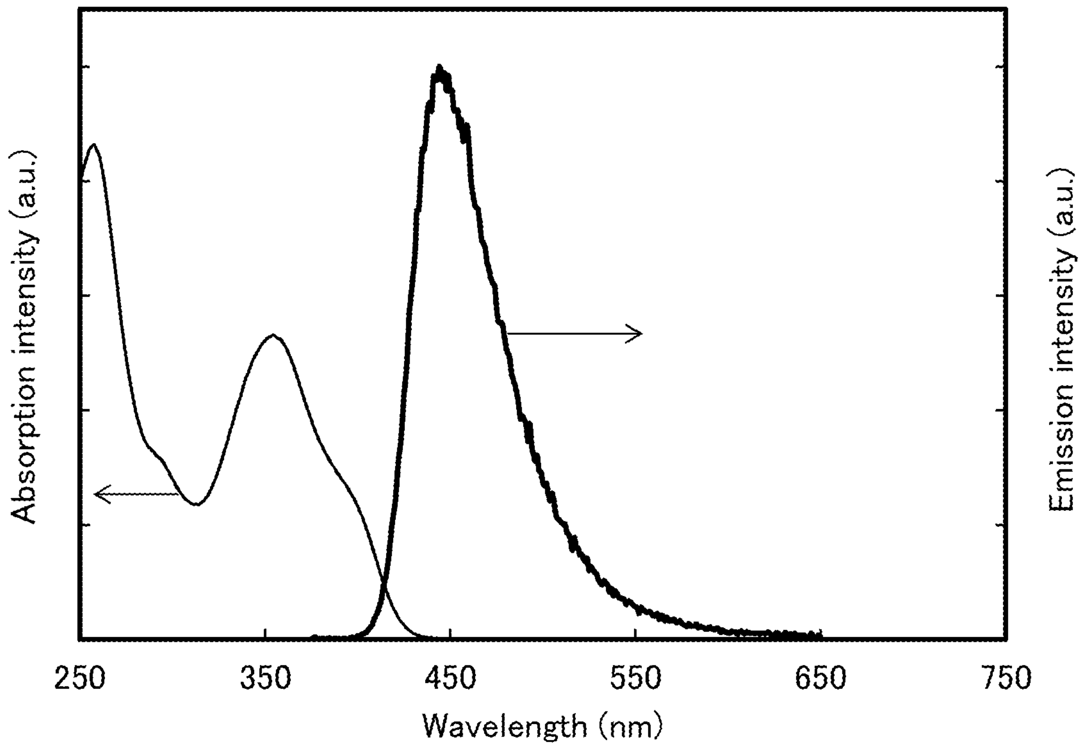
FIG. 21 shows absorption and emission spectra of a thin film of BBA(βN2).

Next, FIG. 20 shows the measurement results of the absorption and emission spectra of BBA(βN2) in a toluene solution. FIG. 21 shows the absorption and emission spectra of a thin film of BBA(βN2). The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectra were measured with a fluorescence spectrophotometer (FS920, manufactured by Hamamatsu Photonics K.K.).

FIG. 20 shows that BBA(βN2) in the toluene solution has absorption peaks at around 350 nm and 290 nm and an emission wavelength peak at 426 nm (excitation wavelength: 360 nm). FIG. 21 shows that the thin film of BBA(βN2) has absorption peaks at around 400 nm, 354 nm, 295 nm, 258 nm, and 208 nm and an emission wavelength peak at around 444 nm (excitation wavelength: 370 nm). These results indicate that BBA(βN2) emits blue light. Furthermore, the compound of one embodiment of the present invention can be used as a host for a light-emitting substance or a substance which emits fluorescence in the visible region.

Furthermore, the thin film of BBA(βN2) was found to be a high-quality film that is not easily aggregated even in the air and is less likely to change in shape.

The HOMO level and the LUMO level of BBA(βN2) were calculated by cyclic voltammetry (CV) measurement. The calculation method is the same as the method described in Example 1 and therefore will not be described here.

According to the results, BBA(βN2) has a HOMO level of −5.45 eV and a LUMO level of −2.40 eV Furthermore, the oxidation-reduction wave was repeatedly measured, and the waveform in the first cycle was compared with that in the hundredth cycle; 87% of the peak intensity of the oxidation potential Ea and 86% of the peak intensity of the reduction potential Ec were maintained. Accordingly, BBA(βN2) is highly resistant to oxidation and reduction.

Differential scanning calorimetry (DSC) measurement of BBA(βN2) was performed with Pyris1DSC manufactured by PerkinElmer, Inc. The DSC measurement was performed in the following manner: the temperature was raised from −10° C. to 250° C. at a temperature rising rate of 40° C./min and held for a minute; then, the temperature was decreased to −10° C. at a temperature decreasing rate of 50° C./min and held at −10° C. for three minutes. This operation was performed twice in succession. The result of the DSC measurement in the second cycle proves that BBA(βN2) has a glass transition point of 95° C. and a melting point of 210° C.

The thermogravimetry-differential thermal analysis of BBA(βN2) was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 453° C. or higher, which shows that BBA(βN2) is a substance with high heat resistance.

Example 3

Synthesis Example 3

In this synthesis example, a synthesis method of 4-(3;2'-binaphthyl-2-yl)-4',4"-diphenyltriphenylamine (abbreviation: BBA(βN2)B-02), which is the organic compound of one embodiment of the present invention represented by the structural formula (116) in Embodiment 1, will be described. The structural formula of BBA(βN2)B-02 is shown below.

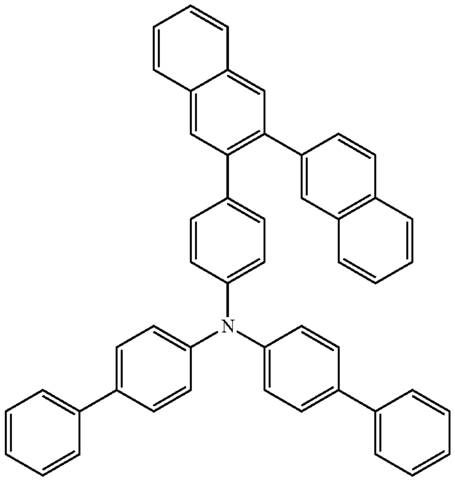 [SMILES: c1ccc(-c2ccc(N(c3ccc(-c4ccccc4)cc3)c3ccc(-c4cc5ccccc5cc4-c4ccc5ccccc5c4)cc3)cc2)cc1]

Step 1: Synthesis of 3-bromo-2,2'-binaphthyl

Into a 200-mL three-neck flask with a reflux pipe, 3.0 g (11 mmol) of 2,3-dibromonaphthalene, 1.8 g (11 mmol) of 2-naphthylboronic acid, 96 mg (0.031 mmol) of tri(ortho-tolyl)phosphine, 50 mL of toluene, 15 mL of ethanol, and an aqueous solution of potassium carbonate (potassium carbonate: 2.9 g/water: 11 mL) were put, the resulting mixture was degassed under reduced pressure, and then, the air in the system was replaced with nitrogen. After that, 24 mg (0.011 mmol) of palladium(II) acetate was added to the mixture, and stirring was performed at room temperature for 4 hours. Water was added to the obtained mixture to extract an aqueous layer with toluene. The extracted solution was combined with an organic layer, and the resulting mixture was washed with water and saturated saline and dried with magnesium sulfate. This mixture was gravity-filtered, and the obtained filtrate was concentrated to give a solid. The obtained solid was purified by high performance liquid chromatography (HPLC; mobile phase: chloroform) to give a white solid of the target compound, 3-bromo-2,2'-binaphthyl (yield: 1.8 g, 52%). The synthesis scheme of Step 1 is shown below.

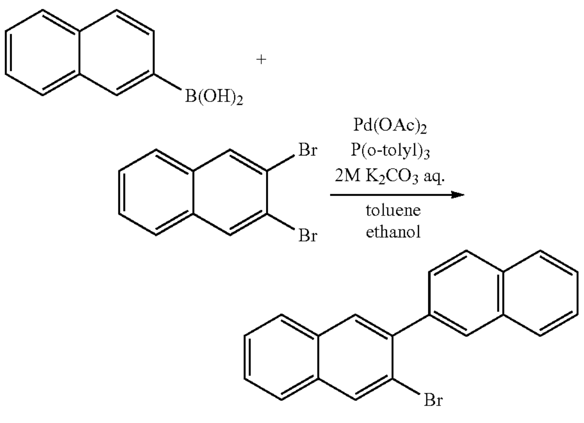

Figure 73A:
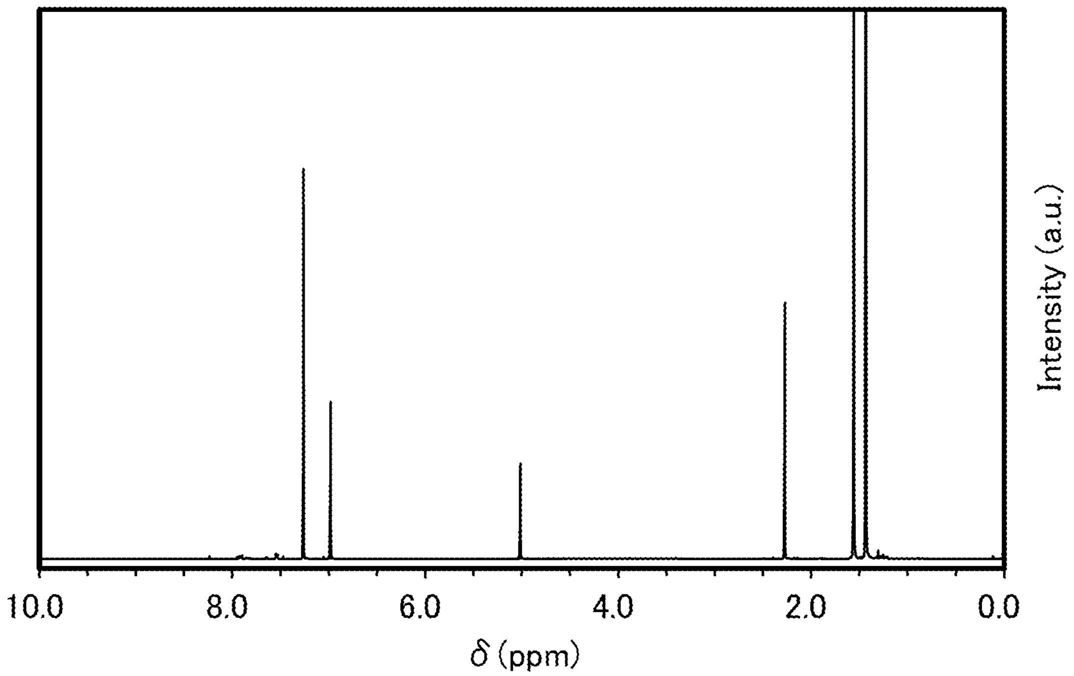
FIGS. 73A and 73B show $^1$H NMR spectra of 3-bromo-2,2'-binaphthyl.
Figure 73B:
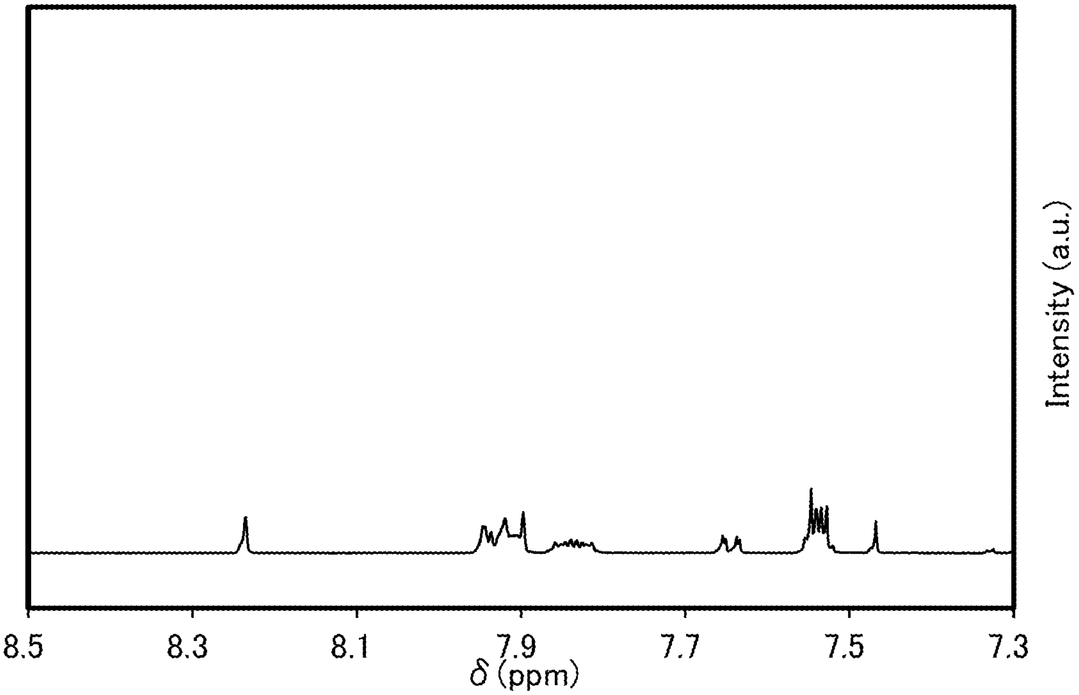

FIGS. 73A and 73B show $^1$H NMR charts of the obtained solid, whose numerical data is shown below. These results indicate that 3-bromo-2,2'-binaphthyl was obtained.

$^1$H NMR (chloroform-d, 500 MHz): δ=8.22 (s, 1H), 7.93-7.88 (m, 5H), 7.85-7.80 (m, 2H), 7.63 (dd, J=9.0, 2.0 Hz, 1H), 7.54-7.46 (m, 4H).

Step 2: Synthesis of 4,4'-diphenyl-4"-(4,4,5,5-tetramethyl-1,3,2-dioxaborolan-2-yl)triphenylamine In a manner similar to Step 2 of Example 1, 4,4'-diphenyl-4"-(4,4,5,5-tetramethyl-1,3,2-dioxaborolan-2-yl)triphenylamine was synthesized.

Step 3: Synthesis of 4-(3;2'-binaphthyl-2-yl)-4',4"-diphenyltriphenylamine (Abbreviation: BBA(βN2)B-02)

Into a 1-L three-neck flask with a reflux pipe, 3.0 g (5.5 mmol) of 4,4'-diphenyl-4"-(4,4,5,5-tetramethyl-1,3,2-dioxaborolan-2-yl)triphenylamine, 1.8 g (5.5 mmol) of 3-bromo-2,2'-binaphthyl, 50 mg (0.17 mmol) of tri(ortho-tolyl)phosphine, 1.5 g/6 mL (11 mmol) of an aqueous solution of potassium carbonate, 50 mL of toluene, and 15 mL of ethanol were put, the mixture was degassed under reduced pressure, and then, the air in the system was replaced with nitrogen. The mixture was heated at 80° C., and 12 mg (0.055 mmol) of palladium(II) acetate was added to this mixture. This mixture was stirred at 100° C. for 10 hours. Water was added to the obtained mixture, and an aqueous layer was extracted with toluene. The extracted solution was combined with an organic layer, and the resulting mixture was washed with water and saturated saline and dried with magnesium sulfate. This mixture was gravity-filtered, and the obtained filtrate was concentrated to give a solid. This solid was purified by HPLC (mobile phase: chloroform) to give 1.1 g of a target pale yellow solid in a yield of 31%. By a train sublimation method, 1.1 g of the obtained solid was purified. In the sublimation purification, the solid was heated at 310° C. for 16 hours under a pressure of 4.2 Pa with an argon flow rate of 15 mL/min. After the sublimation purification, 660 mg of a pale yellow solid was obtained at a collection rate of 60%. The synthesis scheme of Step 3 is shown below.

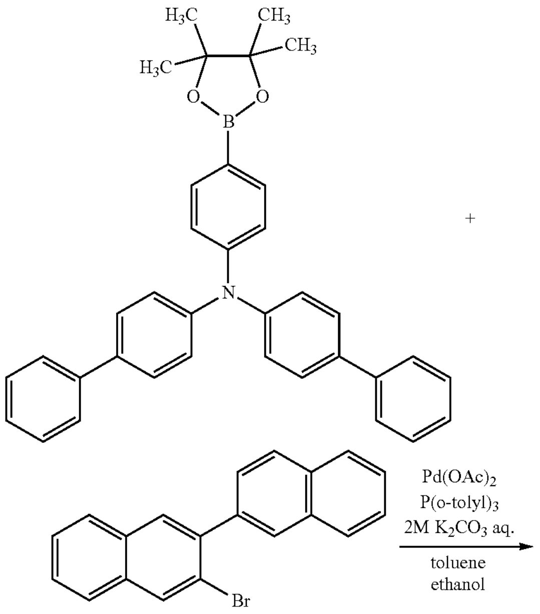

-continued

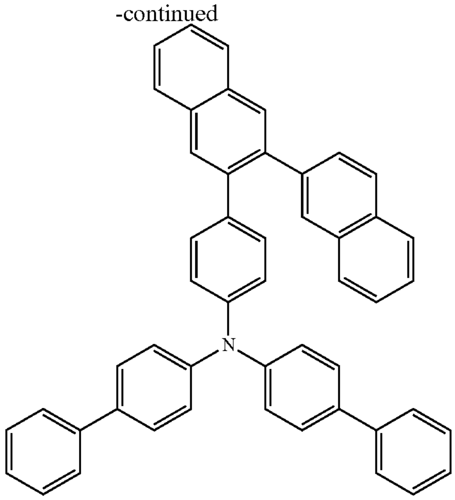

Figure 22A:
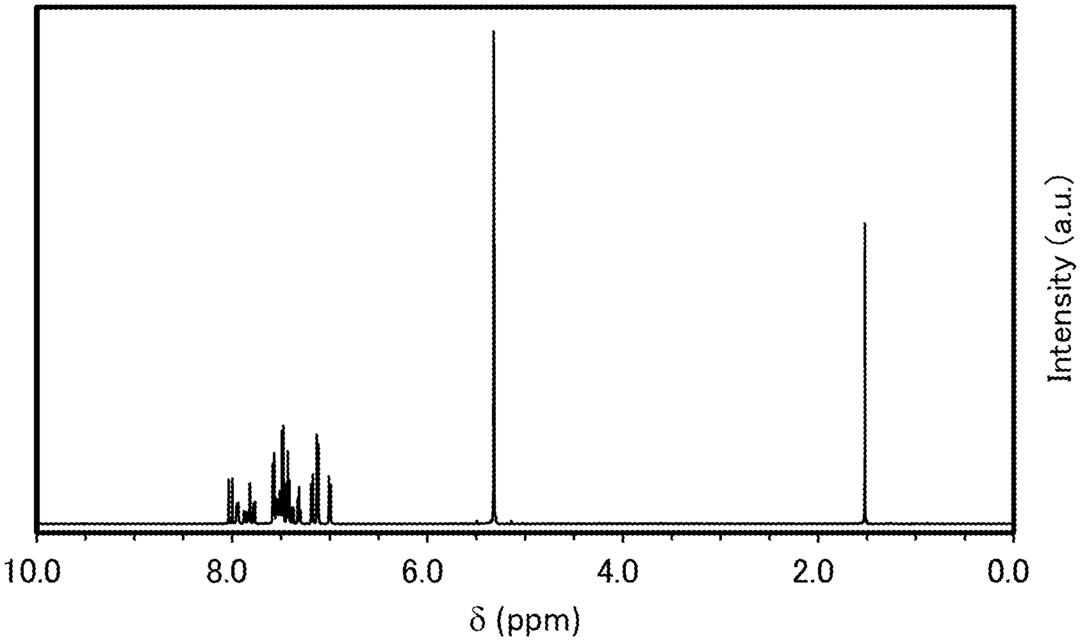
FIGS. 22A and 22B show $^{1}$H NMR spectra of BBA(βN2)B-02.
Figure 22B:
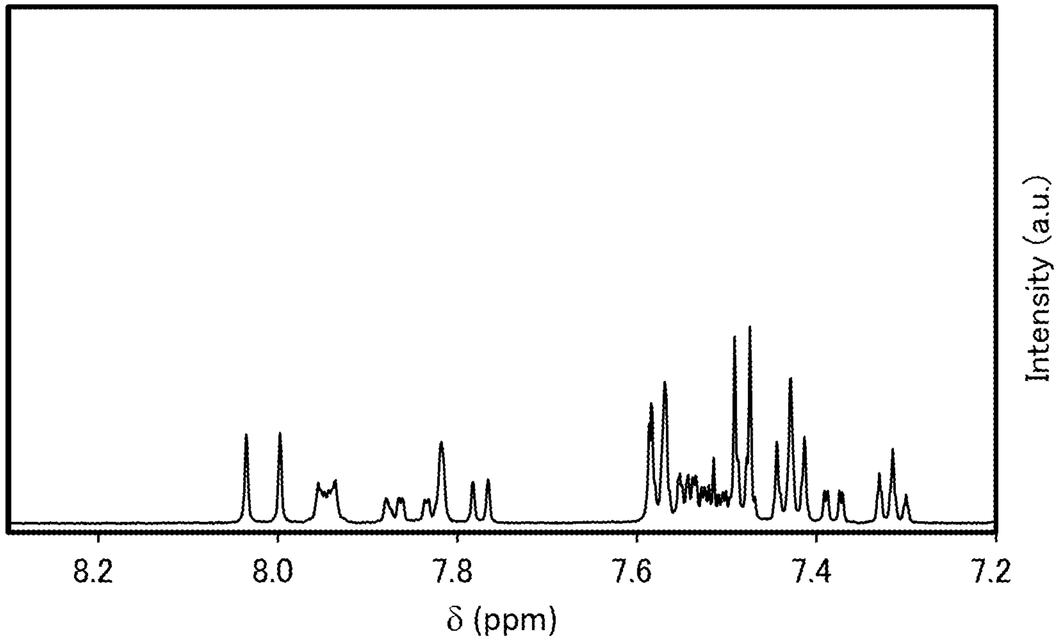

FIGS. 22A and 22B show $^1$H NMR data of the obtained substance, whose numerical data is shown below. These results indicate that BBA(βN2)B-02 was obtained in this synthesis example.

$^1$H NMR (dichloromethane-d2, 500 MHz): δ=8.03 (s, 1H), 7.99 (s, 1H), 7.94 (dd, J=5.5, 4.0 Hz, 2H), 7.87-7.82 (m, 3H), 7.77 (d, J=8.0 Hz, 1H), 7.57 (d, 4H), 7.55-7.47 (m, 8H), 7.43 (t, J=7.5 Hz, 4H), 7.38 (dd, J=8.5, 1.5 Hz, 1H), 7.31 (t, J=7.5 Hz, 2H), 7.18 (d, J=8.5 Hz, 2H), 7.12 (d, J=8.5 Hz, 4H), 7.00 (d, J=8.5 Hz, 2H).

Figure 23:
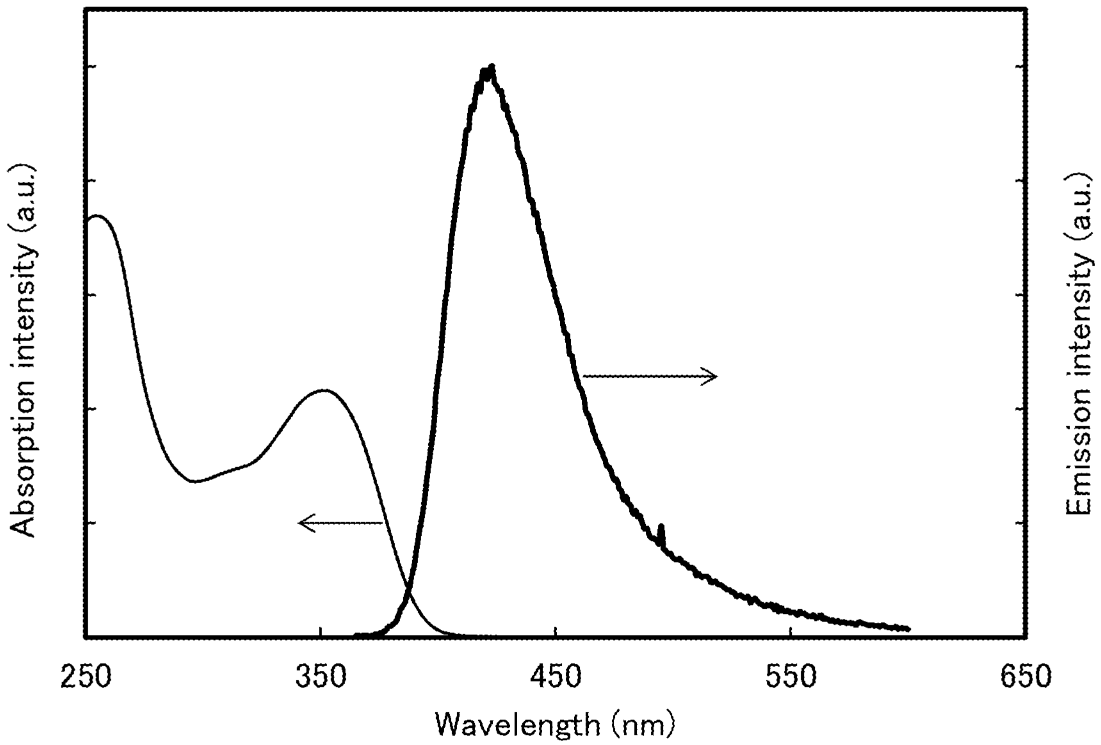
FIG. 23 shows absorption and emission spectra of a thin film of BBA(βN2)B-02.

Next, FIG. 23 shows the measurement results of the absorption and emission spectra of a thin film of BBA(βN2)B-02. The solid thin film was formed over a quartz substrate by a vacuum evaporation method. The absorption spectrum of the thin film was measured with a spectrophotometer (U-4100 Spectrophotometer, manufactured by Hitachi High-Technologies Corporation). The emission spectra were measured with a fluorescence spectrophotometer (FS920, manufactured by Hamamatsu Photonics K.K.).

FIG. 23 shows that the thin film of BBA(βN2)B-02 has absorption peaks at around 351 nm, 310 nm, 255 nm, and 210 nm and an emission wavelength peak at around 422 nm (excitation wavelength: 360 nm). These results indicate that BBA(βN2)B-02 emits blue light and the compound of one embodiment of the present invention can be used as a host for a light-emitting substance or a substance which emits fluorescence in the visible region.

Furthermore, the thin film of BBA(βN2)B-02 was found to be a high-quality film that is not easily aggregated even in the air and is less likely to change in shape.

The HOMO level and the LUMO level of BBA(βN2)B-02 were calculated by cyclic voltammetry (CV) measurement. The calculation method is the same as the method described in Example 1 and therefore will not be described here.

According to the results, BBA(βN2)B-02 has a HOMO level of −5.48 eV and a LUMO level of −2.30 eV Furthermore, the oxidation-reduction wave was repeatedly measured, and the waveform in the first cycle was compared with that in the hundredth cycle; 92% of the peak intensity of the oxidation potential Ea was maintained. Accordingly, BBA(βN2)B-02 is highly resistant to oxidation.

Differential scanning calorimetry (DSC) measurement of BBA(βN2)B-02 was performed with Pyris1DSC manufactured by PerkinElmer, Inc. The DSC measurement was performed in the following manner: the temperature was raised from −10° C. to 335° C. at a temperature rising rate of 40° C./min and held for a minute; then, the temperature was decreased to −10° C. at a temperature decreasing rate of 100° C./min and held at −10° C. for three minutes. This operation was performed twice in succession, and the second measurement result was employed. The DSC measurement proves that BBA(βN2)B-02 has a glass transition point of 116° C. and is thus a compound with favorable heat resistance.

The thermogravimetry-differential thermal analysis of BBA(βN2)B-02 was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be around 430° C., which shows that BBA(βN2)B-02 is a substance with high heat resistance.

Example 4

Synthesis Example 4

In this synthesis example, a synthesis method of 4-(2;2'-binaphthyl-7-yl)-4',4"-diphenyltriphenylamine (abbreviation: BBA(βN2)B-03), which is the organic compound of one embodiment of the present invention represented by the structural formula (110) in Embodiment 1, will be described. The structural formula of BBA(βN2)B-03 is shown below.

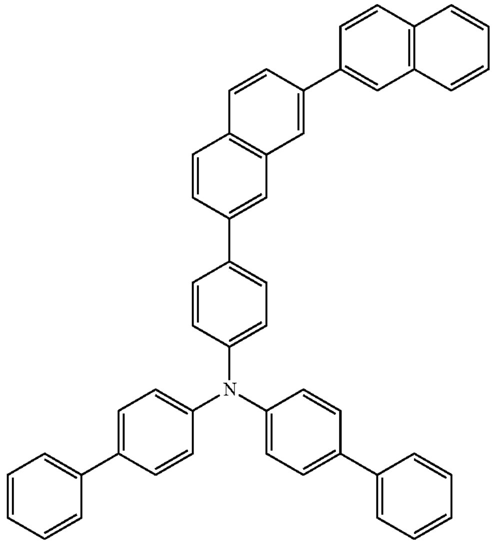 [SMILES: c1ccc(-c2ccc(N(c3ccc(-c4ccccc4)cc3)c3ccc(-c4ccc5ccc(-c6ccc7ccccc7c6)cc5c4)cc3)cc2)cc1]

Step 1: Synthesis of 4,4'-diphenyl-4"-(4,4,5,5-tetramethyl-1,3,2-dioxaborolan-2-yl)triphenylamine In a manner similar to Step 2 of Synthesis Example 1, 4,4'-diphenyl-4"-(4,4,5,5-tetramethyl-1,3,2-dioxaborolan-2-yl)triphenylamine was synthesized.

Step 2: Synthesis of 4-(2;2'-binaphthyl-7-yl)-4',4"-diphenyltriphenylamine (Abbreviation: BBA(βN2)B-03)

Into a 200-mL three-neck flask with a reflux pipe, 3.7 g (6.8 mmol) of 4,4'-diphenyl-4"-(4,4,5,5-tetramethyl-1,3,2-dioxaborolan-2-yl)triphenylamine, 2.3 g (6.8 mmol) of 7-bromo-2,2'-binaphthyl, 42 mg (0.13 mmol) of tri(ortho-tolyl)phosphine, 1.9 g/15 mL (14 mmol) of an aqueous solution of potassium carbonate, 70 mL of toluene, and 25 mL of ethanol were put, the mixture was degassed under reduced pressure, and then, the air in the system was replaced with nitrogen. The mixture was heated at 70° C., and 15 mg (0.068 mmol) of palladium(II) acetate was added to this mixture. This mixture was stirred at 100° C. for 7 hours. Water was added to the obtained mixture, and an aqueous layer was extracted with toluene. The extracted solution was combined with an organic layer, and the resulting mixture was washed with water and saturated saline and dried with magnesium sulfate. This mixture was gravity-filtered, and the obtained filtrate was concentrated to give a white solid. This solid was purified by HPLC (mobile phase: chloroform) to give 3.5 g of a target pale yellow solid in a yield of 79%. By a train sublimation method, 3.5 g of the obtained solid was purified. In the sublimation purification, the solid was heated at 320° C. for 16 hours under a pressure of 4.1 Pa with an argon flow rate of 15 mL/min. After the sublimation purification, 3.0 g of a pale yellow solid was obtained at a collection rate of 85%. The synthesis scheme of Step 2 is shown below.

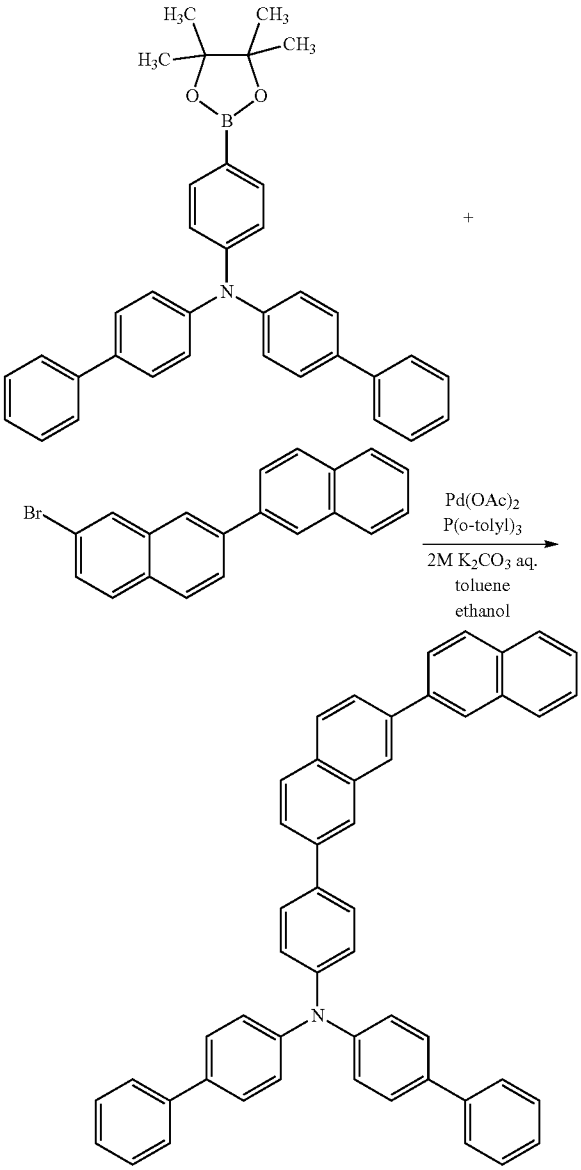

Figure 24A:
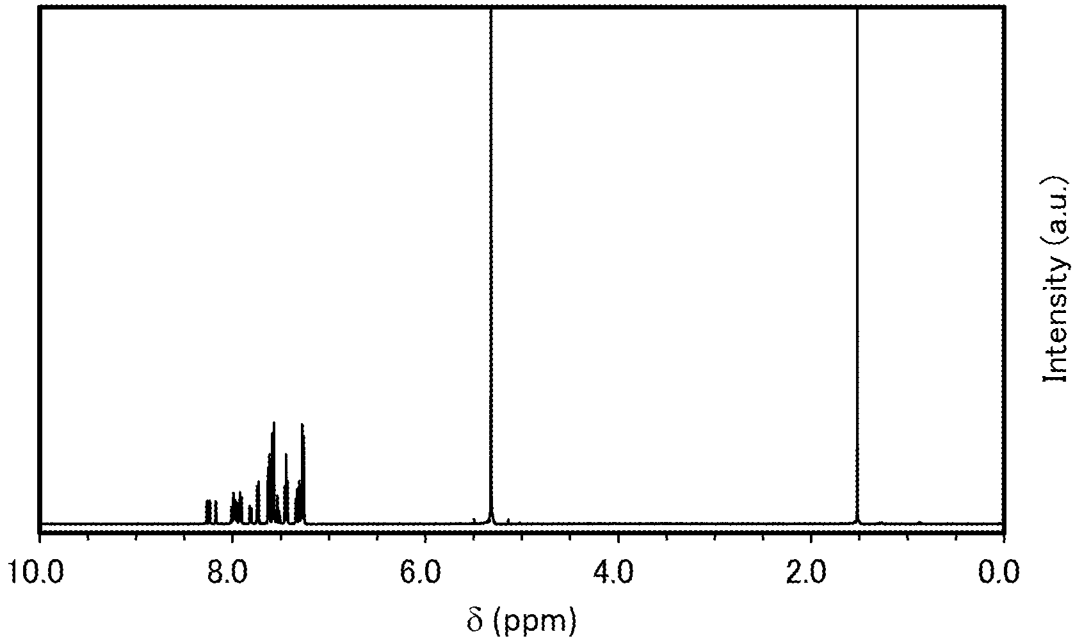
FIGS. 24A and 24B show $^{1}$H NMR spectra of BBA(βN2)B-03.
Figure 24B:
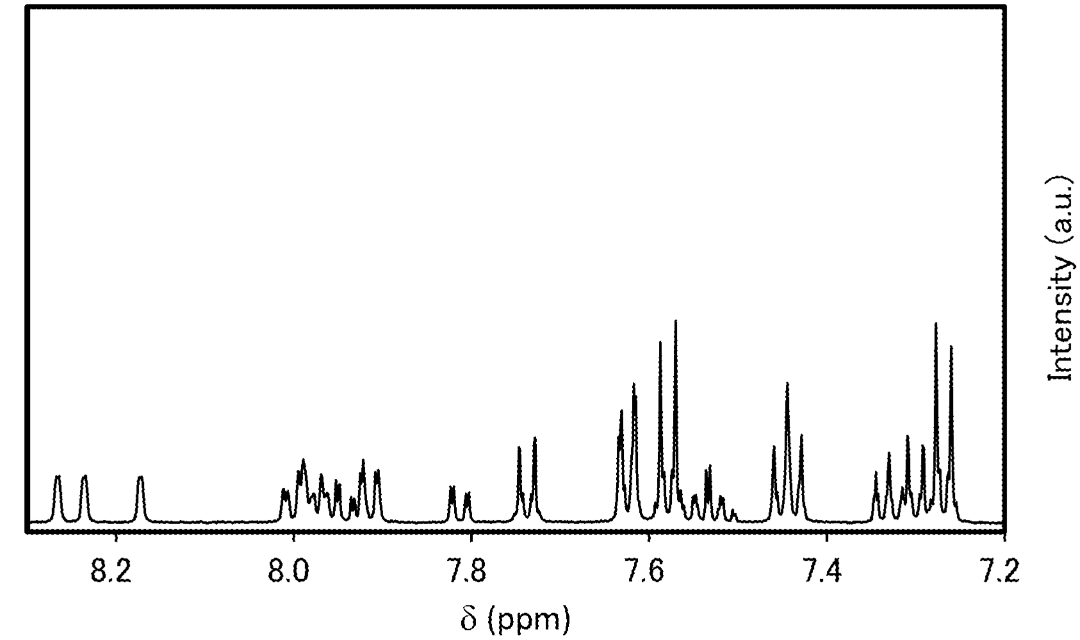

FIGS. 24A and 24B show $^1$H NMR data of the obtained substance, whose numerical data is shown below. These results indicate that BBA(βN2)B-03 was obtained in this synthesis example.

$^1$H NMR (dichloromethane-d2, 500 MHz): δ=8.26 (s, 1H), 8.24 (s, 1H), 8.17 (s, 1H), 8.01-7.90 (m, 7H), 7.81 (dd, J=8.5, 1.5 Hz, 1H), 7.73 (d, J=9.5 Hz, 2H), 7.62 (d, J=8.5 Hz, 4H), 7.59-7.50 (m, 6H), 7.44 (t, J=7.5 Hz, 4H), 7.34-7.26 (m, 8H).

Next, measurement results of the absorption and emission spectra of BBA(βN2)B-03 in a toluene solution and measurement results of the absorption and emission spectra of its thin film will be shown. The method for forming a sample, the measurement method, and the measurement apparatus are similar to those described in the above example and therefore will not be described here.

The measurement results show that BBA(βN2)B-03 in the toluene solution has an absorption peak at around 351 nm and an emission wavelength peak at 411 nm (excitation wavelength: 351 nm). The thin film of BBA(βN2)B-03 has absorption peaks at around 356 nm, 266 nm, and 210 nm and an emission wavelength peak at around 435 nm (excitation wavelength: 360 nm). These results indicate that BBA(βN2)B-03 emits blue light. Furthermore, the compound of one embodiment of the present invention can be used as a host for a light-emitting substance or a substance which emits fluorescence in the visible region.

Furthermore, the thin film of BBA(βN2)B-03 was found to be a high-quality film that is not easily aggregated even in the air and is less likely to change in shape.

The HOMO level and the LUMO level of BBA(βN2)B-03 were calculated by cyclic voltammetry (CV) measurement. The calculation method is the same as the method described in Example 1 and therefore will not be described here.

According to the results, BBA(βN2)B-03 has a HOMO level of −5.47 eV and a LUMO level of −2.41 eV Furthermore, the oxidation-reduction wave was repeatedly measured, and the waveform in the first cycle was compared with that in the hundredth cycle; 89% of the peak intensity of the oxidation potential Ea was maintained. Accordingly, BBA(βN2)B-03 is highly resistant to oxidation.

The thermogravimetry-differential thermal analysis of BBA(βN2)B-03 was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be around 474° C., which shows that BBA(βN2)B-03 is a substance with high heat resistance.

Differential scanning calorimetry (DSC) measurement of BBA(βN2)B-03 was performed with Pyris1DSC manufactured by PerkinElmer, Inc. The DSC measurement was performed in the following manner: the temperature was raised from −10° C. to 355° C. at a temperature rising rate of 40° C./min and held for a minute; then, the temperature was decreased to −10° C. at a temperature decreasing rate of 100° C./min and held at −10° C. for three minutes. This operation was performed three times in succession, and the second measurement result was employed. The DSC measurement proves that BBA(βN2)B-03 has a glass transition point of 116° C. and is thus a compound with favorable heat resistance.

Example 5

Synthesis Example 5

In this synthesis example, a synthesis method of 4-(2;1'-binaphthyl-6-yl)-4',4"-diphenyltriphenylamine (abbreviation: BBAαNβNB), which is the organic compound of one embodiment of the present invention represented by the structural formula (114) in Embodiment 1, will be described. The structural formula of BBAαNβNB is shown below.

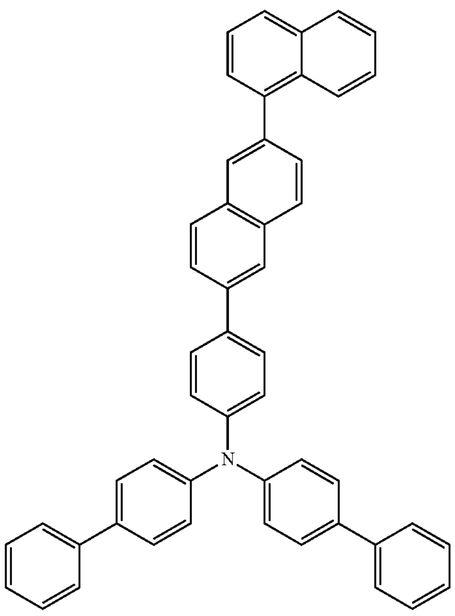 [SMILES: c1ccc(-c2ccc(N(c3ccc(-c4ccccc4)cc3)c3ccc(-c4ccc5cc(-c6cccc7ccccc67)ccc5c4)cc3)cc2)cc1]

Step 1: Synthesis of 4,4'-diphenyl-4"-(4,4,5,5-tetramethyl-1,3,2-dioxaborolan-2-yl)triphenylamine In a manner similar to Step 2 of Synthesis Example 1, 4,4'-diphenyl-4"-(4,4,5,5-tetramethyl-1,3,2-dioxaborolan-2-yl)triphenylamine was synthesized.

Step 2: Synthesis of 4-(2;1'-binaphthyl-6-yl)-4',4"-diphenyltriphenylamine (Abbreviation: BBAαNβNB)

Into a 200-mL three-neck flask with a reflux pipe, 3.5 g (6.7 mmol) of 4,4'-diphenyl-4"-(4,4,5,5-tetramethyl-1,3,2-dioxaborolan-2-yl)triphenylamine, 2.2 g (6.7 mmol) of 6-bromo-2,1'-binaphthyl, 40 mg (0.13 mmol) of tri(ortho-tolyl)phosphine, 1.85 g/6.5 mL (13 mmol) of an aqueous solution of potassium carbonate, 50 mL of toluene, and 15 mL of ethanol were put, the mixture was degassed under reduced pressure, and then, the air in the system was replaced with nitrogen. The mixture was heated at 70° C., and 15.0 mg (0.067 mmol) of palladium(II) acetate was added thereto. This mixture was stirred at 100° C. for 3 hours. Water was added to the obtained mixture, and an aqueous layer was extracted with toluene. The extracted solution was combined with an organic layer, and the resulting mixture was washed with water and saturated saline and dried with magnesium sulfate. The reacted solution was concentrated to give 3.5 g of a target yellow solid in a yield of 82%. By a train sublimation method, 3.55 g of the obtained solid was purified. In the sublimation purification, the solid was heated at 310° C. for 15 hours under a pressure of 4.1 Pa with an argon flow rate of 15 mL/min. After the sublimation purification, 2.5 g of a target pale yellow solid was obtained at a collection rate of 72%. The synthesis scheme of Step 2 is shown below.

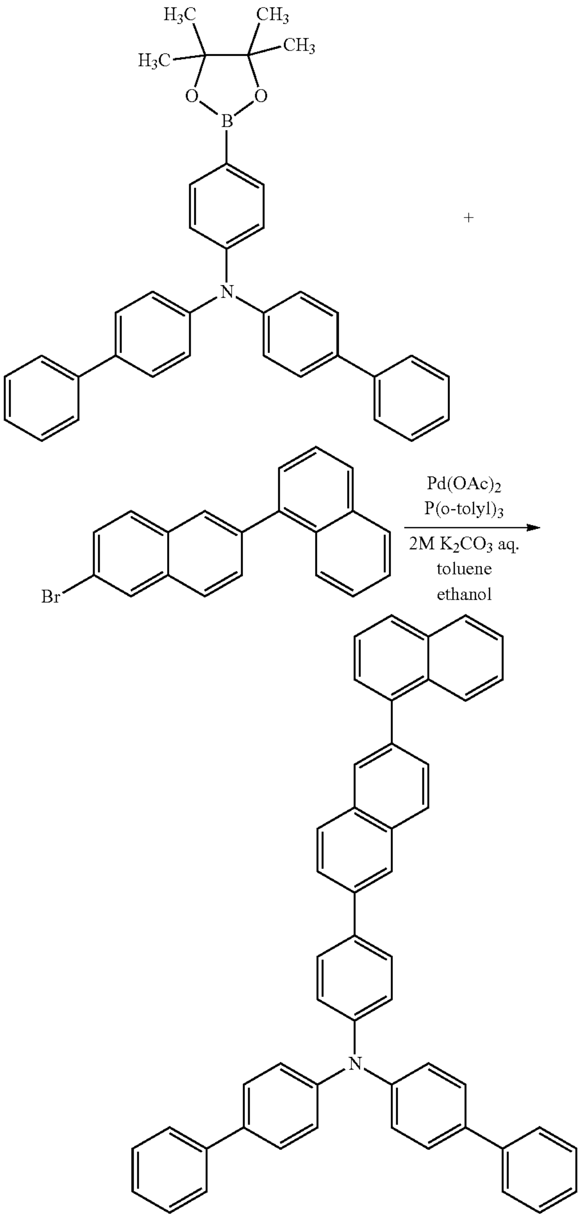

Figure 25A:
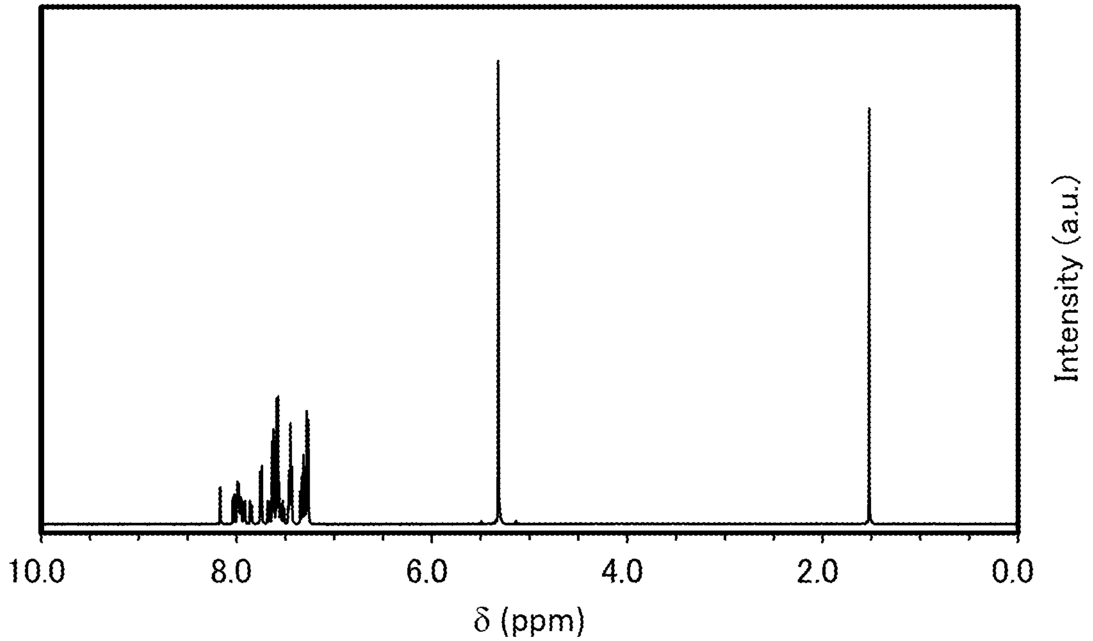
FIGS. 25A and 25B show $^{1}$H NMR spectra of BBAαNβNB.
Figure 25B:
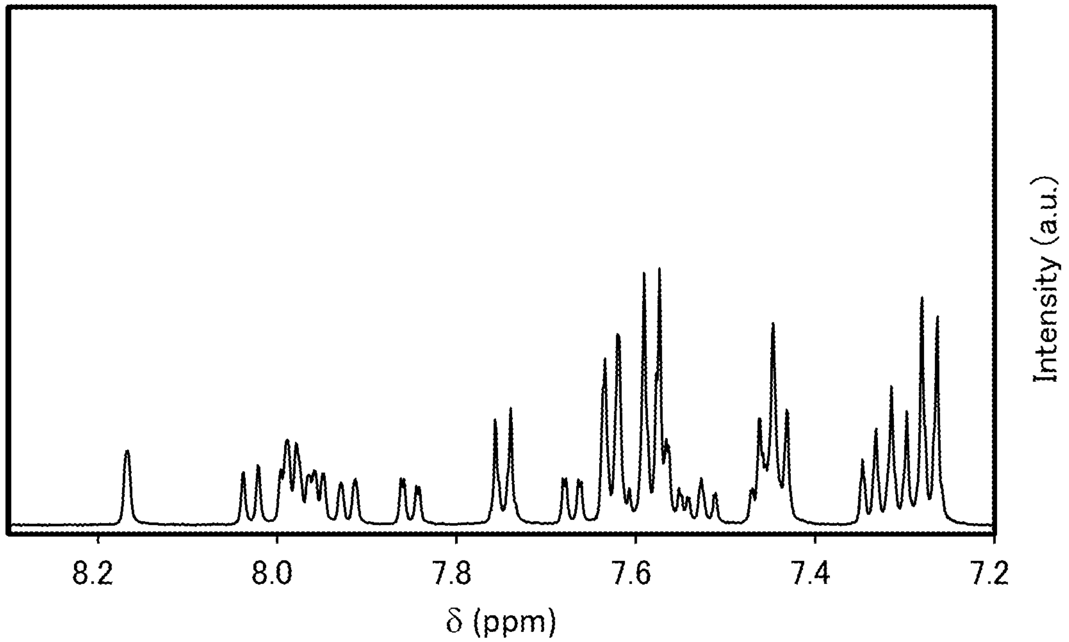

FIGS. 25A and 25B show $^{1}H$ NMR data of the obtained substance, whose numerical data is shown below. These results indicate that BBAαNβNB was obtained in this synthesis example.

$^{1}H$ NMR (dichloromethane-d2, 500 MHz): δ=8.16 (s, 1H), 8.29 (d, J=8.5 Hz, 1H), 7.99-7.95 (m, 4H), 7.92 (d, J=8.0 Hz, 1H), 7.85 (dd, J=8.0, 1.5 Hz, 1H), 7.74 (d, J=8.5 Hz, 2H), 7.67 (dd, J=9.0, 1.5 Hz, 1H), 7.63-7.51 (m, 11H), 7.47-7.43 (m, 5H), 7.34-7.26 (m, 8H).

Next, measurement results of the absorption and emission spectra of BBAαNβNB in a toluene solution and measurement results of the absorption and emission spectra of its thin film will be shown. The method for forming a sample, the measurement method, and the measurement apparatus are similar to those described in the above example and therefore will not be described here.

The measurement results show that BBAαNβNB in the toluene solution has an absorption peak at around 354 nm and an emission wavelength peak at 419 nm (excitation wavelength: 354 nm). The thin film of BBAαNβNB has absorption peaks at around 358 nm, 299 nm, 251 nm, and 212 nm and emission wavelength peaks at around 432 nm and 449 nm (excitation wavelength: 375 nm). These results indicate that BBAαNβNB emits blue light. Furthermore, the compound of one embodiment of the present invention can be used as a host for a light-emitting substance or a substance which emits fluorescence in the visible region.

Furthermore, the thin film of BBAαNβNB was found to be a high-quality film that is not easily aggregated even in the air and is less likely to change in shape.

The HOMO level and the LUMO level of BBAαNβNB were calculated by cyclic voltammetry (CV) measurement. The calculation method is the same as the method described in Example 1 and therefore will not be described here.

According to the results, BBAαNβNB has a HOMO level of −5.47 eV and a LUMO level of −2.40 eV Furthermore, the oxidation-reduction wave was repeatedly measured, and the waveform in the first cycle was compared with that in the hundredth cycle; 89% of the peak intensity of the oxidation potential Ea was maintained. Accordingly, BBAαNβNB is highly resistant to oxidation.

The thermogravimetry-differential thermal analysis of BBAαNβNB was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 470° C., which shows that BBAαNβNB is a substance with high heat resistance.

Differential scanning calorimetry (DSC) measurement of BBAαNβNB was performed with Pyris1DSC manufactured by PerkinElmer, Inc. The DSC measurement was performed in the following manner: the temperature was raised from −10° C. to 290° C. at a temperature rising rate of 40° C./min and held for a minute; then, the temperature was decreased to −10° C. at a temperature decreasing rate of 100° C./min and held at −10° C. for three minutes. This operation was performed twice in succession, and the second measurement result was employed. The DSC measurement proves that BBAαNβNB has a glass transition point of 113° C. and is thus a compound with favorable heat resistance.

Example 6

Synthesis Example 6

In this synthesis example, a synthesis method of 4-(2;1'-binaphthyl-3-yl)-4',4"-diphenyltriphenylamine (abbreviation: BBAαNβNB-02) represented by the structural formula (117) in Embodiment 1 will be described. The structural formula of BBAαNβNB-02 is shown below.

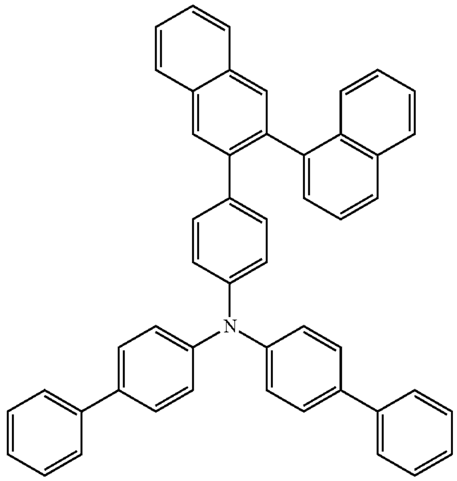 [SMILES: c1ccc(-c2ccc(N(c3ccc(-c4ccccc4)cc3)c3ccc(-c4cc5ccccc5cc4-c4cccc5ccccc45)cc3)cc2)cc1]

Step 1: Synthesis of 3-bromo-2,1'-binaphthyl

Into a 200-mL three-neck flask with a reflux pipe, 3.0 g (11 mmol) of 2,3-dibromonaphthalene, 1.8 g (11 mmol) of 1-naphthylboronic acid, 96 mg (0.031 mmol) of tri(ortho-tolyl)phosphine, 50 mL of toluene, 15 mL of ethanol, and a 2M potassium carbonate aqueous solution (potassium carbonate: 2.9 g/water: 11 mL) were put, the mixture was degassed under reduced pressure, and then, the air in the system was replaced with nitrogen. After that, 24 mg (0.011 mmol) of palladium acetate was added, and stirring was performed at room temperature for 7 hours. Water was added to the obtained mixture, and an aqueous layer was extracted with toluene. The extracted solution was combined with an organic layer, and the resulting mixture was washed with water and saturated saline and dried with magnesium sulfate. This mixture was gravity-filtered, and the obtained filtrate was concentrated to give a pale yellow solid. This solid was purified by HPLC (mobile phase: chloroform) to give 1.8 g of a target white solid in a yield of 53%. The synthesis scheme of Step 1 is shown below.

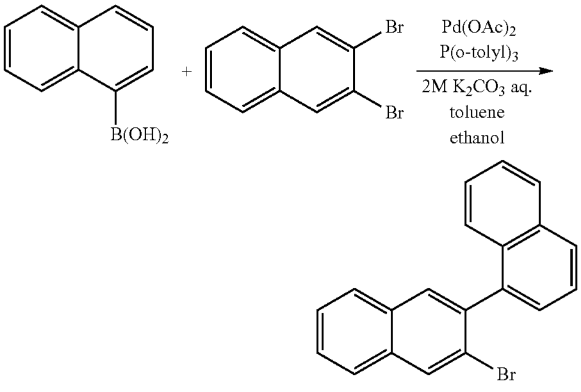

Figure 74A:
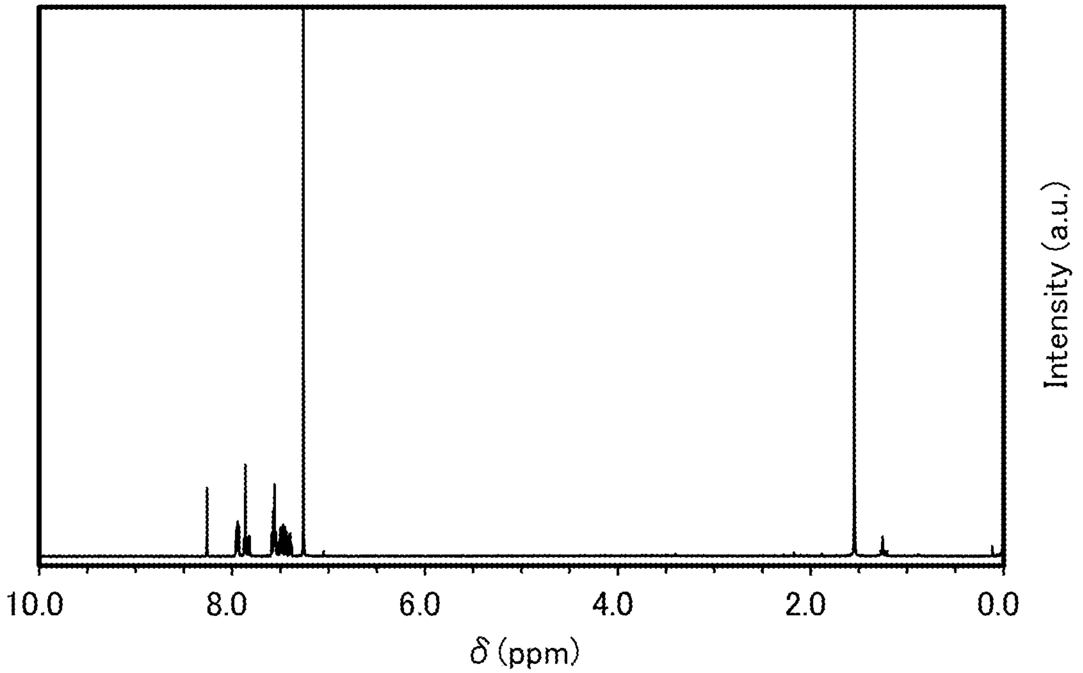
FIGS. 74A and 74B show $^1$H NMR spectra of 3-bromo-2,1'-binaphthyl.
Figure 74B:
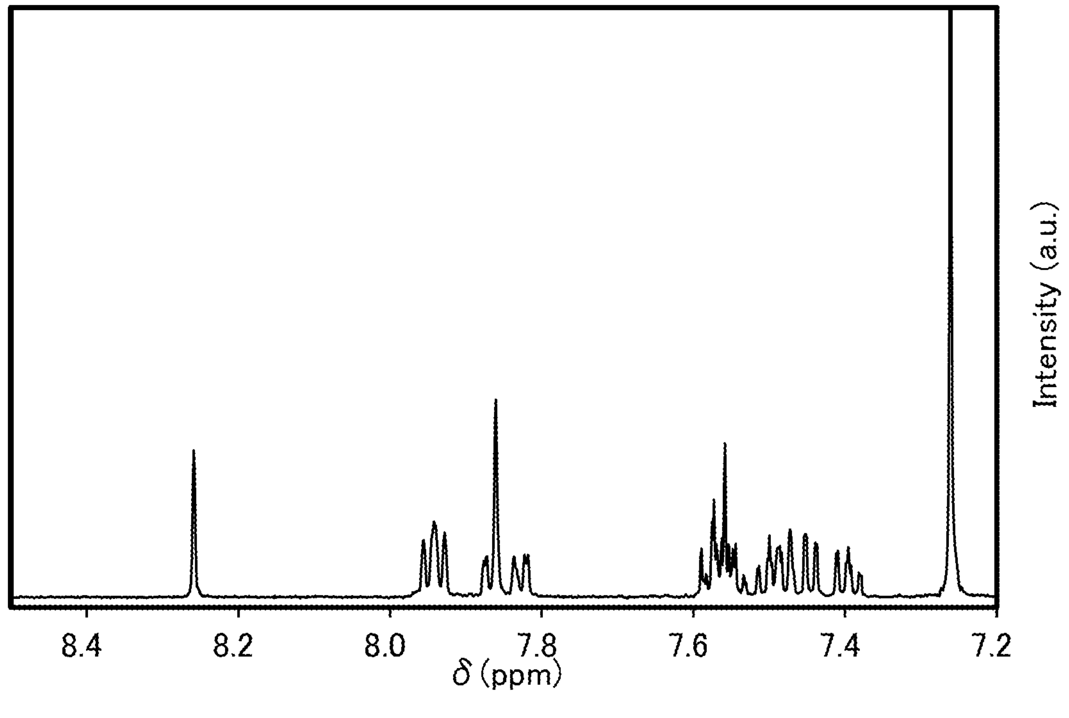

FIGS. 74A and 74B show $^1$H NMR charts of the obtained solid, whose numerical data is shown below. These results indicate that 3-bromo-2,1'-binaphthyl was obtained.

$^1$H NMR (chloroform-d, 500 MHz): δ=8.26 (s, 1H), 7.94 (t, J=7.0 Hz, 2H), 7.87-7.80 (m, 3H), 7.59-7.38 (m, 7H).

Step 2: Synthesis of 4,4'-diphenyl-4"-(4,4,5,5-tetramethyl-1,3,2-dioxaborolan-2-yl)triphenylamine In a manner similar to Step 2 of Synthesis Example 1, 4,4'-diphenyl-4"-(4,4,5,5-tetramethyl-1,3,2-dioxaborolan-2-yl)triphenylamine was synthesized.

Step 3: Synthesis of 4-(2;1'-binaphthyl-3-yl)-4',4"-diphenyltriphenylamine (Abbreviation: BBAαNβNB-02)

Into a 1-L three-neck flask with a reflux pipe, 3.0 g (5.5 mmol) of 4,4'-diphenyl-4"-(4,4,5,5-tetramethyl-1,3,2-dioxaborolan-2-yl)triphenylamine, 1.8 g (5.5 mmol) of 3-bromo-2,1'-binaphthyl, 50 mg (0.17 mmol) of tri(ortho-tolyl)phosphine, 1.5 g/6 mL (11 mmol) of an aqueous solution of potassium carbonate, 50 mL of toluene, and 15 mL of ethanol were put, the mixture was degassed under reduced pressure, and then, the air in the system was replaced with nitrogen. This mixture was heated at 80° C., and 12 mg (0.055 mmol) of palladium(II) acetate was added to the mixture. This mixture was stirred at 100° C. for 4 hours. Water was added to the obtained mixture, and an aqueous layer was extracted with toluene. The extracted solution was combined with an organic layer, and the resulting mixture was washed with water and saturated saline and dried with magnesium sulfate. This mixture was gravity-filtered, and the obtained filtrate was concentrated to give a pale brown solid. This solid was purified by HPLC (mobile phase: chloroform) to give 910 mg of a target pale yellow solid in a yield of 25%. By a train sublimation method, 910 mg of the obtained solid was purified. In the sublimation purification, the solid was heated at 290° C. for 15 hours under a pressure of 4.1 Pa with an argon flow rate of 15 mL/min. After the sublimation purification, 640 mg of a pale yellow solid was obtained at a collection rate of 70%. The synthesis scheme of Step 3 is shown below.

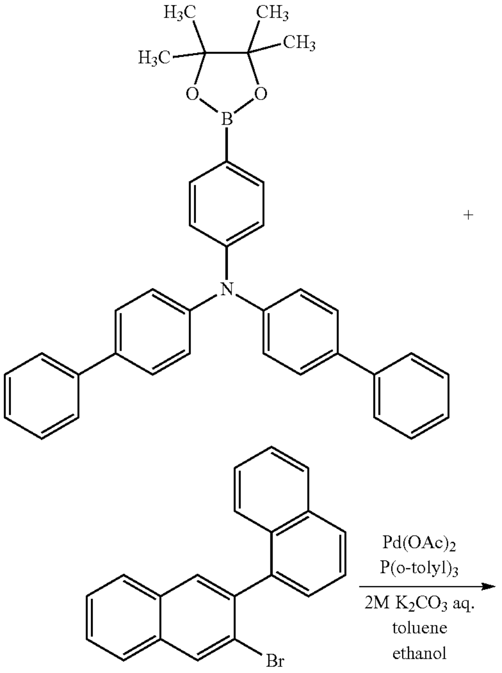

-continued

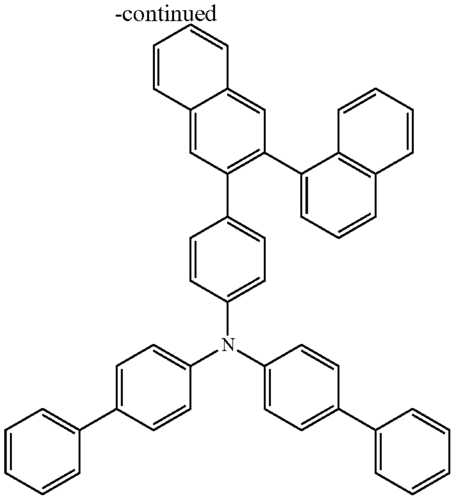

Figure 26A:
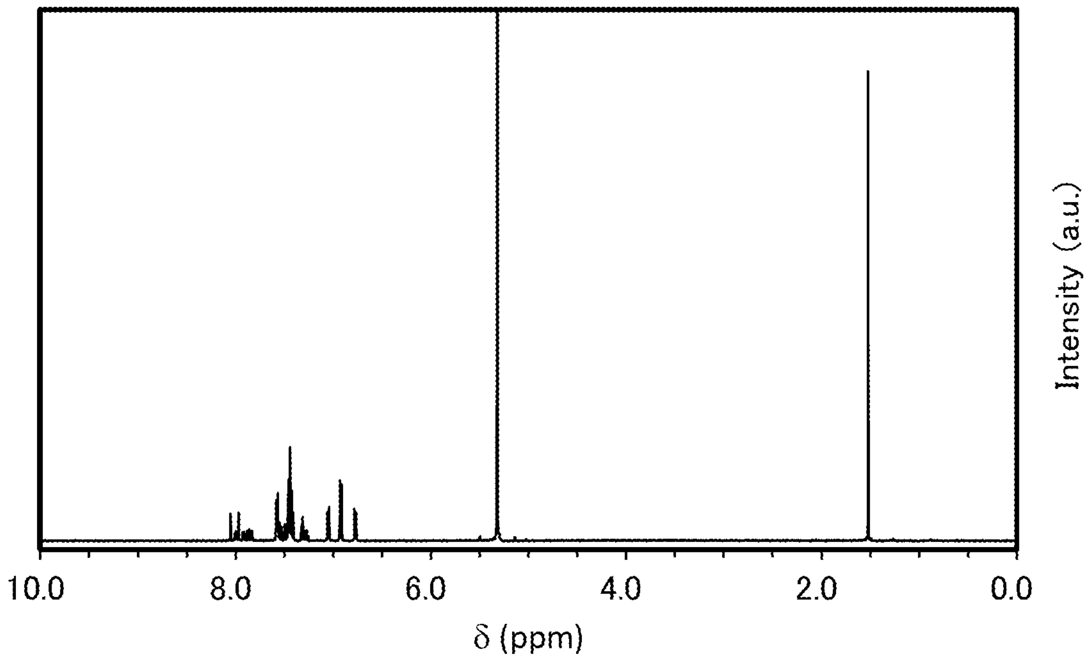
FIGS. 26A and 26B show $^{1}$H NMR spectra of BBAαNβNB-02.
Figure 26B:
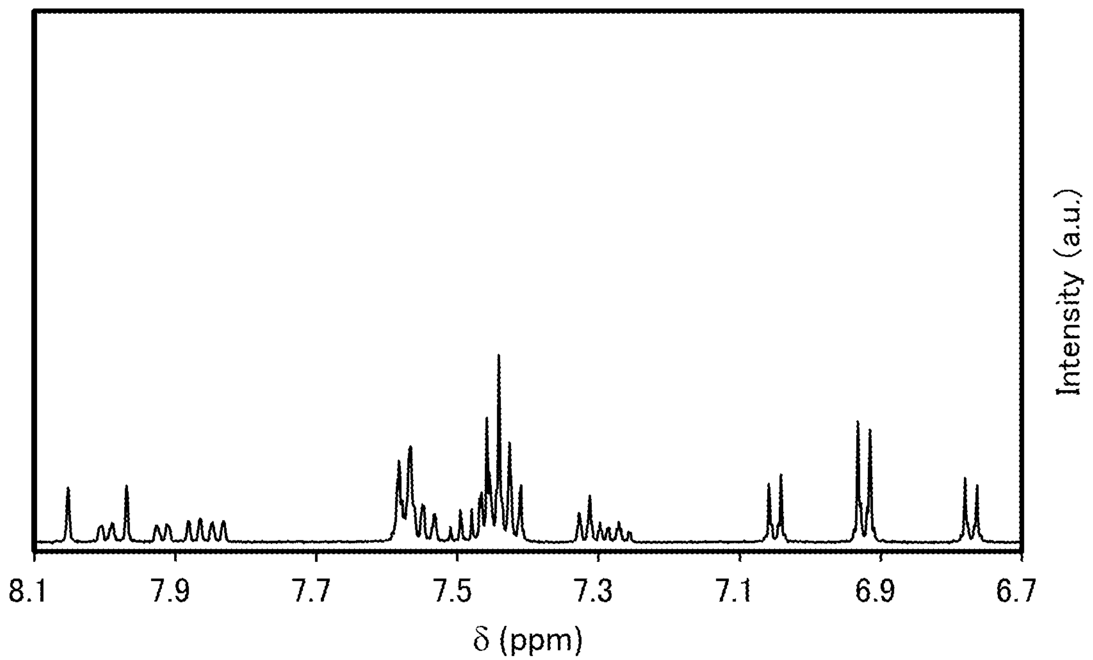

FIGS. 26A and 26B show $^1$H NMR data of the obtained substance, whose numerical data is shown below. These results indicate that BBAαNβNB-02 was obtained in this synthesis example.

$^1$H NMR (dichloromethane-d2, 500 MHz): δ=8.05 (s, 1H), 7.99 (d, J=7.5 Hz, 1H), 7.97 (s, 1H), 7.92 (d, J=7.0 Hz, 1H), 7.87 (d, J=8.0 Hz, 1H), 7.39 (d, J=8.0 Hz, 1H), 7.58-7.41 (m, 18H), 7.33-7.26 (m, 3H), 7.50 (d, J=8.5 Hz, 2H), 6.92 (d, J=8.5 Hz, 4H), 6.78 (d, J=8.5 Hz, 2H).

Next, measurement results of the absorption and emission spectra of BBAαNβNB-02 in a toluene solution and measurement results of the absorption and emission spectra of its thin film will be shown. The method for forming a sample, the measurement method, and the measurement apparatus are similar to those described in the above example and therefore will not be described here.

The measurement results show that BBAαNβNB-02 in the toluene solution has an absorption peak at around 349 nm and an emission wavelength peak at 405 nm (excitation wavelength: 350 nm). The thin film of BBAαNβNB-02 has absorption peaks at around 352 nm, 294 nm, 253 nm, 224 nm, and 213 nm and an emission wavelength peak at around 423 nm (excitation wavelength: 364 nm). These results indicate that BBAαNβNB-02 emits blue light. Furthermore, the compound of one embodiment of the present invention can be used as a host for a light-emitting substance or a substance which emits fluorescence in the visible region.

Furthermore, the thin film of BBAαNβNB-02 was found to be a high-quality film that is not easily aggregated even in the air and is less likely to change in shape.

The HOMO level and the LUMO level of BBAαNβNB-02 were calculated by cyclic voltammetry (CV) measurement. The calculation method is the same as the method described in Example 1 and therefore will not be described here.

According to the results, BBAαNβNB-02 has a HOMO level of −5.48 eV and a LUMO level of −2.25 eV. Furthermore, the oxidation-reduction wave was repeatedly measured, and the waveform in the first cycle was compared with that in the hundredth cycle; 90% of the peak intensity of the oxidation potential Ea was maintained. Accordingly, BBAαNβNB-02 is highly resistant to oxidation.

Differential scanning calorimetry (DSC) measurement of BBAαNβNB-02 was performed with Pyris1DSC manufactured by PerkinElmer, Inc. The DSC measurement was performed in the following manner: the temperature was raised from −10° C. to 290° C. at a temperature rising rate of 40° C./min and held for a minute; then, the temperature was decreased to −10° C. at a temperature decreasing rate of 100° C./min and held at −10° C. for three minutes. The DSC measurement proves that BBAαNβNB-02 has a glass transition point of 125° C. and a crystallization temperature of 226° C. and is thus a substance with extremely high heat resistance.

The thermogravimetry-differential thermal analysis of BBAαNβNB-02 was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 430° C., which shows that BBAαNβNB-02 is a substance with high heat resistance.

Example 7

Synthesis Example 7

In this synthesis example, a synthesis method of 4,4'-diphenyl-4"-(7;1'-binaphthyl-2-yl)triphenylamine (abbreviation: BBAαNβNB-03) represented by the structural formula (115) in Embodiment 1 will be described. The structural formula of BBAαNβNB-03 is shown below.

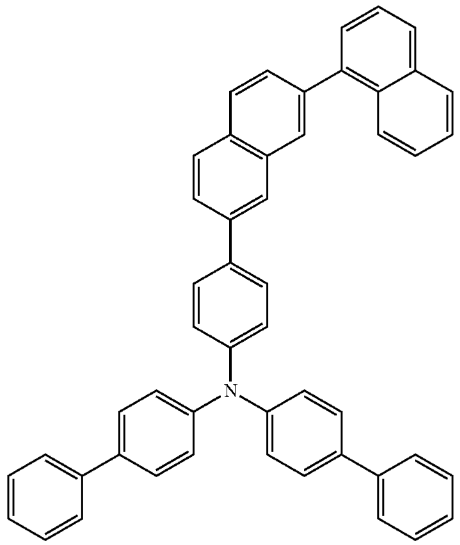 [SMILES: c1ccc(-c2ccc(N(c3ccc(-c4ccccc4)cc3)c3ccc(-c4ccc5ccc(-c6cccc7ccccc67)cc5c4)cc3)cc2)cc1]

Step 1: Synthesis of 4,4'-diphenyl-4"-(4,4,5,5-tetramethyl-1,3,2-dioxaborolan-2-yl)triphenylamine In a manner similar to Step 2 of Synthesis Example 1, 4,4'-diphenyl-4"-(4,4,5,5-tetramethyl-1,3,2-dioxaborolan-2-yl)triphenylamine was synthesized.

Step 2: Synthesis method of 4,4'-diphenyl-4"-(7;1'-binaphthyl-2-yl)triphenylamine (Abbreviation: BBAαNβNB-03)

Into a 200-mL three-neck flask with a reflux pipe, 3.6 g (6.7 mmol) of 4,4'-diphenyl-4"-(4,4,5,5-tetramethyl-1,3,2-dioxaborolan-2-yl)triphenylamine, 2.2 g (6.7 mmol) of 7-bromo-2,1'-binaphthyl, 41 mg (0.13 mmol) of tri(ortho-tolyl)phosphine, 1.8 g/6 mL (13 mmol) of an aqueous solution of potassium carbonate, 50 mL of toluene, and 15 mL of ethanol were put, the mixture was degassed under reduced pressure, and then, the air in the system was replaced with nitrogen. This mixture was heated at 70° C., and 15 mg (0.067 mmol) of palladium(II) acetate was added to the mixture. The mixture was stirred at 100° C. for 7 hours. Water was added to the obtained mixture, and an aqueous layer was extracted with toluene. The extracted solution was combined with an organic layer, and the resulting mixture was washed with water and saturated saline and dried with magnesium sulfate. This mixture was gravity-filtered, and the obtained filtrate was concentrated to give 3.4 g of a yellow solid in a yield of 78%. By a train sublimation method, 3.4 g of the obtained solid was purified. In the sublimation purification, the solid was heated at 295° C. for 15 hours under a pressure of 3.4 Pa with an argon flow rate of 15 mL/min. After the sublimation purification, 1.4 g of a pale yellow solid was obtained at a collection rate of 42%. The synthesis scheme of Step 2 is shown below.

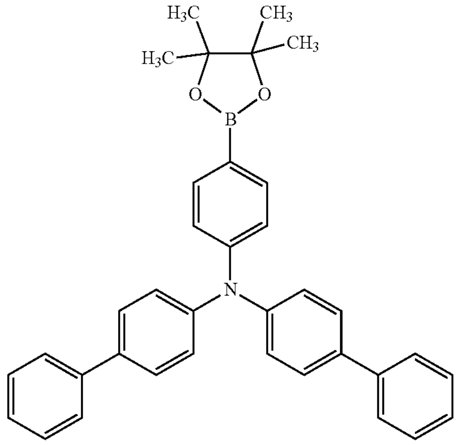

+

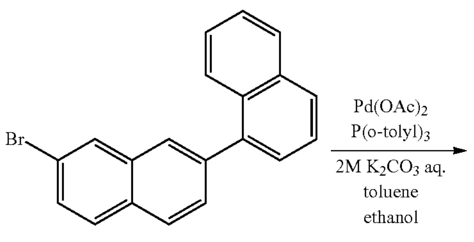

-continued

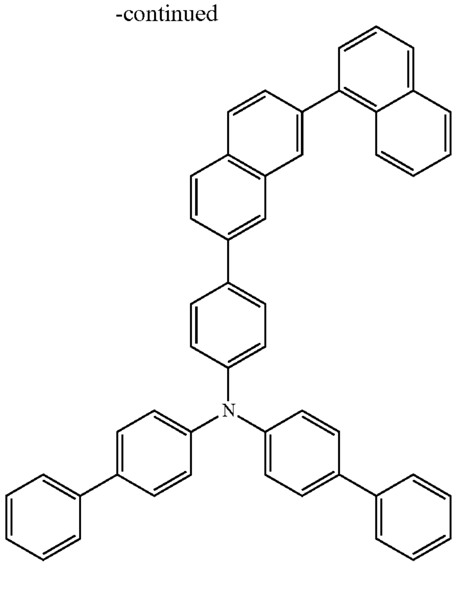

Figure 27A:
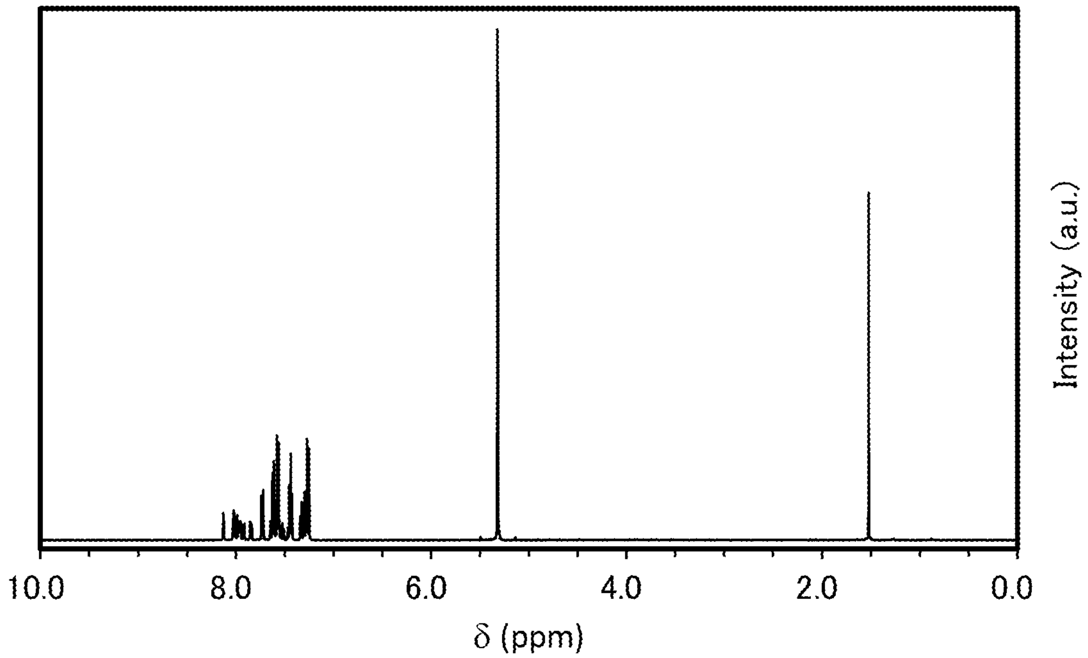
FIGS. 27A and 27B show $^{1}$H NMR spectra of BBAαNβNB-03.
Figure 27B:
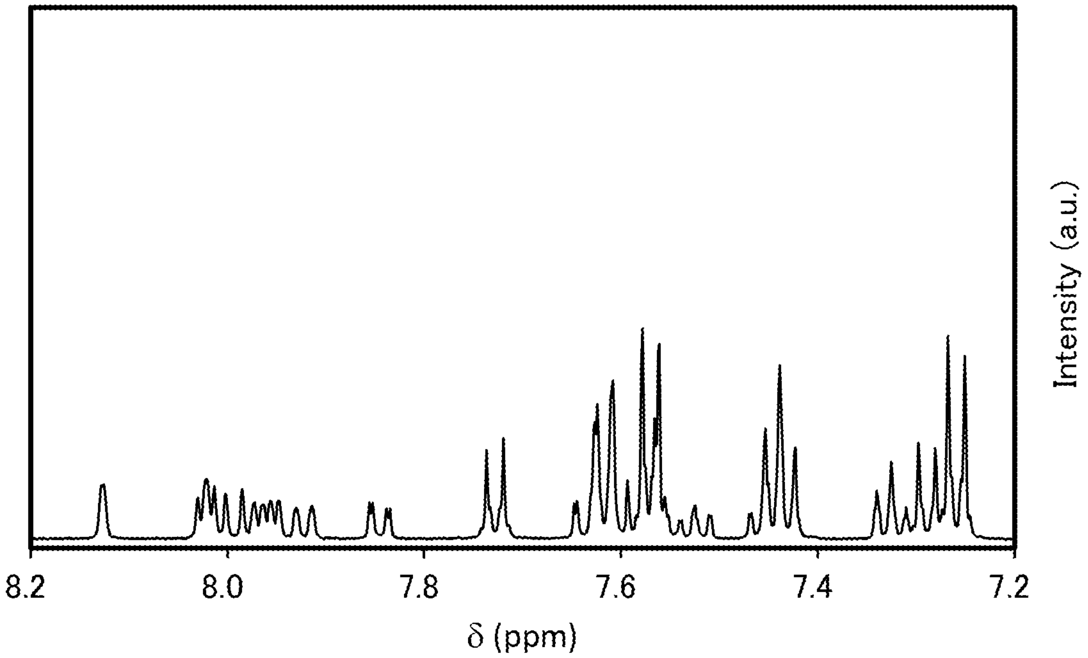

FIGS. 27A and 27B shows $^1$H NMR data of the obtained substance, whose numerical data is shown below. These results indicate that BBAαNβNB-03 was obtained in this synthesis example.

$^1$H NMR (dichloromethane-d2, 500 MHz): δ=8.12 (s, 1H), 8.03-8.01 (m, 2H), 7.94 (d, J=8.5 Hz, 1H), 7.97-7.94 (m, 2H), 7.92 (d, J=8.0 Hz, 1H), 7.84 (dd, J=8.5, 1.5 Hz, 1H), 7.72 (d, J=8.5 Hz, 2H), 7.64-7.55 (m, 11H), 7.52 (t, J=7.0 Hz, 1H), 7.47-7.42 (m, 5H), 7.34-7.25 (m, 8H).

Next, measurement results of the absorption and emission spectra of BBAαNβNB-03 in a toluene solution and measurement results of the absorption and emission spectra of its thin film will be shown. The method for forming a sample, the measurement method, and the measurement apparatus are similar to those described in the above example and therefore will not be described here.

The measurement results show that BBAαNβNB-03 in the toluene solution has an absorption peak at around 352 nm and an emission wavelength peak at 427 nm (excitation wavelength: 360 nm). The thin film of BBAαNβNB-03 has absorption peaks at around 355 nm, 295 nm, 254 nm, and 210 nm and an emission wavelength peak at around 427 nm (excitation wavelength: 360 nm). These results indicate that BBAαNβNB-03 emits blue light. Furthermore, the compound of one embodiment of the present invention can be used as a host for a light-emitting substance or a substance which emits fluorescence in the visible region.

Furthermore, the thin film of BBAαNβNB-03 was found to be a high-quality film that is not easily aggregated even in the air and is less likely to change in shape.

The HOMO level and the LUMO level of BBAαNβNB-03 were calculated by cyclic voltammetry (CV) measurement. The calculation method is the same as the method described in Example 1 and therefore will not be described here.

According to the results, BBAαNβNB-03 has a HOMO level of −5.47 eV and a LUMO level of −2.35 eV. Furthermore, the oxidation-reduction wave was repeatedly measured, and the waveform in the first cycle was compared with that in the hundredth cycle; 89% of the peak intensity of the oxidation potential Ea was maintained. Accordingly, BBAαNβNB-03 is highly resistant to oxidation.

The thermogravimetry-differential thermal analysis of BBAαNβNB-03 was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 490° C., which shows that BBAαNβNB-03 is a substance with high heat resistance.

Differential scanning calorimetry (DSC) measurement of BBAαNβNB-03 was performed with Pyris1DSC manufactured by PerkinElmer, Inc. The DSC measurement was performed in the following manner: the temperature was raised from −10° C. to 290° C. at a temperature rising rate of 40° C./min and held for a minute; then, the temperature was decreased to −10° C. at a temperature decreasing rate of 100° C./min and held at −10° C. for three minutes. This operation was performed twice in succession, and the second measurement result was employed. The DSC measurement proves that BBAαNβNB-03 has a glass transition point of 122° C. and is thus a compound with favorable heat resistance.

Example 8

In this example, light-emitting elements 1 and 2 which correspond to the light-emitting element of one embodiment of the present invention described in the above embodiment will be described. The structural formulae of organic compounds used for the light-emitting elements 1 and 2 are shown below.

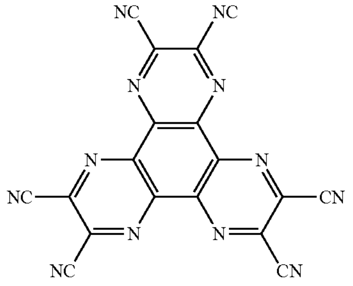

(i) HAT-CN

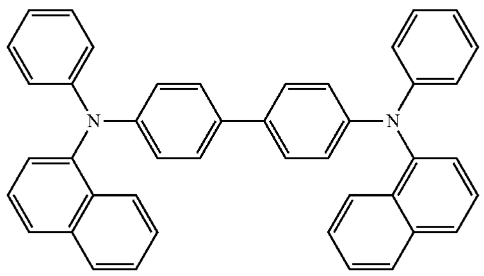

(ii) NPB

-continued
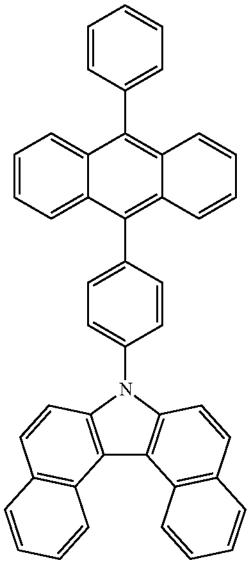
(iii) cgDBCzPA
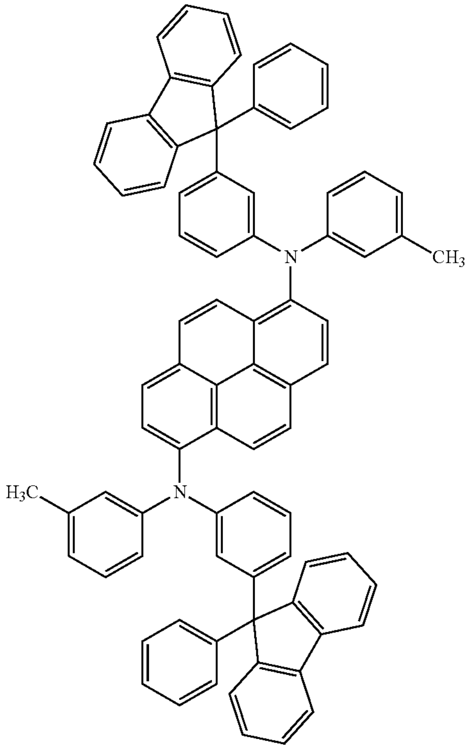
(iv) 1,6mMemFLPAPrn
-continued
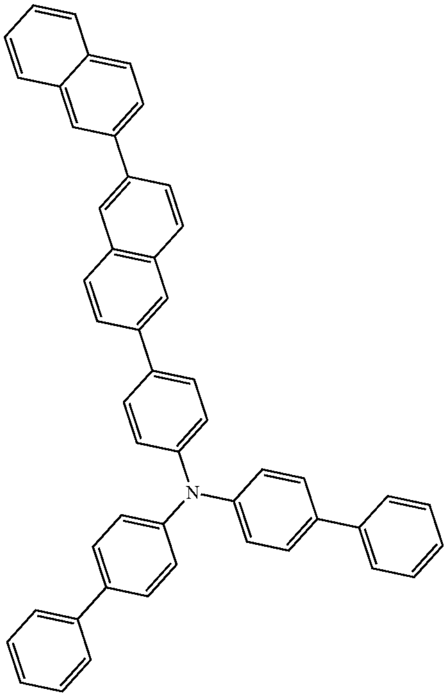
(101) BBA(βN2)B
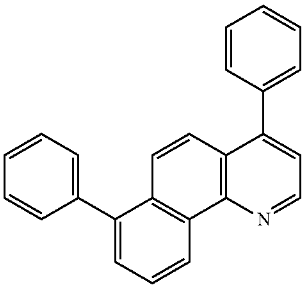
(v) BPhen
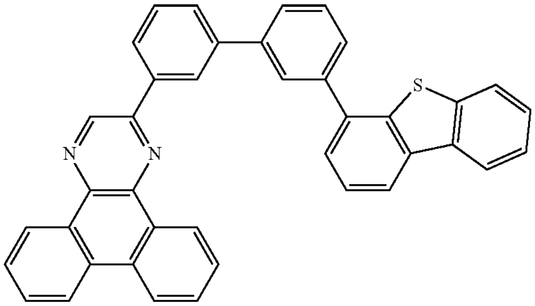
(vi) 2mDBTBPDPq-II -continued

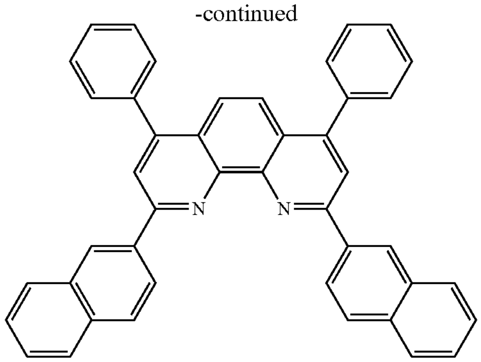

(vii) NBPhen (Method for Fabricating Light-Emitting Element 1)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 20 nm by evaporation, and then, 4-(6;2'-binaphthyl-2-yl)-4',4''-diphenyltriphenylamine (abbreviation: BBA(βN2)B) represented by the structural formula (101) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 10 nm by evaporation, and then, bathophenanthroline (abbreviation: BPhen) represented by the structural formula (v) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 1 of this example was fabricated.

(Method for Fabricating Light-Emitting Element 2)

The light-emitting element 2 was fabricated in the same manner as the light-emitting element 1 except that, in the electron-transport layer 114, 2-[3'-(dibenzothiophen-4-yl)biphenyl-3-yl]dibenzo[f,h]quinoxaline (abbreviation: 2mDBTBPDBq-II) represented by the structural formula (vi) was used instead of cgDBCzPA and 2,9-bis(naphthalen-2-yl)-4,7-diphenyl-1,10-phenanthroline (abbreviation: NBPhen) represented by the structural formula (vii) was used instead of BPhen.

The element structures of the light-emitting elements 1 and 2 are shown in the following table.

TABLE 1

| | Hole-injection layer | Hole-transport layer | | Light-emitting layer | Electron-transport layer | | Electron-injection layer |
|---|---|---|---|---|---|---|---|
| | 5 nm | 20 nm | 10 nm | 25 nm | 10 nm | 15 nm | 1 nm |
| Element 1 | HAT-CN | NPB | BBA(βN2)B | cgDBCzPA: 1,6mMemFLPAPrn (1:0.03) | cgDBCzPA | BPhen | LiF |
| Element 2 | | | | | 2mDBTBPDBq-II | NBPhen | |

The light-emitting elements 1 and 2 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 28:
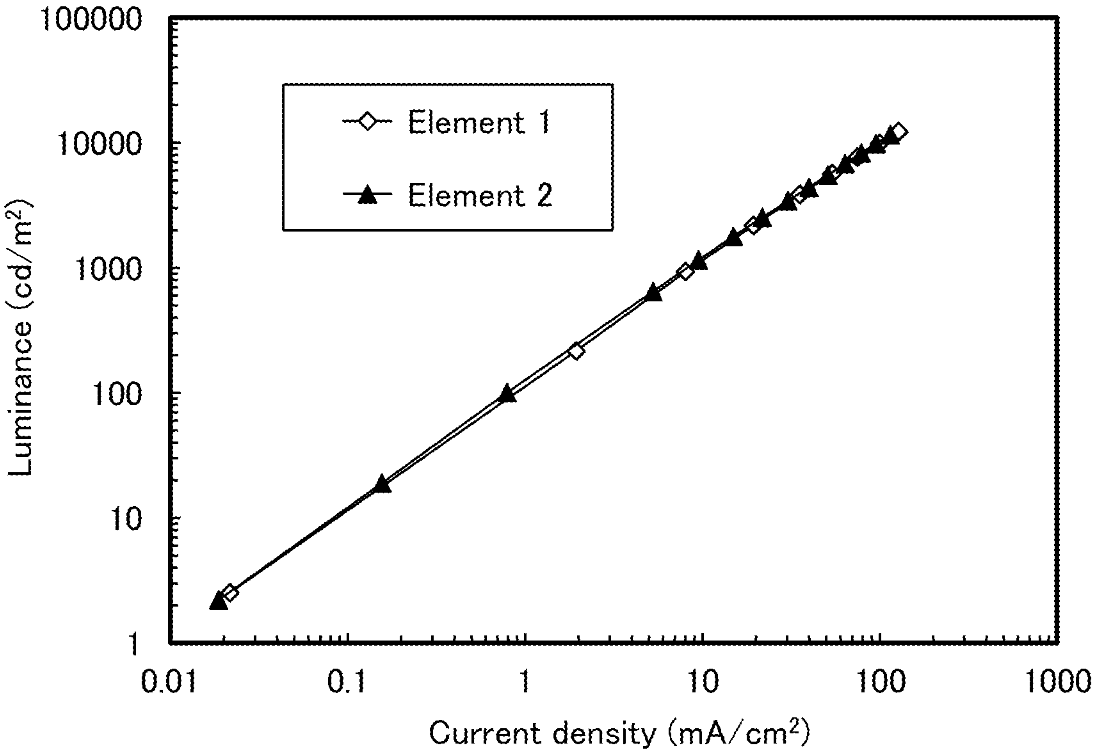
FIG. 28 shows luminance-current density characteristics of light-emitting elements 1 and 2.
Figure 29:
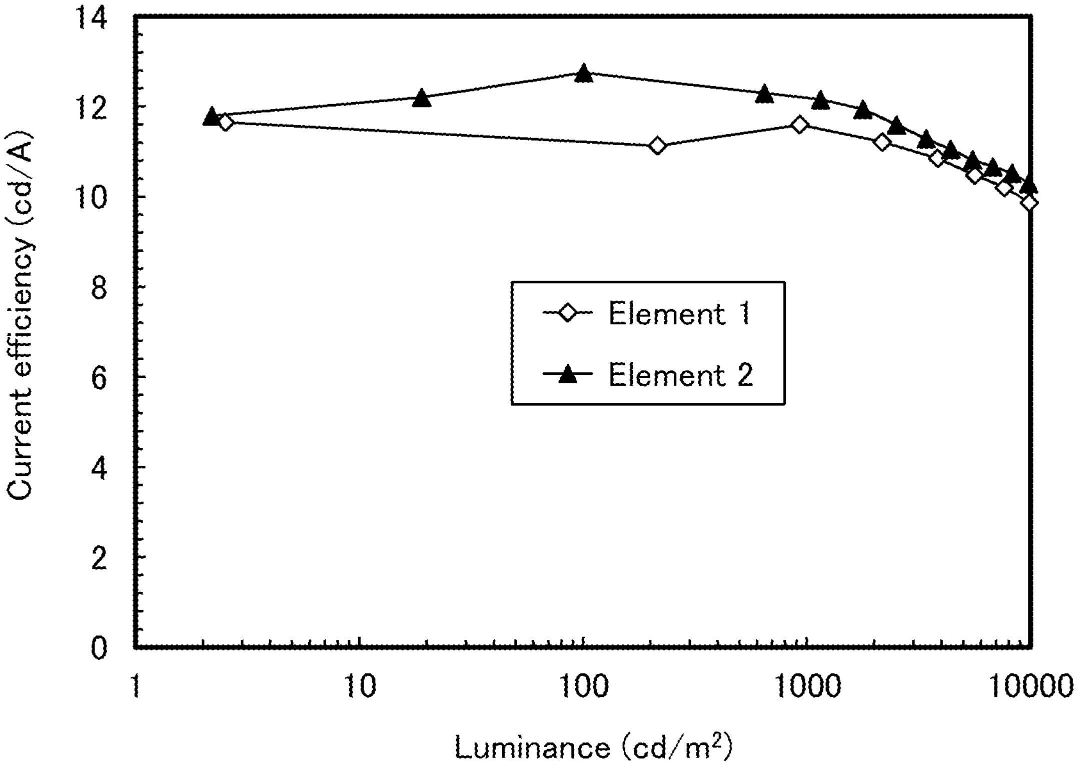
FIG. 29 shows current efficiency-luminance characteristics of the light-emitting elements 1 and 2.
Figure 30:
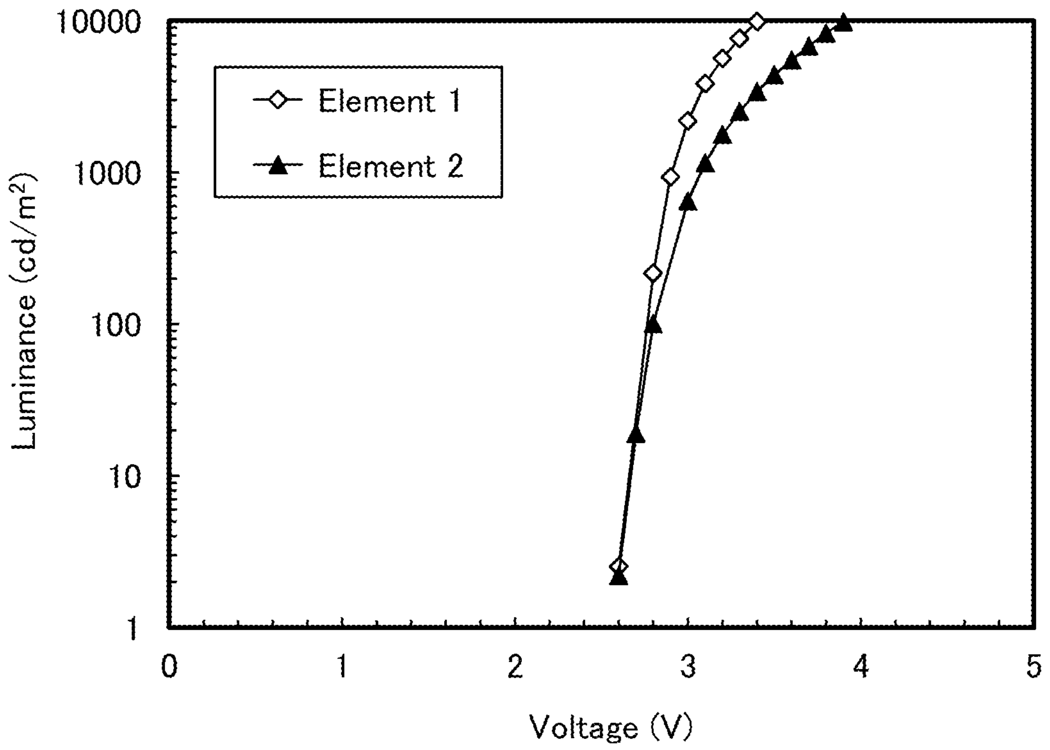
FIG. 30 shows luminance-voltage characteristics of the light-emitting elements 1 and 2.
Figure 31:
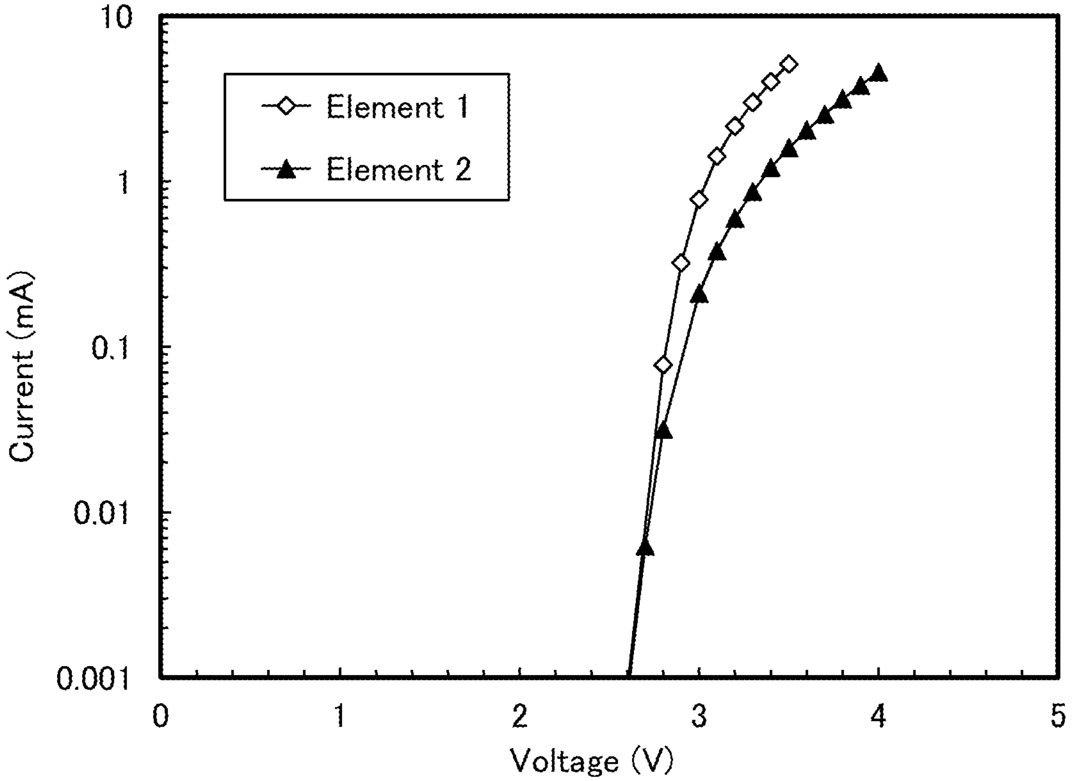
FIG. 31 shows current-voltage characteristics of the light-emitting elements 1 and 2.
Figure 32:
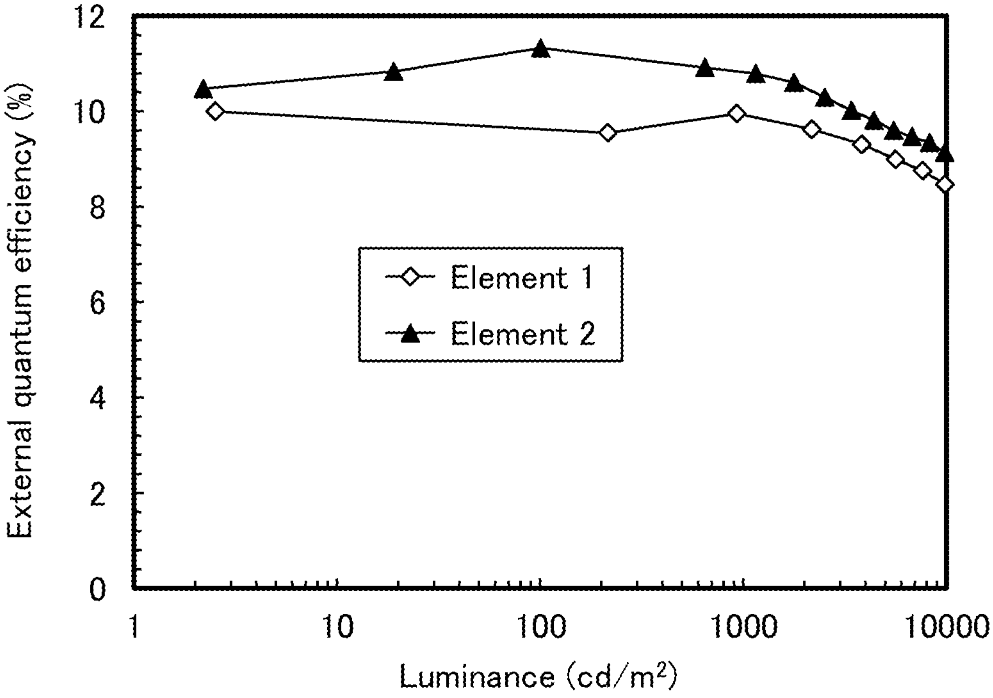
FIG. 32 shows external quantum efficiency-luminance characteristics of the light-emitting elements 1 and 2.
Figure 33:
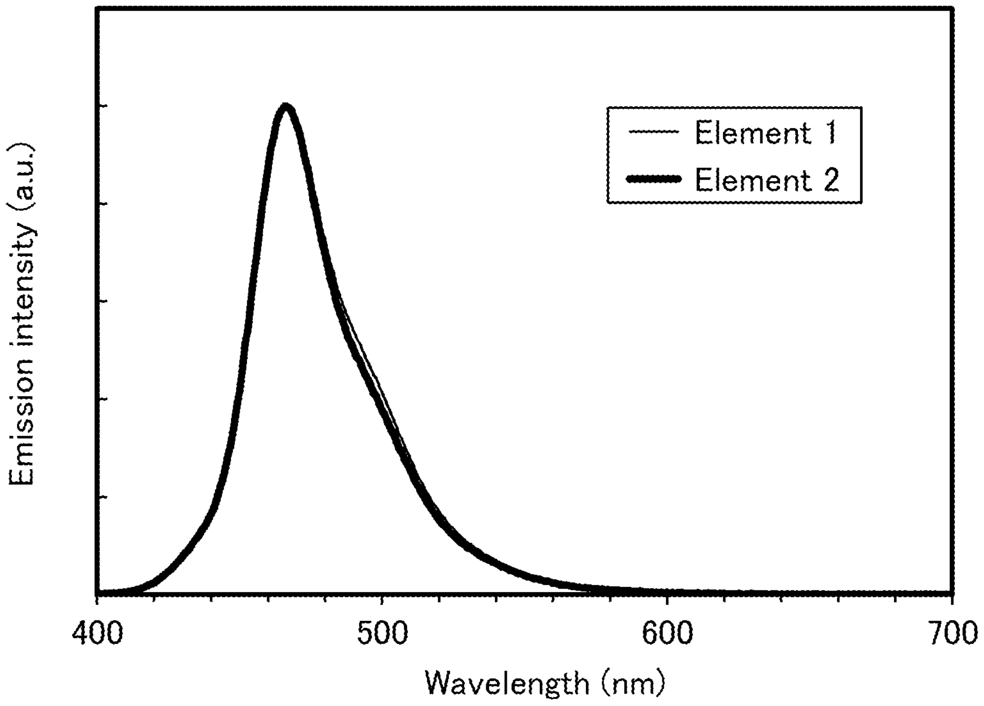
FIG. 33 shows emission spectra of the light-emitting elements 1 and 2.

FIG. 28 shows luminance-current density characteristics of the light-emitting elements 1 and 2. FIG. 29 shows current efficiency-luminance characteristics thereof. FIG. 30 shows luminance-voltage characteristics thereof. FIG. 31 shows current-voltage characteristics thereof. FIG. 32 shows external quantum efficiency-luminance characteristics thereof. FIG. 33 shows emission spectra thereof.

TABLE 2

| | Voltage | Current | Current density | Chromaticity | | Current efficiency | External quantum |
|---|---|---|---|---|---|---|---|
| | (V) | (mA) | ($mA/cm^2$) | x | y | (cd/A) | efficiency (%) |
| Element 1 | 2.9 | 0.32 | 8.0 | 0.14 | 0.16 | 12 | 10 |
| Element 2 | 3.1 | 0.38 | 9.5 | 0.14 | 0.15 | 12 | 11 |

According to FIG. 28, FIG. 29, FIG. 30, FIG. 31, FIG. 32, FIG. 33, and Table 2, the light-emitting elements 1 and 2 have high external quantum efficiencies of 10% and 11%, respectively, at 1000 $cd/m^2$.

Figure 34:
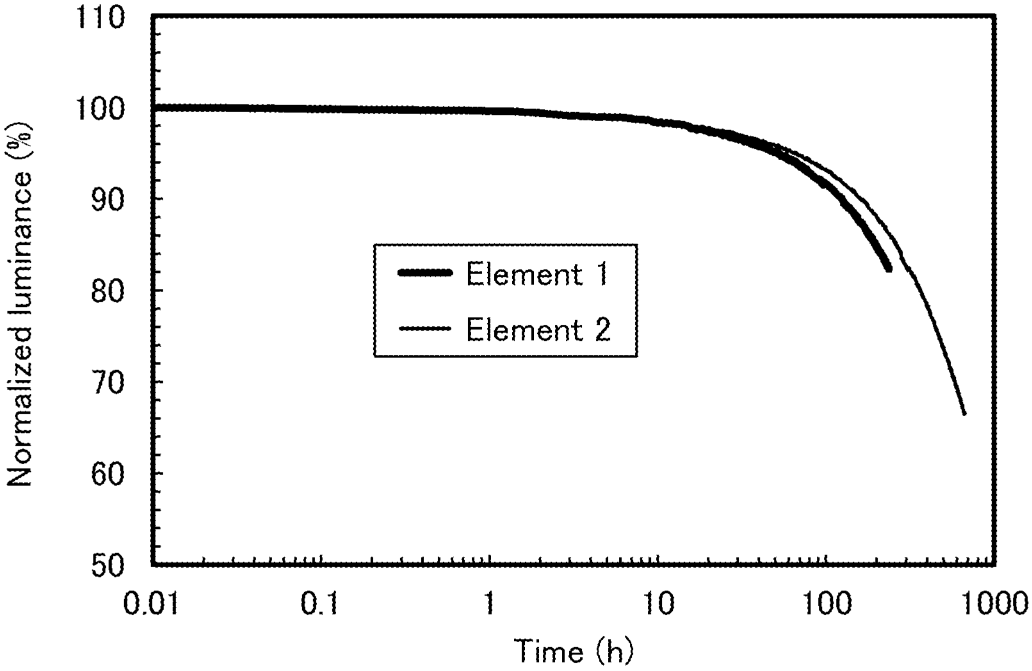
FIG. 34 shows time dependence of normalized luminance of the light-emitting elements 1 and 2.

FIG. 34 is a graph showing driving time-dependent change in luminance under the conditions where the current value was 2 mA and the current density was constant. As shown in FIG. 34, each of the light-emitting elements 1 and 2 maintained 90% or more of the initial luminance after 100-hour-driving and was found to be a long-life light-emitting element whose luminance was only slightly decreased over driving time.

Example 9

In this example, light-emitting elements 3 and 4 which correspond to the light-emitting element of one embodiment of the present invention described in the above embodiment will be described. The structural formulae of organic compounds used for the light-emitting elements 3 and 4 are shown below.

(i)

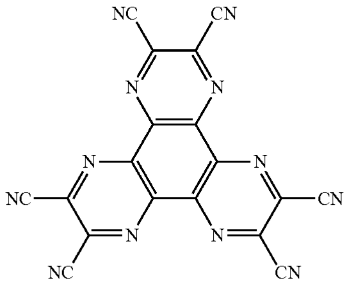

HAT-CN (ii)

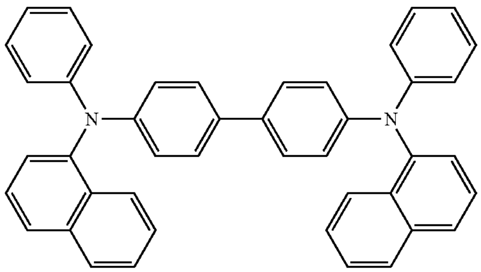

NPB

-continued (iii)

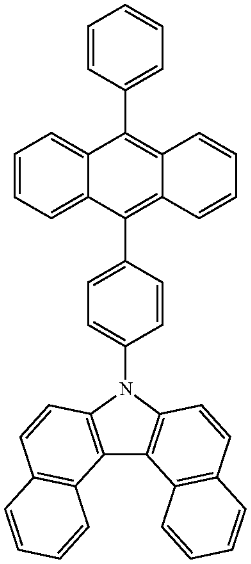

cgDBCzPA (iv)

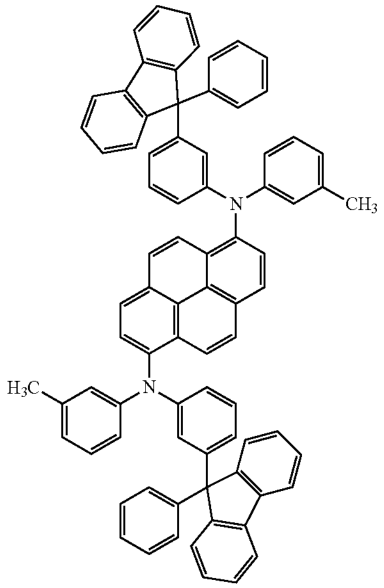

1,6mMemFLPAPrn

-continued (v)

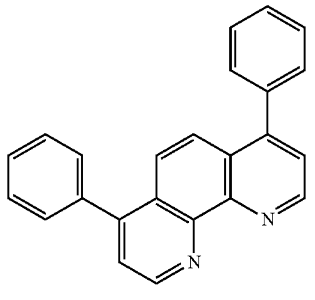

BPhen (vi)

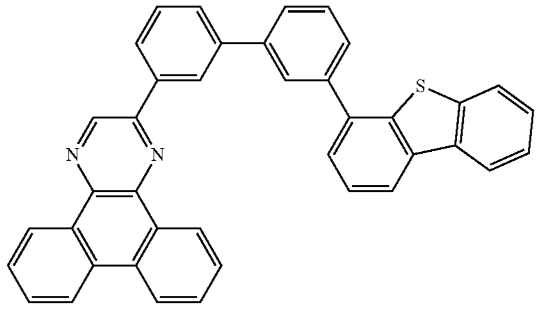

2mDBTBPDBq-II (vii)

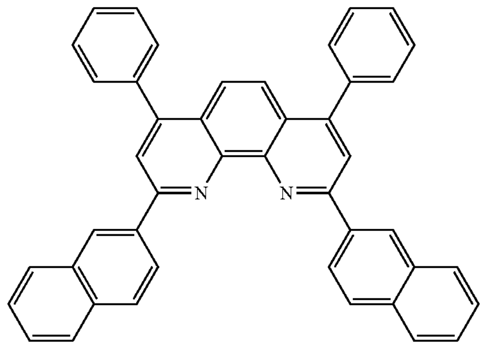

NBPhen (viii)

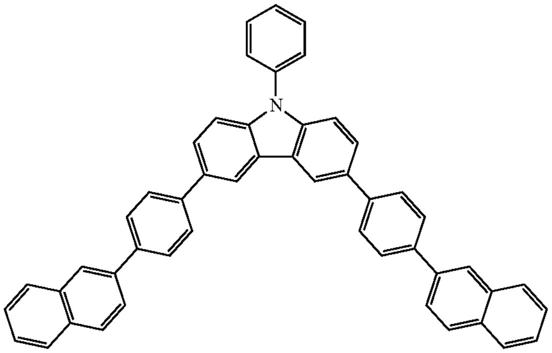

β NP2PC

-continued (101)

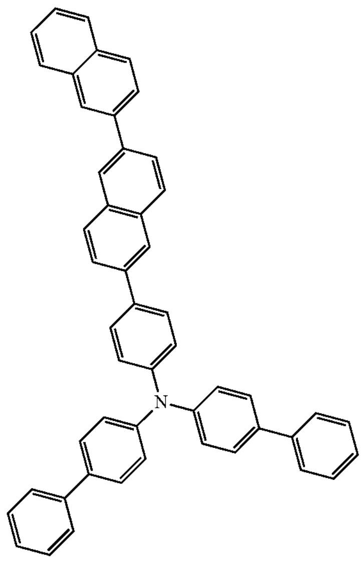

BBA(β N2)B (Method for Fabricating Light-Emitting Element 3)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 10 nm by evaporation, 4-(6;2'-binaphthyl-2-yl)-4',4''-diphenyltriphenylamine (abbreviation: BBA (βN2)B) represented by the structural formula (101) was deposited to a thickness of 10 nm by evaporation, and then, 3,6-bis[4-(2-naphthyl)phenyl]-9-phenyl-9H-carbazole (abbreviation: βNP2PC) represented by the structural formula (viii) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation:

1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 10 nm by evaporation, and bathophenanthroline (abbreviation: BPhen) represented by the structural formula (v) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 3 of this example was fabricated.

(Method for Fabricating Light-Emitting Element 4)

The light-emitting element 4 was fabricated in the same manner as the light-emitting element 3 except that, in the electron-transport layer 114, 2-[3'-(dibenzothiophen-4-yl)biphenyl-3-yl]dibenzo[f,h]quinoxaline (abbreviation: 2mDBTBPDBq-II) represented by the structural formula (vi) was used instead of cgDBCzPA and 2,9-bis(naphthalen-2-yl)-4,7-diphenyl-1,10-phenanthroline (abbreviation: NBPhen) represented by the structural formula (vii) was used instead of BPhen.

The element structures of the light-emitting elements 3 and 4 are shown in the following table.

TABLE 3

| | Hole-injection layer | Hole-transport layer | | | Light-emitting layer | Electron-transport layer | | Electron-injection layer |
|---|---|---|---|---|---|---|---|---|
| | 5 nm | 10 nm | 10 nm | 10 nm | 25 nm | 10 nm | 15 nm | 1 nm |
| Element 3 | HAT-CN | NPB | BBA(βN2)B | βNP2PC | cgDBCzPA:1,6mMemFLPAPrn (1:0.03) | cgDBCzPA | BPhen | LiF |
| Element 4 | | | | | | 2mDBTBPDBq-II | NBPhen | |

The light-emitting elements 3 and 4 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 35:
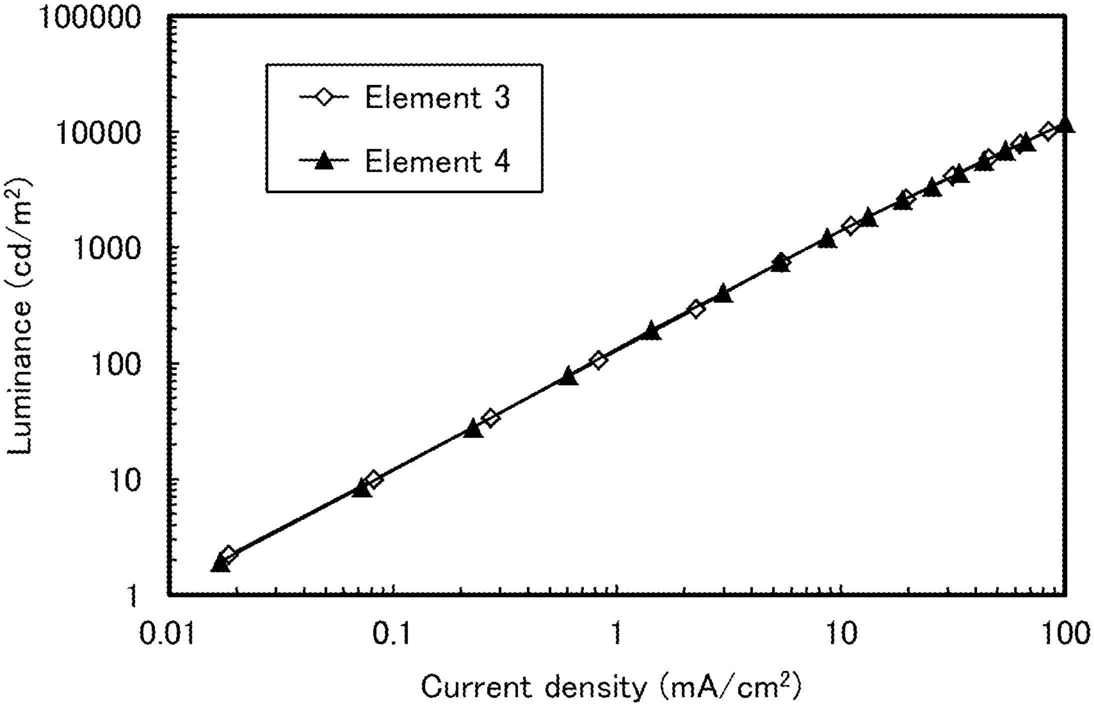
FIG. 35 shows luminance-current density characteristics of light-emitting elements 3 and 4.
Figure 36:
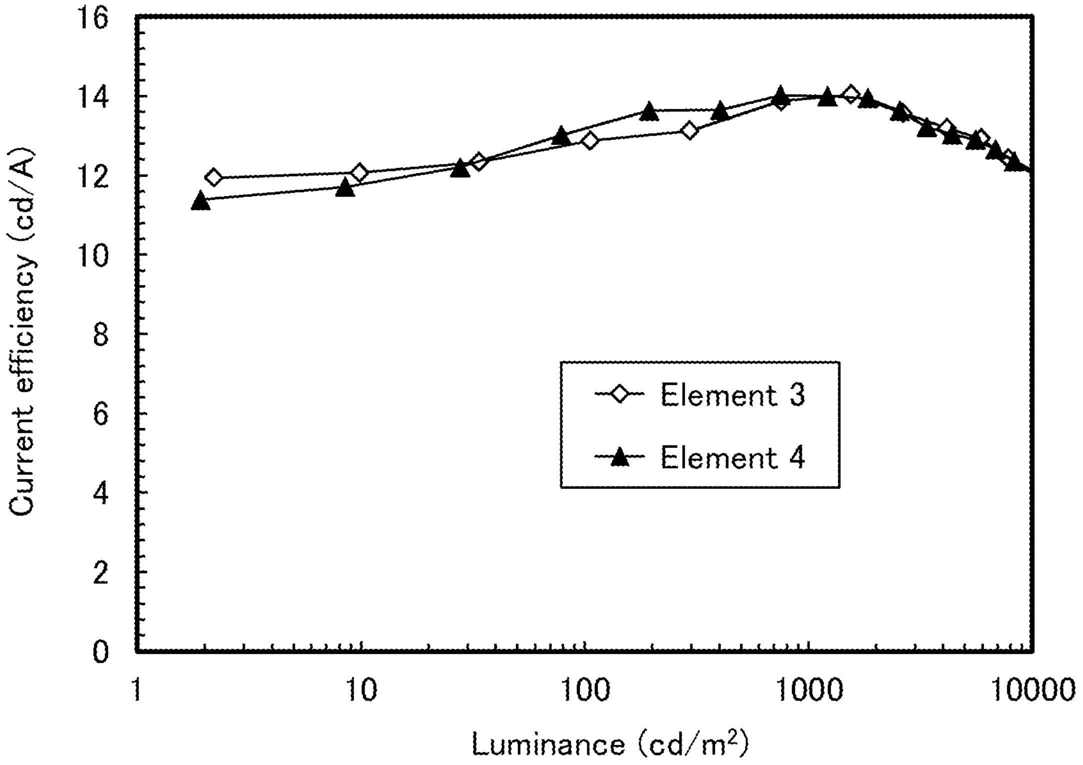
FIG. 36 shows current efficiency-luminance characteristics of the light-emitting elements 3 and 4.
Figure 37:
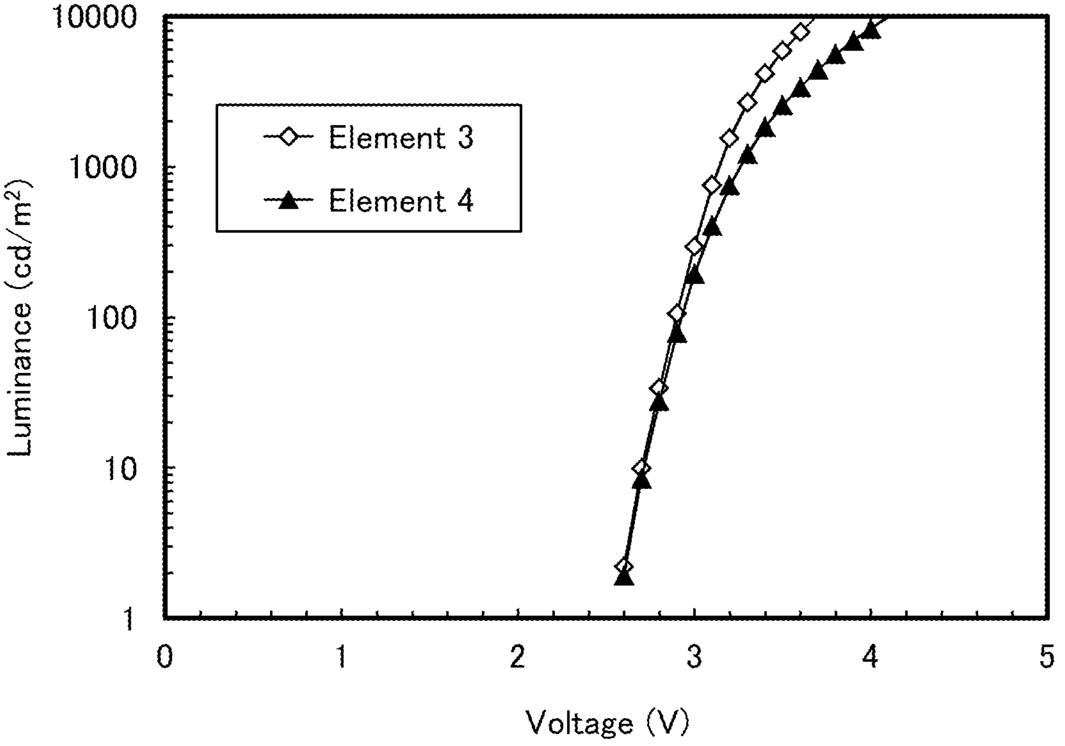
FIG. 37 shows luminance-voltage characteristics of the light-emitting elements 3 and 4.
Figure 38:
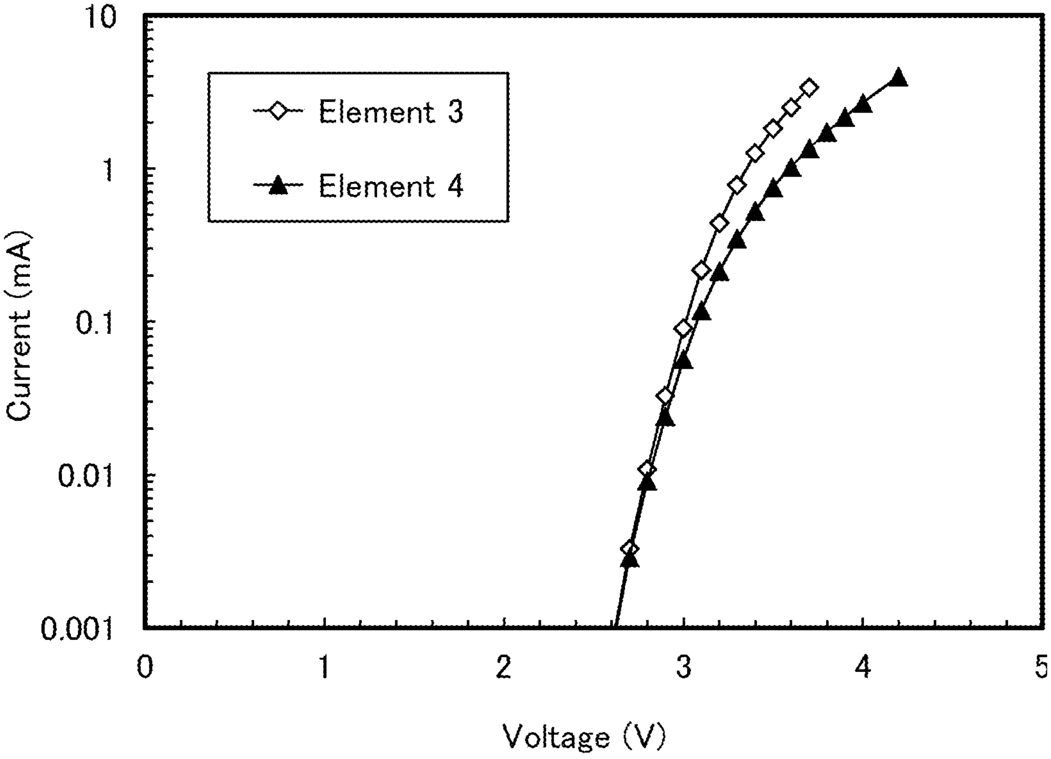
FIG. 38 shows current-voltage characteristics of the light-emitting elements 3 and 4.
Figure 39:
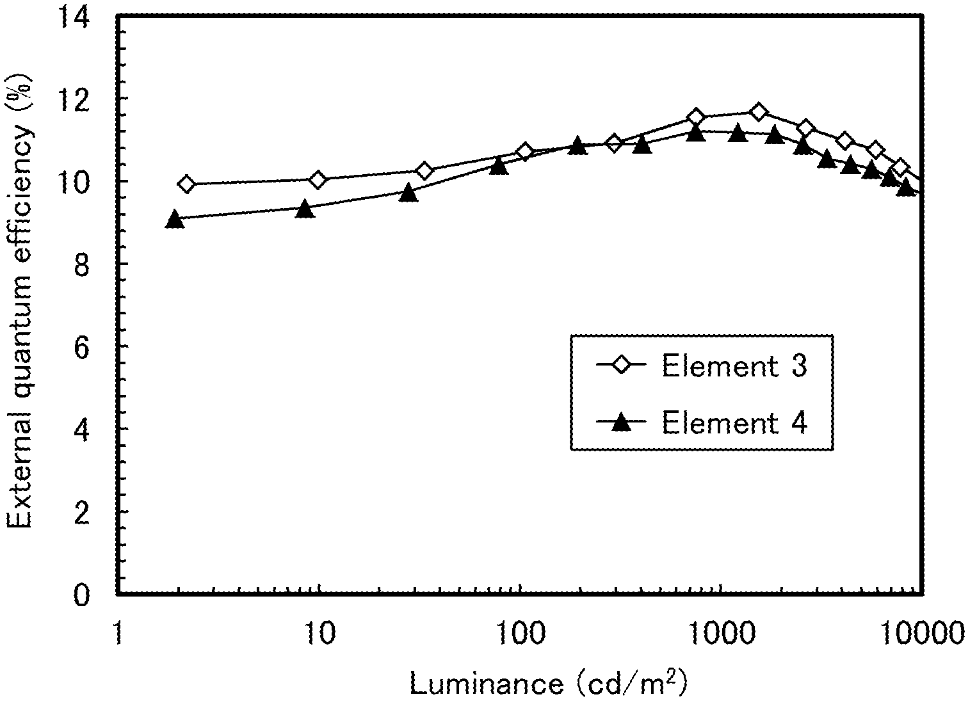
FIG. 39 shows external quantum efficiency-luminance characteristics of the light-emitting elements 3 and 4.
Figure 40:
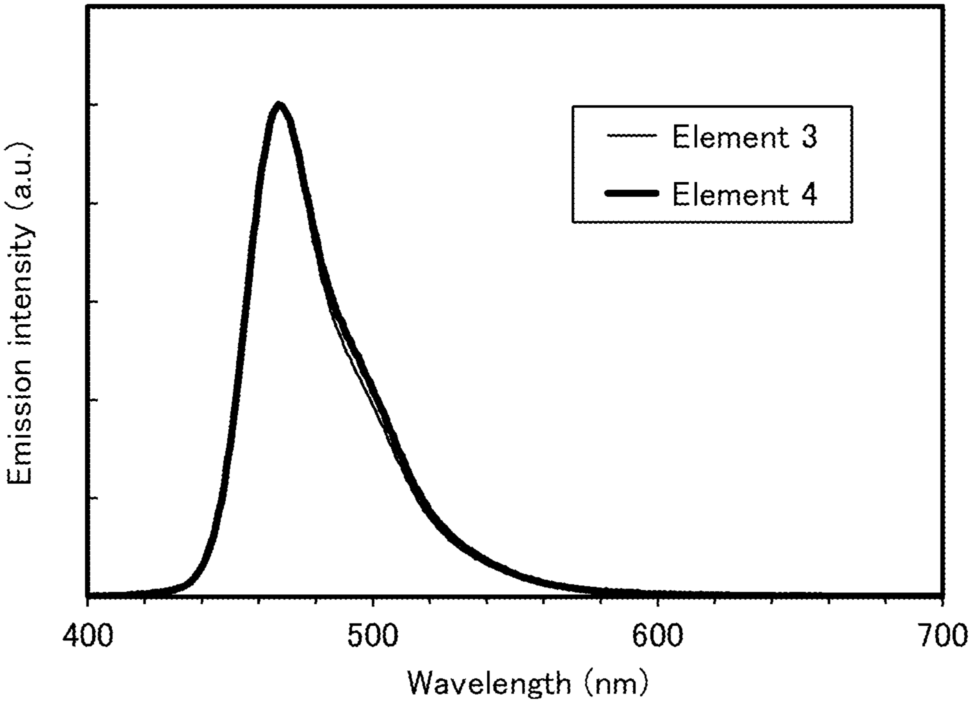
FIG. 40 shows emission spectra of the light-emitting elements 3 and 4.

FIG. 35 shows luminance-current density characteristics of the light-emitting elements 3 and 4. FIG. 36 shows current efficiency-luminance characteristics thereof. FIG. 37 shows luminance-voltage characteristics thereof. FIG. 38 shows current-voltage characteristics thereof. FIG. 39 shows external quantum efficiency-luminance characteristics thereof. FIG. 40 shows emission spectra thereof.

TABLE 4

| | Voltage (V) | Current (mA) | Current density ($mA/cm^2$) | Chromaticity x | Chromaticity y | Current efficiency (cd/A) | External quantum efficiency (%) |
|---|---|---|---|---|---|---|---|
| Element 3 | 3.1 | 0.22 | 5.4 | 0.14 | 0.18 | 14 | 12 |
| Element 4 | 3.3 | 0.35 | 8.7 | 0.14 | 0.17 | 14 | 11 |

According to FIG. 35, FIG. 36, FIG. 37, FIG. 38, FIG. 39, FIG. 40, and Table 4, the light-emitting elements 3 and 4 have high external quantum efficiencies of 12% and 11%, respectively, at 1000 $cd/m^2$.

Figure 41:
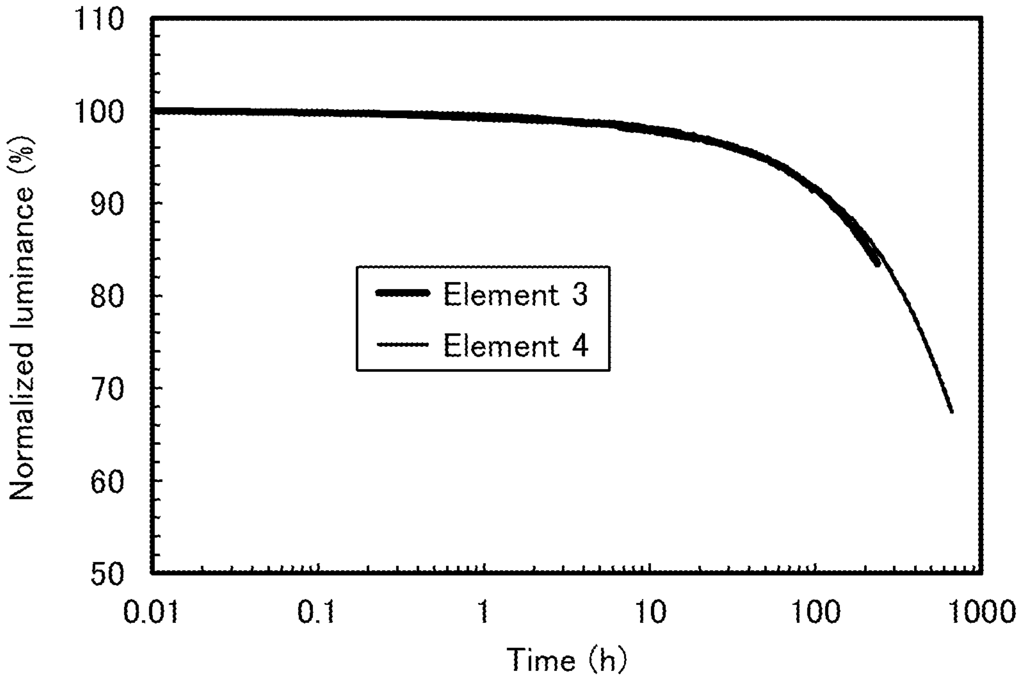
FIG. 41 shows time dependence of normalized luminance of the light-emitting elements 3 and 4.

FIG. 41 is a graph showing driving time-dependent change in luminance under the conditions where the current value was 2 mA and the current density was constant. As shown in FIG. 41, each of the light-emitting elements 3 and 4 maintained 90% or more of the initial luminance after 100-hour-driving and was found to be a long-life light-emitting element whose luminance was only slightly decreased over driving time.

Example 10

In this example, light-emitting elements 5 and 6 which correspond to the light-emitting element of one embodiment of the present invention described in the above embodiment will be described. The structural formulae of organic compounds used for the light-emitting elements 5 and 6 are shown below.

(i)

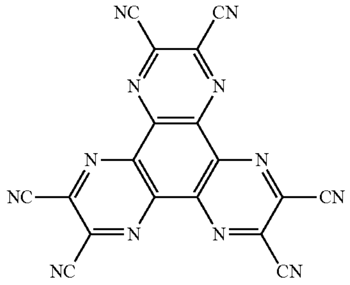

HAT-CN

-continued
(ii)
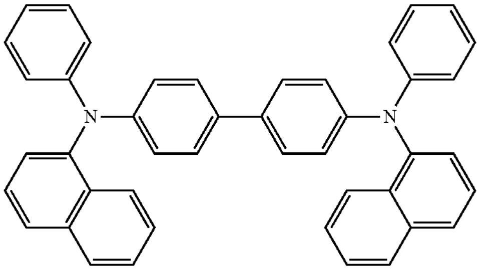
NPB
(iii)
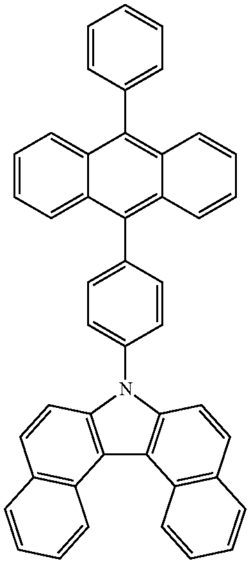
cgDBCzPA
(iv)
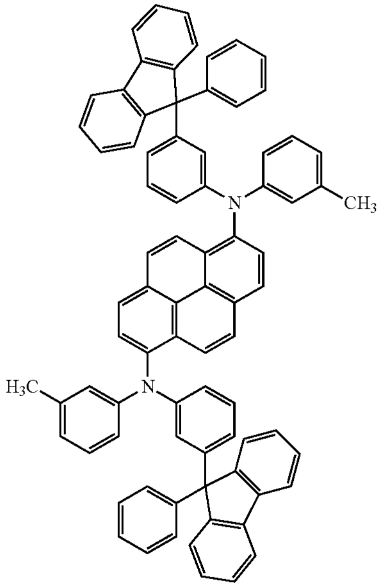
1,6mMemFLPAPrn
-continued
(v)
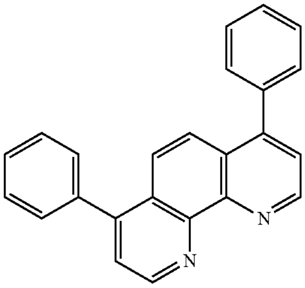
BPhen
(vi)
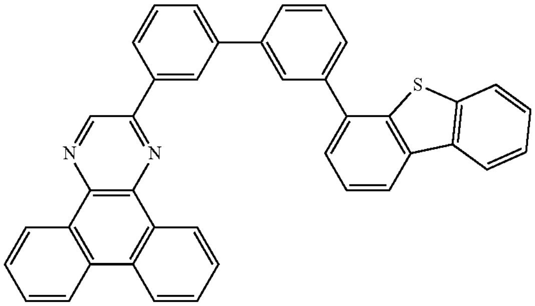
2mDBTBPDBq-II
(vii)
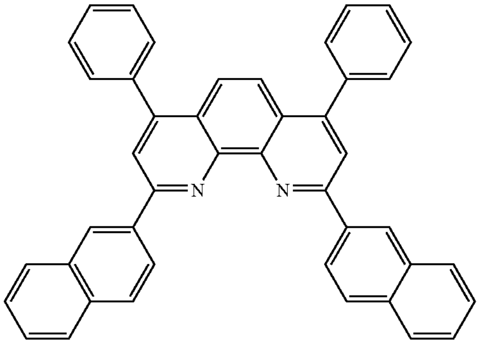
NBPhen
(viii)
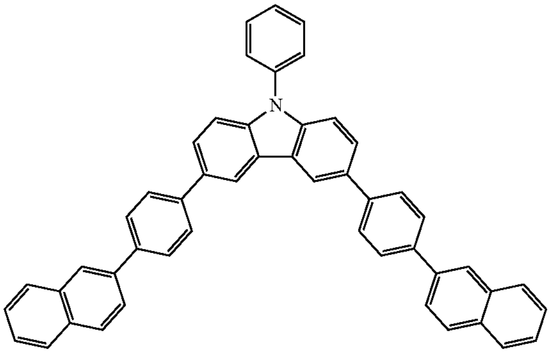
β NP2PC -continued (122)

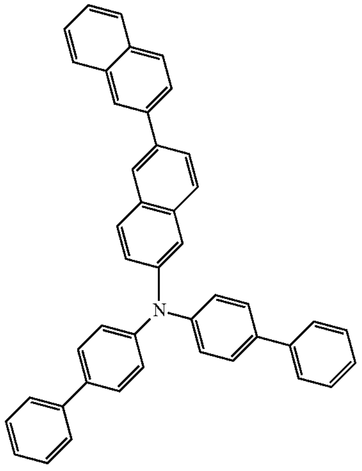

BBA(β N2)B (Method for Fabricating Light-Emitting Element 5)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 10 nm by evaporation, N,N-bis(4-biphenylyl)-2,2'-binaphthyl-6-amine (abbreviation: BBA(βN2)) represented by the structural formula (122) was deposited to a thickness of 10 nm by evaporation, and then, 3,6-bis[4-(2-naphthyl)phenyl]-9-phenyl-9H-carbazole (abbreviation: βNP2PC) represented by the structural formula (viii) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 10 nm by evaporation, and then, bathophenanthroline (abbreviation: BPhen) represented by the structural formula (v) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 5 of this example was fabricated.

(Method for Fabricating Light-Emitting Element 6)

The light-emitting element 6 was fabricated in the same manner as the light-emitting element 5 except that, in the electron-transport layer 114, 2-[3'-(dibenzothiophen-4-yl)biphenyl-3-yl]dibenzo[f,h]quinoxaline (abbreviation: 2mDBTBPDBq-II) represented by the structural formula (vi) was used instead of cgDBCzPA and 2,9-bis(naphthalen-2-yl)-4,7-diphenyl-1,10-phenanthroline (abbreviation: NBPhen) represented by the structural formula (vii) was used instead of BPhen.

The element structures of the light-emitting elements 5 and 6 are shown in the following table.

TABLE 5

| | Hole-injection layer | Hole-transport layer | | | Light-emitting layer | Electron-transport layer | | Electron-injection layer |
|---|---|---|---|---|---|---|---|---|
| | 5 nm | 10 nm | 10 nm | 10 nm | 25 nm | 10 nm | 15 nm | 1 nm |
| Element 5 | HAT-CN | NPB | BBA(βN2) | βNP2PC | cgDBCzPA: | cgDBCzPA | BPhen | LiF |
| Element 6 | | | | | 1,6mMemFLPAPrn | 2mDBTBPDBq-II | NBPhen | |
| | | | | | (1:0.03) | | | |

The light-emitting elements 5 and 6 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 42:
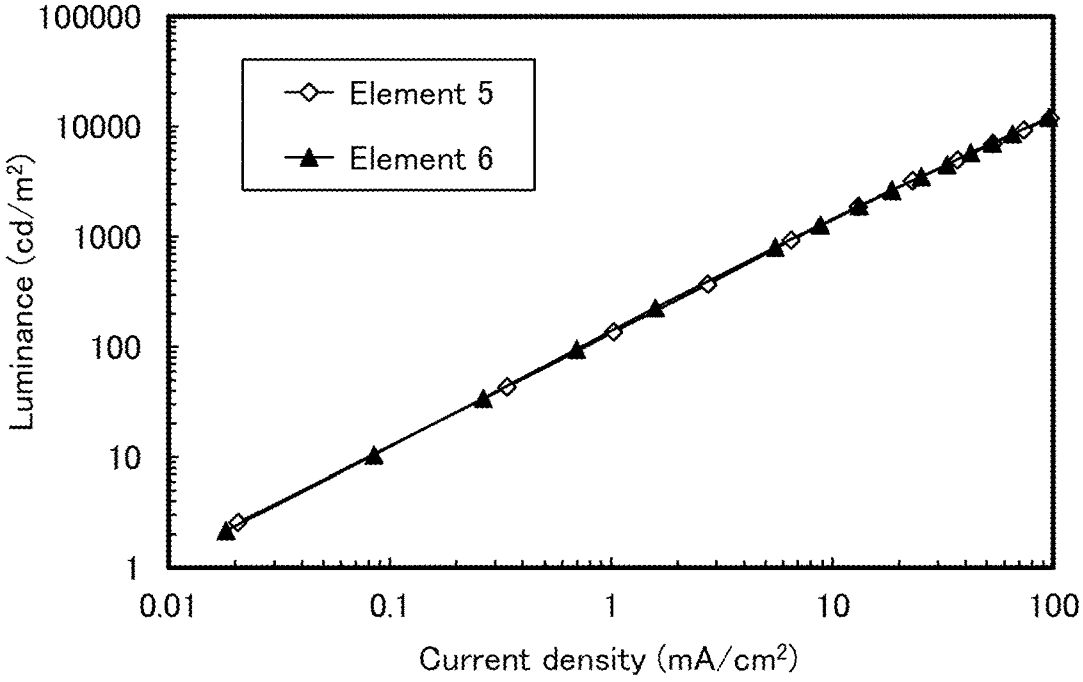
FIG. 42 shows luminance-current density characteristics of light-emitting elements 5 and 6.
Figure 43:
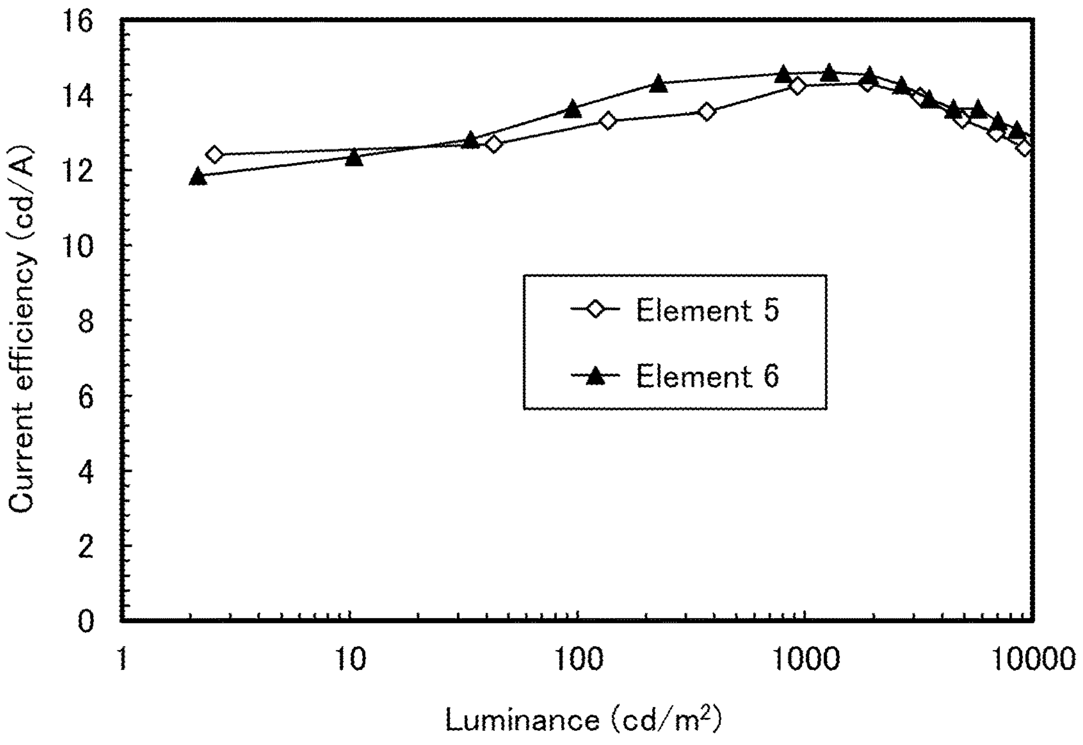
FIG. 43 shows current efficiency-luminance characteristics of the light-emitting elements 5 and 6.
Figure 44:
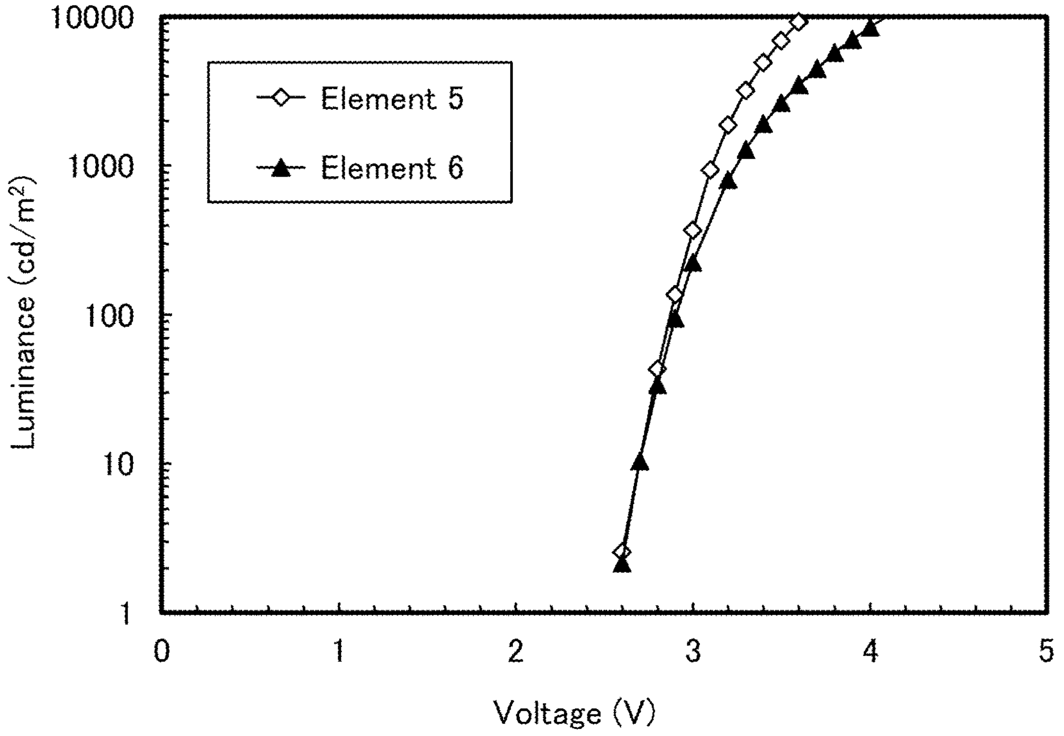
FIG. 44 shows luminance-voltage characteristics of the light-emitting elements 5 and 6.
Figure 45:
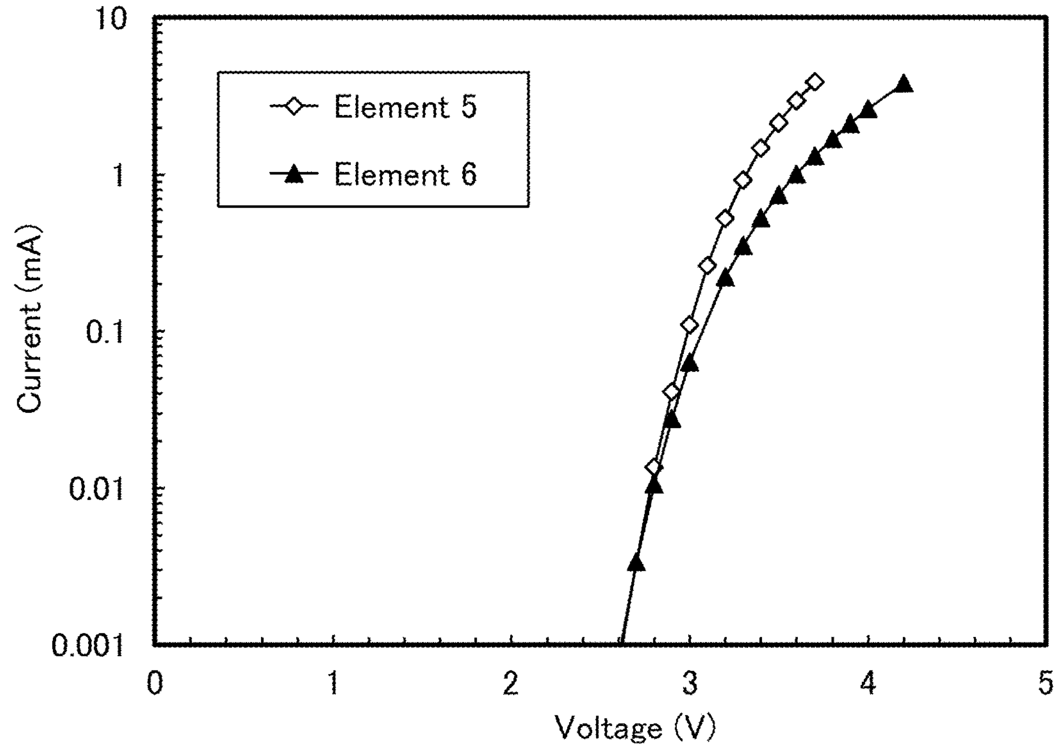
FIG. 45 shows current-voltage characteristics of the light-emitting elements 5 and 6.
Figure 46:
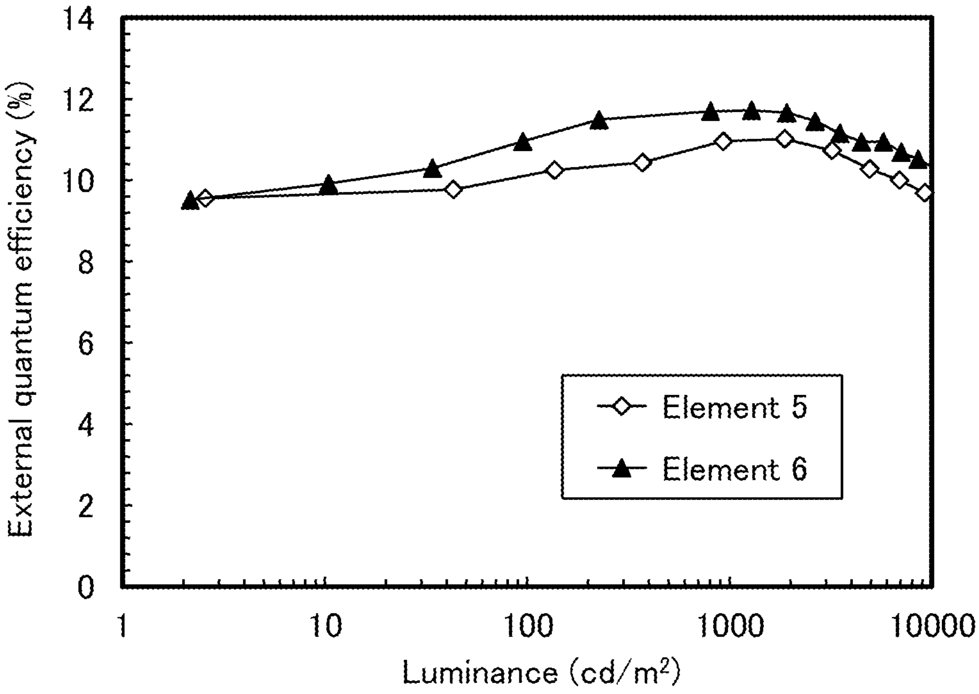
FIG. 46 shows external quantum efficiency-luminance characteristics of the light-emitting elements 5 and 6.
Figure 47:
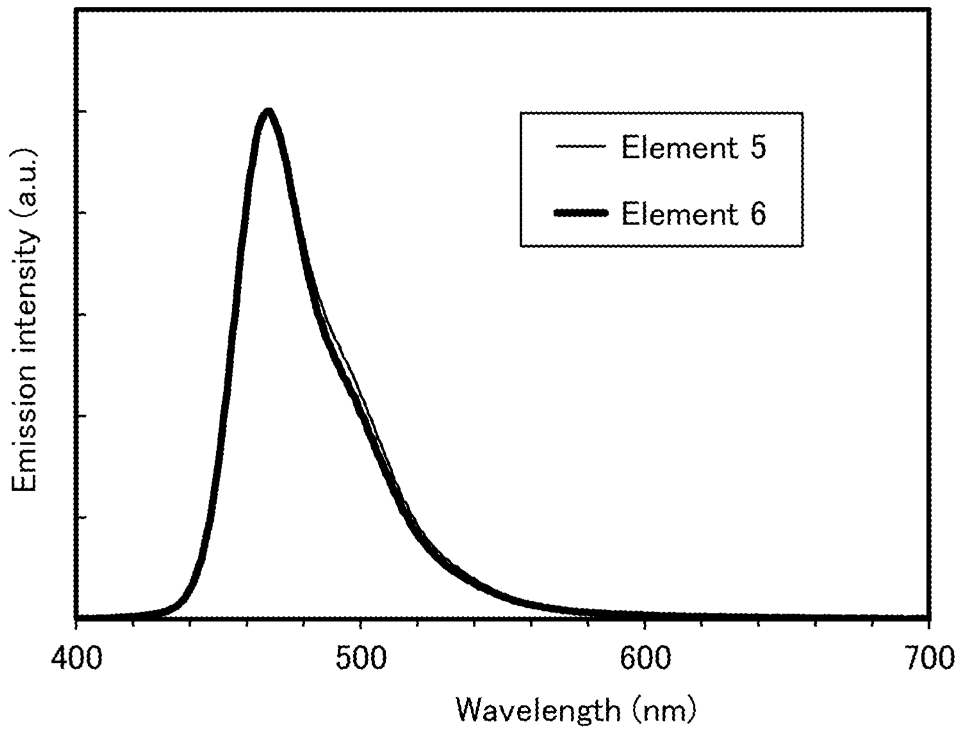
FIG. 47 shows emission spectra of the light-emitting elements 5 and 6.

FIG. 42 shows luminance-current density characteristics of the light-emitting elements 5 and 6. FIG. 43 shows current efficiency-luminance characteristics thereof. FIG. 44 shows luminance-voltage characteristics thereof. FIG. 45 shows current-voltage characteristics thereof. FIG. 46 shows external quantum efficiency-luminance characteristics thereof. FIG. 47 shows emission spectra thereof.

TABLE 6

| | Voltage (V) | Current (mA) | Current density ($mA/cm^2$) | Chromaticity x | Chromaticity y | Current efficiency (cd/A) | External quantum efficiency (%) |
|---|---|---|---|---|---|---|---|
| Element 5 | 3.1 | 0.26 | 6.5 | 0.14 | 0.19 | 14 | 11 |
| Element 6 | 3.2 | 0.22 | 5.5 | 0.14 | 0.18 | 15 | 12 |

According to FIG. 42, FIG. 43, FIG. 44, FIG. 45, FIG. 46, FIG. 47, and Table 6, the light-emitting elements 5 and 6 have very high external quantum efficiencies of 11% and 12%, respectively, at 1000 $cd/m^2$.

Figure 48:
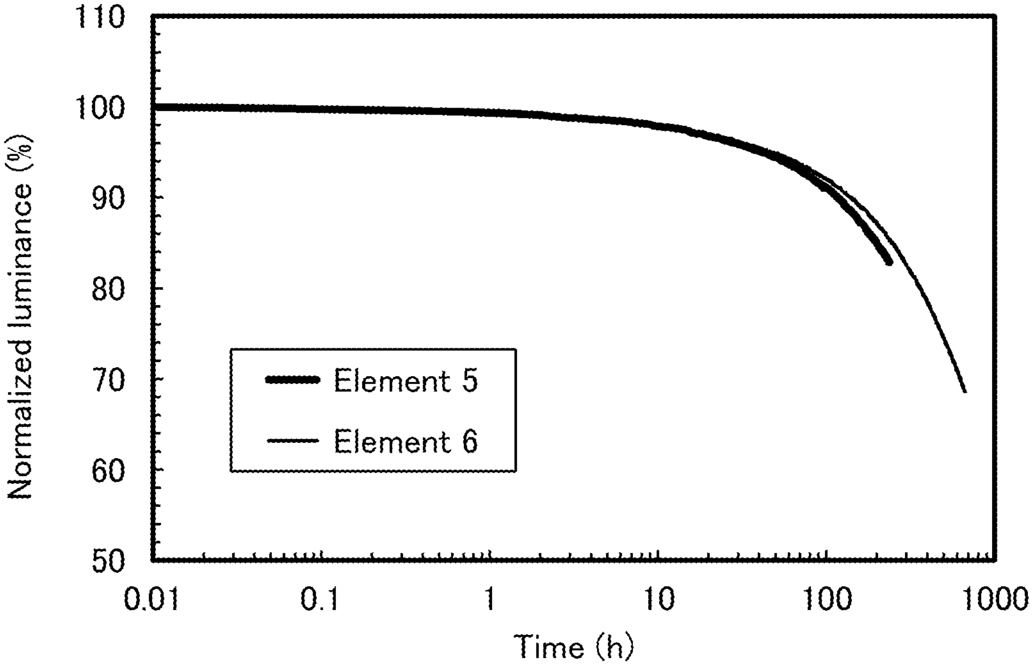
FIG. 48 shows time dependence of normalized luminance of the light-emitting elements 5 and 6.

FIG. 48 is a graph showing driving time-dependent change in luminance under the conditions where the current value was 2 mA and the current density was constant. As shown in FIG. 48, each of the light-emitting elements 5 and 6 maintained 90% or more of the initial luminance after 100-hour-driving and was found to be a long-life light-emitting element whose luminance was only slightly decreased over driving time.

Example 11

In this example, light-emitting elements 7 and 8 which correspond to the light-emitting element of one embodiment of the present invention described in the above embodiment will be described. The structural formulae of organic compounds used for the light-emitting elements 7 and 8 are shown below.

(i)

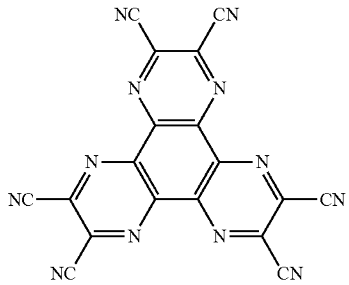

HAT-CN (ii)

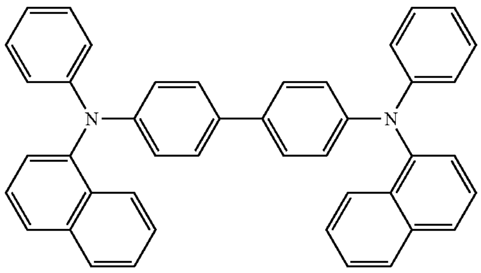

NPB

-continued (iii)

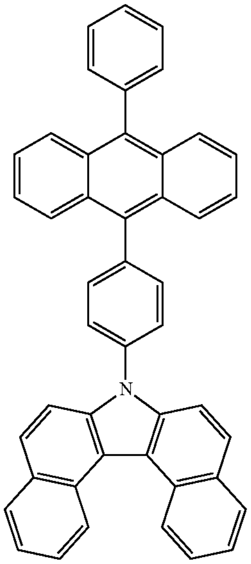

cgDBCzPA (iv)

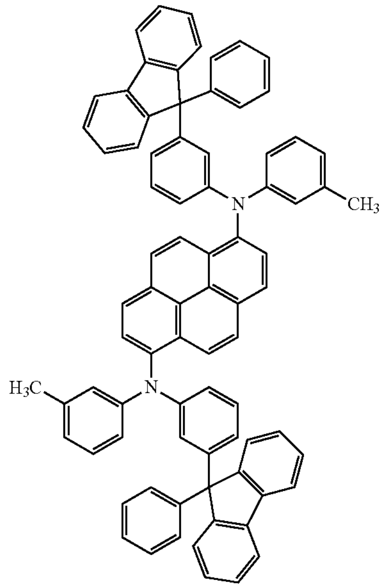

1,6mMemFLPAPrn

-continued (v)

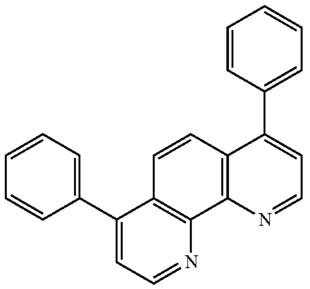

BPhen (vi)

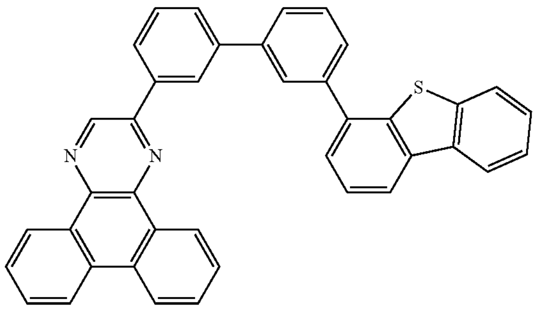

2mDBTBPDBq-II (vii)

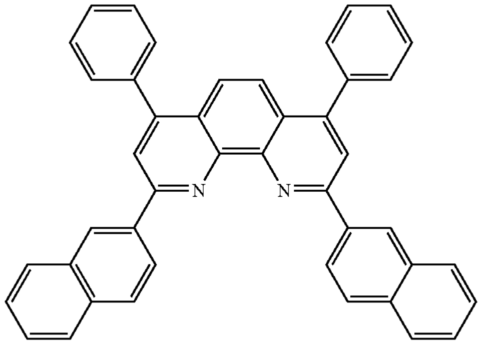

NBPhen (viii)

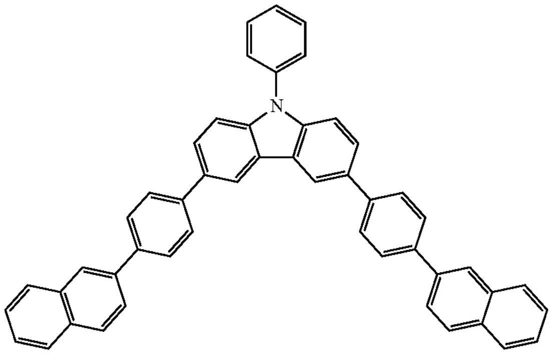

β NP2PC

-continued (116)

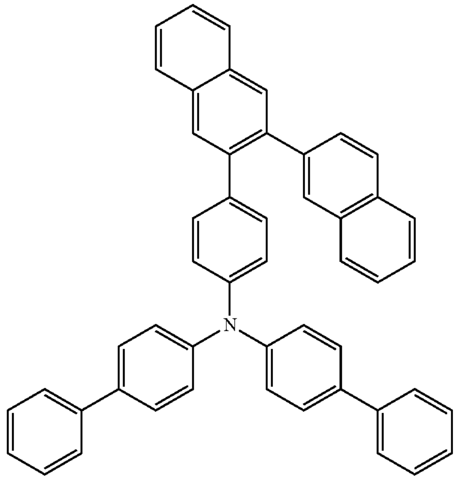

BBA(β N2)B-02

(Method for Fabricating Light-Emitting Element 7)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 20 nm by evaporation, and then, 4-(3;2'-binaphthyl-2-yl)-4',4"-diphenyltriphenylamine (abbreviation: BBA(βN2)B-02) represented by the structural formula (116) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 15 nm by evaporation, and then, bathophenanthroline (abbreviation: BPhen) represented by the structural formula (v) was deposited to a thickness of 10 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 7 of this example was fabricated.

(Method for Fabricating Light-Emitting Element 8)

The light-emitting element 8 was fabricated in the same manner as the light-emitting element 7 except for the following differences: in the electron-transport layer 114, 2-[3'-(dibenzothiophen-4-yl)biphenyl-3-yl]dibenzo[f,h]quinoxaline (abbreviation: 2mDBTBPDBq-J) represented by the structural formula (vi) and having a thickness of 10 nm was used instead of cgDBCzPA, and 2,9-bis(naphthalen-2-yl)-4,7-diphenyl-1,10-phenanthroline (abbreviation: NB Phen) represented by the structural formula (vii) and having a thickness of 15 nm was used instead of BPhen.

The element structures of the light-emitting elements 7 and 8 are shown in the following table.

TABLE 7

| | Hole-injection layer | Hole-transport layer | | Light-emitting layer | | | Electron-injection layer |
|---|---|---|---|---|---|---|---|
| | 5 nm | 20 nm | 10 nm | 25 nm | Electron-transport layer | | 1 nm |
| Element 7 | HAT-CN | NPB | BBA(βN2)B-02 | cgDBCzPA: 1,6mMemFLPAPrn (1:0.03) | cgDBCzPA 15 nm | BPhen 10 nm | LiF |
| Element 8 | | | | | 2mDBTBPDBq-II 10 nm | NBPhen 15 mn | |

The light-emitting elements 7 and 8 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 49:
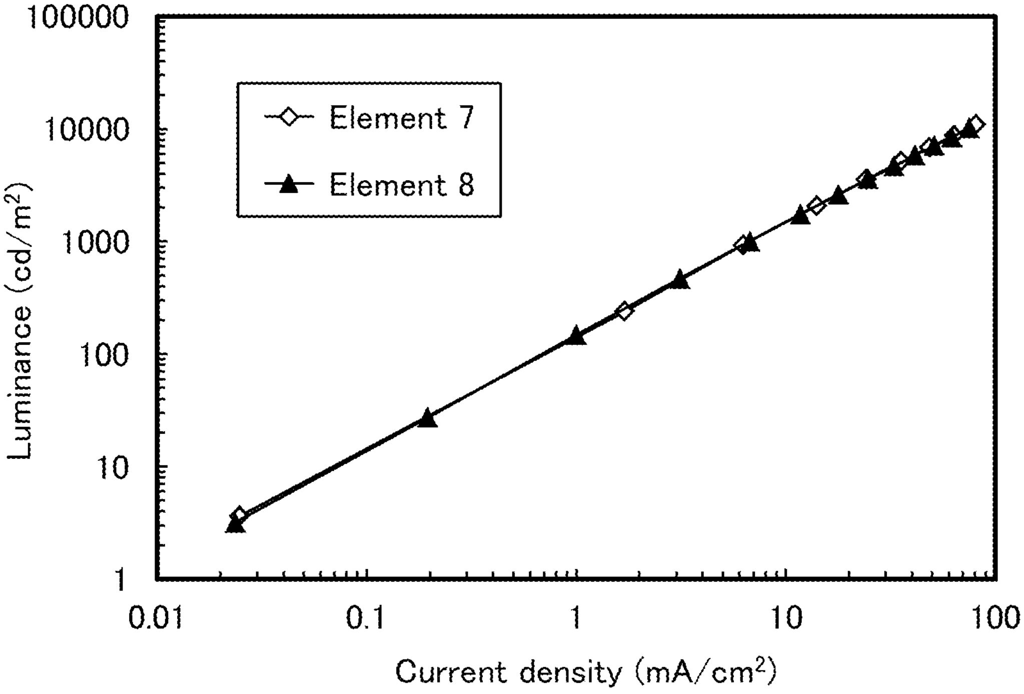
FIG. 49 shows luminance-current density characteristics of light-emitting elements 7 and 8.
Figure 50:
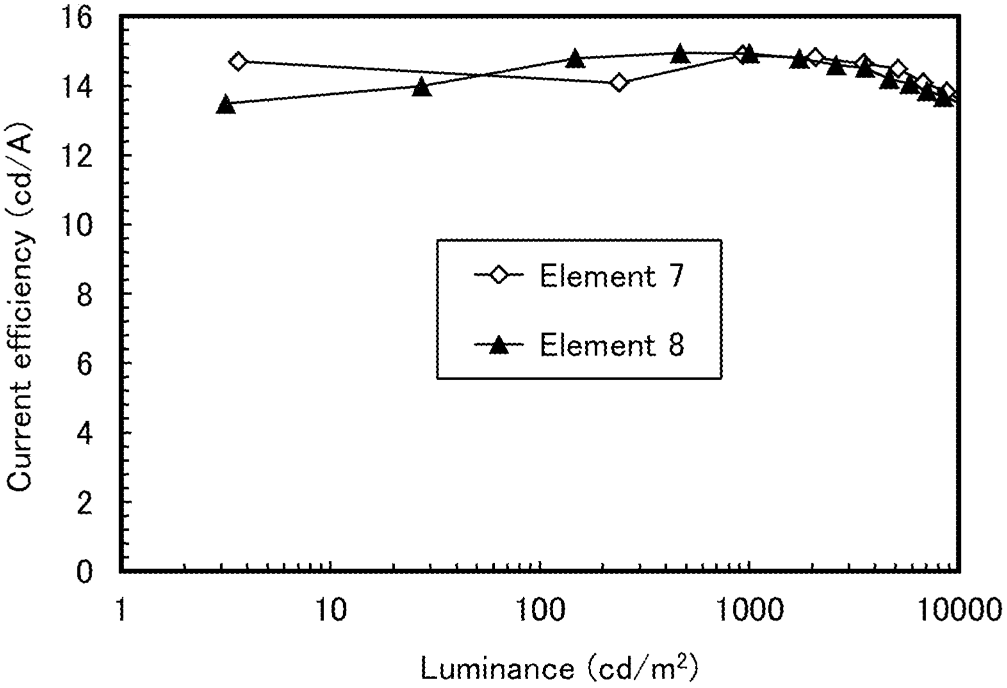
FIG. 50 shows current efficiency-luminance characteristics of the light-emitting elements 7 and 8.
Figure 51:
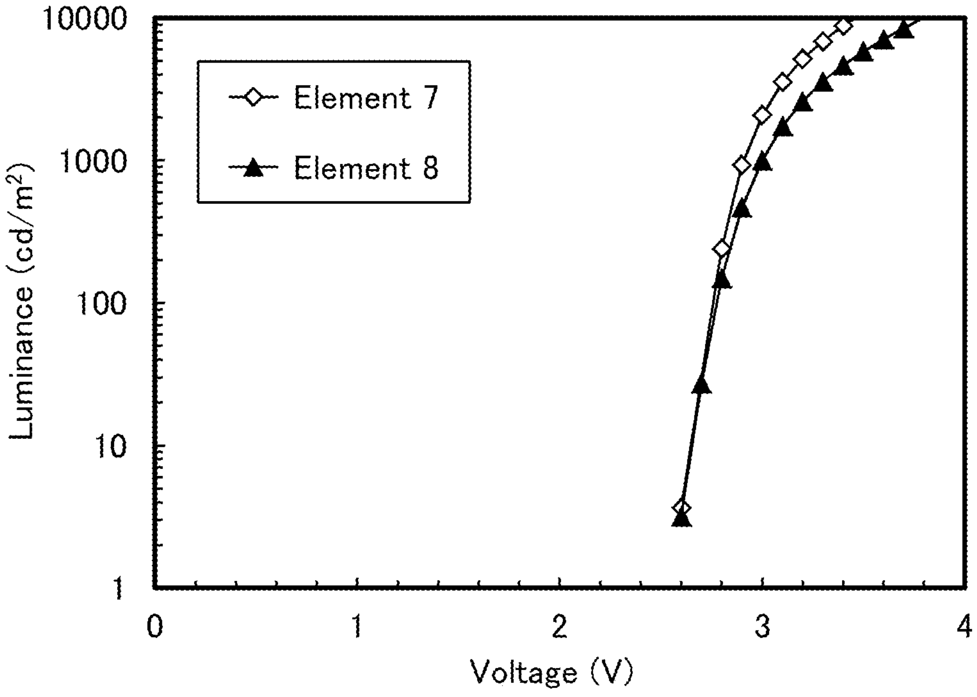
FIG. 51 shows luminance-voltage characteristics of the light-emitting elements 7 and 8.
Figure 52:
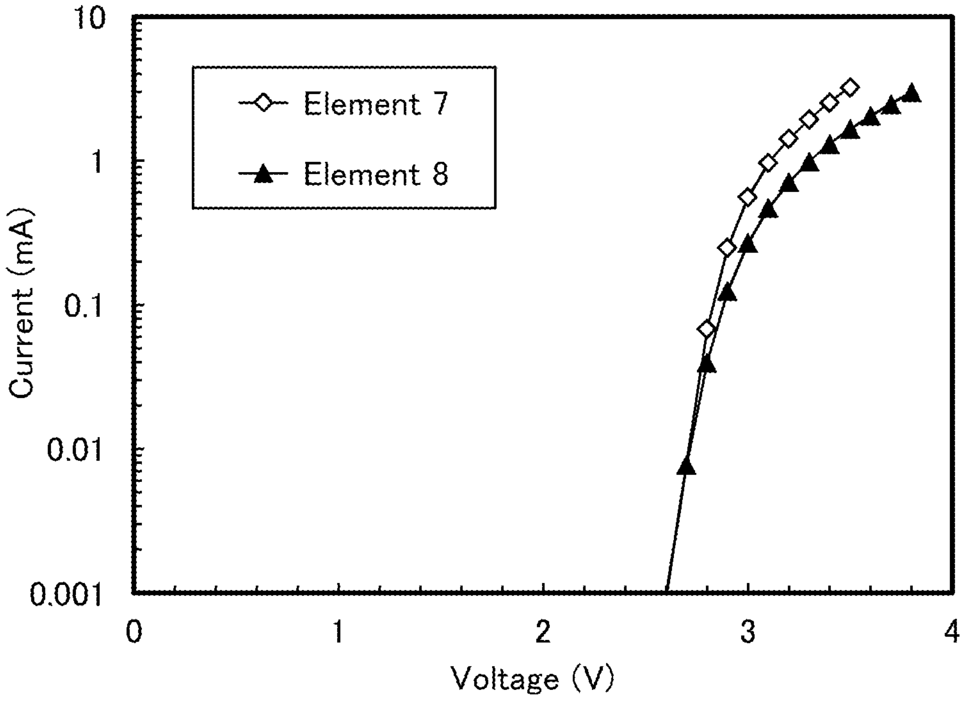
FIG. 52 shows current-voltage characteristics of the light-emitting elements 7 and 8.
Figure 53:
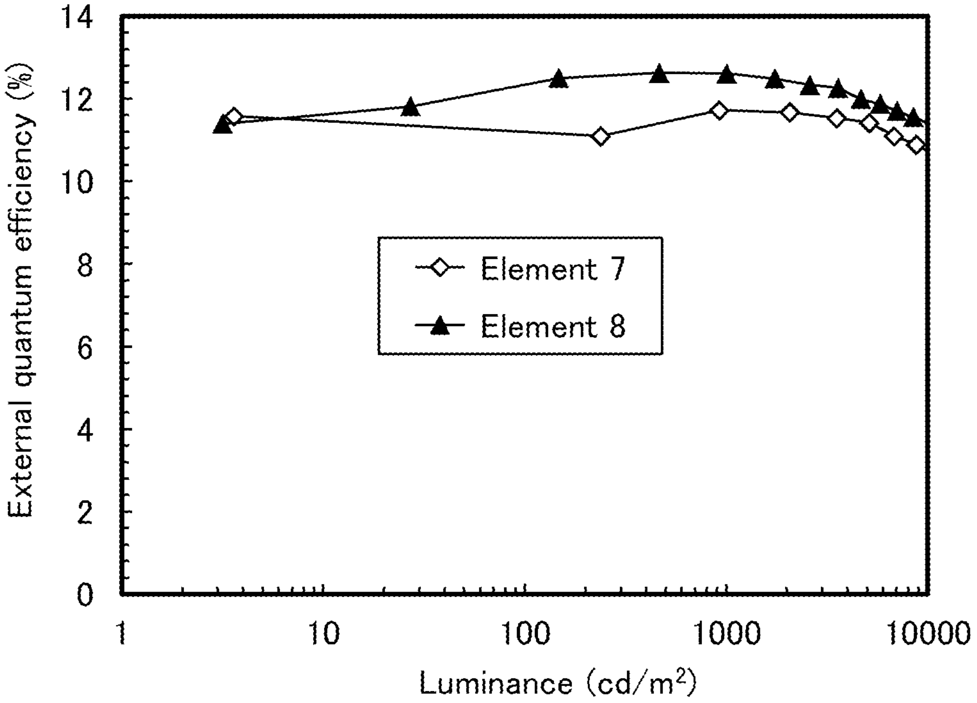
FIG. 53 shows external quantum efficiency-luminance characteristics of the light-emitting elements 7 and 8.
Figure 54:
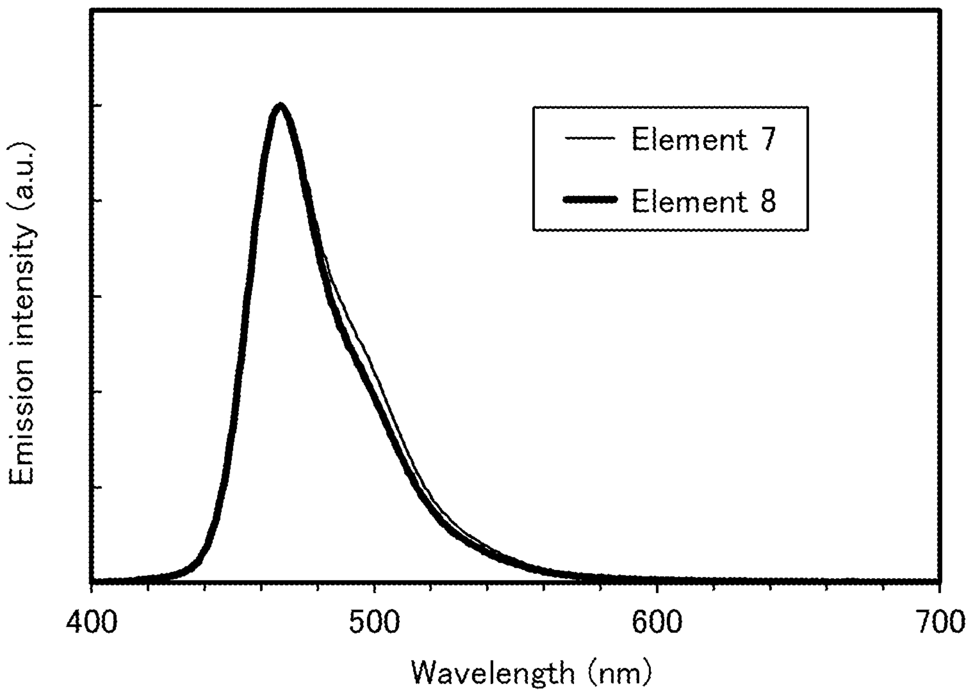
FIG. 54 shows emission spectra of the light-emitting elements 7 and 8.

FIG. 49 shows luminance-current density characteristics of the light-emitting elements 7 and 8. FIG. 50 shows current efficiency-luminance characteristics thereof. FIG. 51 shows luminance-voltage characteristics thereof. FIG. 52 shows current-voltage characteristics thereof. FIG. 53 shows external quantum efficiency-luminance characteristics thereof. FIG. 54 shows emission spectra thereof.

TABLE 8

| | Voltage | Current | Current density | Chromaticity | | Current efficiency | External quantum efficiency |
|---|---|---|---|---|---|---|---|
| | (V) | (mA) | ($mA/cm^2$) | x | y | (cd/A) | (%) |
| Element 7 | 2.9 | 0.25 | 6.2 | 0.14 | 0.19 | 15 | 12 |
| Element 8 | 3.0 | 0.27 | 6.7 | 0.14 | 0.17 | 15 | 13 |

According to FIG. 49, FIG. 50, FIG. 51, FIG. 52, FIG. 53, FIG. 54, and Table 8, the light-emitting elements 7 and 8 have very high external quantum efficiencies of 12% and 13%, respectively, at 1000 $cd/m^2$.

Example 12

In this example, light-emitting elements 9 and 10 which correspond to the light-emitting element of one embodiment of the present invention described in the above embodiment will be described. The structural formulae of organic compounds used for the light-emitting elements 9 and 10 are shown below.

(i)

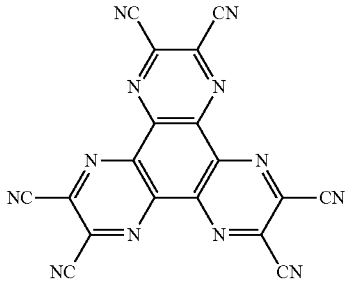

HAT-CN

-continued
(ii)
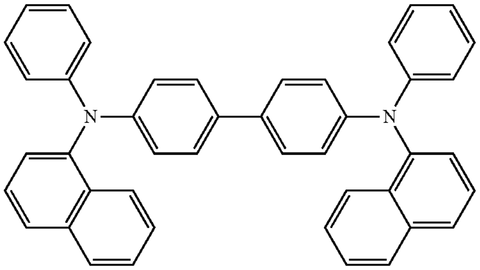
NPB
(iii)
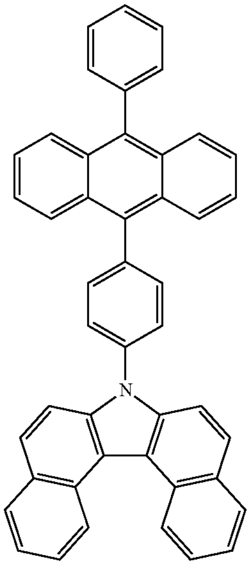
cgDBCzPA
(iv)
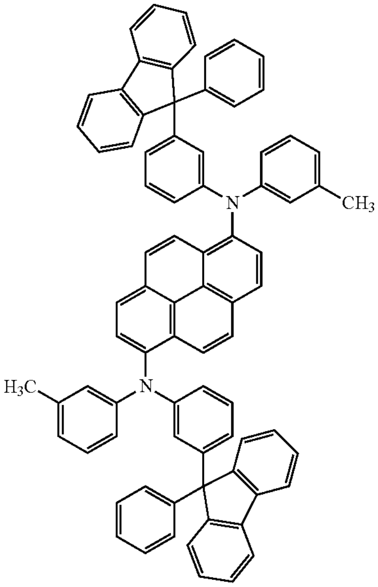
1,6mMemFLPAPrn
-continued
(v)
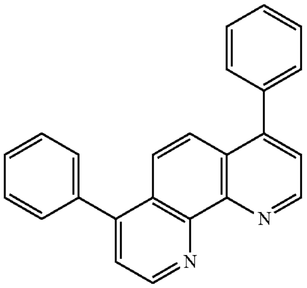
BPhen
(vi)
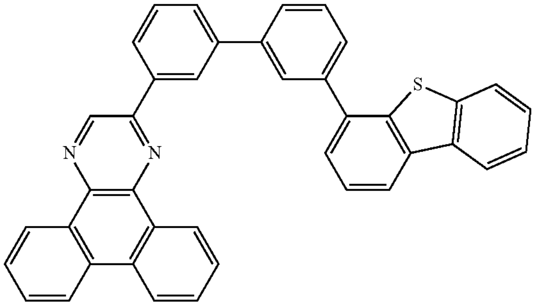
2mDBTBPDBq-II
(vii)
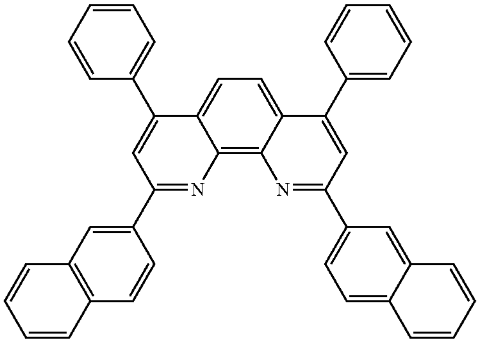
NBPhen
(viii)
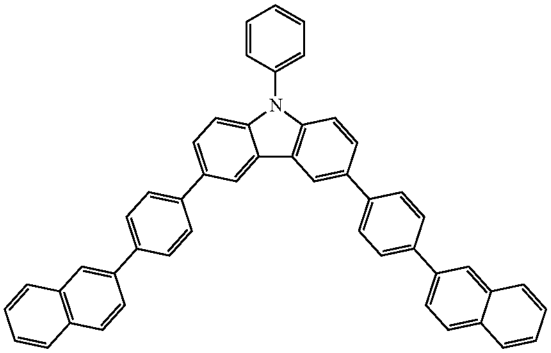
β NP2PC -continued (116)

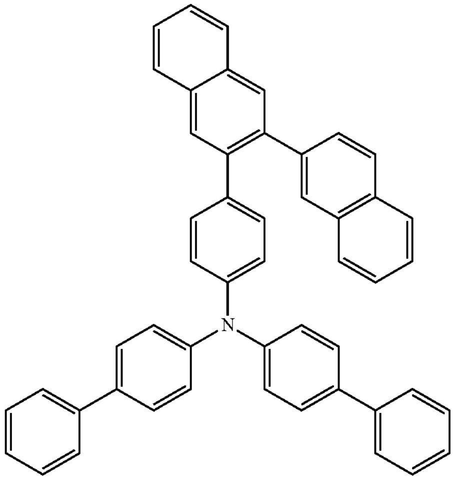

BBA(β N2)B-02

(Method for Fabricating Light-Emitting Element 9)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis [N-(1-naphthyl)-N-phenylamino]biphenyl (abbreviation: NPB) represented by the structural formula (ii) was deposited to a thickness of 10 nm by evaporation, 4-(3;2'-binaphthyl-2-yl)-4',4''-diphenyltriphenylamine (abbreviation: BBA (βN2)B-02) represented by the structural formula (116) was deposited to a thickness of 10 nm by evaporation, and then, 3,6-bis[4-(2-naphthyl)phenyl]-9-phenyl-9H-carbazole (abbreviation: βNP2PC) represented by the structural formula (viii) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 15 nm by evaporation, and then, bathophenanthroline (abbreviation: BPhen) represented by the structural formula (v) was deposited to a thickness of 10 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 9 of this example was fabricated.

(Method for Fabricating Light-Emitting Element 10)

The light-emitting element 10 was fabricated in the same manner as the light-emitting element 9 except for the following differences: in the electron-transport layer 114, 2-[3'-(dibenzothiophen-4-yl)biphenyl-3-yl]dibenzo[f,h]quinoxaline (abbreviation: 2mDBTBPDBq-J) represented by the structural formula (vi) and having a thickness of 10 nm was used instead of cgDBCzPA, and 2,9-bis(naphthalen-2-yl)-4,7-diphenyl-1,10-phenanthroline (abbreviation: NBPhen) represented by the structural formula (vii) and having a thickness of 15 nm was used instead of BPhen.

The element structures of the light-emitting elements 9 and 10 are shown in the following table.

TABLE 9

| Hole-injection layer | Hole-transport layer | | | Light-emitting layer | Electron-transport | | Electron-injection layer |
|---|---|---|---|---|---|---|---|
| 5 nm | 10 nm | 10 nm | 10 nm | 25 nm | layer | | 1 nm |
| HAT-CN | NPB | BBA(βN2)B-02 | βNP2PC | cgDBCzPA: 1,6mMemFLPAPrn (1:0.03) | *1 | *2 | LiF |

*1 Element 9: cgDBCzPA (15 nm), Element 10: 2mDBTBPDBq-II (10 nm)

*2 Element 9: BPhen (10 nm), Element 10: NBPhen (15 nm)

The light-emitting elements 9 and 10 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 55:
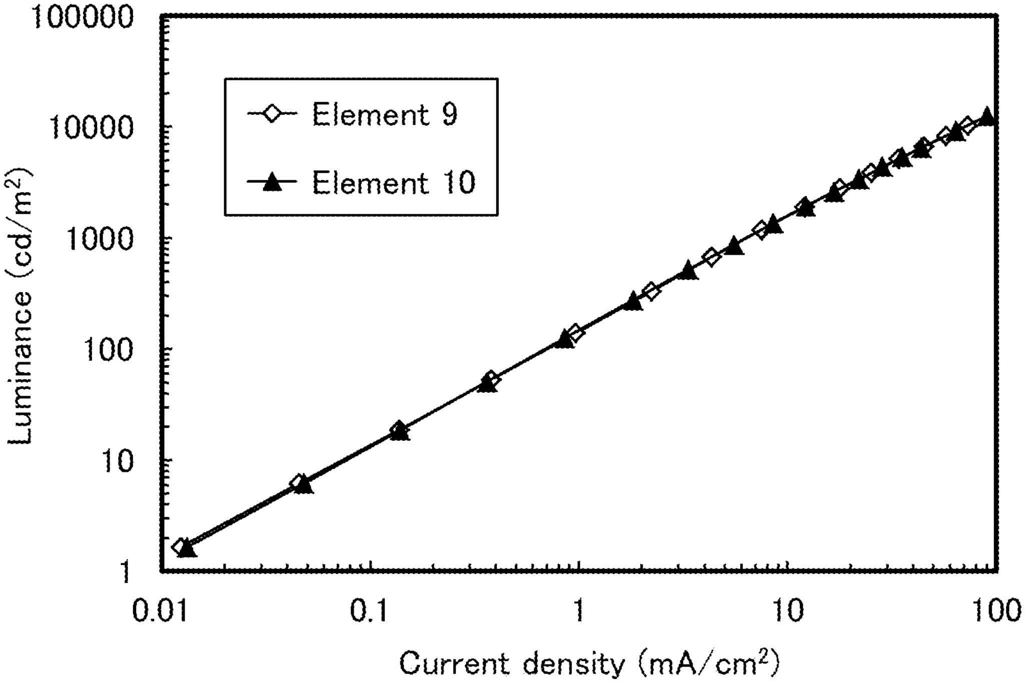
FIG. 55 shows luminance-current density characteristics of light-emitting elements 9 and 10.
Figure 56:
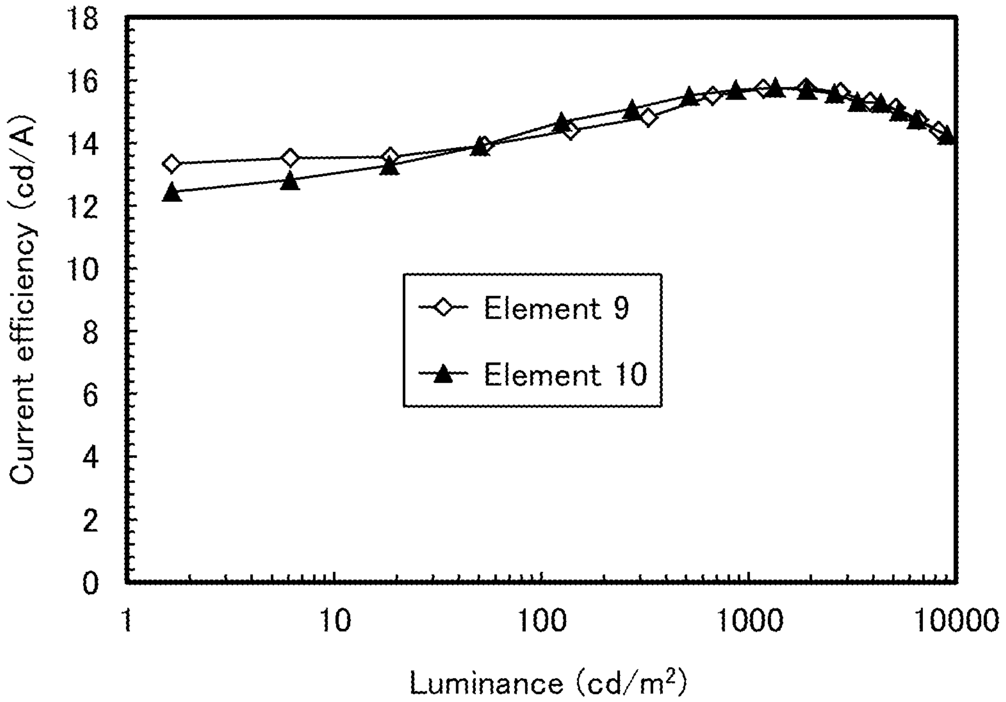
FIG. 56 shows current efficiency-luminance characteristics of the light-emitting elements 9 and 10.
Figure 57:
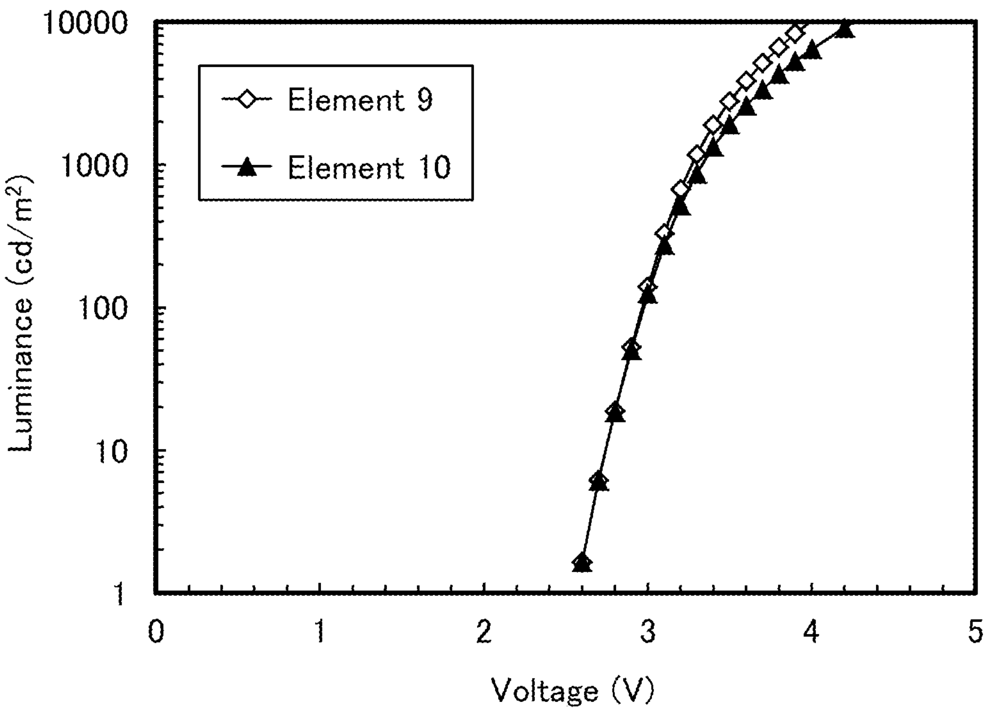
FIG. 57 shows luminance-voltage characteristics of the light-emitting elements 9 and 10.
Figure 58:
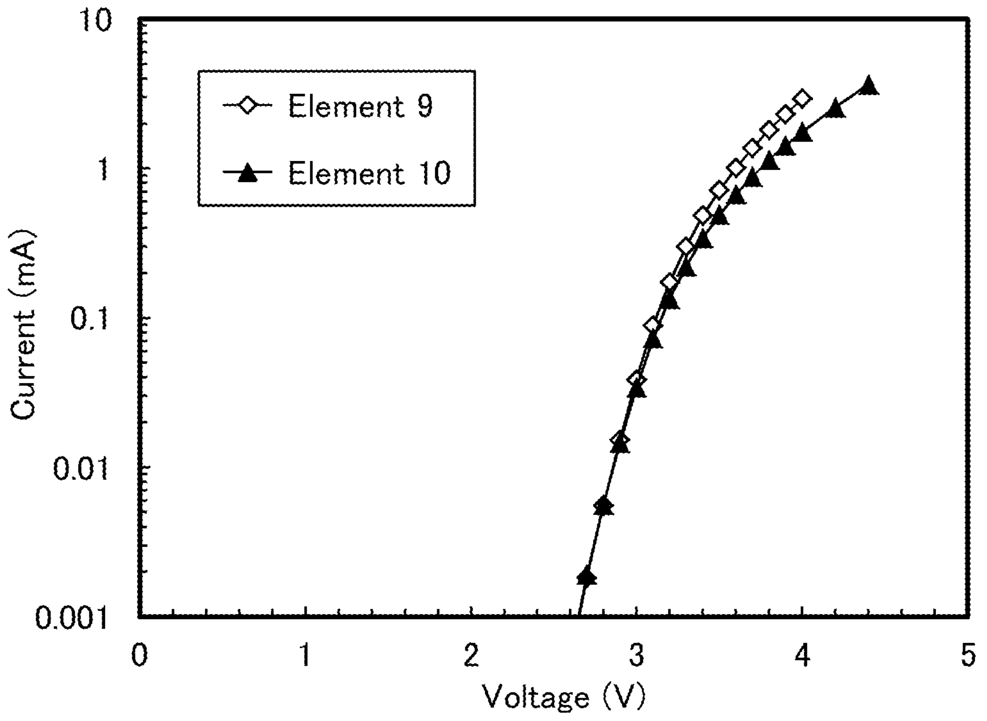
FIG. 58 shows current-voltage characteristics of the light-emitting elements 9 and 10.
Figure 59:
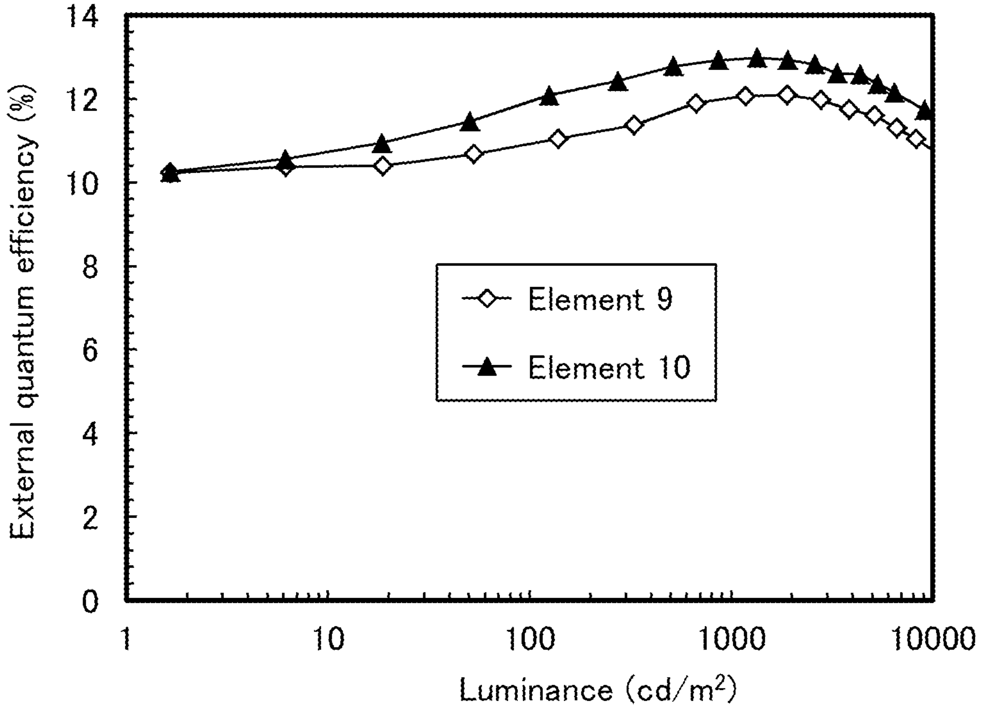
FIG. 59 shows external quantum efficiency-luminance characteristics of the light-emitting elements 9 and 10.
Figure 60:
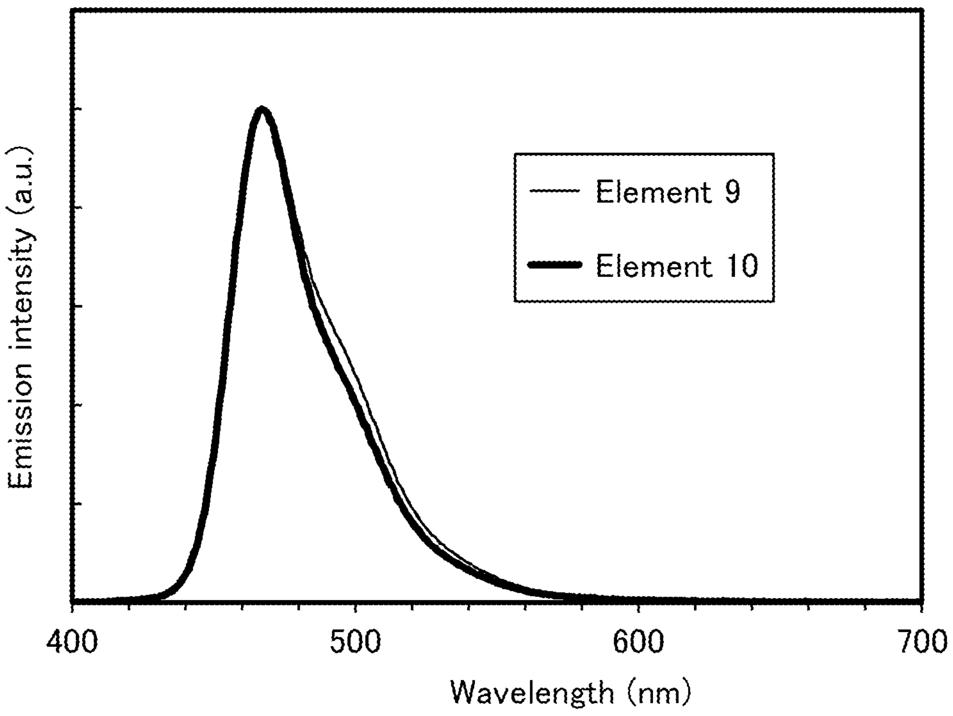
FIG. 60 shows emission spectra of the light-emitting elements 9 and 10.

FIG. 55 shows luminance-current density characteristics of the light-emitting elements 9 and 10. FIG. 56 shows current efficiency-luminance characteristics thereof. FIG. 57 shows luminance-voltage characteristics thereof. FIG. 58 shows current-voltage characteristics thereof. FIG. 59 shows external quantum efficiency-luminance characteristics thereof. FIG. 60 shows emission spectra thereof.

TABLE 10

| | Voltage | Current | Current density | Chromaticity | | Current efficiency | External quantum efficiency |
|---|---|---|---|---|---|---|---|
| | (V) | (mA) | (mA/cm$^2$) | x | y | (cd/A) | (%) |
| Element 9 | 3.3 | 0.30 | 7.5 | 0.14 | 0.20 | 16 | 12 |
| Element 10 | 3.3 | 0.22 | 5.5 | 0.14 | 0.18 | 16 | 13 |

According to FIG. 55, FIG. 56, FIG. 57, FIG. 58, FIG. 59, FIG. 60, and Table 10, the light-emitting elements 9 and 10 have very high external quantum efficiencies of 12% and 13%, respectively, at 1000 cd/m$^2$.

Example 13

In this example, light-emitting elements 11 and 12 which correspond to the light-emitting element of one embodiment of the present invention described in the above embodiment will be described. The structural formulae of organic compounds used for the light-emitting elements 11 and 12 are shown below.

(i)

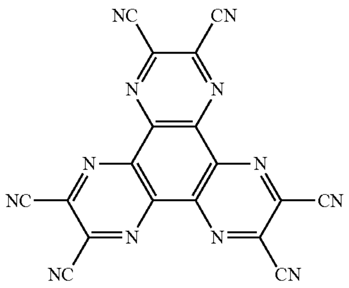

HAT-CN (ii)

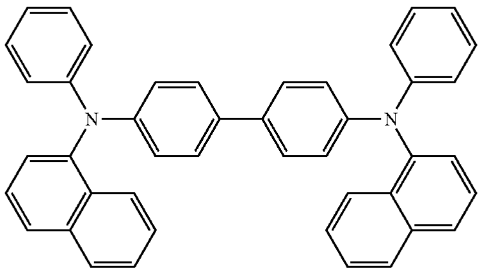

NPB

-continued (iii)

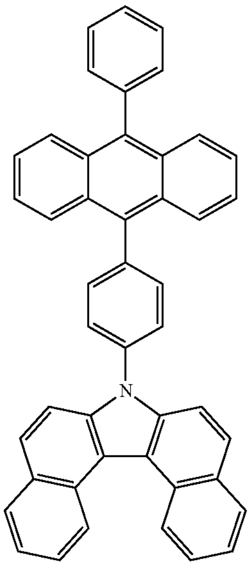

cgDBCzPA (iv)

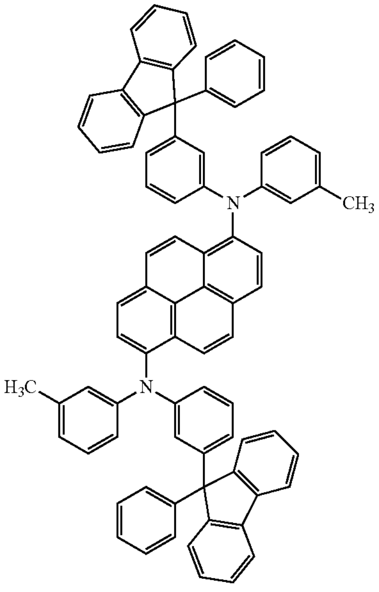

1,6mMemFLPAPrn

-continued (v)

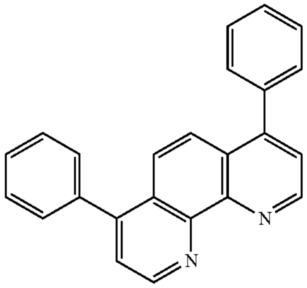

BPhen (vi)

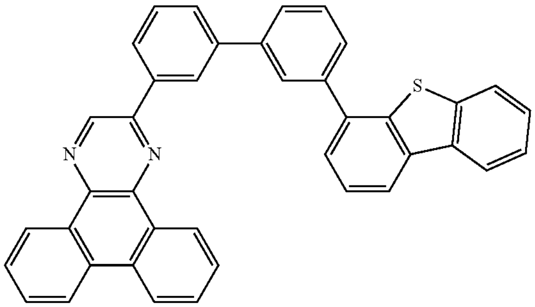

2mDBTBPDBq-II (vii)

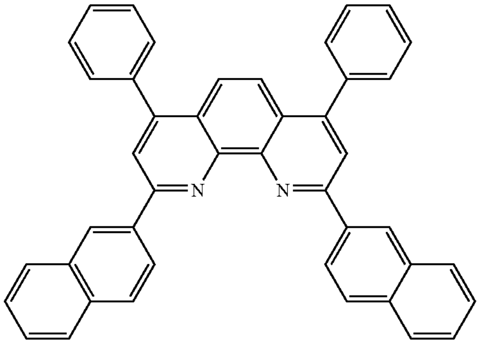

NBPhen (viii)

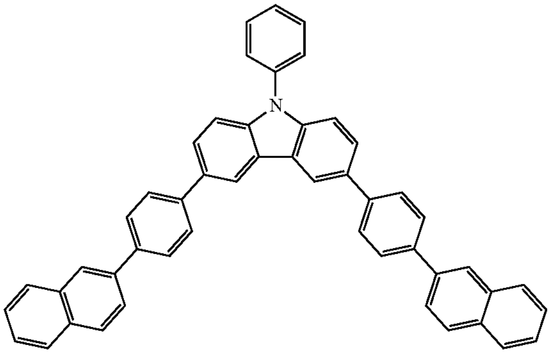

β NP2PC

-continued (117)

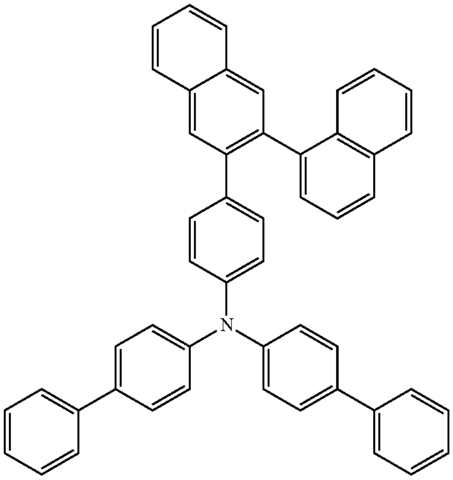

BBAαNβNB-02

(Method for Fabricating Light-Emitting Element 11)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 20 nm by evaporation, and then, 4-(2;1'-binaphthyl-3-yl)-4',4"-diphenyltriphenylamine (abbreviation: BBAαNβNB-02) represented by the structural formula (117) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 15 nm by evaporation, and then, bathophenanthroline (abbreviation: BPhen) represented by the structural formula (v) was deposited to a thickness of 10 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 11 of this example was fabricated.

(Method for Fabricating Light-Emitting Element 12)

The light-emitting element 12 was fabricated in the same manner as the light-emitting element 11 except for the following differences: in the electron-transport layer 114, 2-[3'-(dibenzothiophen-4-yl)biphenyl-3-yl]dibenzo[f,h]quinoxaline (abbreviation: 2mDBTBPDBq-J) represented by the structural formula (vi) and having a thickness of 10 nm was used instead of cgDBCzPA, and 2,9-bis(naphthalen-2-yl)-4,7-diphenyl-1,10-phenanthroline (abbreviation: NBPhen) represented by the structural formula (vii) and having a thickness of 15 nm was used instead of BPhen.

The element structures of the light-emitting elements 11 and 12 are shown in the following table.

TABLE 11

| | Hole-injection | Hole-transport layer | | Light-emitting layer | | | Electron-injection layer |
|---|---|---|---|---|---|---|---|
| | 5 mn | 20 mn | 10 mn | 25 mn | Electron-transport layer | | 1 nm |
| Element 11 | HAT-CN | NPB | BBAαNβNB-02 | cgDBCzPA: 1,6mMemFLPAPrn (1:0.03) | cgDBCzPA 15 mn | BPhen 10 mn | LiF |
| Element 12 | | | | | 2mDBTBPDBq-II 10 nm | NBPhen 15 nm | |

The light-emitting elements 11 and 12 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 61:
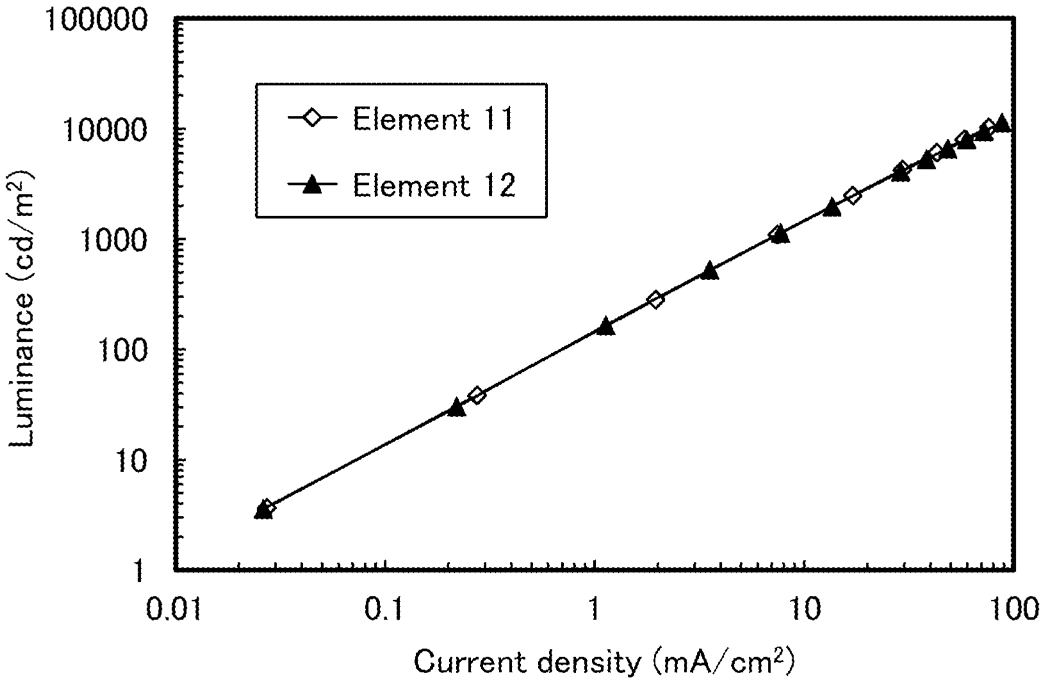
FIG. 61 shows luminance-current density characteristics of light-emitting elements 11 and 12.
Figure 62:
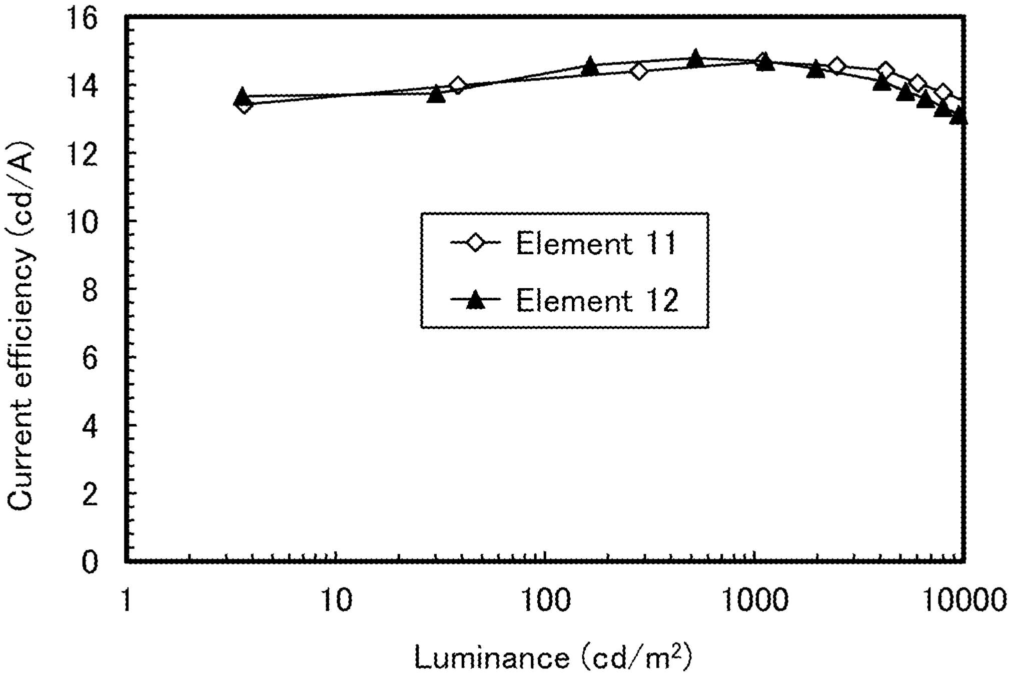
FIG. 62 shows current efficiency-luminance characteristics of the light-emitting elements 11 and 12.
Figure 63:
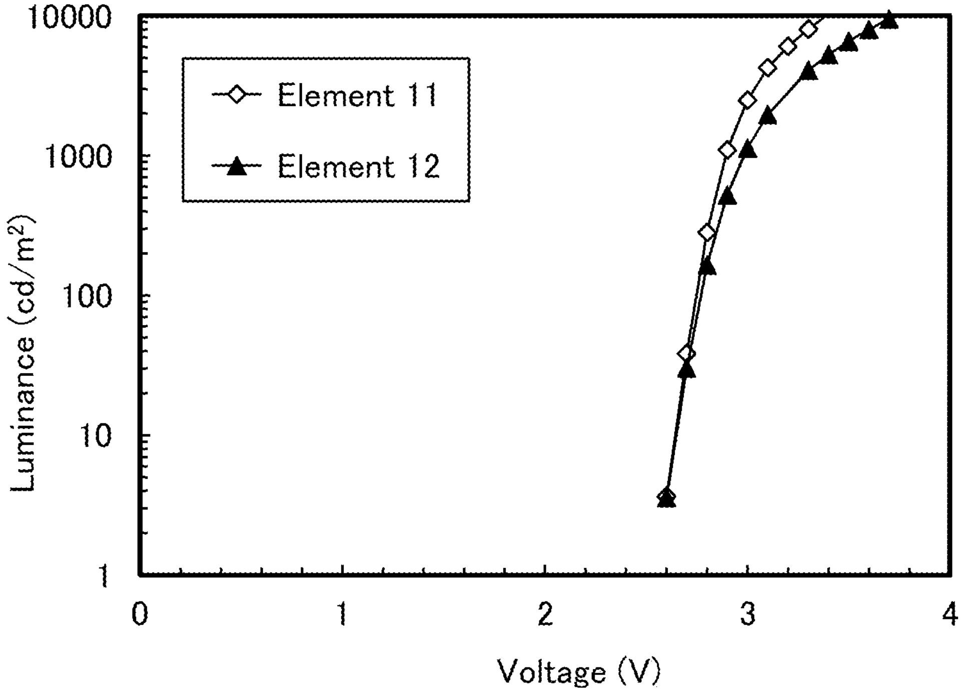
FIG. 63 shows luminance-voltage characteristics of the light-emitting elements 11 and 12.
Figure 64:
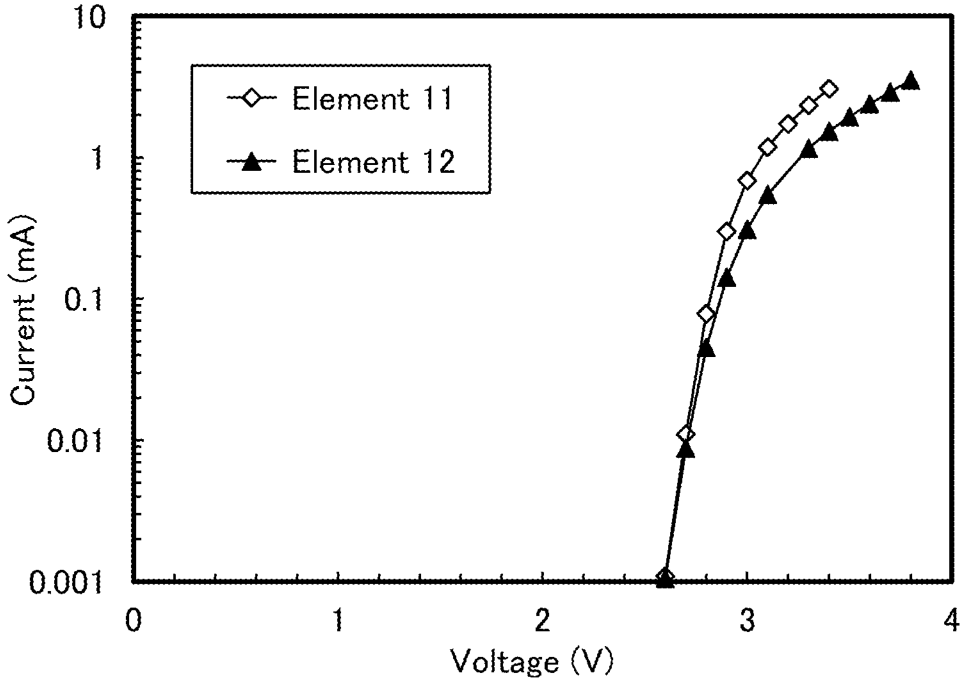
FIG. 64 shows current-voltage characteristics of the light-emitting elements 11 and 12.
Figure 65:
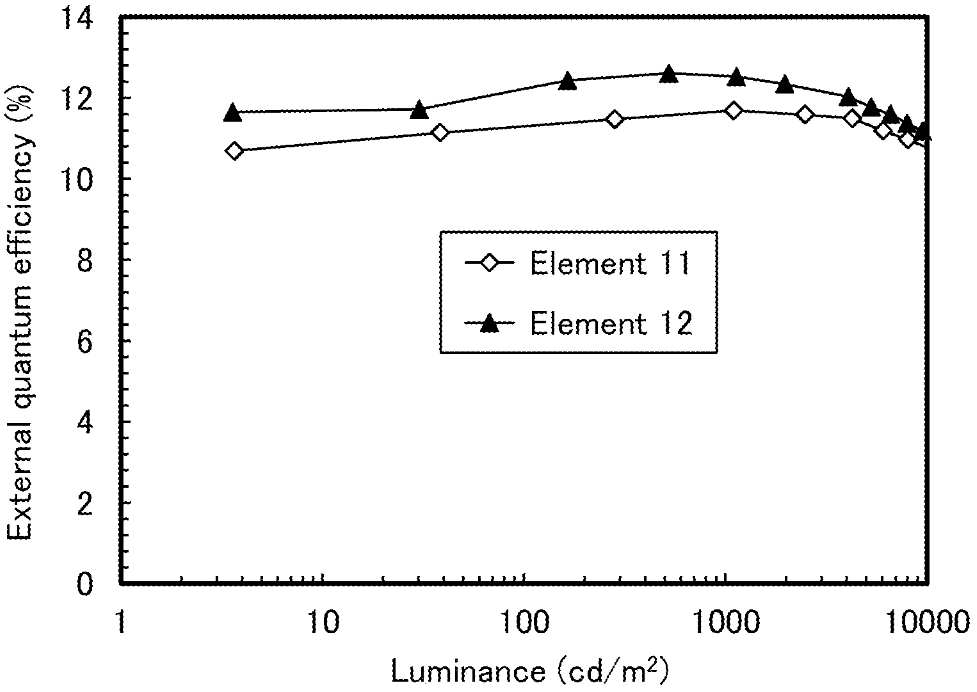
FIG. 65 shows external quantum efficiency-luminance characteristics of the light-emitting elements 11 and 12.
Figure 66:
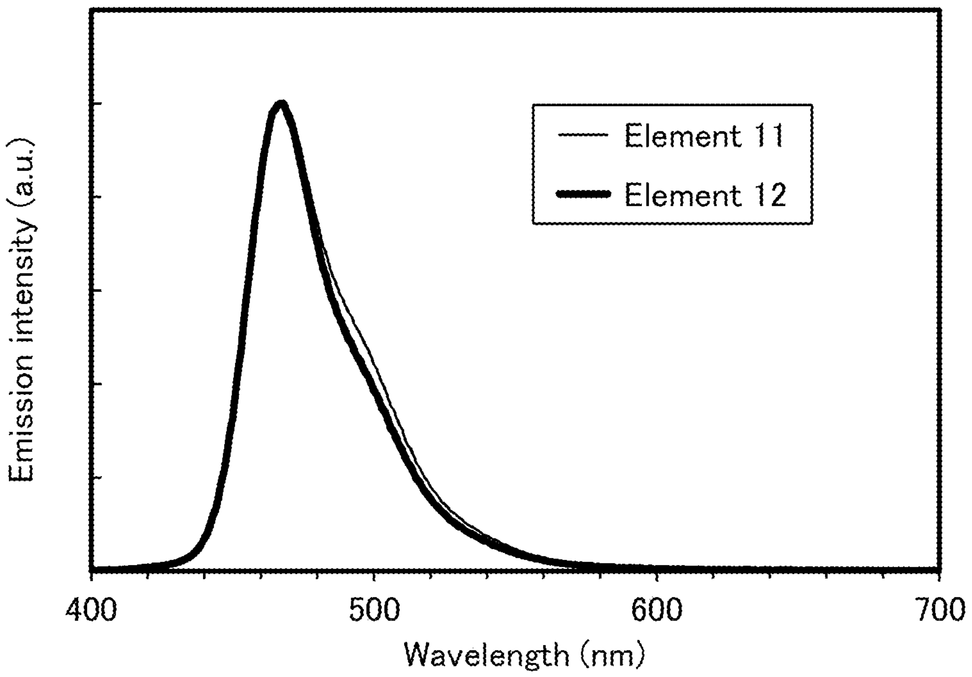
FIG. 66 shows emission spectra of the light-emitting elements 11 and 12.

FIG. 61 shows luminance-current density characteristics of the light-emitting elements 11 and 12. FIG. 62 shows current efficiency-luminance characteristics thereof. FIG. 63 shows luminance-voltage characteristics thereof. FIG. 64 shows current-voltage characteristics thereof. FIG. 65 shows external quantum efficiency-luminance characteristics thereof. FIG. 66 shows emission spectra thereof.

TABLE 12

| | Voltage | Current | Current density | Chromaticity | | Current efficiency | External quantum efficiency |
|---|---|---|---|---|---|---|---|
| | (V) | (mA) | (mA/cm$^2$) | x | y | (cd/A) | (%) |
| Element 11 | 2.9 | 0.30 | 7.5 | 0.14 | 0.19 | 15 | 12 |
| Element 12 | 3.0 | 0.31 | 7.7 | 0.14 | 0.17 | 15 | 13 |

According to FIG. 61, FIG. 62, FIG. 63, FIG. 64, FIG. 65, FIG. 66, and Table 12, the light-emitting elements 11 and 12 have external quantum efficiencies of 12% and 13%, respectively, at 1000 cd/m$^2$.

Example 14

In this example, light-emitting elements 13 and 14 which correspond to the light-emitting element of one embodiment of the present invention described in the above embodiment will be described. The structural formulae of organic compounds used for the light-emitting elements 13 and 14 are shown below.

(i)

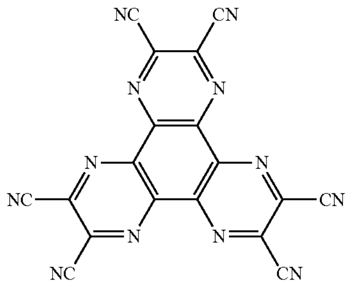

HAT-CN

-continued
(ii)
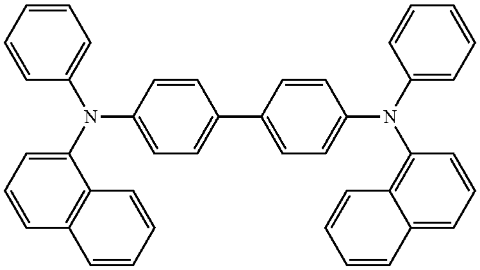
NPB
(iii)
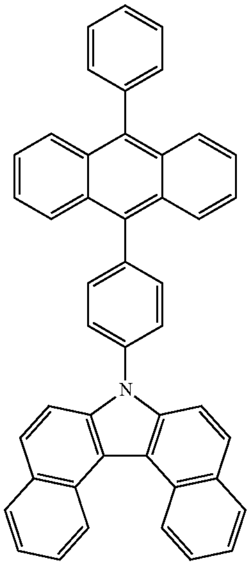
cgDBCzPA
(iv)
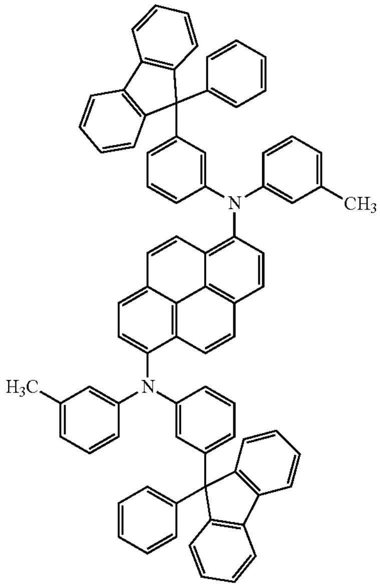
1,6mMemFLPAPrn
-continued
(v)
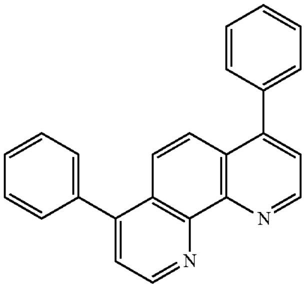
BPhen
(vi)
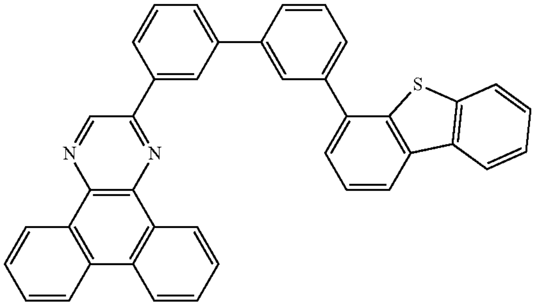
2mDBTBPDBq-II
(vii)
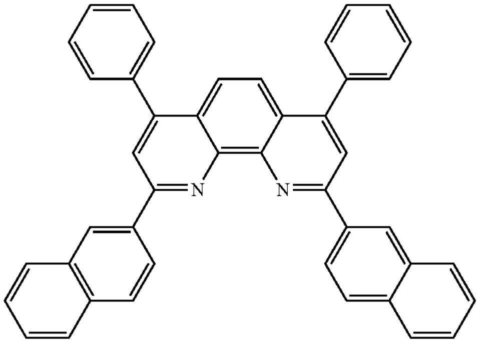
NBPhen
(viii)
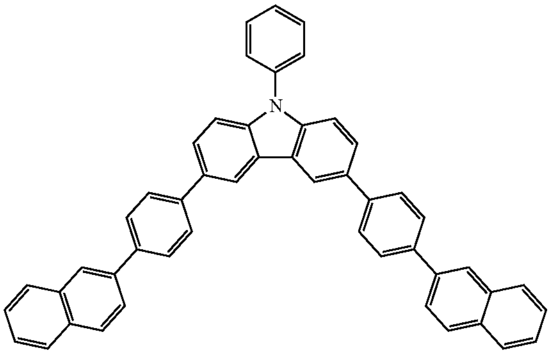
β NP2PC -continued (117)

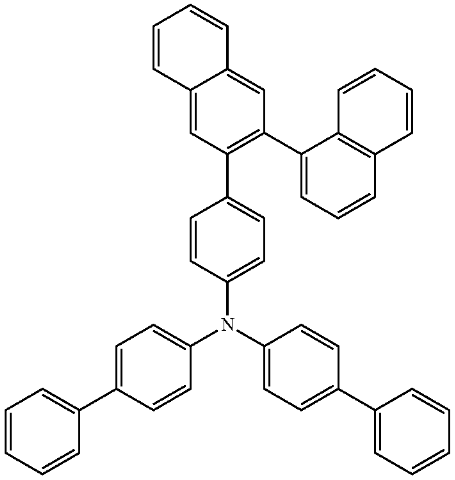

BBAαNβNB-02

(Method for Fabricating Light-Emitting Element 13)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 10 nm by evaporation, 4-(2;1'-binaphthyl-3-yl)-4',4"-diphenyltriphenylamine (abbreviation: BBAαNβNB-02) represented by the structural formula (117) was deposited to a thickness of 10 nm by evaporation, and then, 3,6-bis[4-(2-naphthyl)phenyl]-9-phenyl-9H-carbazole (abbreviation: βNP2PC) represented by the structural formula (viii) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 15 nm by evaporation, and then, bathophenanthroline (abbreviation: BPhen) represented by the structural formula (v) was deposited to a thickness of 10 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 13 of this example was fabricated.

(Method for Fabricating Light-Emitting Element 14)

The light-emitting element 14 was fabricated in the same manner as the light-emitting element 13 except for the following differences: in the electron-transport layer 114, 2-[3'-(dibenzothiophen-4-yl)biphenyl-3-yl]dibenzo[f,h]quinoxaline (abbreviation: 2mDBTBPDBq-II) represented by the structural formula (vi) and having a thickness of 10 nm was used instead of cgDBCzPA, and 2,9-bis(naphthalen-2-yl)-4,7-diphenyl-1,10-phenanthroline (abbreviation: NBPhen) represented by the structural formula (vii) and having a thickness of 15 nm was used instead of BPhen.

The element structures of the light-emitting elements 13 and 14 are shown in the following table.

TABLE 13

| Hole-injection layer | Hole-transport layer | | | Light-emitting layer | Electron-transport layer | | Electron-injection layer |
|---|---|---|---|---|---|---|---|
| 5 nm | 10 nm | 10 nm | 10 nm | 25 nm | | | 1 nm |
| HAT-CN | NPB | BBAαNβNB-02 | βNP2PC | cgDBCzPA: 1,6mMemFLPAPrn (1:0.03) | *3 | *4 | LiF |

*3 Element 13: cgDBCzPA (15 nm), Element 14: 2mDBTBPDBq-II (10 nm)

*4 Element 13: BPhen (10 nm), Element 14: NBPhen (15 nm)

The light-emitting elements 13 and 14 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

Figure 67:
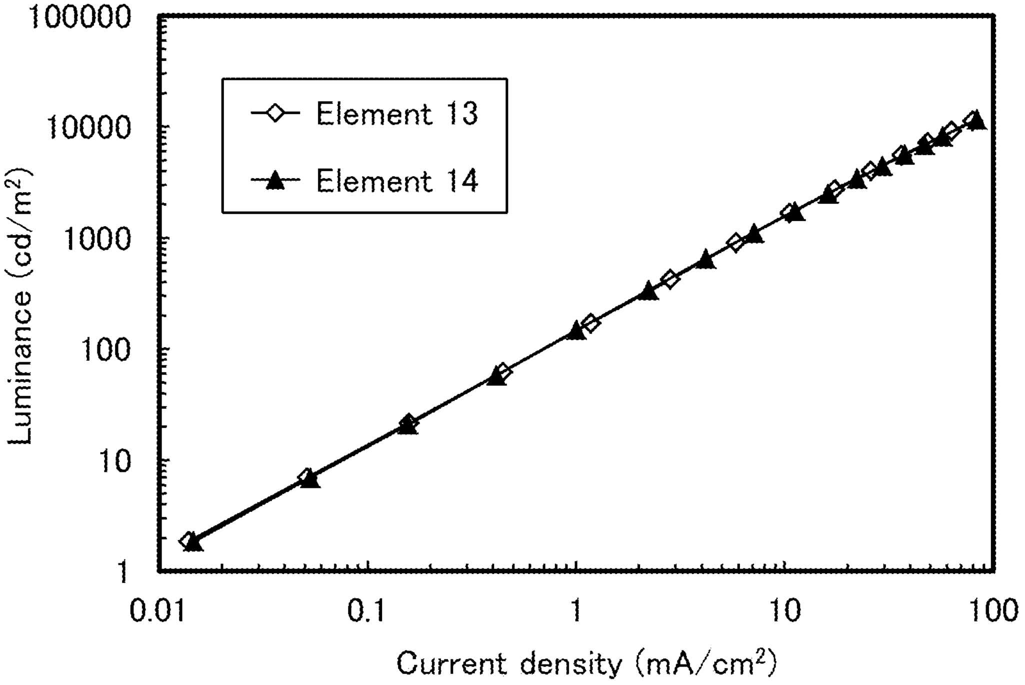
FIG. 67 shows luminance-current density characteristics of light-emitting elements 13 and 14.
Figure 68:
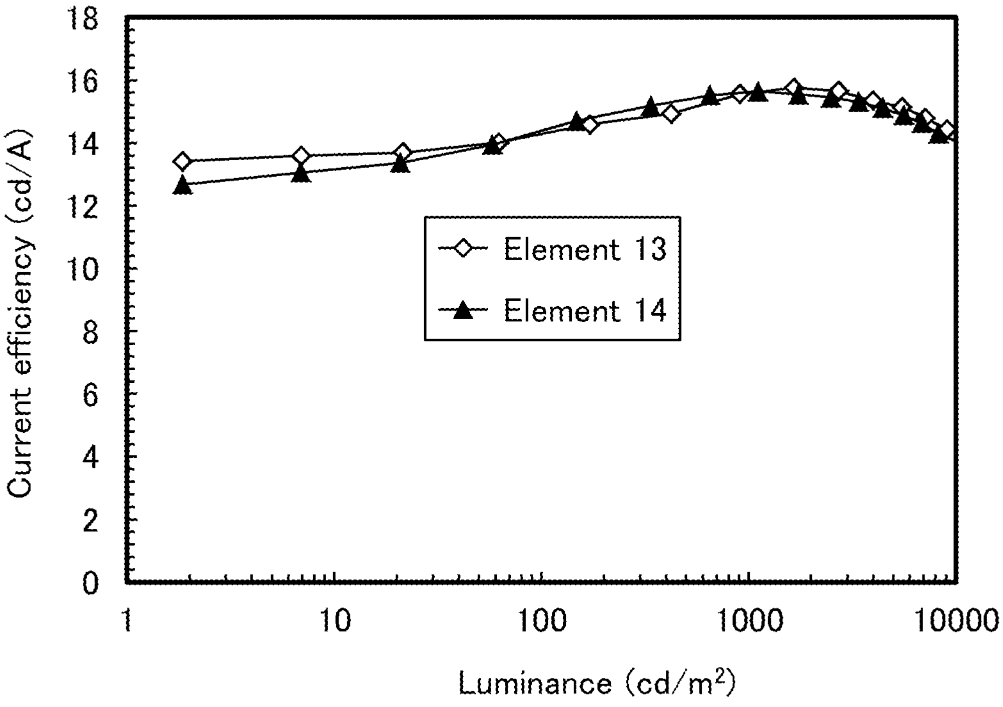
FIG. 68 shows current efficiency-luminance characteristics of the light-emitting elements 13 and 14.
Figure 69:
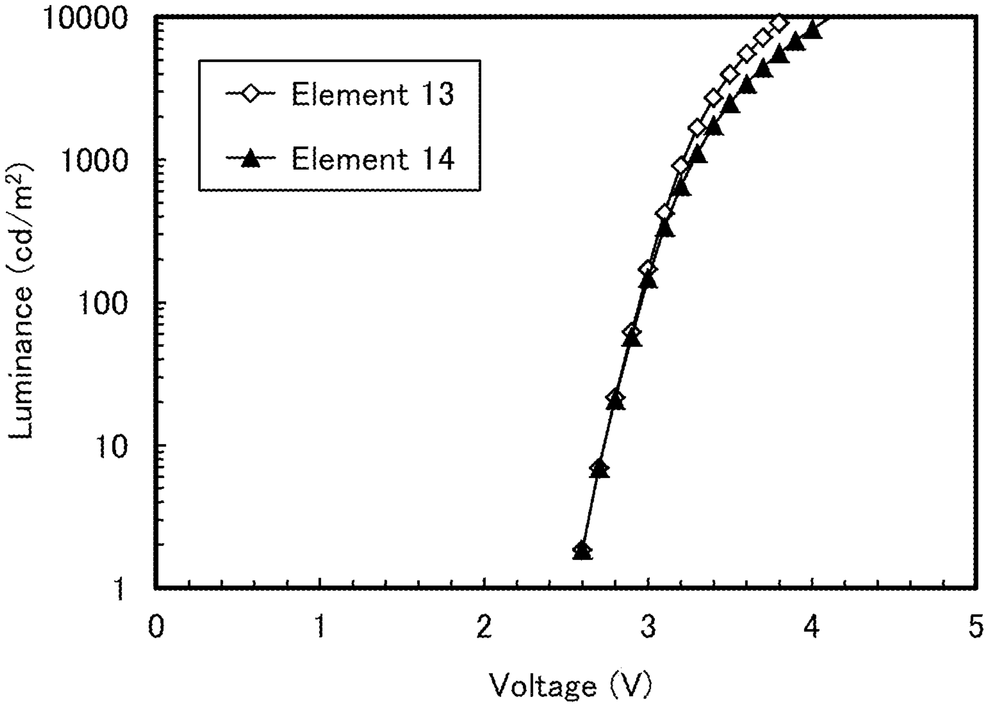
FIG. 69 shows luminance-voltage characteristics of the light-emitting elements 13 and 14.
Figure 70:
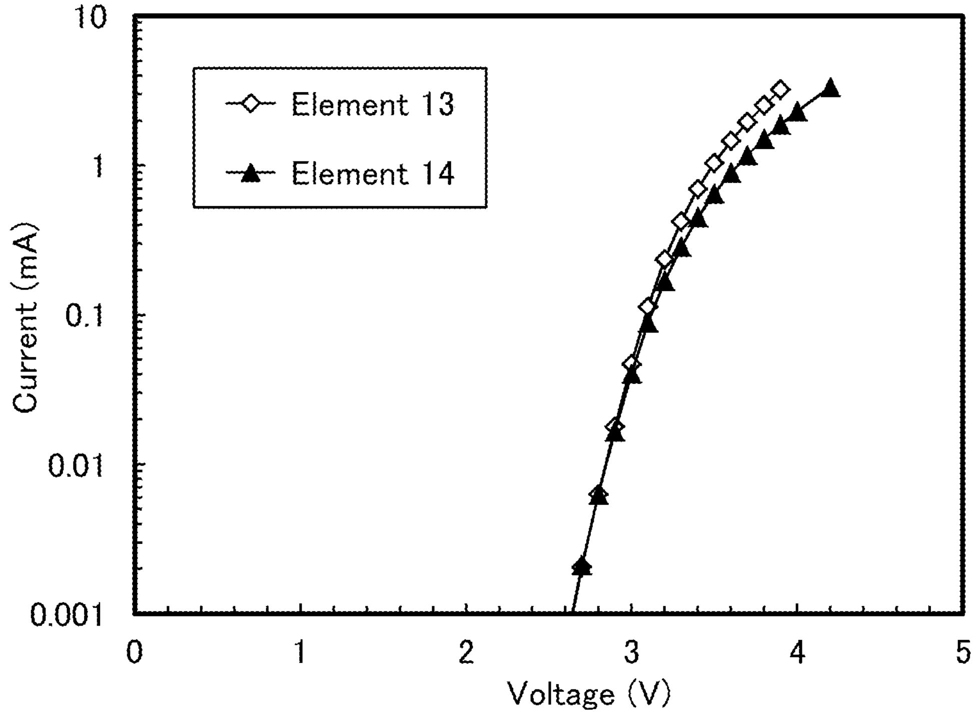
FIG. 70 shows current-voltage characteristics of the light-emitting elements 13 and 14.
Figure 71:
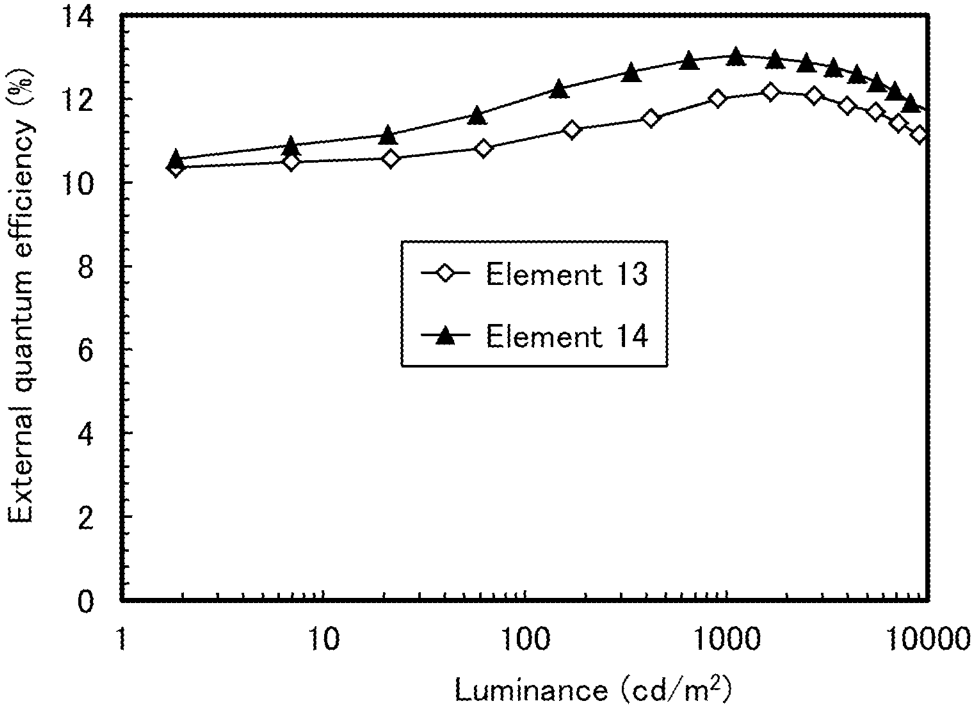
FIG. 71 shows external quantum efficiency-luminance characteristics of the light-emitting elements 13 and 14.
Figure 72:
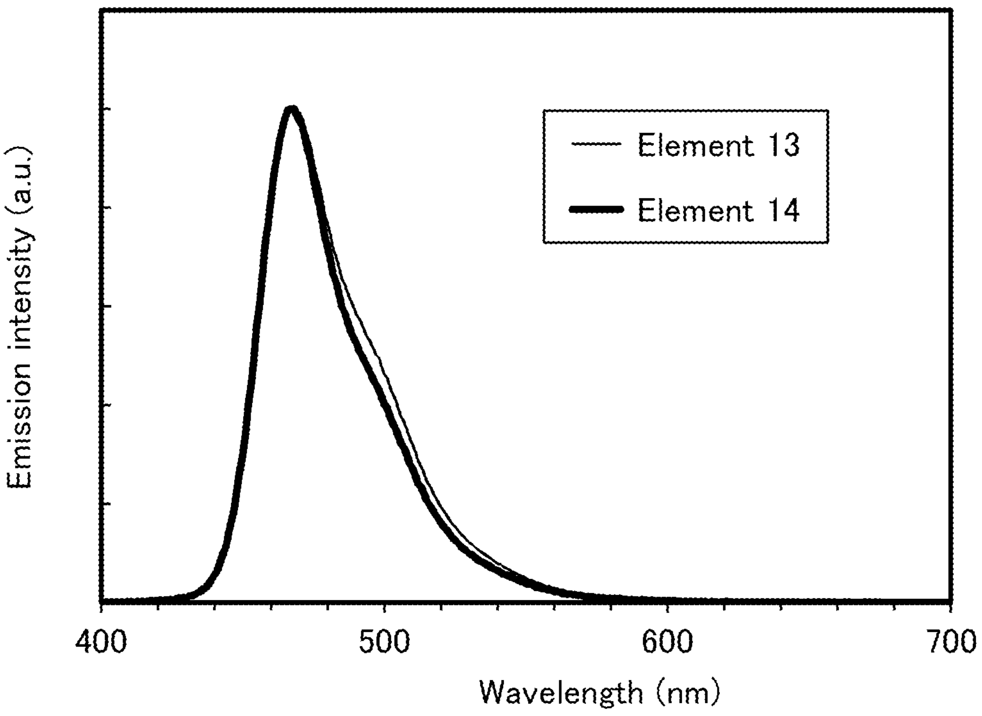
FIG. 72 shows emission spectra of the light-emitting elements 13 and 14.

FIG. 67 shows luminance-current density characteristics of the light-emitting elements 13 and 14. FIG. 68 shows current efficiency-luminance characteristics thereof. FIG. 69 shows luminance-voltage characteristics thereof. FIG. 70 shows current-voltage characteristics thereof. FIG. 71 shows external quantum efficiency-luminance characteristics thereof. FIG. 72 shows emission spectra thereof.

TABLE 14

| | Voltage | Current | Current density | Chromaticity | | Current efficiency | External quantum efficiency |
|---|---|---|---|---|---|---|---|
| | (V) | (mA) | ($mA/cm^2$) | x | y | (cd/A) | (%) |
| Element 13 | 3.2 | 0.23 | 5.8 | 0.14 | 0.20 | 16 | 12 |
| Element 14 | 3.3 | 0.28 | 7.1 | 0.14 | 0.18 | 16 | 13 |

According to FIG. 67, FIG. 68, FIG. 69, FIG. 70, FIG. 71, FIG. 72, and Table 14, the light-emitting elements 13 and 14 have very high external quantum efficiencies of 12% and 13%, respectively, at 1000 $cd/m^2$.

Example 15

Synthesis Example 8

In this synthesis example, a synthesis method of 4-(1;2'-binaphthyl-4-yl)-4',4"-diphenyltriphenylamine (abbreviation: BBAβNαNB), which is the organic compound of one embodiment of the present invention represented by the structural formula (118) in Embodiment 1, will be described in detail. The structural formula of BBAβNαNB is shown below.

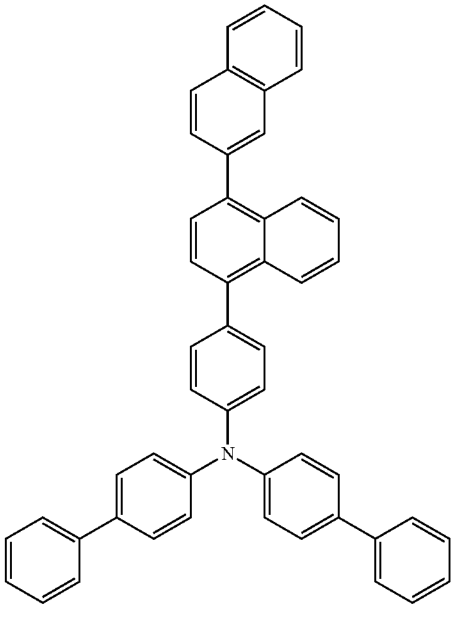 [SMILES: c1ccc(-c2ccc(N(c3ccc(-c4ccccc4)cc3)c3ccc(-c4ccc(-c5ccc6ccccc6c5)c5ccccc45)cc3)cc2)cc1]

Step 1: Synthesis of 4,4'-diphenyl-4"-(4,4,5,5-tetramethyl-1,3,2-dioxaborolan-2-yl)triphenylamine In a manner similar to Step 2 of Synthesis Example 1, 4,4'-diphenyl-4"-(4,4,5,5-tetramethyl-1,3,2-dioxaborolan-2-yl)triphenylamine was synthesized.

Step 2: Synthesis of 4-(1;2'-binaphthyl-4-yl)-4',4"-diphenyltriphenylamine (Abbreviation: BBAβNαNB)

Into a 200-mL three-neck flask with a reflux pipe, 2.5 g (4.6 mmol) of 4,4'-diphenyl-4"-(4,4,5,5-tetramethyl-1,3,2-dioxaborolan-2-yl)triphenylamine, 1.5 g (4.6 mmol) of 1-bromo-4,2'-binaphthyl, 28 mg (92 μmol) of tri(ortho-tolyl) phosphine, 20 mL (2.0 mol/L) of an aqueous solution of potassium carbonate, 50 mL of toluene, and 10 mL of ethanol were put, the mixture was degassed under reduced pressure, and then, the air in the flask was replaced with nitrogen. This mixture was heated at 60° C., 10 mg (46 μmol) of palladium(II) acetate was added thereto, and then, stirring was performed at 100° C. for 3 hours. After the stirring, the precipitated solid was collected by suction filtration. Water was added to the obtained filtrate to separate an aqueous layer and an organic layer from each other, and then, the aqueous layer was extracted with toluene. The extracted solution was washed with water and saturated saline and dried with magnesium sulfate. This mixture was gravity-filtered. The obtained filtrate was concentrated to give 1.5 g of a target light black solid in a yield of 50%. The synthesis scheme of Step 2 is shown below.

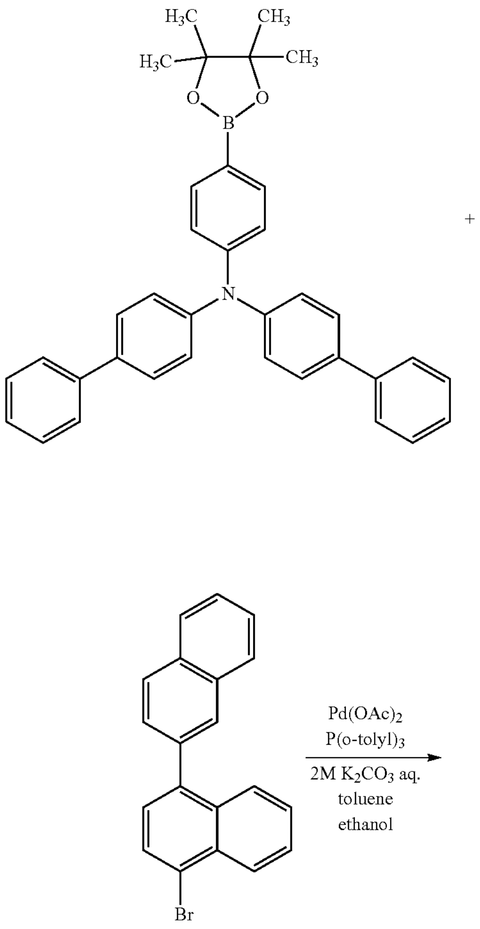

-continued

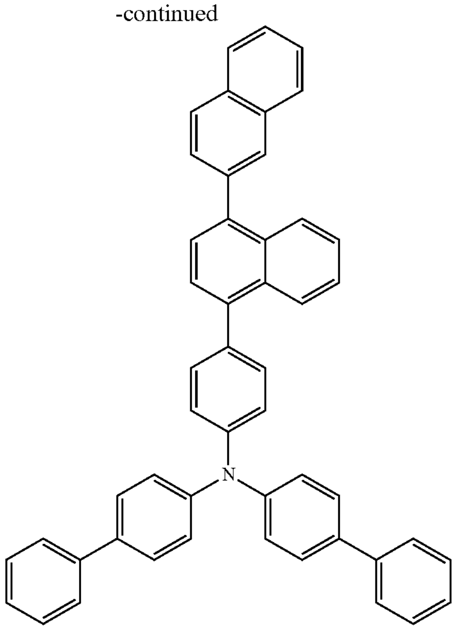

Figure 75A:
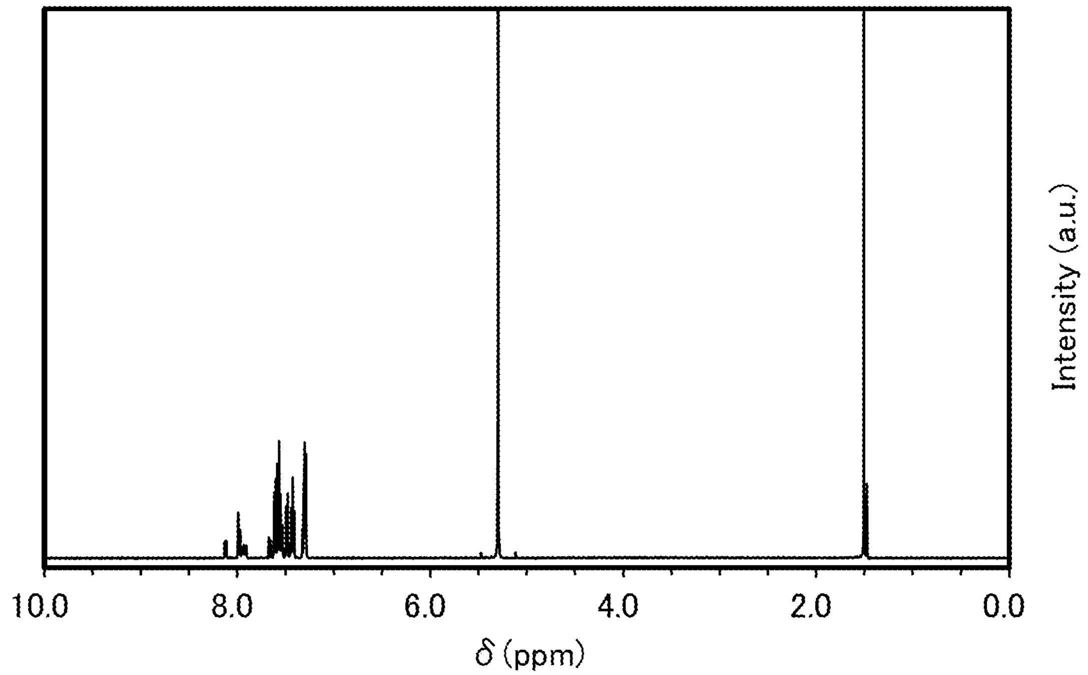
FIGS. 75A and 75B show $^1$H NMR spectra of BBAβNαNB.
Figure 75B:
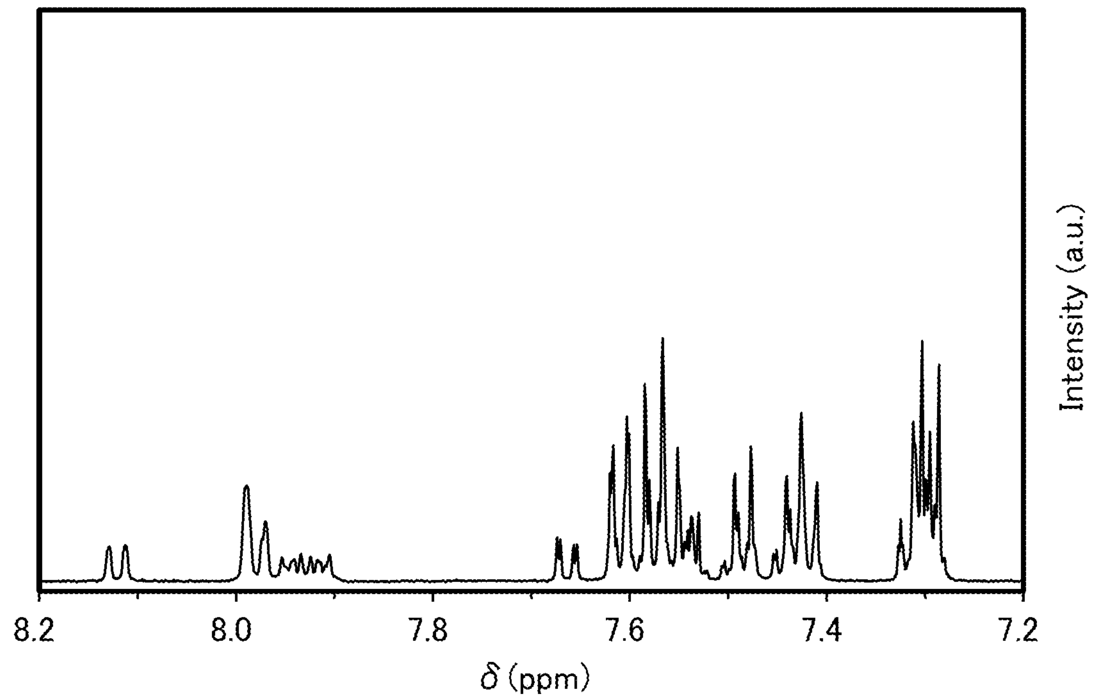

FIGS. 75A and 75B show H NMR charts of the obtained solid, whose numerical data is shown below.

$^1$H NMR (chloroform-d, 500 MHz): δ=8.12 (d, J=8.0 Hz, 1H), 7.99-7.91 (m, 5H), 7.66 (dd, $J_1$=8.0 Hz, $J_2$=1.5 Hz, 1H), 7.62-7.52 (m, 12H), 7.50-7.48 (m, 3H), 7.46-7.41 (m, 5H), 7.33-7.28 (m, 8H).

By a train sublimation method, 1.5 g of the obtained solid was purified. As the sublimation purification, heating was performed at 310° C. for 15 hours under a pressure of 3.6 Pa with an argon flow rate of 15 mL/min. After the sublimation purification, 1.1 g of a target pale yellow solid was obtained at a collection rate of 73%.

Next, measurement results of the absorption and emission spectra of BBAβNαNB in a toluene solution and measurement results of the absorption and emission spectra of its thin film will be shown. The method for forming a sample, the measurement method, and the measurement apparatus are similar to those described in the above example and therefore will not be described here.

The measurement results show that BBAβNαNB in the toluene solution has an absorption peak at around 348 nm and an emission wavelength peak at 430 nm (excitation wavelength: 348 nm). The thin film of BBAβNαNB has absorption peaks at around 351 nm, 300 nm, 245 nm, and 215 nm and an emission wavelength peak at 439 nm (excitation wavelength: 353 nm). These results indicate that BBAβNαNB emits blue light. The compound of one embodiment of the present invention can be used as a host for a light-emitting substance or a substance which emits fluorescence in the visible region.

Furthermore, the thin film of BBAβNαNB was found to be a high-quality film that is not easily aggregated even in the air and is less likely to change in shape.

The HOMO level and the LUMO level of BBAβNαNB were calculated by cyclic voltammetry (CV) measurement. Furthermore, CV measurement was repeated 100 times, and the oxidation-reduction wave in the hundredth cycle was compared with the oxidation-reduction wave in the first cycle to examine the electrical stability of the compound. The measurement methods are similar to those of Example 1 and therefore will not be described here.

According to the results of measuring the oxidation potential Ea [V] of BBAβNαNB, its HOMO level and LUMO level are −5.49 eV and −2.40 eV, respectively. Furthermore, the oxidation-reduction wave was repeatedly measured, and the waveform in the first cycle was compared with that in the hundredth cycle; in the Ea measurement, 91% of the peak intensity was maintained. Accordingly, BBAβNαNB is highly resistant to oxidation.

The thermogravimetry-differential thermal analysis of BBAβNαNB was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 462° C., which shows that BBAβNαNB is a substance with high heat resistance.

Differential scanning calorimetry (DSC) measurement of BBAβNαNB was performed with Pyris1DSC manufactured by PerkinElmer, Inc. The DSC measurement was performed in the following manner: the temperature was raised from −10° C. to 320° C. at a temperature rising rate of 40° C./min and held for a minute; then, the temperature was decreased to −10° C. at a temperature decreasing rate of 100° C./min and held at −10° C. for three minutes. This operation was performed twice in succession, and the second measurement result was employed. The DSC measurement proves that BBAβNαNB has a glass transition point of 123° C. and is thus a compound with favorable heat resistance.

Example 16

Synthesis Example 9

In this synthesis example, a synthesis method of 4-(1;2'-binaphthyl-5-yl)-4',4"-diphenyltriphenylamine (abbreviation: BBAβNαNB-02) represented by the structural formula (120) in Embodiment 1 will be described. The structural formula of BBAβNαNB-02 is shown below.

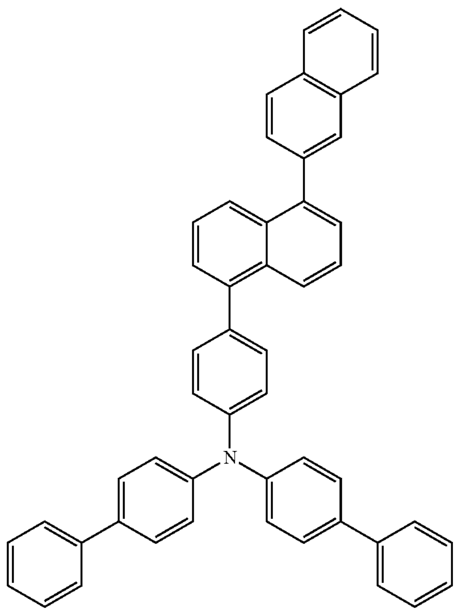

Step 1: Synthesis of 4,4'-diphenyl-4"-(4,4,5,5-tetramethyl-1,3,2-dioxaborolan-2-yl)triphenylamine In a manner similar to Step 2 of Synthesis Example 1, 4,4'-diphenyl-4"-(4,4,5,5-tetramethyl-1,3,2-dioxaborolan-2-yl)triphenylamine was synthesized.

2: Synthesis of 4-(1;2'-binaphthyl-5-yl)-4',4"-diphenyltriphenylamine (Abbreviation: BBAβNαNB-02)>

Into a 200-mL three-neck flask with a reflux pipe, 2.5 g (4.6 mmol) of 4,4'-diphenyl-4"-(4,4,5,5-tetramethyl-1,3,2-dioxaborolan-2-yl)triphenylamine, 1.5 g (4.6 mmol) of 5-bromo-1,2'-binaphthyl, 28 mg (92 μmol) of tri(ortho-tolyl) phosphine, 20 mL (2.0 mol/L) of an aqueous solution of potassium carbonate, 50 mL of toluene, and 10 mL of ethanol were put, the mixture was degassed under reduced pressure, and then, the air in the flask was replaced with nitrogen. This mixture was heated at 60° C., 10 mg (46 μmol) of palladium(II) acetate was added thereto, and then, stirring was performed at 100° C. for 9 hours. After the stirring, the precipitated solid was collected by suction filtration. Water was added to the obtained filtrate to separate an organic layer and an aqueous layer from each other, and then, the aqueous layer was extracted with toluene. The extracted solution was combined with the organic layer, and the resulting mixture was washed with water and saturated saline and dried with magnesium sulfate. This mixture was gravity-filtered. The obtained filtrate was concentrated to give 1.6 g of a white solid in a yield of 53%. The synthesis scheme of Step 2 is shown below.

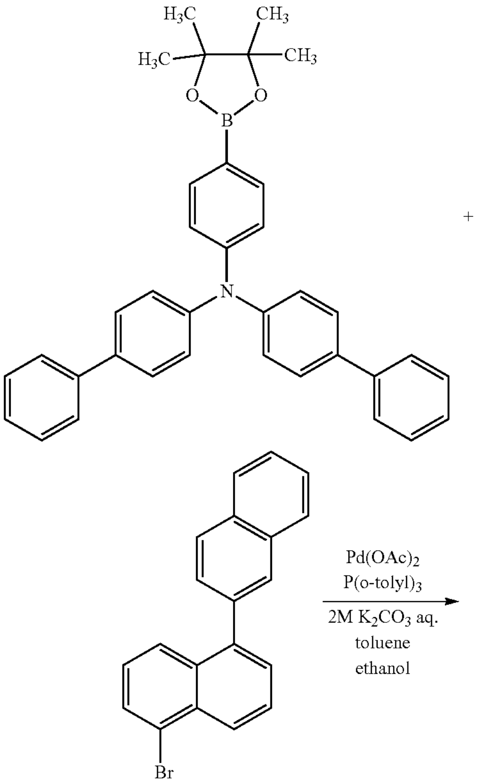

-continued

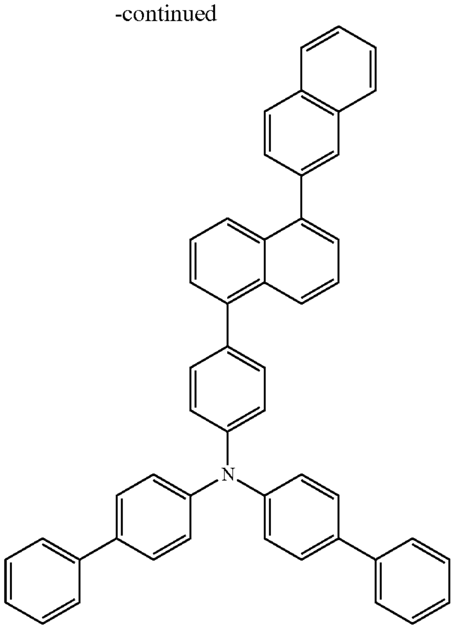

Figure 76A:
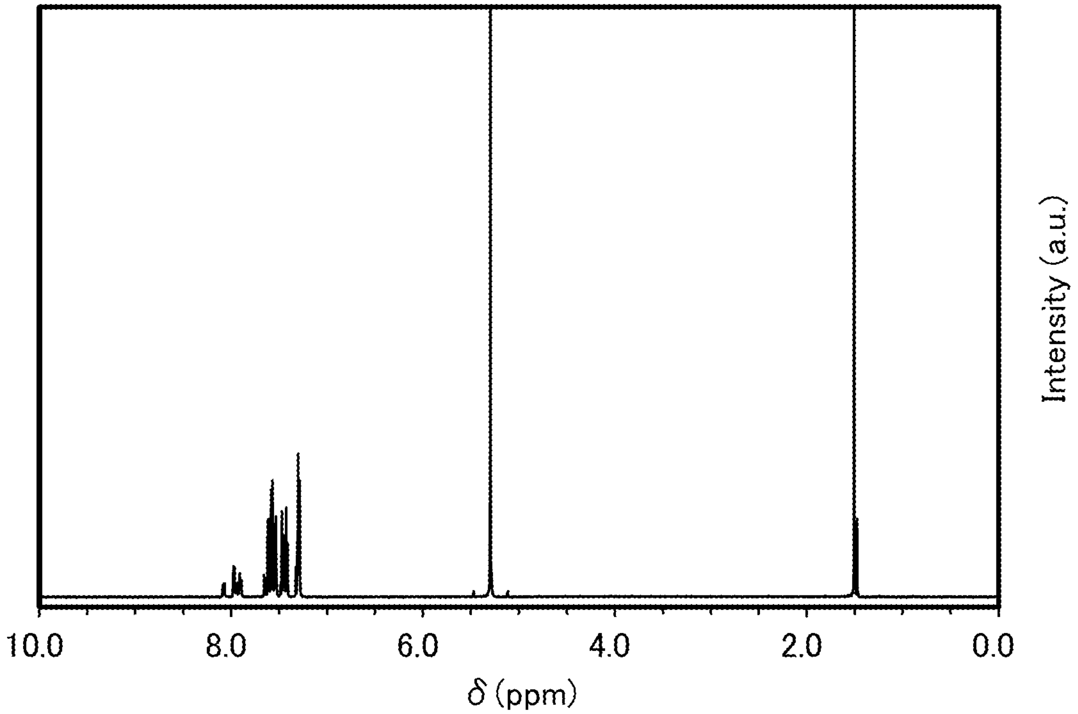
FIGS. 76A and 76B show $^1$H NMR spectra of BBAβNαNB-02.
Figure 76B:
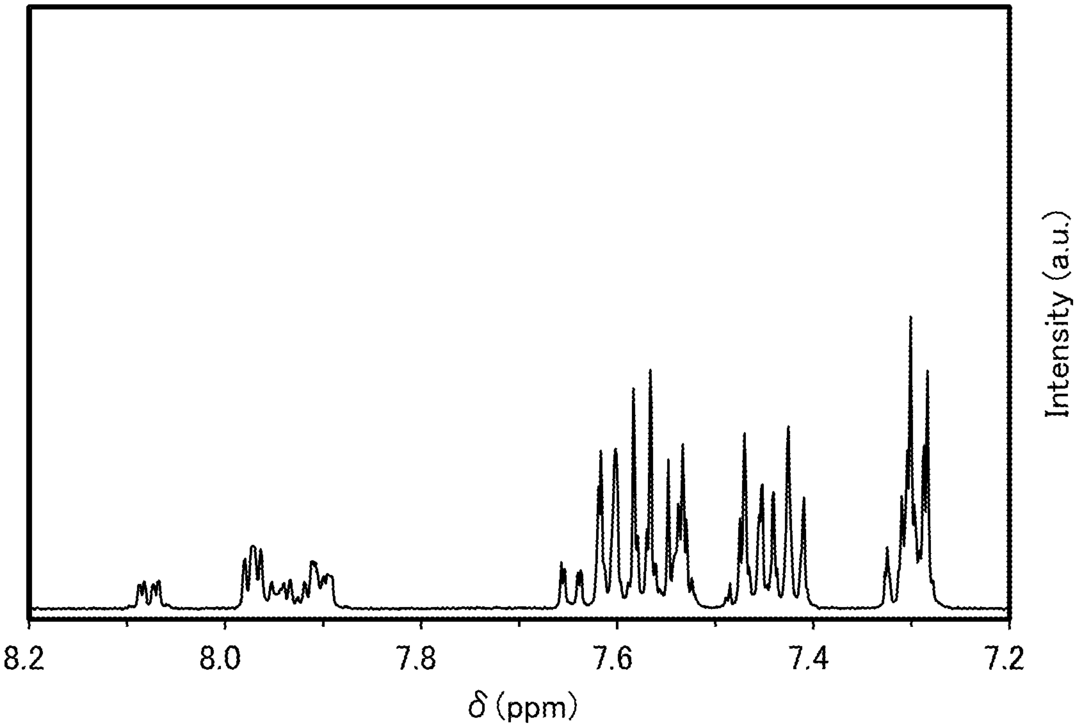

FIGS. 76A and 76B show $^1$H NMR charts of the obtained solid, whose numerical data is shown below.

$^1$H NMR (chloroform-d, 500 MHz): δ=8.10 (dd, $J_1$=7.0 Hz, $J_2$=2.5 Hz, 1H), 8.00-7.92 (m, 5H), 7.67 (dd, $J_1$=8.0 Hz, $J_2$=1.5 Hz, 1H), 7.64-7.62 (m, 4H), 7.59 (d, J=8.5 Hz, 4H), 7.57-7.55 (m, 4H), 7.51-7.43 (m, 8H), 7.35-7.31 (m, 8H).

By a train sublimation method, 1.6 g of the obtained solid was purified. As the sublimation purification, heating was performed at 310° C. for 15 hours under a pressure of 3.6 Pa with an argon flow rate of 15 mL/min. After the sublimation purification, 1.3 g of a target pale yellow solid was obtained at a collection rate of 81%.

Next, measurement results of the absorption and emission spectra of BBAβNαNB-02 in a toluene solution and measurement results of the absorption and emission spectra of its thin film will be shown. The method for forming a sample, the measurement method, and the measurement apparatus are similar to those described in the above example and therefore will not be described here.

The measurement results show that BBAβNαNB-02 in the toluene solution has an absorption peak at around 346 nm and an emission wavelength peak at 419 nm (excitation wavelength: 348 nm). The thin film of BBAβNαNB-02 has absorption peaks at around 350 nm, 300 nm, 243 nm, and 215 nm and an emission wavelength peak at 427 nm (excitation wavelength: 350 nm). These results indicate that BBAβNαNB-02 emits blue light. Thus, the compound of one embodiment of the present invention can be used as a host for a light-emitting substance or a substance which emits fluorescence in the visible region.

Furthermore, the thin film of BBAβNαNB-02 was found to be a high-quality film that is not easily aggregated even in the air and is less likely to change in shape.

The HOMO level and the LUMO level of BBAβNαNB-02 were calculated by cyclic voltammetry (CV) measurement. Furthermore, CV measurement was repeated 100 times, and the oxidation-reduction wave in the hundredth cycle was compared with the oxidation-reduction wave in the first cycle to examine the electrical stability of the compound. The measurement methods have already been explained in Example 1 and therefore will not be described here.

According to the results of measuring the oxidation potential Ea [V] of BBAβNαNB-02, its HOMO level and LUMO level are −5.49 eV and −2.35 eV, respectively. Furthermore, the oxidation-reduction wave was repeatedly measured, and the waveform in the first cycle was compared with that in the hundredth cycle; in the Ea measurement, 91% of the peak intensity was maintained. Accordingly, BBAβNαNB-02 is highly resistant to oxidation.

The thermogravimetry-differential thermal analysis of BBAβNαNB-02 was performed. The measurement was conducted using a high vacuum differential type differential thermal balance (TG-DTA 2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the decomposition temperature, i.e. the temperature at which the weight obtained by thermogravimetry reduced by 5% of the initial weight, was found to be 477° C., which shows that BBAβNαNB-02 is a substance with high heat resistance.

Differential scanning calorimetry (DSC) measurement of BBAβNαNB-02 was performed with Pyris1DSC manufactured by PerkinElmer, Inc. The DSC measurement was performed in the following manner: the temperature was raised from −10° C. to 330° C. at a temperature rising rate of 40° C./min and held for a minute; then, the temperature was decreased to −10° C. at a temperature decreasing rate of 100° C./min and held at −10° C. for three minutes. This operation was performed twice in succession, and the second measurement result was employed. The DSC measurement proves that BBAβNαNB-02 has a glass transition point of 111° C. and is thus a compound with favorable heat resistance.

Example 17

In this example, light-emitting elements 15 to 24 which correspond to the light-emitting element of one embodiment of the present invention described in the above embodiment will be described. The structural formulae of organic compounds used for the light-emitting elements 15 to 24 are shown below.

(i)

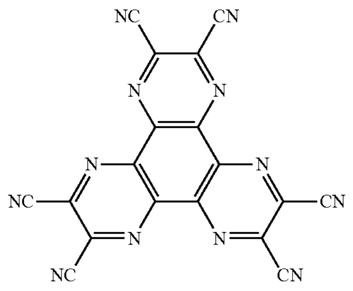

HAT-CN (ii)

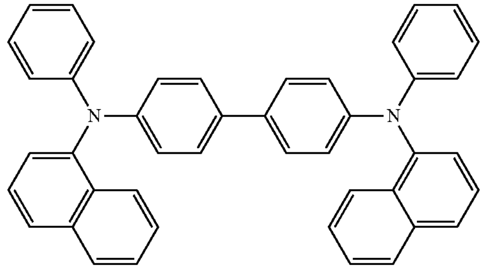

NPB

-continued (iii)

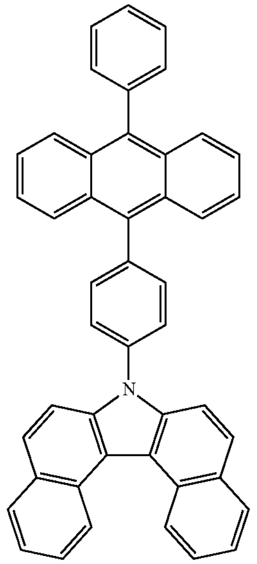

egDBCzPA (iv)

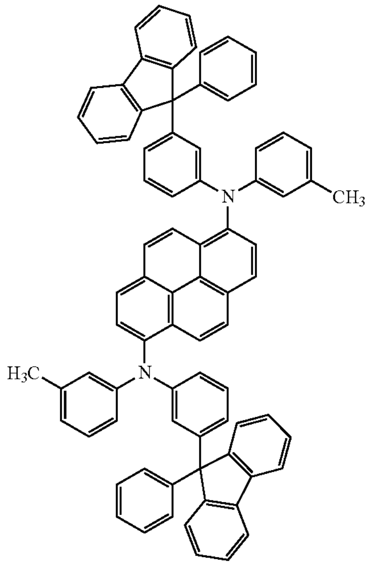

1,6mMemFLPAPrn

-continued
(ix)
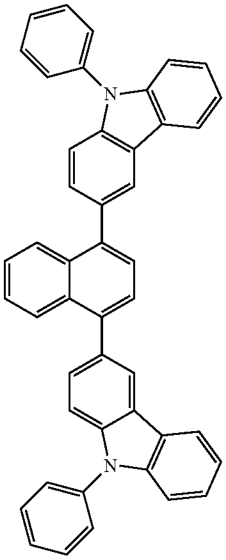
PCzN2
(v)
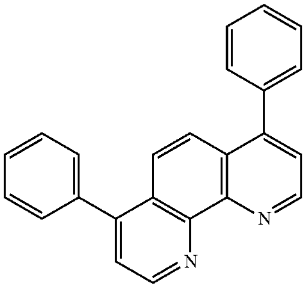
BPhen
(vi)
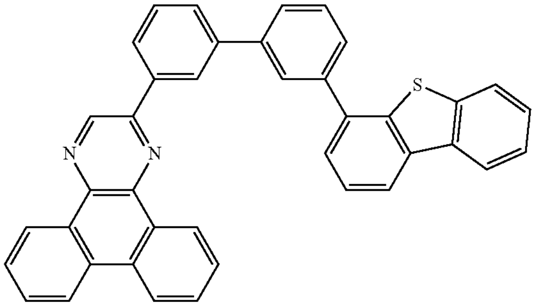
2mDBTBPDBq-II
-continued
(vii)
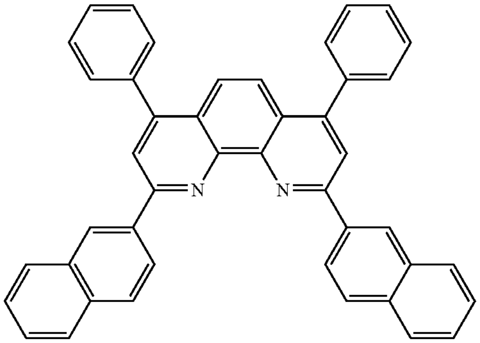
NBPhen
(viii)
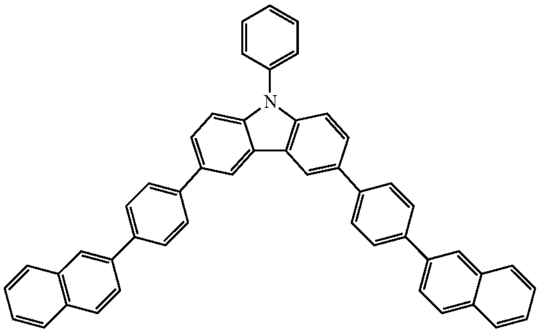
β NP2PC
(110)
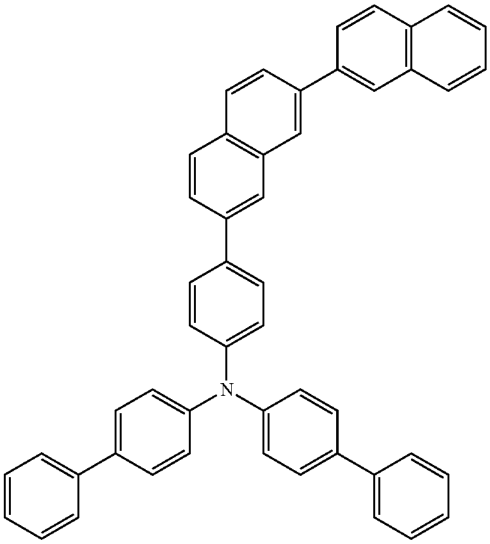
BBA(β N2)B-03

-continued (114)

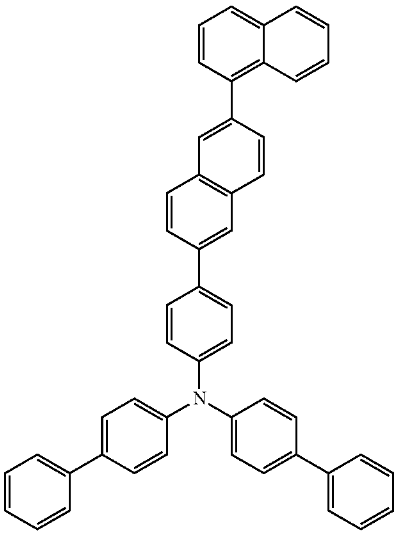

BBA α N β NB (115)

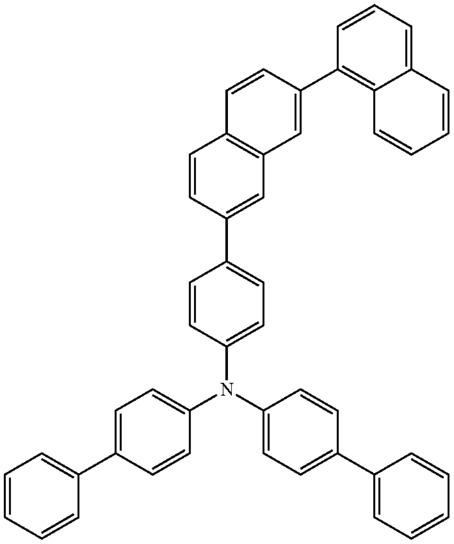

BBA α N β NB-03

-continued (118)

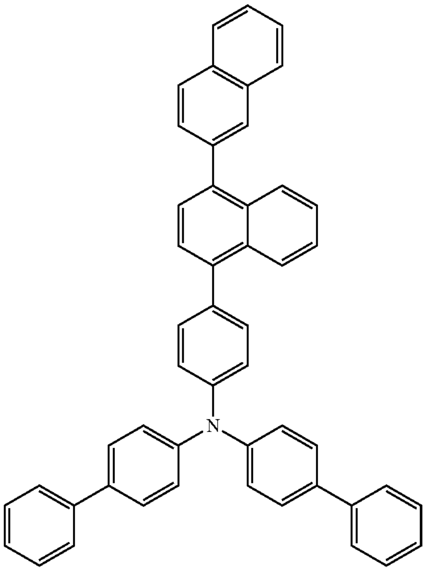

BBA β N α NB (120)

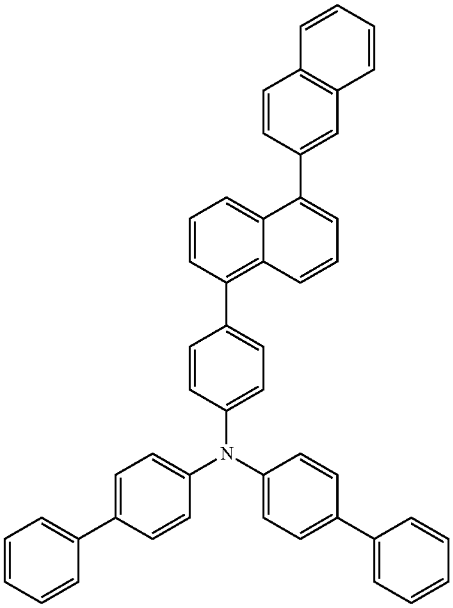

BBA β N α NB-02

(Method for Fabricating Light-Emitting Element 15)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 10 nm by evaporation, 4-(2;2'-binaphthyl-7-yl)-4',4"-diphenyltriphenylamine (abbreviation: BBA(βN2)B-03) represented by the structural formula (110) was deposited to a thickness of 10 nm by evaporation, and then, 3,6-bis[4-(2-naphthyl)phenyl]-9-phenyl-9H-carbazole (abbreviation: βNP2PC) represented by the structural formula (viii) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 15 nm by evaporation, and then, bathophenanthroline (abbreviation: BPhen) represented by the structural formula (v) was deposited to a thickness of 10 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 15 of this example was fabricated.

(Method for Fabricating Light-Emitting Element 16)

The light-emitting element 16 was fabricated in the same manner as the light-emitting element 15 except for the following differences: to form the electron-transport layer 114, 2-[3'-(dibenzothiophen-4-yl)biphenyl-3-yl]dibenzo[f,h]quinoxaline (abbreviation: 2mDBTBPDBq-II) represented by the structural formula (vi) was formed to a thickness of 10 nm, and then, 2,9-bis(naphthalen-2-yl)-4,7-diphenyl-1,10-phenanthroline (abbreviation: NBPhen) was deposited to a thickness of 15 nm by evaporation.

(Method for Fabricating Light-Emitting Element 17)

The light-emitting element 17 was fabricated in the same manner as the light-emitting element 15 except for the following differences: in the hole-transport layer 112, 4,4'-diphenyl-4"-(7;1'-binaphthyl-2-yl)triphenylamine (abbreviation: BBAαNβNB-03) represented by the structural formula (115) was used instead of BBA(βN2)B-03, and 3,3'-(naphthalene-1,4-diyl)bis(9-phenyl-9H-carbazole) (abbreviation: PCzN2) represented by the structural formula (ix) was used instead of βNP2PC; and in the electron-transport layer 114, NBPhen was used instead of BPhen.

(Method for Fabricating Light-Emitting Element 18)

The light-emitting element 18 was fabricated in the same manner as the light-emitting element 17 except that, in the electron-transport layer, 2mDBTBPDBq-II was used instead of cgDBCzPA.

(Method for Fabricating Light-Emitting Element 19)

The light-emitting element 19 was fabricated in the same manner as the light-emitting element 17 except that, in the hole-transport layer, 4-(2;1'-binaphthyl-6-yl)-4',4"-diphenyltriphenylamine (abbreviation: BBAαNβNB) represented by the structural formula (114) was used instead of BBAαNβNB-03.

(Method for Fabricating Light-Emitting Element 20)

The light-emitting element 20 was fabricated in the same manner as the light-emitting element 19 except that, in the electron-transport layer 114, 2mDBTBPDBq-II was used instead of cgDBCzPA.

(Method for Fabricating Light-Emitting Element 21)

The light-emitting element 21 was fabricated in the same manner as the light-emitting element 17 except that, in the hole-transport layer 112, 4-(1;2'-binaphthyl-4-yl)-4',4"-diphenyltriphenylamine (abbreviation: BBAβNαNB) represented by the structural formula (118) was used instead of BBAαNβNB-03.

(Method for Fabricating Light-Emitting Element 22)

The light-emitting element 22 was fabricated in the same manner as the light-emitting element 21 except that, in the electron-transport layer, 2mDBTBPDBq-II was used instead of cgDBCzPA.

(Method for Fabricating Light-Emitting Element 23)

The light-emitting element 23 was fabricated in the same manner as the light-emitting element 17 except that, in the hole-transport layer 112, 4-(1;2'-binaphthyl-5-yl)-4',4"-diphenyltriphenylamine (abbreviation: BBAβNαNB-02) represented by the structural formula (120) was used instead of BBAαNβNB-03.

(Method for Fabricating Light-Emitting Element 24)

The light-emitting element 24 was fabricated in the same manner as the light-emitting element 23 except that, in the electron-transport layer 114, 2mDBTBPDBq-II was used instead of cgDBCzPA.

The element structures of the light-emitting elements 15 to 24 are shown in the following tables.

TABLE 15

| | Hole-injection layer | Hole-transport layer | | | Light-emitting layer | Electron-transport layer | | Electron-injection layer |
|---|---|---|---|---|---|---|---|---|
| | 5 nm | 10 nm | 10 nm | 10 nm | 25 nm | | | 1 mm |
| Element 15 | HAT-CN | NPB | BBA(βN2)B-03β | βNP2PC | cgDBCzPA: 1,6mMemFLPAPrn (1:0.03) | *5 | *6 | LiF |
| Element 16 | | | | | | | | |
| Element 17 | | | BBAαNβNB-03 | PCzN2 | | | | |
| Element 18 | | | | | | | | |
| Element 19 | | | BBAαNβNB | | | | | |
| Element 20 | | | | | | | | |

TABLE 15-continued

| | Hole-injection layer | Hole-transport layer | | | Light-emitting layer | Electron-transport | Electron-injection layer |
|---|---|---|---|---|---|---|---|
| | 5 nm | 10 nm | 10 nm | 10 nm | 25 nm | layer | 1 mm |
| Element 21 | | | BBAβNαNB | | | | |
| Element 22 | | | | | | | |
| Element 23 | | | BBAβNαNB-02 | | | | |
| Element 24 | | | | | | | |

TABLE 16

| | *5 | | *6 | |
|---|---|---|---|---|
| | Material | Thickness (nm) | Material | Thickness (nm) |
| Element 15 | cgDBCzPA | 15 | BPhen | 10 |
| Element 16 | 2mDBTBPDBq-II | 10 | NBPhen | 15 |
| Element 17 | cgDBCzPA | 15 | | 10 |
| Element 18 | 2mDBTBPDBq-II | | | |
| Element 19 | cgDBCzPA | | | |
| Element 20 | 2mDBTBPDBq-II | | | |
| Element 21 | cgDBCzPA | | | |
| Element 22 | 2mDBTBPDBq-II | | | |
| Element 23 | cgDBCzPA | | | |
| Element 24 | 2mDBTBPDBq-II | | | |

The light-emitting elements 15 to 24 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

The table below shows main characteristics of the light-emitting elements 15 to 24 at around 1000 cd/$m^2$.

TABLE 17

| | Voltage (V) | Current (mA) | Current density ($mA/cm^2$) | Chromaticity x | Chromaticity y | Current efficiency (cd/A) | External quantum efficiency (%) |
|---|---|---|---|---|---|---|---|
| Element 15 | 3.2 | 0.23 | 5.9 | 0.14 | 0.19 | 15 | 12 |
| Element 16 | 3.3 | 0.21 | 5.3 | 0.14 | 0.18 | 15 | 12 |
| Element 17 | 3.1 | 0.22 | 5.4 | 0.14 | 0.18 | 16 | 13 |
| Element 18 | 3.2 | 0.22 | 5.6 | 0.14 | 0.18 | 17 | 14 |
| Element 19 | 3.1 | 0.20 | 5.0 | 0.14 | 0.16 | 14 | 12 |
| Element 20 | 3.2 | 0.26 | 6.5 | 0.14 | 0.16 | 14 | 12 |
| Element 21 | 3.2 | 0.25 | 6.2 | 0.14 | 0.17 | 15 | 13 |
| Element 22 | 3.3 | 0.28 | 6.9 | 0.14 | 0.16 | 15 | 13 |
| Element 23 | 3.2 | 0.25 | 6.2 | 0.14 | 0.16 | 14 | 12 |
| Element 24 | 3.3 | 0.30 | 7.4 | 0.14 | 0.16 | 14 | 12 |

Table 17 shows that the light-emitting elements 15 to 24 each have a very high external quantum efficiency in a range of 12% to 14% at around 1000 cd/$m^2$. Moreover, each of the light-emitting elements 15 to 24 has a low drive voltage, indicating favorable emission efficiency.

Furthermore, driving time-dependent change in luminance was measured under the conditions where the current value was 2 mA and the current density was constant. The table below shows the ratio (%) of the luminance after 100 hours to the initial luminance of each of the light-emitting elements.

TABLE 18

| | Ratio of luminance after 100 h to initial luminance (%) |
|---|---|
| Element 15 | 89 |
| Element 16 | 89 |
| Element 17 | 91 |
| Element 18 | 93 |
| Element 19 | 92 |
| Element 20 | 92 |
| Element 21 | 92 |
| Element 22 | 93 |
| Element 23 | 92 |
| Element 24 | 93 |

Even after being driven for 100 hours, the light-emitting elements 17 to 24 each maintained 90% or more of the initial luminance, and the light-emitting elements 15 and 16 each maintained 85% or more of the initial luminance. Each of the light-emitting elements was found to be a long-life light-emitting element whose luminance was only slightly decreased over driving time.

Example 18

In this example, light-emitting elements 25 to 34 which correspond to the light-emitting element of one embodiment of the present invention described in the above embodiment will be described. The structural formulae of organic compounds used for the light-emitting elements 25 to 34 are shown below.

(i)
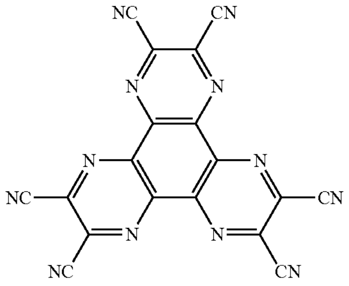
HAT-CN
(ii)
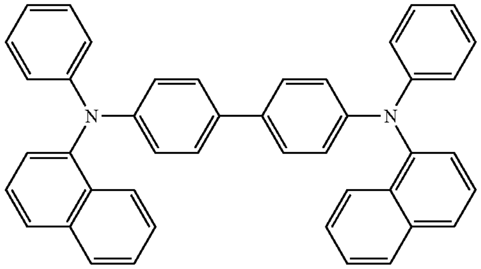
NPB
(iii)
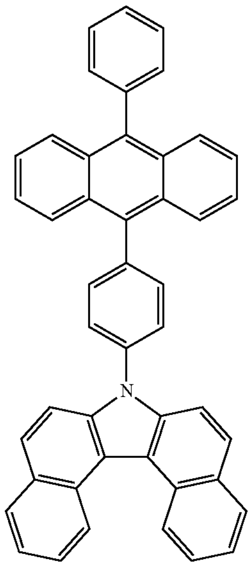
egDBCzPA
-continued
(iv)
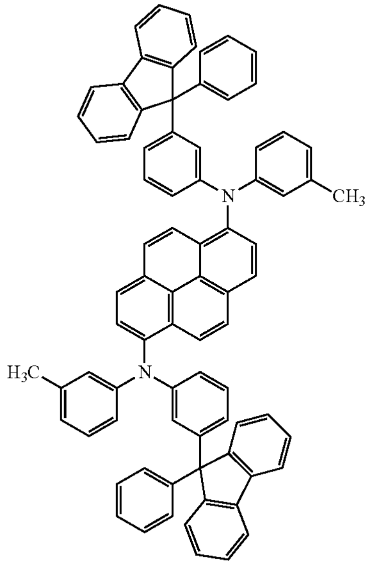
1,6mMemFLPAPrn
(v)
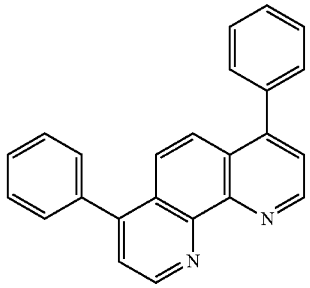
BPhen
(vi)
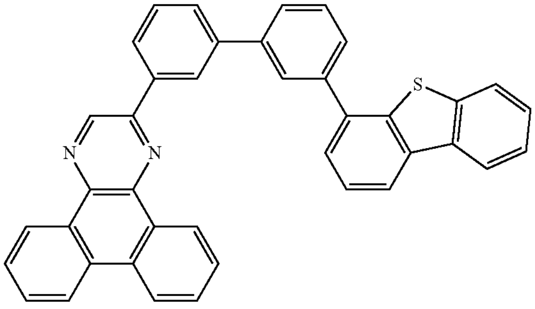
2mDBTBPDBq-II -continued
(vii)
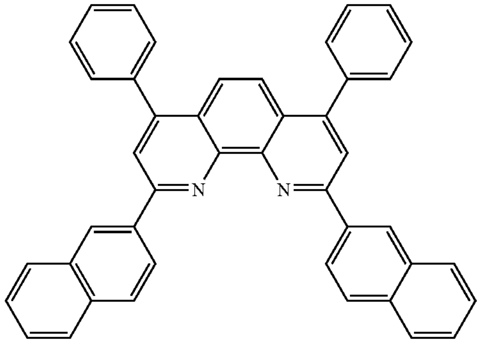
NBPhen
(110)
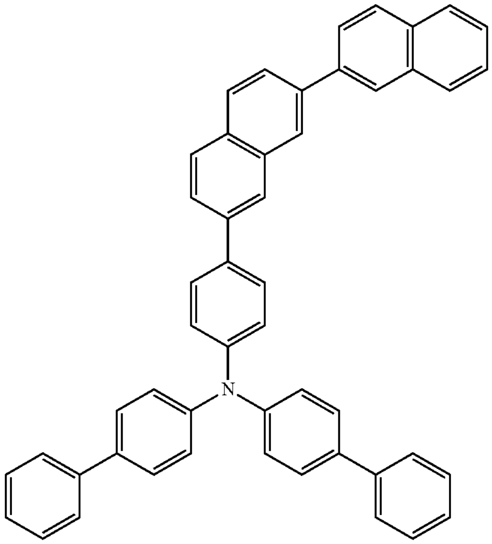
BBA(β N2)B-03
(114)
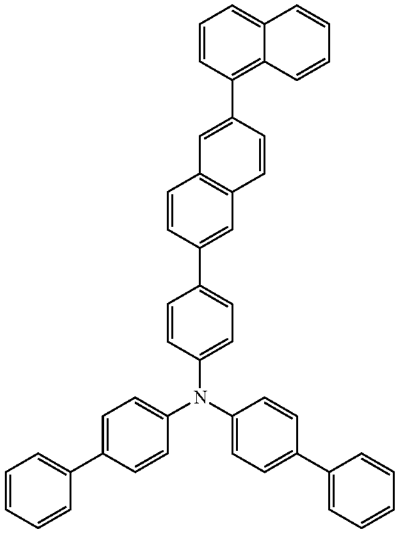
BBA α N β NB
-continued
(115)
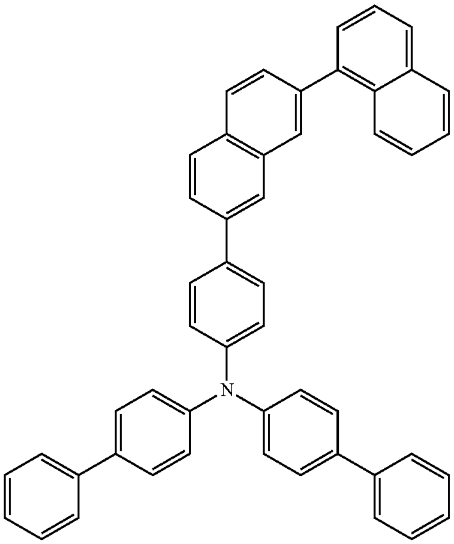
BBA α N β NB-03
(118)
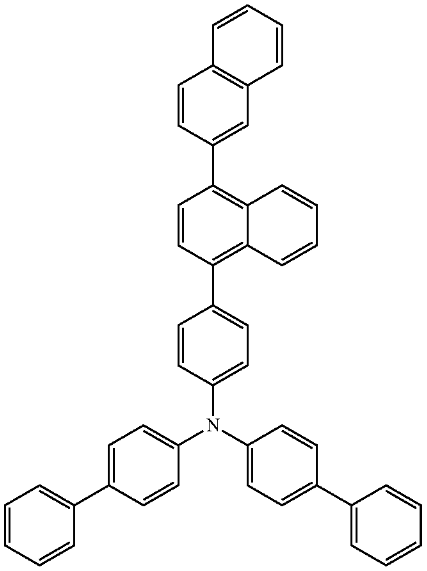
BBA β N α NB -continued (120)

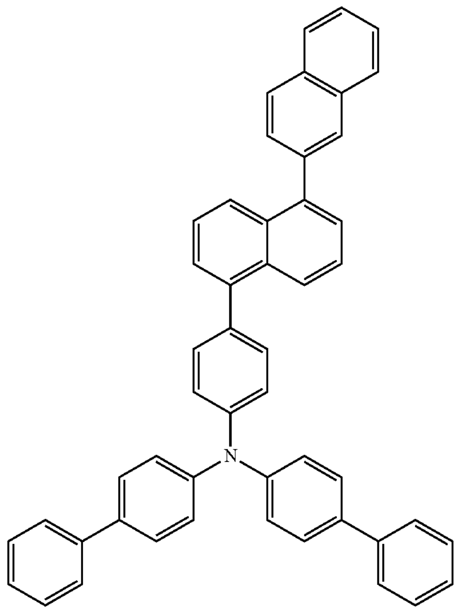 [SMILES: c1ccc(-c2ccc(N(c3ccc(-c4ccccc4)cc3)c3ccc(-c4cccc5c(-c6ccc7ccccc7c6)cccc45)cc3)cc2)cc1]

BBAβNαNB-02

(Method for Fabricating Light-Emitting Element 25)

First, indium tin oxide containing silicon oxide (ITSO) was deposited over a glass substrate by a sputtering method to form the anode 101. The thickness of the anode 101 was 70 nm, and the electrode area was 4 $mm^2$ (2 mm×2 mm).

Next, in pretreatment for forming the light-emitting element over the substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate over which the anode 101 was formed was fixed to a substrate holder provided in the vacuum evaporation apparatus such that the side on which the anode 101 was formed faced downward. Then, 2,3,6,7,10,11-hexacyano-1,4,5,8,9,12-hexaazatriphenylene (abbreviation: HAT-CN) represented by the structural formula (i) was deposited to a thickness of 5 nm over the anode 101 by an evaporation method using resistance heating, whereby the hole-injection layer 111 was formed.

Subsequently, over the hole-injection layer 111, 4,4'-bis[N-(1-naphthyl)-N-phenylamino]biphenyl (abbreviation: NPB) represented by the structural formula (ii) was deposited to a thickness of 20 nm by evaporation, and then, 4-(2;2'-binaphthyl-7-yl)-4',4"-diphenyltriphenylamine (abbreviation: BBA(βN2)B-03) represented by the structural formula (110) was deposited to a thickness of 10 nm by evaporation, whereby the hole-transport layer 112 was formed.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by the structural formula (iii) and N,N'-bis (3-methylphenyl)-N,N'-bis[3-(9-phenyl-9H-fluoren-9-yl)phenyl]pyrene-1,6-diamine (abbreviation: 1,6mMemFLPAPrn) represented by the structural formula (iv) in a weight ratio of 1:0.03 (=cgDBCzPA:1,6mMemFLPAPrn).

After that, over the light-emitting layer 113, cgDBCzPA was deposited to a thickness of 15 nm by evaporation, and then, bathophenanthroline (abbreviation: BPhen) represented by the structural formula (v) was deposited to a thickness of 10 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 25 of this example was fabricated.

(Method for Fabricating Light-Emitting Element 26)

The light-emitting element 26 was fabricated in the same manner as the light-emitting element 25 except for the following differences: to form the electron-transport layer 114, 2-[3'-(dibenzothiophen-4-yl)biphenyl-3-yl]dibenzo[f,h]quinoxaline (abbreviation: 2mDBTBPDBq-II) represented by the structural formula (vi) was formed to a thickness of 10 nm, and then, 2,9-bis(naphthalen-2-yl)-4,7-diphenyl-1,10-phenanthroline (abbreviation: NBPhen) was deposited to a thickness of 15 nm by evaporation.

(Method for Fabricating Light-Emitting Element 27)

The light-emitting element 27 was fabricated in the same manner as the light-emitting element 25 except for the following differences: in the hole-transport layer 112, 4,4'-diphenyl-4"-(7;1'-binaphthyl-2-yl)triphenylamine (abbreviation: BBAαNβNB-03) represented by the structural formula (115) was used instead of BBA(βN2)B-03; and in the electron-transport layer 114, NBPhen was used instead of BPhen.

(Method for Fabricating Light-Emitting Element 28)

The light-emitting element 28 was fabricated in the same manner as the light-emitting element 27 except that, in the electron-transport layer 114, 2mDBTBPDBq-II was used instead of cgDBCzPA.

(Method for Fabricating Light-Emitting Element 29)

The light-emitting element 29 was fabricated in the same manner as the light-emitting element 27 except that 4-(2;1'-binaphthyl-6-yl)-4',4"-diphenyltriphenylamine (abbreviation: BBAαNβNB) represented by the structural formula (114) was used instead of BBAαNβNB-03.

(Method for Fabricating Light-Emitting Element 30)

The light-emitting element 30 was fabricated in the same manner as the light-emitting element 28 except that 4-(2;1'-binaphthyl-6-yl)-4',4"-diphenyltriphenylamine (abbreviation: BBAαNβNB) represented by the structural formula (114) was used instead of BBAαNβNB-03.

(Method for Fabricating Light-Emitting Element 31)

The light-emitting element 31 was fabricated in the same manner as the light-emitting element 27 except that 4-(1;2'-binaphthyl-4-yl)-4',4"-diphenyltriphenylamine (abbreviation: BBAβNαNB) represented by the structural formula (118) was used instead of BBAαNβNB-03.

(Method for Fabricating Light-Emitting Element 32)

The light-emitting element 32 was fabricated in the same manner as the light-emitting element 28 except that 4-(1;2'-binaphthyl-4-yl)-4',4"-diphenyltriphenylamine (abbreviation: BBAβNαNB) represented by the structural formula (118) was used instead of BBAαNβNB-03.

(Method for Fabricating Light-Emitting Element 33)

The light-emitting element 33 was fabricated in the same manner as the light-emitting element 27 except that 4-(1;2'-binaphthyl-5-yl)-4',4"-diphenyltriphenylamine (abbreviation: BBAβNαNB-02) represented by the structural formula (120) was used instead of BBAαNβNB-03.

(Method for Fabricating Light-Emitting Element 34)

The light-emitting element 34 was fabricated in the same manner as the light-emitting element 28 except that 4-(1;2'-binaphthyl-5-yl)-4',4"-diphenyltriphenylamine (abbreviation: BBAβNαNB-02) represented by the structural formula (120) was used instead of BBAαNβNB-03.

The element structures of the light-emitting elements 25 to 34 are shown in the following table.

TABLE 19

| | Hole-injection layer | Hole-transport layer | | Light-emitting layer | Electron-transport layer | | Electron-injection layer |
|---|---|---|---|---|---|---|---|
| | 5 nm | 20 nm | 10 nm | 25 nm | 15 nM*7 | 10 nm*8 | 1 nm |
| Element 25 | HAT-CN | NPB | BBA(βN2)B-03 | cgDBCzPA: | cgDBCzPA | BPhen | LiF |
| Element 26 | | | | 1,6mMemFLPAPrn | 2mDBTBPDBq-II | NBPhen | |
| Element 27 | | | BBAαNβNB-03 | (1:0.03) | cgDBCzPA | | |
| Element 28 | | | | | 2mDBTBPDBq-II | | |
| Element 29 | | | BBAαNβNB | | cgDBCzPA | | |
| Element 30 | | | | | 2mDBTBPDBq-II | | |
| Element 31 | | | BBAβNαNB | | cgDBCzPA | | |
| Element 32 | | | | | 2mDBTBPDBq-II | | |
| Element 33 | | | BBAβNαNB-02 | | cgDBCzPA | | |
| Element 34 | | | | | 2mDBTBPDBq-II | | |

*7Element 26: 10 nm,
*8Element 26: 15 nm

The light-emitting elements 25 to 34 were each sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, initial characteristics of these light-emitting elements were measured. Note that the measurement was performed at room temperature (in an atmosphere kept at 25° C.).

The table below shows main characteristics of the light-emitting elements 25 to 34 at around 1000 cd/m$^2$.

TABLE 20

| | Voltage | Current | Current density | Chromaticity | | Current efficiency | External quantum efficiency |
|---|---|---|---|---|---|---|---|
| | (V) | (mA) | (mA/cm$^2$) | x | y | (cd/A) | (%) |
| Element 25 | 3.0 | 0.28 | 7.1 | 0.14 | 0.18 | 15 | 12 |
| Element 26 | 3.1 | 0.29 | 7.2 | 0.14 | 0.18 | 15 | 12 |
| Element 27 | 3.0 | 0.37 | 9.3 | 0.14 | 0.18 | 15 | 12 |
| Element 28 | 3.1 | 0.29 | 7.3 | 0.14 | 0.17 | 15 | 13 |
| Element 29 | 2.9 | 0.19 | 4.6 | 0.14 | 0.16 | 13 | 11 |
| Element 30 | 3.0 | 0.24 | 5.9 | 0.14 | 0.16 | 13 | 12 |
| Element 31 | 3.0 | 0.28 | 6.9 | 0.14 | 0.17 | 14 | 12 |
| Element 32 | 3.1 | 0.30 | 7.4 | 0.14 | 0.16 | 14 | 12 |
| Element 33 | 3.0 | 0.29 | 7.2 | 0.14 | 0.16 | 14 | 12 |
| Element 34 | 3.1 | 0.33 | 8.3 | 0.14 | 0.16 | 14 | 12 |

Table 20 shows that the light-emitting elements 25 to 34 each have a very high external quantum efficiency in a range of 11% to 13% at around 1000 cd/m$^2$. Moreover, each of the light-emitting elements 25 to 34 has a low drive voltage, indicating favorable emission efficiency.

Furthermore, driving time-dependent change in luminance was measured under the conditions where the current value was 2 mA and the current density was constant. The table below shows the ratio (%) of the luminance after 100 hours to the initial luminance of each of the light-emitting elements.

TABLE 21

| | Ratio of luminance after 100 h to initial luminance (%) |
|---|---|
| Element 25 | 87 |
| Element 26 | 89 |
| Element 27 | 87 |
| Element 28 | 91 |
| Element 29 | 87 |
| Element 30 | 91 |
| Element 31 | 89 |

TABLE 21-continued

| | Ratio of luminance after 100 h to initial luminance (%) |
|---|---|
| Element 32 | 91 |
| Element 33 | 89 |
| Element 34 | 91 |

The light-emitting elements 25 to 34 each maintained 85% or more of the initial luminance even after being driven for 100 hours. Each of the light-emitting elements was found to be a long-life light-emitting element whose luminance was only slightly decreased over driving time.

This application is based on Japanese Patent Application Serial No. 2016-255514 filed with Japan Patent Office on Dec. 28, 2016, the entire contents of which are hereby incorporated by reference.

What is claimed is:

1. An organic compound represented by the following formula (G1), (G1)

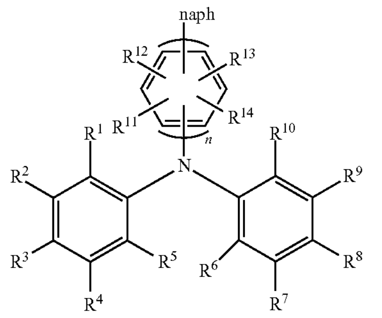

wherein each of $R^{11}$ to $R^{14}$ independently represents any one of hydrogen, an alkyl group having 1 to 6 carbon atoms, and a cycloalkyl group having 3 to 6 carbon atoms, wherein one of $R^1$ to $R^5$ represents a group selected from the following formulae (R-2) to (R-4), and the others represent hydrogen, wherein one of $R^6$ to $R^{10}$ represents a group selected from the following formulae (R-2) to (R-4), and the others represent hydrogen, (R-2)

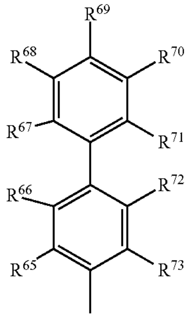

(R-3)

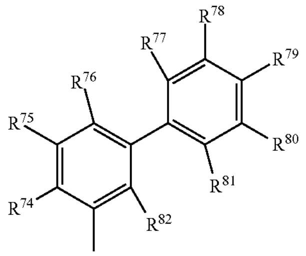

(R-4)

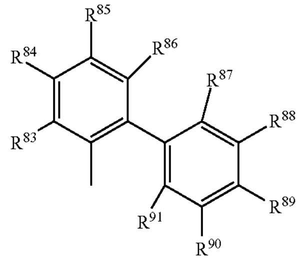

wherein each of $R^{65}$ to $R^{91}$ independently represents any one of hydrogen, an alkyl group having 1 to 6 carbon atoms, and a cycloalkyl group having 3 to 6 carbon atoms, wherein n represents 0, 1 or 2, wherein naph represents a group represented by the following formula (g1-1), (g1-1)

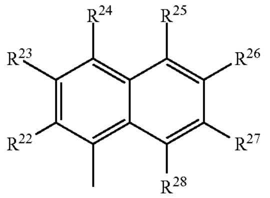

wherein one of $R^{22}$ to $R^{28}$ represents a group represented by formula (g2-1) or (g2-2), wherein each of the others of $R^{22}$ to $R^{28}$ independently represents any one of hydrogen, an alkyl group having 1 to 6 carbon atoms, and a cycloalkyl group having 3 to 6 carbon atoms, (g2-1)

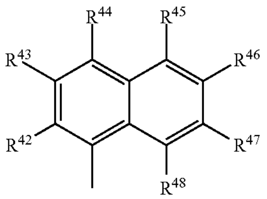

(g2-2)

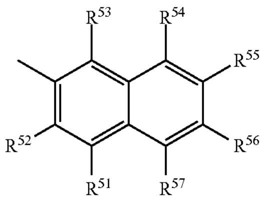

wherein each of $R^{42}$ to $R^{48}$ independently represents any one of hydrogen, an alkyl group having 1 to 6 carbon atoms, and a cycloalkyl group having 3 to 6 carbon atoms, and wherein each of $R^{51}$ to $R^{57}$ independently represents any one of hydrogen, an alkyl group having 1 to 6 carbon atoms, and a cycloalkyl group having 3 to 6 carbon atoms.

2. The organic compound according to claim 1, wherein the organic compound is represented by the following formula (G3), (G3)

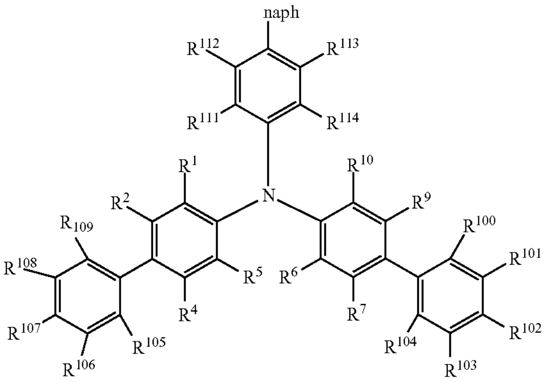

wherein one of $R^{100}$ to $R^{104}$ represents a phenyl group and the others represent hydrogen, wherein one of $R^{105}$ to $R^{109}$ represents a phenyl group and the others represent hydrogen, and wherein each of $R^{111}$ to $R^{114}$ independently represents any one of hydrogen, an alkyl group having 1 to 6 carbon atoms, and a cycloalkyl group having 3 to 6 carbon atoms.

3. The organic compound according to claim 1, wherein the organic compound is represented by the following formula (G4), and (G4)

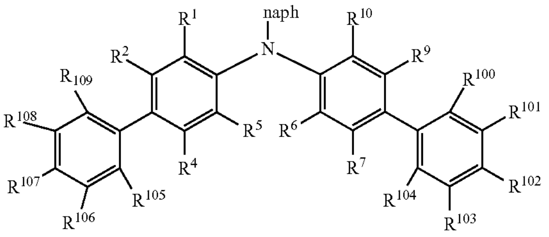

wherein one of $R^{100}$ to $R^{104}$ represents a phenyl group and the others represent hydrogen, and wherein one of $R^{105}$ to $R^{109}$ represents a phenyl group and the other represent hydrogen.

4. A light-emitting device comprising:

a hole-transport layer comprising the organic compound according to claim 1;

a light-emitting layer over the hole-transport layer; and an electron-transport layer over the light-emitting layer.

5. An electronic device comprising:

the light-emitting device according to claim 4; and any one of a sensor, an operation button, a speaker and a microphone.

6. A lighting device comprising:

the light-emitting device according to claim 4; and a housing.

* * * * *